US008147856B2

(12) United States Patent
Carozzi et al.

(10) Patent No.: US 8,147,856 B2
(45) Date of Patent: Apr. 3, 2012

(54) AXMI-031, AXMI-039, AXMI-040 AND AXMI-049, A FAMILY OF NOVEL DELTA-ENDOTOXIN GENES AND METHODS FOR THEIR USE

(75) Inventors: Nadine Carozzi, Raleigh, NC (US); **Nicholas Du

AXMI-031, AXMI-039, AXMI-040 AND AXMI-049, A FAMILY OF NOVEL DELTA-ENDOTOXIN GENES AND METHODS FOR THEIR USE

CROSS REFERENCE TO RELATED APPLICATION

This application is a divisional of U.S. application Ser. No. 11/762,886, filed Jun. 14, 2007, which claims the benefit of U.S. Provisional Application Ser. No. 60/813,774, filed Jun. 14, 2006, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "366899_SequenceListing.txt", created on Jan. 31, 2009, and having a size of 347 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus thuringiensis* family tree. In Advanced Engineered Pesticides, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Hofte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer there is a continual need to discover new forms of *Bacillus thuringiensis* delta-endotoxins.

SUMMARY OF INVENTION

Compositions and methods for conferring pest resistance to bacteria, plants, plant cells, tissues and seeds are provided. Compositions include nucleic acid molecules encoding sequences for delta-endotoxin polypeptides, vectors comprising those nucleic acid molecules, and host cells comprising the vectors. Compositions also include the polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in SEQ ID NO:2, 4, 6, 8, 10, 12, 15, 17, 19, 21, 23, 25, 27, 29, 31, 33, 35, or 38, a nucleotide sequence set forth in SEQ ID NO:1, 3, 5, 7, 9, 11, 14, 16, 18, 20, 22, 24, 26, 28, 30, 32, 34, or 37, or the delta-endotoxin nucleotide sequences deposited in bacterial hosts as Accession Nos. B-30935, B-30936, B-30937, and B-50046, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran or coleopteran pest. Methods and kits for detecting the nucleic acids and polypeptides of the invention in a sample are also included.

Methods for controlling or killing a nematode pest population are further provided. The methods comprise introducing into a plant a polynucleotide encoding a nematode-active polypeptide with a molecular size greater than 22 kDa. These nematode-active polypeptides are useful for controlling or killing plant-parasitic nematodes, particularly cyst nematodes.

The compositions and methods of the invention are useful for the production of organisms with pesticide resistance, specifically bacteria and plants. These organisms and compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

DETAILED DESCRIPTION

The present invention is drawn to compositions and methods for regulating pest resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered pesticidal proteins by methods known in the art, such as domain swapping or DNA shuffling. The proteins find use in controlling or killing lepidopteran, coleopteran, and nematode pest populations, and for producing compositions with pesticidal activity.

Plasmids containing the nucleotide sequences of the invention were deposited in the permanent collection of the Agricultural Research Service Culture Collection, Northern Regional Research Laboratory (NRRL), 1815 North University Street, Peoria, Ill. 61604, United States of America, on Jun. 9, 2006, and assigned Accession Nos. NRRL B-30935 (for axmi-031), NRRL B-30936 (for axmi-039), and NRRL B-30937 (for axmi-040); and on May 29, 2007 and assigned NRRL B-50046 (axmi-049). These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

By "delta-endotoxin" is intended a toxin from *Bacillus thuringiensis* that has toxic activity against one or more pests, including, but not limited to, members of the Lepidoptera, Diptera, and Coleoptera orders or members of the Nematoda phylum, or a protein that has homology to such a protein. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Provided herein are novel isolated nucleotide sequences that confer pesticidal activity. Also provided are the amino acid sequences of the delta-endotoxin proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1, 3, 5, 34, and 37, the delta endotoxin nucleotide sequences deposited in bacterial hosts as Accession Nos. NRRL B-30935, B-30936, B-30937, and B-50046, and variants, fragments, and complements thereof (for example, SEQ ID NO:7, 9, 11, 14, 16, 18, 20, 22, 24, 26, 28, 30, and 32). By "complement" is intended a nucleotide sequence that is sufficiently complementary to a given nucleotide sequence such that it can hybridize to the given nucleotide sequence to thereby form a stable duplex. The corresponding amino acid sequence for the delta-endotoxin protein encoded by this nucleotide sequence are set forth in SEQ ID NO:2, 4, 6, 8, 10, 12, 14, 16, 18, 20, 22, 24, 26, 28, 30, 32, 34, and 37.

Nucleic acid molecules that are fragments of these delta-endotoxin encoding nucleotide sequences are also encompassed by the present invention (for example, SEQ ID NO:9, 11, 14, 18, 20, 22, and 24). By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length delta-endotoxin encoding nucleotide sequence disclosed herein (for example, 3558 nucleotides for SEQ ID NO:1, 3984 nucleotides for SEQ ID NO:3, 3720 nucleotides for SEQ ID NO:5, and 3669 nucleotides for SEQ ID NO:34) depending upon the intended use. By "contiguous" nucleotides is intended nucleotide residues that are immediately adjacent to one another. Fragments of the nucleotide sequences of the present invention will encode protein fragments that retain the biological activity of the delta-endotoxin protein and, hence, retain pesticidal activity. By "retains activity" is intended that the fragment will have at least about 30%, at least about 50%, at least about 70%, 80%, 90%, 95% or higher of the pesticidal activity of the delta-endotoxin protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100 contiguous amino acids, or up to the total number of amino acids present in a full-length delta-endotoxin protein of the invention (for example, 1185 amino acids for SEQ ID NO:2, 1327 amino acids for SEQ ID NO:4, 1239 amino acids for SEQ ID NO:6, and 1223 amino acids for SEQ ID NO:35).

Preferred delta-endotoxin proteins of the present invention are encoded by a nucleotide sequence sufficiently identical to the nucleotide sequence of SEQ ID NO:1, 3, 5, 7, 9, 11, 14, 16, 18, 20, 22, 24, 26, 28, 30, 32, 34, or 37. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin-like nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A nonlimiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules (for example, SEQ ID NO:7, 9, 11, 16, 18, 22, 24, 26, 28, 30, and 32). "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743, 477, all of which are herein incorporated by reference in their entirety.

The skilled artisan will further appreciate that changes can be introduced by mutation of the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of the amino acid sequences of the present invention and known delta-endotoxin sequences. Examples of residues that are conserved but that may allow conservative amino acid substitutions and still retain activity include, for example, residues that have only conservative substitutions between all proteins contained in an alignment of the amino acid sequences of the present invention and known delta-endotoxin sequences. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the delta-endotoxin nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of delta-endotoxin encoding nucleotide sequence of the invention or a fragment or variant thereof. Methods for the preparation of probes for hybridization are generally known in the art and are disclosed in Sambrook and Russell, 2001, supra herein incorporated by reference.

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NO:2, 4, 6, 8, 10, 12, 15, 17, 19, 21, 23, 25, 27, 29, 31, 33, 35, or 38. Fragments, biologically active portions, and variants thereof are also provided, and may be used to practice the methods of the present invention.

"Fragments" or "biologically active portions" include polypeptide fragments comprising amino acid sequences sufficiently identical to the amino acid sequence set forth in SEQ ID NO:2, 4, 6, 8, 10, 12, 16, 17, 19, 21, 23, 25, 27, 29, 31, 33, 35, or 38 and that exhibit pesticidal activity (for example, SEQ ID NO:15, 19, 21, 23, or 25). A biologically active portion of a delta-endotoxin protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2, 4, 6, 8, 10, 12, 15, 17, 19, 21, 23, 25, 27, 29, 31, 33, 35, or 38. The invention encompasses other fragments, however, such as any fragment in the protein greater than about 10, 20, 30, 50, 100, 150, 200, 250, 300, 350, 400, 400, 450, 500, 550, 600, 650, 700, 750, 800, 850, 900, 950, 1000, 1050, 1100, 1150, 1200, 1250, or 1300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO:2, 4, 6, 8, 10, 12, 16, 17, 19, 21, 23, 25, 27, 29, 31, 33, 35, or 38 (e.g., SEQ ID NO:10, 12, 17, 19, 23, 25, 27, 29, 31, or 33). Variants also include polypeptides encoded by a nucleic acid molecule that hybridizes to the nucleic acid molecule of SEQ ID NO:1, 3, 5, 7, 9, 11, 14, 16, 18, 20, 22, 24, 26, 28, 30, 32, 34, or 37, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi-031, axmi-039, axmi-040, and axmi-049 genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. These delta-endotoxin proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a delta-endotoxin may be altered by various methods, and that these alterations may result in DNA sequences encoding proteins with amino acid sequences different than that encoded by a delta-endotoxin of the present invention. This protein may be altered in various ways including amino acid substitutions, deletions, truncations, and insertions of one or more amino acids of SEQ ID NO:2, 4, 6, 8, 10, 12, 15, 17, 19, 21, 23, 25, 27, 29, 31, 33, 35, or 38, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of a delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a delta-endotoxin to confer pesticidal activity may be improved by the use of such techniques upon the compositions of this invention. For example, one may express a delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J.*

*Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A delta-endotoxin sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" (i.e., SEQ ID NO:9, 11, 28, 30, and 32) to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence (i.e., SEQ ID NO:10, 12, 29, 31, and 33) sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the delta-endotoxin is targeted to the chloroplast for expression. In this manner, where the delta-endotoxin is not directly inserted into the chloroplast, the expression cassette will additionally contain a nucleic acid encoding a transit peptide to direct the delta-endotoxin to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The delta-endotoxin gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell.

"Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The delta-endotoxin gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the delta-endotoxin are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (Agrobacterium-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western blot, biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Pesticidal Activity in Plants

In another aspect of the invention, one may generate transgenic plants expressing a delta-endotoxin that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a delta-endotoxin may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Pest Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a delta-endotoxin gene into a cellular host. Expression of the delta-endotoxin gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

Nematode Control

Plant-parasitic nematodes, including cyst nematodes, root knot nematodes, and other nematodes, cause billions of dollars in damage to crops every year. Plant-parasitic nematodes pierce plant cell walls with their stylet, which is formed by some of the mouth and esophagus parts, and pump up the plant cell just into their digestive system. Numerous publications in the art conclude that sedentary plant parasitic nematodes do not ingest molecules larger than about 23-28 kDa in vivo. This has led to the widespread belief that the feeding tube produced by these nematodes acts as a molecular sieve, restricting the size of molecules that can be ingested. Bockenhoff and Grundler ((1994) *Parasitology* 109:249-254) injected fluorescently labeled dextrans into syncytia that were being fed upon by *Heterodera schachtii*. They found that the nematodes ingested 22 kDa dextrans, but not 40 kDa dextrans. Urwin et al. ((1998) *Planta* 204:472-479) found that a 23 kDa fusion protein expressed in transgenic *Arabidopsis* could not be ingested by *H. schachtii*, although a protein of about 11 kDa could be ingested. Similarly, Unwin et al. ((1997) *Molecular Plant-Microbe Interactions* 10:394-400) found that 28 kDa green fluorescent protein (GFP) expressed in transgenic *Arabidopsis* could not be ingested by *H. schachtii*. Thus, it was not previously recognized or demonstrated that nematodes could be controlled by expressing a protein greater than 22 kDa in a plant since it was understood that nematodes would not ingest such a protein.

Provided herein are methods and compositions for conferring resistance to nematodes in plants. The methods comprise introducing into a plant at least one nucleotide sequence encoding a nematode-active polypeptide and growing the plant in a field containing nematodes. By "nematode-active polypeptide" is intended a polypeptide that, when ingested by the nematode, results in the death or stunting of growth or proliferation of at least one nematode. In one embodiment, the nematode-active polypeptide has a molecular weight greater than about 22 kDa, about 23 kDa, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80 kDa, or greater.

In another embodiment, the nematode-active polypeptide has activity against plant-parasitic nematodes. Expression of the nematode-active polypeptide in a plant reduces the ability of nematodes to infest or feed on roots of the plant. Examples of plant-parasitic nematodes sensitive to the compositions of the present invention include root knot nematodes (*Meloidogyne* sp.), stunt nematode (*Tylenchorhynchus* sp.), lance nematode (*Hoplolaimus* sp.), spiral nematode (*Helicotylenchus* sp.), lesion nematode (*Pratylenchus* sp.), cyst nematode (*Heterodera* sp. and *Globodera* sp.), and ring nematode (*Criconema* sp.).

Pesticidal Compositions

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, coleopteran, or nematode pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrimidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypli*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis*; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise introducing into a plant or plant cell a polynucleotide comprising a pesticidal sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing a pesticidal protein disclosed herein. Expression of the pesticidal protein results in a reduced ability of a pest to infest or feed on the plant, thus improving plant yield.

The following examples are offered by way of illustration and not by way of limitation.

EXPERIMENTAL

Example 1

Growth of ATX9387 and Preparation of Extracts

Strain ATX9387, identified as a member of the *Bacillus cereus/Bacillus thuringiensis* group by MIDI analysis, was grown in T3 medium at 30 degrees for times ranging from 16 hours to 5 days. Cultures were centrifuged and the supernatants were passed through 0.2 micron filters, resulting in sterile supernatants Example 2

*C. elegans* Bioassay

*Caenorhabitis elegans* ("*C. elegans*") hermaphrodites were reared as known in the art, to generate populations of healthy animals for bioassay. General procedures for growth, harvesting, and genetic manipulation of *C. elegans* including growth media, etc. may be found in the art, for example, in Wood, ed. (1988) *The Nematode Caenorhabditis elegans* (Cold Spring Harbor Laboratory Press, Cold Spring Harbor, N.Y.).

Sterile supernatants from strain ATX9387 were tested for activity on *C. elegans*. Bioassays were performed in 96-well plates. Five to ten nematodes were added to 80 μl of S medium (Wood, supra) and were mixed with 20 μl of sterile supernatant, 0.5 μl of concentrated HB101 (prepared as described in Wood, supra) and rifampicin (final concentration of 0.1 μg/l). Assays were allowed to proceed at room temperature for 3 days and nematodes were quantitated. Negative control samples (T3 medium or sterile supernatants from inactive strains) contained hundreds of active nematodes, while test samples (containing ATX9387 supernatant) contained 5 to 10 nematodes that were sluggish or dead. The results of the bioassay of ATX9387 extracts on *C. elegans* are shown in Table 1.

TABLE 1

Activity of ATX9387 extracts on *C. elegans*

| Growth Time | ATX9387 | Control |
|---|---|---|
| 16 hours | − | − |
| 1 day | − | − |
| 2 days | − | − |
| 3 days | ++ | − |
| 4 days | ++ | − |
| 5 days | ++ | − |

Example 3

Activity of ATX9387 on Soybean Cyst Nematodes

A sterile supernatant of a 5-day culture of ATX9387 was concentrated 40-fold and fed to SCN J2 nematodes. Nematodes feeding on sterile supernatant were reproducibly observed to be sluggish, and exhibited higher motility than nematodes fed extract of a negative control concentrated to the same extent.

Example 4

Anti-Nematode Activity from ATX9387 is Conferred by a Protein

To identify the anti-nematode activity in ATX9387, the following tests were performed. First, the ability of the activity to be destroyed by heating was tested by heating samples of sterile supernatant from ATX9387 to 100° C. for 10 minutes, then assaying heated material in a nematode bioassay. Heat treatment of sterile supernatants from ATX9387 resulted in a loss of anti-nematode activity. Next, active samples were treated with pronase to degrade proteins. This treatment resulted in loss of activity. Sterile supernatants from ATX9387 were passed through a 3 kDa molecular weight cut-off ("MWCO") concentration unit. The active ingredient was retained by the 3 kDa MWCO filter while the flow-through showed no activity. This indicates that the active molecule was larger than 3 kDa in size.

Example 5

Fractionation of Activity from ATX9387

The sterile supernatant of a 4-day culture of ATX9387 was fractionated by liquid chromatography on an anion exchange column in 20 mM Tris pH 8, using a gradient from 0 M to 1 M NaCl. Several consecutive fractions were active. The most active fraction was subjected to SDS-PAGE, and two prominent bands of approximately 130 kd and approximately 70 kd were observed.

In another experiment strain ATX9387 was grown for 5 days in T3 medium at 30° C. The culture was centrifuged at 8,000×g for 10 minutes, and the supernatant was passed through a 0.2 μm filter. The filtered supernatant was dialyzed against 20 mM Tris pH 8 using Spectra/Por 1 dialysis tubing (6-8,000 MWCO), and was then fractionated on an anion exchange column (Mono Q) using a gradient from 0 to 1 M NaCl over 20 bed volumes. The fractions were dialyzed against 20 mM Tris pH 8 using Slide-A-Lyzer (Pierce Biotechnology, Rockford, Ill.) mini dialysis units (7,000 MWCO), and bioassayed on *C. elegans* using 20 μl of sample in a 100 μl bioassay volume, as described herein. Fractions 12 and 13 were found to be active, and were pooled and then concentrated 7-fold using an Amicon Ultra-4 5,000 MWCO concentrator. The concentrated material was fractionated on a gel filtration column (Superdex 200) in 50 mM sodium phosphate, 150 mM NaCl, pH 7. Fractions were concentrated 10-fold using Centricon YM-3 concentrators, and were bioassayed on *C. elegans* as above. Fractions 5 and 6 were the most active, and fraction 7 was somewhat active. SDS-PAGE of the fractions showed that fractions 5-7 shared several proteins: a protein at about 130 kDa, a doublet at about 75 kDa, and a protein at about 53 kDa. The most prominent bands were subjected to N-terminal protein sequencing by Edman degradation. The 130 kDa protein and the 70 kDa protein had very similar N-terminal sequences (cysteine could not be detected by the method used), and thus are likely to result from the same initial protein. This protein was designated as AXMI-031 (SEQ ID NO:2).

TABLE 2

N-terminal sequence of the ~130 kDa protein from ATX9387

| 1 | A, S + S', M |
| 2 | D, Q |

TABLE 2-continued

N-terminal sequence of the ~130 kDa protein from ATX9387

| 3 | ?, P, N |
| 4 | N |
| 5 | L |
| 6 | Q |
| 7 | S |
| 8 | Q |
| 9 | ?, Q |
| 10 | N |
| 11 | I |
| 12 | P |
| 13 | Y |
| 14 | N |
| 15 | V |

TABLE 3

N-terminal sequence of the about ~70 kDa protein from ATX9387

| 1 | A, G, S + S' |
| 2 | F |
| 3 | P |
| 4 | N |
| 5 | L |
| 6 | Q |
| 7 | V? |
| 8 | Q |
| 9 | ? |
| 10 | N?, V? |
| 11 | I |
| 12 | P |
| 13 | Y, Q |
| 14 | ?, N |
| 15 | ?, V |

A search of protein databases with the N-terminal sequences of the ~130 kDa protein and the ~70 kDa protein demonstrated that the N-terminal amino acids of the AXMI-031 proteins have significant similarity to the N-terminus of the endotoxin Cry14Aa (SEQ ID NO:13).

N-terminal sequence of Cry14A: MDCN-LQSQQNIPYNV (amino acid residues 1 through 15 of SEQ ID NO:13).

Example 6

Cloning of the Axmi-031 Coding Region from ATX9387

A random fragment library of ATX9387 was generated, and a DNA clone (pAX031) containing the DNA sequence encoding the N-terminus of axmi-031 was identified. A second clone, pAX032, was identified as containing the C-terminus of axmi-031. Clones pAX031 and pAX032 overlap substantially, such that it is clear to one skilled in the art that both clones together comprise the entire axmi-031 coding region.

To confirm the nature of the AXMI-031, a genomic clone was amplified using a high fidelity polymerase PFU ULTRA™ (Stratagene) from total DNA using primers designed to the ends of the axmi-031 open reading frame. The resulting PCR product was cloned into the PCR-TOPOII-Blunt vector (Invitrogen) to create pAX980. The DNA sequence pAX980 was determined and found to contain the same open reading frame as in the random fragment library clones pAX031 and pAX032. Translation of this open reading frame generates a protein sequence consistent with the N-terminal sequence obtained from the purified AXMI-031 protein. Thus, this open reading frame was designated axmi- 031 (SEQ ID NO:1). The plasmid clone pAX2515, containing axmi-031 was deposited on Jun. 9, 2006 and assigned the accession number NRRL B-30935.

Example 7

Comparison of AXMI-031 to Other Known Endotoxins

Database searches using the AXMI-031 protein sequence demonstrate that AXMI-031 is a member of the delta-endotoxin class of insecticidal proteins. AXMI-031 is most similar to the cry14Aa1 endotoxin. The amino acid sequence of AXMI-031 is 86.6% identical to CRY14Aa1 (SEQ ID NO:13).

Example 8

Expression of the AXMI-031 Polypeptide in *E. coli*

For soluble expression in *E. coli*, primers were designed to include the translation start and stop codons from the axmi-031 ORF. The primers added an optimal RBS and Gateway attB recombination sites. Stratagene Pfu I polymerase was used to consistently amplify the ORF from the pAX980, and recombined with pDONR221 (Invitrogen, Carlsbad, Calif.) to create the entry vector pAX2515 (as per protocols from Invitrogen). The clone was sequenced for verification. A further recombination was performed to introduce the ORF into pDEST 17 to be expressed by the T7 promoter, yielding pAX2530. The presence and orientation of the inserted axmi-031 fragment were verified by restriction digest, and transformed into *E. coli* BL21 (DE3) cells. This vector produces a translational fusion of 26 amino acids (3.17 kDa), including a 6× His tag, on the N-terminus of AXMI-031.

His-AXMI-031 was expressed from pAX2530 in BL21* (DE3) cells as follows. A starter culture of pAX2530 was grown overnight at 37° C. in LB with 50 µg/ml carbenicillin. The following day the saturated culture was diluted 1:100 into fresh medium, and the fresh culture grown at 37° to an OD of 0.4, at which time the culture was placed at room temperature with shaking overnight. As a control, an expression vector carrying the axmi-004 gene (pAX2530) was constructed as for axmi-031, and the AXMI-004 protein (U.S. patent application Ser. No. 10/782,020) was expressed from pAX2504 in the same *E. coli* host. Whole cultures were analyzed by SDS-PAGE. Cultures containing pAX2530 produced a prominent protein band at approximately 135 kDa, the expected size for His-AXMI-031 protein, while cultures containing pAX2504 did not.

Example 9

Antibodies to AXMI-031

To generate anti-AXMI-031 antibodies, affinity purified AXMI-031 (SEQ ID NO:2) protein was inoculated into rabbits, and antisera to AXMI-031 isolated and titered as known in the art. The selected antisera were found to also react with SYNAXMI-031 protein (SEQ ID NO:8).

Example 10

Activity of AXMI-031 on *C. elegans*

Cultures of *E. coli* containing pAX2530, were prepared, and found to produce a 135 kDa protein not present in control strains, suggesting the expression of AXMI-031 in pAX2530 containing strains. These cultures were tested for activity on *C. elegans* and were active against *C. elegans*, while control cultures showed no activity against *C. elegans*.

Example 11

Expression of AXMI-031 in *Bacillus*

The insecticidal gene axmi-031 is amplified by PCR from pAX980, and the PCR product is cloned into the *Bacillus* expression vector pAX916, or another suitable vector, by methods well known in the art. The resulting *Bacillus* strain, containing the vector with axmi-031 is cultured on a conventional growth media, such as CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared, and AXMI-031 protein was tested for activity in bioassays against *C. elegans*, and found to have activity.

Example 12

Synaxmi-031, Synaxmi-031(apo) and Synaxmi-031 (ER)

In one aspect of the invention, synthetic axmi-031 sequences are generated, for example synaxmi-031 (SEQ ID NO:7). These synthetic sequences have an altered DNA sequence relative to the axmi-031 sequence, and encode a protein that is collinear with the original AXMI-031 protein, but lacks the C-terminal "crystal domain" present in AXMI-031. The synaxmi-031 gene sequence encodes SYNAXMI-031 protein (SEQ ID NO:8), which comprises the first 685 amino acids of the AXMI-031 protein.

In another aspect of the invention, modified versions of synaxmi-031 are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White *Lupin Lupinus albus* (Genebank ID GI:14276838; Miller et al. (2001) Plant Physiology 127: 594-606) is known in the art to result in endoplasmic reticulum targeting of heterologous proteins. If the resulting fusion protein also contains an endoplasmic retention sequence comprising the peptide N-terminus-lysine-aspartic acid-glutamic acid-leucine (i.e. the "KDEL" motif (SEQ ID NO:36) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, the synaxmi-031ER gene (SEQ ID NO:11) encodes a fusion protein that contains the N-terminal thirty-one amino acids of the acid phosphatase gene from the White *Lupin Lupinus albus* fused to the N-terminus of SYNAXMI-031, as well as the KDEL sequence at the C-terminus. Thus, the resulting protein AXMI-031ER (SEQ ID NO:12), is predicted to be targeted the plant endoplasmic reticulum upon expression in a plant cell.

The synaxmi-031(apo) gene (SEQ ID NO:9) encodes a fusion protein that contains the N-terminal thirty-one amino acids of the acid phosphatase gene from the White *Lupin Lupinus albus* fused to the N-terminus of SYNAXMI-031, but lacks the KDEL sequence at the C-terminus. Thus, the resulting protein AXMI-031 (APO) (SEQ ID NO:10), is predicted to be targeted to the plant apoplast upon expression in a plant cell.

Example 13

Truncations of Synaxmi-031 to Yield Alternate AXMI-031 Proteins

DNA constructs that resulted in expression of variants of AXMI-031 protein were developed and expressed, in addition to synthetic sequences encoding AXMI-031 and variants and fragments thereof (SEQ ID NO:15-27). A subset of these genes were tested for nematode activity in vitro.

TABLE 4

Nematicidal Activity of AXMI-031 variants in vitro

| Protein | Nucleotide SEQ ID NO: | Amino acid SEQ ID NO: | Active on C. elegans? |
| --- | --- | --- | --- |
| Bacterial Expression | | | |
| AXMI-031-truncated | 14 | 15 | Yes |
| AXMI-031(m1) | 16 | 17 | Yes |
| AXMI-031(m1)-truncated | 18 | 19 | Yes |
| AXMI-031(A-D) | 20 | 21 | Yes |
| SYNAXMI-031 (A-D) | 26 | 27 | NT |
| AXMI-031(B-C) | 22 | 23 | Yes |
| AXMI-031(B-D) | 24 | 25 | Yes |

NT = not tested

Example 14

Truncations and Addition of Cellular Targeting Domain(s) for Plant Expression In another aspect of the invention, modified versions of the synaxmi-031 sequences are designed such that the resulting peptide is targeted to a plant organelle, such as the endoplasmic reticulum or the apoplast.

In another aspect of the invention, the genes are truncated such that the resulting peptide is a truncated version of AXMI-031, which may or may not be further modified for targeting to plant organelles, such as the apoplast or the endoplasmic reticulum.

In another aspect of the invention, modified versions are developed that result in expression of truncated variants that contain domains designed to target the resulting protein to plant organelles.

The following variant nucleotide sequences were designed:
aposynaxmi-031 (A-D) (SEQ ID NO:28) encodes the APOAXMI-031 (A-D) protein (SEQ ID NO:29). apoSyn2axmi-031(A-D) (SEQ ID NO:30) encodes the APOAXMI-031(A-D) protein (SEQ ID NO:31). aposynaxmi-031 (fl) (SEQ ID NO:37) encodes the APOSYNAXMI-031(FL) protein (SEQ ID NO:38). Synaxmi031(t)-ER (SEQ ID NO:32) encodes the SYNAXMI-031(FL)-ER protein (SEQ ID NO:33).

Example 15

Extraction of plasmid DNA from Strains ATX16538 ATX16093 and ATX21049

Strains ATX16538, ATX16093, and ATX21049 were selected for analysis. Pure cultures of each strain were grown in large quantities of rich media. The cultures were centrifuged to harvest the cell pellet. The cell pellet was then prepared by treatment with SDS by methods known in the art, resulting in breakage of the cell wall and release of DNA. Proteins and large genomic DNA was then precipitated by a high salt concentration. The plasmid DNA was then precipitated with ethanol. In several instances, the plasmid DNA was separated from any remaining chromosomal DNA by high-speed centrifugation through a cesium chloride gradient. Alternatively, the plasmid DNA was purified by binding to a resin, as known in the art. For each strain, the quality of the DNA was checked by visualization on an agarose gel by methods known in the art.

Example 16

Cloning of Genes from Strains ATX16538 ATX16093 and ATX21049

DNA libraries were prepared from the plasmid DNA or each strain. This may be achieved in many ways as known in the art. For, example, the purified plasmid DNA can be sheared into 5-10 kb sized fragments and the 5' and 3' single stranded overhangs repaired using T4 DNA polymerase and Klenow fragment in the presence of all four dNTPs, as known in the art. Phosphates can then be attached to the 5' ends by treatment with T4 polynucleotide kinase, as known in the art. The repaired DNA fragments can then be ligated overnight into a standard high copy vector (i.e. pBLUESCRIPT® SK+), suitably prepared to accept the inserts as known in the art (for example by digestion with a restriction enzyme producing blunt ends).

The quality of the resulting DNA libraries was analyzed by digesting a subset of clones with a restriction enzyme known to have a cleavage site flanking the cloning site. A high percentage of clones were determined to contain inserts, usually with an average insert size of 5-6 kb.

Example 17

High Throughput Sequencing of Library Plates

Once the DNA library quality was checked and confirmed, colonies were grown in a rich broth in 2 ml 96-well blocks overnight at 37° C., typically at a shaking speed of 350 rpm. The blocks were centrifuged to collect the cells at the bottom of the block. The blocks were then prepared by standard alkaline lysis prep in a high throughput format.

The end sequences of clones from this library were then determined for a large number of clones from each block in the following manner: The DNA sequence of each clone chosen for analysis was determined using the fluorescent dye terminator sequencing technique (Applied Biosystems), by methods known in the art using an automated DNA sequencing machine, and standard oligonucleotide primers that anneal to the plasmid vector in the region flanking the insert.

Example 18

Assembly and Screening of Sequencing Data

DNA sequences obtained were compiled into an assembly project and aligned together to form contigs. This can be done efficiently using a computer program, such as Vector NTi, or alternatively by using the Pred/Phrap suite of DNA alignment and analysis programs as described elsewhere herein. These contigs, along with any individual read that may not have been added to a contig, were compared to a compiled database of all classes of known pesticidal genes. Contigs or individual reads identified as having identity to a known endotoxin or pesticidal gene were analyzed further.

From strain ATX16538, pAX2579 was found to contain an open reading frame with homology to "cry" type delta-endotoxins. This open reading frame was designated as axmi-039 (SEQ ID NO:3), and the encoded protein was designated AXMI-039 (SEQ ID NO:4). The axmi-039 ORF and flanking sequence (151 bp upstream of the start codon and 29 bp downstream of the stop codon) was PCR amplified, cloned into pRSFIB and sequenced to yield pAX2579. pAX2579 was deposited with the ARS Patent Strain Collection on Jun. 9, 2006, and assigned NRRL B-30936. AXMI-039 is 43.9% amino acid sequence identity to Cry5Ba1, which is the closest homolog identified.

From strain ATX16093, pAX4313 was found to contain an open reading frame with homology to "cry" type delta-endotoxins. This open reading frame was designated as axmi-040 (SEQ ID NO:5), and the encoded protein was designated AXMI-040 (SEQ ID NO:6). pAX4313 was deposited with the ARS Patent Strain Collection on Jun. 9, 2006, and assigned NRRL B-30937. AXMI-040 is 42.9% amino acid sequence identity to Cry21Ba1, which is the closest homolog identified.

From strain ATX21049, an open reading frame was identified that exhibited homology to "cry" type delta-endotoxins. This open reading frame was designated as axmi-049 (SEQ ID NO:34), and the encoded protein was designated AXMI-049 (SEQ ID NO:35). This open reading frame was amplified by PCR and cloned into a vector to yield pAX5039. pAX5039 was deposited with the ARS Patent Strain Collection on May 29, 2007, and assigned NRRL B-50046. AXMI-049 has 46.1% amino acid sequence identity to Cry21Ba1, which is the closest homology identified.

Example 19

Vectoring of the Pesticidal genes of the invention for Plant Expression

Each of the coding regions of the genes of the invention are connected independently with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

Example 20

Transformation of the Genes of the Invention into Plant Cells by Agrobacterium-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

Example 21

Transgenic Plants Expressing AXMI-031 and Variants

The plant expression cassettes described herein are combined with an appropriate plant selectable marker to aid in the selections of transformed cells and tissues, and ligated into plant transformation vectors. These may include binary vectors from *Agrobacterium*-mediated transformation or simple plasmid vectors for aerosol or biolistic transformation. synaxmi-031 (apo) was cloned into a plant expression vector, and this vector was introduced into *Agrobacterium tumefaciens* as known in the art. The synaxmi-031 (apo) coding region under control of the *Arabidopsis* UBQ3 promoter (Norris et al. (1993) *J. Plant Mol. Biol.* 21:895-906) was introduced into *Arabidopsis thaliana* by floral dip method as known in the art, and transgenic plants were selected. The presence of synaxmi-031(apo) in the transgenic Ti population was confirmed by PCR analysis as known in the art, using oligonucleotide primers derived from the sequence of synaxmi-031, which also anneal to synaxmi-031 (apo).

Leaf and root tissue from transgenic synaxmi-031 (apo) containing plants was prepared and separated on polyacrylamide gels alongside non-transgenic controls and dilutions of AXMI-031 protein, and transferred to a membrane as known in the art. The samples were tested for the presence of the expression product of synaxmi-031(apo) by Western blot analysis as known in the art, using anti-AXMI-031 antibodies described herein. The expression product of synaxmi-031 (apo) of the expected size was detected in samples of both leaf and root tissue from transgenic synaxmi-031(apo)-containing plants, but not detected in non-transgenic controls.

TABLE 5

Antibody detection of SYNAXMI-031(APO) in transgenic plants

| Source of Tissue | Detection of SYNAXMI-031(APO) |
|---|---|
| Non-transformed control | − |
| synaxmi-031(apo) containing plant 'A' | +++ |
| synaxmi-031(apo) containing plant 'B' | +++ |

Example 22

Reduced Cyst Formation by AXMI-031 Expressing Plants

Transgenic plants expressing synaxmi-031 (apo) were tested for ability to resist infestation by *Heterodera schachtii* compared to control plants. Transgenic plants, as well as control plants transformed with vector alone, were infested with approximately 100 J2 hatchlings, and the number of nematodes entering the roots, as well as the number of cyst formed, was measured. Transgenic plants expressing SYN-AXMI-031 (APO) were found to consistently have reduced numbers of nematodes entering the roots, and reduced numbers of cysts formed relative to controls.

TABLE 6

Reduced cyst formation in AXMI-031 expressing plants

|  | Cyst formation |
|---|---|
| Control plant | ++ |
| Plants expressing AXMI-031(APO) | + |

Example 23

Additional Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet; then, dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*. CRC, Boca Raton, Fla. Alternatively, assays are commonly described in the journals "Arthropod Management Tests" and "Journal of Economic Entomology" or by discussion with members of the Entomological Society of America (ESA).

Example 24

Transformation of Maize Cells with the Pesticidal Genes of the Invention

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/1 nL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240,842).

DNA constructs designed to express the genes of the invention in plant cells are accelerated into plant tissue using an aerosol beam accelerator, using conditions essentially as described in PCT Publication No. WO/0138514. After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | per liter | Source |
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polypeptide with pesticidal activity, selected from the group consisting of:
   a) a polypeptide comprising the amino acid sequence of SEQ ID NO:2, 4, 6, 8, 10, 12, 15, 17, 19, 21, 23, 25, 27, 29, 31, 33, 35, or 38;
   b) a polypeptide comprising an amino acid sequence having at least 95% sequence identity to the amino acid sequence of SEQ ID NO:2, 8, 10, 12, 15, 17, 19, 21, 23, 25, 27, 29, 31, 33 or 38, wherein said amino acid sequence has pesticidal activity against a lepidopteran or a nematode pest;
   c) a polypeptide that is encoded by the nucleotide sequence of SEQ ID NO:1, 3, 5, 7, 9, 11, 14, 16, 18, 20, 22, 24, 26, 28, 30, 32, 34, or 37; and
   d) a polypeptide encoded by the delta endotoxin nucleotide sequence of the DNA insert of the plasmid deposited as Accession No. B-30935.

2. The polypeptide of claim 1 further comprising heterologous amino acid sequences.

3. A composition comprising the polypeptide of claim 1.

4. The composition of claim 3, wherein said composition is selected from the group consisting of a powder, dust, pellet, granule, spray, emulsion, colloid, and solution.

5. The composition of claim 3, wherein said composition is prepared by desiccation, lyophilization, homogenization, extraction, filtration, centrifugation, sedimentation, or concentration of a culture of *Bacillus thuringiensis* cells.

6. The composition of claim 3, comprising from about 1% to about 99% by weight of said polypeptide.

7. A method for controlling a lepidopteran or nematode pest population comprising contacting said population with a pesticidally-effective amount of the polypeptide of claim 1.

8. A method for killing a lepidopteran or nematode pest, said method comprising contacting said pest with, or feeding to said pest, a pesticidally-effective amount of the polypeptide of claim 1.

9. A method for producing a polypeptide with pesticidal activity, said method comprising culturing a host cell comprising a nucleic acid molecule encoding said polypeptide under conditions in which said nucleic acid molecule is expressed, wherein said nucleic acid molecule comprises a nucleotide sequence selected from the group consisting of:
   a) the nucleotide sequence of SEQ ID NO:1, 7, 9, 11, 14, 16, 18, 20, 22, 24, 26, 28, 30, 32, or 37, or a complement thereof;
   b) a nucleotide sequence that encodes a polypeptide comprising the amino acid sequence of SEQ ID NO:2, 8, 10, 12, 15, 17, 19, 21, 23, 25, 27, 29, 31, 33, or 38;
   c) a nucleotide sequence that encodes a polypeptide comprising an amino acid sequence having at least 95% sequence identity to the amino acid sequence of SEQ ID NO:2, 8, 10, 12, 15, 17, 19, 21, 23, 25, 27, 29, 31, 33, or 38, wherein said amino acid sequence has pesticidal activity against a lepidopteran or a nematode pest; and,
   d) the delta endotoxin nucleotide sequence of the DNA insert of the plasmid deposited as Accession Nos. B-30935, or a complement thereof.

* * * * *

SEQUENCE LISTING

<160> NUMBER OF SEQ ID NOS: 38

<210> SEQ ID NO 1
<211> LENGTH: 3558
<212> TYPE: DNA
<213> ORGANISM: Bacillus cereus/Bacillus thuringiensis
<220> FEATURE:
<221> NAME/KEY: CDS
<222> LOCATION: (1)...(3558)

<400> SEQUENCE: 1

```
atg gat tgt aat tta caa tca caa caa aat att cca tat aat gta tta       48
Met Asp Cys Asn Leu Gln Ser Gln Gln Asn Ile Pro Tyr Asn Val Leu
1               5                   10                  15 gca ata cca gta tct aat gtt aat tcg ttg act gat aca gtt gga gat       96
Ala Ile Pro Val Ser Asn Val Asn Ser Leu Thr Asp Thr Val Gly Asp
            20                  25                  30 tta aaa aaa gca tgg gaa gaa ttt caa aaa act ggt tct ttt tca tta      144
Leu Lys Lys Ala Trp Glu Glu Phe Gln Lys Thr Gly Ser Phe Ser Leu
        35                  40                  45 aca gct tta caa caa gga ttt tct gct tca caa gga gga aca ttc aat      192
Thr Ala Leu Gln Gln Gly Phe Ser Ala Ser Gln Gly Gly Thr Phe Asn
    50                  55                  60 tat tta aca tta cta caa tca gga ata tca tta gct ggt tct ttt gtt      240
Tyr Leu Thr Leu Leu Gln Ser Gly Ile Ser Leu Ala Gly Ser Phe Val
65                  70                  75                  80 cct gga ggt act ttt gta gca cct att att aat atg gtt att ggt tgg      288
Pro Gly Gly Thr Phe Val Ala Pro Ile Ile Asn Met Val Ile Gly Trp
                85                  90                  95 tta tgg cca cat aaa aac aaa aat gcg gat aca gaa aat tta ata aat      336
Leu Trp Pro His Lys Asn Lys Asn Ala Asp Thr Glu Asn Leu Ile Asn
            100                 105                 110 tta att gat tca gaa att caa aaa caa tta aac aaa gct tta tta gat      384
Leu Ile Asp Ser Glu Ile Gln Lys Gln Leu Asn Lys Ala Leu Leu Asp
        115                 120                 125 gca gat aga aat gag tgg agc tct tat tta gaa tct ata ttt gat tct      432
Ala Asp Arg Asn Glu Trp Ser Ser Tyr Leu Glu Ser Ile Phe Asp Ser
    130                 135                 140 tca aat aac cta aat ggt gca att gta gat gca cag tgg tca ggc act      480
Ser Asn Asn Leu Asn Gly Ala Ile Val Asp Ala Gln Trp Ser Gly Thr
145                 150                 155                 160 gta aat act aca aat aga aca cta aga aat cca aca gaa tca gat tat      528
Val Asn Thr Thr Asn Arg Thr Leu Arg Asn Pro Thr Glu Ser Asp Tyr
                165                 170                 175 aca aat gtt gtt aca aat ttt att gca gcg gat ggt gac att gca aat      576
Thr Asn Val Val Thr Asn Phe Ile Ala Ala Asp Gly Asp Ile Ala Asn
            180                 185                 190 aat gaa aat cac ata atg aat ggc aac ttt gac gta gct gca gca cct      624
Asn Glu Asn His Ile Met Asn Gly Asn Phe Asp Val Ala Ala Ala Pro
        195                 200                 205 tat ttt gtt ata gga gca aca gca cgt ttt gca gca atg caa tct tat      672
Tyr Phe Val Ile Gly Ala Thr Ala Arg Phe Ala Ala Met Gln Ser Tyr
    210                 215                 220 att aaa ttt tgt aat gct tgg att gat aaa gtt gga ttg agt gac gca      720
Ile Lys Phe Cys Asn Ala Trp Ile Asp Lys Val Gly Leu Ser Asp Ala
225                 230                 235                 240 cag ctt act aca caa aag gct aat tta gat cgc acg aaa caa aat atg      768
Gln Leu Thr Thr Gln Lys Ala Asn Leu Asp Arg Thr Lys Gln Asn Met
                245                 250                 255 cgt aat gca att ctt aac tat aca caa caa gtt atg aaa gtt ttt aaa      816
```

```
                Arg Asn Ala Ile Leu Asn Tyr Thr Gln Gln Val Met Lys Val Phe Lys
                            260                 265                 270 gat tcc aaa aat atg cct aca ata ggt act aat aaa ttt agt gtt gat          864
Asp Ser Lys Asn Met Pro Thr Ile Gly Thr Asn Lys Phe Ser Val Asp
            275                 280                 285 acc tat aat gta tat att aaa gga atg aca tta aat gtt tta gat att          912
Thr Tyr Asn Val Tyr Ile Lys Gly Met Thr Leu Asn Val Leu Asp Ile
    290                 295                 300 gta gca ata tgg cct tca tta tat cca gat gat tat act tca caa aca          960
Val Ala Ile Trp Pro Ser Leu Tyr Pro Asp Asp Tyr Thr Ser Gln Thr
305                 310                 315                 320 gcc tta gaa caa aca cgt gtc act ttt tca aat atg gtt ggc caa gaa         1008
Ala Leu Glu Gln Thr Arg Val Thr Phe Ser Asn Met Val Gly Gln Glu
                325                 330                 335 gaa ggt aca gat gga agc cta aga att tac aat act ttt gat tct ttt         1056
Glu Gly Thr Asp Gly Ser Leu Arg Ile Tyr Asn Thr Phe Asp Ser Phe
            340                 345                 350 agt tat caa cat agt cca ata cct aat aat aat gtt aat tta att tct         1104
Ser Tyr Gln His Ser Pro Ile Pro Asn Asn Asn Val Asn Leu Ile Ser
        355                 360                 365 tat tat aat gat gaa tta caa aat cta gaa tta gga gta tat acc cct         1152
Tyr Tyr Asn Asp Glu Leu Gln Asn Leu Glu Leu Gly Val Tyr Thr Pro
    370                 375                 380 cct aaa aaa gga agt gga tac tct tat cct tat gga ttt gtt tta aat         1200
Pro Lys Lys Gly Ser Gly Tyr Ser Tyr Pro Tyr Gly Phe Val Leu Asn
385                 390                 395                 400 tat gca aac agt aaa tat aaa tat ggt gat agc aat gat cca gaa tct         1248
Tyr Ala Asn Ser Lys Tyr Lys Tyr Gly Asp Ser Asn Asp Pro Glu Ser
                405                 410                 415 cta gga gga tta tct aca cta tct gca cct ata caa caa gtt aat gca         1296
Leu Gly Gly Leu Ser Thr Leu Ser Ala Pro Ile Gln Gln Val Asn Ala
            420                 425                 430 gca act caa aac agt aaa tat cta gat gga gaa atc cta aat gga ata         1344
Ala Thr Gln Asn Ser Lys Tyr Leu Asp Gly Glu Ile Leu Asn Gly Ile
        435                 440                 445 gga gca tcc tta cct ggt tat tgt act aca gga tgt tca cca aca gaa         1392
Gly Ala Ser Leu Pro Gly Tyr Cys Thr Thr Gly Cys Ser Pro Thr Glu
    450                 455                 460 cca cct ttt agt tgt act tct acc gct aat ggc tat aaa gca agc tgt         1440
Pro Pro Phe Ser Cys Thr Ser Thr Ala Asn Gly Tyr Lys Ala Ser Cys
465                 470                 475                 480 aat cct tca gat aca aat caa aaa att aac gct tta tat cct ttt aca         1488
Asn Pro Ser Asp Thr Asn Gln Lys Ile Asn Ala Leu Tyr Pro Phe Thr
                485                 490                 495 caa gct aat gta aag gga aac aca gga aaa tta gga gta ctg gca agt         1536
Gln Ala Asn Val Lys Gly Asn Thr Gly Lys Leu Gly Val Leu Ala Ser
            500                 505                 510 ctt gtt tca tat gat tta aat cct aaa aat gta ttt ggt gaa tta gat         1584
Leu Val Ser Tyr Asp Leu Asn Pro Lys Asn Val Phe Gly Glu Leu Asp
        515                 520                 525 tca gat aca aat aat gtt atc tta aaa gga att cct gca gaa aaa gga         1632
Ser Asp Thr Asn Asn Val Ile Leu Lys Gly Ile Pro Ala Glu Lys Gly
    530                 535                 540 tat ttt cct aat aat gcg cgt cct act gtt gta aaa gaa tgg att aat         1680
Tyr Phe Pro Asn Asn Ala Arg Pro Thr Val Val Lys Glu Trp Ile Asn
545                 550                 555                 560 ggt gca agt gct gta cca ctt gat tca gga aat acc tta ttt atg acg         1728
Gly Ala Ser Ala Val Pro Leu Asp Ser Gly Asn Thr Leu Phe Met Thr
                565                 570                 575 gct acg aat tta aca gct act caa tat aga att aga ata cgt tat gca         1776
```

```
                     Ala Thr Asn Leu Thr Ala Thr Gln Tyr Arg Ile Arg Ile Arg Tyr Ala
                                 580                 585                 590 aat cca aat tca aat act caa atc ggt gta cga att aca caa aat ggt           1824
Asn Pro Asn Ser Asn Thr Gln Ile Gly Val Arg Ile Thr Gln Asn Gly
            595                 600                 605 tct cta att tcc agt agt aat cta aca ctt tat agt act act gat atg           1872
Ser Leu Ile Ser Ser Ser Asn Leu Thr Leu Tyr Ser Thr Thr Asp Met
            610                 615                 620 aat aat act tta cca cta aat gta tat gta ata gga gaa aat gga aat           1920
Asn Asn Thr Leu Pro Leu Asn Val Tyr Val Ile Gly Glu Asn Gly Asn
625                 630                 635                 640 tat aca ctt caa gat tta tat aat act act aat gtt tta tca aca gga           1968
Tyr Thr Leu Gln Asp Leu Tyr Asn Thr Thr Asn Val Leu Ser Thr Gly
                645                 650                 655 gat att aca tta caa att aca gga gga gat caa aaa ata ttt att gat           2016
Asp Ile Thr Leu Gln Ile Thr Gly Gly Asp Gln Lys Ile Phe Ile Asp
            660                 665                 670 cga ata gaa ttt gtt cct act atg cct gta cct ggt aat act aac aac           2064
Arg Ile Glu Phe Val Pro Thr Met Pro Val Pro Gly Asn Thr Asn Asn
            675                 680                 685 aat aac ggt aat aat aac ggt aat aat aat ccc cca cac cac gtt tgt           2112
Asn Asn Gly Asn Asn Asn Gly Asn Asn Asn Pro Pro His His Val Cys
690                 695                 700 gca ata gct ggt aca caa caa tct tgt tct gga ccg ccc aaa ttt gaa           2160
Ala Ile Ala Gly Thr Gln Gln Ser Cys Ser Gly Pro Pro Lys Phe Glu
705                 710                 715                 720 caa gta agt gat tta gaa aaa att aca aca caa gta tat atg tta ttc           2208
Gln Val Ser Asp Leu Glu Lys Ile Thr Thr Gln Val Tyr Met Leu Phe
                725                 730                 735 aaa tct tct ccg tat gaa gaa tta gct cta gaa gtt tcc agc tat caa           2256
Lys Ser Ser Pro Tyr Glu Glu Leu Ala Leu Glu Val Ser Ser Tyr Gln
            740                 745                 750 att agt caa gta gca tta aaa gtt atg gca tta tct gat gaa cta ttt           2304
Ile Ser Gln Val Ala Leu Lys Val Met Ala Leu Ser Asp Glu Leu Phe
            755                 760                 765 tgt gaa gaa aaa aac gta tta cga aaa tta gtc aat aaa gca aaa caa           2352
Cys Glu Glu Lys Asn Val Leu Arg Lys Leu Val Asn Lys Ala Lys Gln
770                 775                 780 tta tta gaa gca agt aac tta cta gta ggt gga aat ttt gaa aca act           2400
Leu Leu Glu Ala Ser Asn Leu Leu Val Gly Gly Asn Phe Glu Thr Thr
785                 790                 795                 800 caa aat tgg gta ctt gga aca aat gct tat ata aat tat gat tcg ttt           2448
Gln Asn Trp Val Leu Gly Thr Asn Ala Tyr Ile Asn Tyr Asp Ser Phe
                805                 810                 815 tta ttt aat gga aat tat tta tct tta caa cca gca agt gga ttt ttc           2496
Leu Phe Asn Gly Asn Tyr Leu Ser Leu Gln Pro Ala Ser Gly Phe Phe
            820                 825                 830 aca tct tat gct tat caa aaa ata gat gag tca aca tta aaa cca tat           2544
Thr Ser Tyr Ala Tyr Gln Lys Ile Asp Glu Ser Thr Leu Lys Pro Tyr
            835                 840                 845 aca cga tat aaa gtt tct ggg ttc att ggg caa agt aat caa gta gaa           2592
Thr Arg Tyr Lys Val Ser Gly Phe Ile Gly Gln Ser Asn Gln Val Glu
850                 855                 860 ctt att att tct cgt tat gga aaa gaa att gat aaa ata tta aat gtt           2640
Leu Ile Ile Ser Arg Tyr Gly Lys Glu Ile Asp Lys Ile Leu Asn Val
865                 870                 875                 880 cca tat gca gga cct ctt cct atc act gct gat gca tca ata act tgt           2688
Pro Tyr Ala Gly Pro Leu Pro Ile Thr Ala Asp Ala Ser Ile Thr Cys
                885                 890                 895 tgt gca cca gaa ata ggc caa tgt gat ggg gaa caa tct gat tct cat           2736
```

| | | |
|---|---|---|
| Cys Ala Pro Glu Ile Gly Gln Cys Asp Gly Glu Gln Ser Asp Ser His<br>900 905 910 | | |
| ttc ttt aac tat agc atc gat gta ggt gca ctt cac cca gaa tta aac<br>Phe Phe Asn Tyr Ser Ile Asp Val Gly Ala Leu His Pro Glu Leu Asn<br>915 920 925 | 2784 | |
| cct ggc att gaa att ggt ctt aaa att gtg caa tca aat ggt tat ata<br>Pro Gly Ile Glu Ile Gly Leu Lys Ile Val Gln Ser Asn Gly Tyr Ile<br>930 935 940 | 2832 | |
| aca att agt aat cta gaa att att gaa gaa cgt cca ctt aca gaa atg<br>Thr Ile Ser Asn Leu Glu Ile Ile Glu Glu Arg Pro Leu Thr Glu Met<br>945 950 955 960 | 2880 | |
| gaa att caa gca gtc aat cga aaa aat caa aaa tgg gaa aga gaa aaa<br>Glu Ile Gln Ala Val Asn Arg Lys Asn Gln Lys Trp Glu Arg Glu Lys<br>965 970 975 | 2928 | |
| ctt cta gaa tgt gca agt att agt gaa ctt tta caa cca att att aat<br>Leu Leu Glu Cys Ala Ser Ile Ser Glu Leu Leu Gln Pro Ile Ile Asn<br>980 985 990 | 2976 | |
| caa atc gat tca ttg ttt aaa gat gga aac tgg tat aat gat att ctt<br>Gln Ile Asp Ser Leu Phe Lys Asp Gly Asn Trp Tyr Asn Asp Ile Leu<br>995 1000 1005 | 3024 | |
| cct cat gtc aca tat caa gat tta aaa aat att ata ata ccc gag tta<br>Pro His Val Thr Tyr Gln Asp Leu Lys Asn Ile Ile Ile Pro Glu Leu<br>1010 1015 1020 | 3072 | |
| cca aaa tta aaa cat tgg ttc ata gag aat ctc cca ggt gaa tat cat<br>Pro Lys Leu Lys His Trp Phe Ile Glu Asn Leu Pro Gly Glu Tyr His<br>1025 1030 1035 1040 | 3120 | |
| gaa att gaa caa aaa atg aaa gaa gct cta aaa tat gca ttt aca caa<br>Glu Ile Glu Gln Lys Met Lys Glu Ala Leu Lys Tyr Ala Phe Thr Gln<br>1045 1050 1055 | 3168 | |
| tta gac gag aaa aat tta atc cac aat ggt cac ttt aca act aac tta<br>Leu Asp Glu Lys Asn Leu Ile His Asn Gly His Phe Thr Thr Asn Leu<br>1060 1065 1070 | 3216 | |
| ata gat tgg caa gta gaa ggt gat gct caa atg aaa gta tta gaa aat<br>Ile Asp Trp Gln Val Glu Gly Asp Ala Gln Met Lys Val Leu Glu Asn<br>1075 1080 1085 | 3264 | |
| gat gct ctt gca tta caa ctt ttc aac tgg gat gct agt gct tca caa<br>Asp Ala Leu Ala Leu Gln Leu Phe Asn Trp Asp Ala Ser Ala Ser Gln<br>1090 1095 1100 | 3312 | |
| tct ata aat ata tta gaa ttt gat gaa gat aag gca tat aaa ctt cgc<br>Ser Ile Asn Ile Leu Glu Phe Asp Glu Asp Lys Ala Tyr Lys Leu Arg<br>1105 1110 1115 1120 | 3360 | |
| gta tat gct caa gga agc gga aca atc caa ttt gga aac tgt gaa gat<br>Val Tyr Ala Gln Gly Ser Gly Thr Ile Gln Phe Gly Asn Cys Glu Asp<br>1125 1130 1135 | 3408 | |
| gaa gct atc caa ttt aat aca aac tca ttc ata tat caa gaa aaa ata<br>Glu Ala Ile Gln Phe Asn Thr Asn Ser Phe Ile Tyr Gln Glu Lys Ile<br>1140 1145 1150 | 3456 | |
| gtc tat ttc gat acc cca tca gtt aat tta cac ata caa tca gaa ggt<br>Val Tyr Phe Asp Thr Pro Ser Val Asn Leu His Ile Gln Ser Glu Gly<br>1155 1160 1165 | 3504 | |
| tct gaa ttt att gta agt agt atc gat cta att gaa tta tca gac gac<br>Ser Glu Phe Ile Val Ser Ser Ile Asp Leu Ile Glu Leu Ser Asp Asp<br>1170 1175 1180 | 3552 | |
| caa taa<br>Gln *<br>1185 | 3558 | |

<210> SEQ ID NO 2
<211> LENGTH: 1185
<212> TYPE: PRT
<213> ORGANISM: Bacillus cereus/Bacillus thuringiensis

<400> SEQUENCE: 2

```
Met Asp Cys Asn Leu Gln Ser Gln Gln Asn Ile Pro Tyr Asn Val Leu
 1               5                  10                  15

Ala Ile Pro Val Ser Asn Val Asn Ser Leu Thr Asp Thr Val Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Thr Phe Asn
    50                  55                  60

Tyr Leu Thr Leu Leu Gln Ser Gly Ile Ser Leu Ala Gly Ser Phe Val
 65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
            115                 120                 125

Ala Asp Arg Asn Glu Trp Ser Ser Tyr Leu Glu Ser Ile Phe Asp Ser
130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Val Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
    290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Val Asn Leu Ile Ser
        355                 360                 365

Tyr Tyr Asn Asp Glu Leu Gln Asn Leu Glu Leu Gly Val Tyr Thr Pro
    370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415
```

```
Leu Gly Gly Leu Ser Thr Leu Ser Ala Pro Ile Gln Val Asn Ala
            420                 425                 430
Ala Thr Gln Asn Ser Lys Tyr Leu Asp Gly Glu Ile Leu Asn Gly Ile
        435                 440                 445
Gly Ala Ser Leu Pro Gly Tyr Cys Thr Gly Cys Ser Pro Thr Glu
    450                 455                 460
Pro Pro Phe Ser Cys Thr Ser Thr Ala Asn Gly Tyr Lys Ala Ser Cys
465                 470                 475                 480
Asn Pro Ser Asp Thr Asn Gln Lys Ile Asn Ala Leu Tyr Pro Phe Thr
                485                 490                 495
Gln Ala Asn Val Lys Gly Asn Thr Gly Lys Leu Gly Val Leu Ala Ser
                500                 505                 510
Leu Val Ser Tyr Asp Leu Asn Pro Lys Asn Val Phe Gly Glu Leu Asp
            515                 520                 525
Ser Asp Thr Asn Asn Val Ile Leu Lys Gly Ile Pro Ala Glu Lys Gly
    530                 535                 540
Tyr Phe Pro Asn Asn Ala Arg Pro Thr Val Val Lys Glu Trp Ile Asn
545                 550                 555                 560
Gly Ala Ser Ala Val Pro Leu Asp Ser Gly Asn Thr Leu Phe Met Thr
                565                 570                 575
Ala Thr Asn Leu Thr Ala Thr Gln Tyr Arg Ile Arg Ile Arg Tyr Ala
            580                 585                 590
Asn Pro Asn Ser Asn Thr Gln Ile Gly Val Arg Ile Thr Gln Asn Gly
        595                 600                 605
Ser Leu Ile Ser Ser Ser Asn Leu Thr Leu Tyr Ser Thr Thr Asp Met
    610                 615                 620
Asn Asn Thr Leu Pro Leu Asn Val Tyr Val Ile Gly Glu Asn Gly Asn
625                 630                 635                 640
Tyr Thr Leu Gln Asp Leu Tyr Asn Thr Thr Asn Val Leu Ser Thr Gly
                645                 650                 655
Asp Ile Thr Leu Gln Ile Thr Gly Gly Asp Gln Lys Ile Phe Ile Asp
            660                 665                 670
Arg Ile Glu Phe Val Pro Thr Met Pro Val Pro Gly Asn Thr Asn Asn
        675                 680                 685
Asn Asn Gly Asn Asn Gly Asn Asn Pro His His Val Cys
    690                 695                 700
Ala Ile Ala Gly Thr Gln Gln Ser Cys Ser Gly Pro Pro Lys Phe Glu
705                 710                 715                 720
Gln Val Ser Asp Leu Glu Lys Ile Thr Thr Gln Val Tyr Met Leu Phe
                725                 730                 735
Lys Ser Ser Pro Tyr Glu Glu Leu Ala Leu Glu Val Ser Ser Tyr Gln
            740                 745                 750
Ile Ser Gln Val Ala Leu Lys Val Met Ala Leu Ser Asp Glu Leu Phe
        755                 760                 765
Cys Glu Glu Lys Asn Val Leu Arg Lys Leu Val Asn Lys Ala Lys Gln
    770                 775                 780
Leu Leu Glu Ala Ser Asn Leu Val Gly Gly Asn Phe Glu Thr Thr
785                 790                 795                 800
Gln Asn Trp Val Leu Gly Thr Asn Ala Tyr Ile Asn Tyr Asp Ser Phe
                805                 810                 815
Leu Phe Asn Gly Asn Tyr Leu Ser Leu Gln Pro Ala Ser Gly Phe Phe
            820                 825                 830
Thr Ser Tyr Ala Tyr Gln Lys Ile Asp Glu Ser Thr Leu Lys Pro Tyr
```

```
                835                 840                 845
Thr Arg Tyr Lys Val Ser Gly Phe Ile Gly Gln Ser Asn Gln Val Glu
        850                 855                 860
Leu Ile Ile Ser Arg Tyr Gly Lys Glu Ile Asp Lys Ile Leu Asn Val
865                 870                 875                 880
Pro Tyr Ala Gly Pro Leu Pro Ile Thr Ala Asp Ala Ser Ile Thr Cys
                885                 890                 895
Cys Ala Pro Glu Ile Gly Gln Cys Asp Gly Glu Gln Ser Asp Ser His
            900                 905                 910
Phe Phe Asn Tyr Ser Ile Asp Val Gly Ala Leu His Pro Glu Leu Asn
        915                 920                 925
Pro Gly Ile Glu Ile Gly Leu Lys Ile Val Gln Ser Asn Gly Tyr Ile
    930                 935                 940
Thr Ile Ser Asn Leu Glu Ile Ile Glu Glu Arg Pro Leu Thr Glu Met
945                 950                 955                 960
Glu Ile Gln Ala Val Asn Arg Lys Asn Gln Lys Trp Glu Arg Glu Lys
                965                 970                 975
Leu Leu Glu Cys Ala Ser Ile Ser Glu Leu Leu Gln Pro Ile Ile Asn
            980                 985                 990
Gln Ile Asp Ser Leu Phe Lys Asp Gly Asn Trp Tyr Asn Asp Ile Leu
        995                 1000                1005
Pro His Val Thr Tyr Gln Asp Leu Lys Asn Ile Ile Pro Glu Leu
    1010                1015                1020
Pro Lys Leu Lys His Trp Phe Ile Glu Asn Leu Pro Gly Glu Tyr His
1025                1030                1035                1040
Glu Ile Glu Gln Lys Met Lys Glu Ala Leu Lys Tyr Ala Phe Thr Gln
                1045                1050                1055
Leu Asp Glu Lys Asn Leu Ile His Asn Gly His Phe Thr Thr Asn Leu
            1060                1065                1070
Ile Asp Trp Gln Val Gly Asp Ala Gln Met Lys Val Leu Glu Asn
        1075                1080                1085
Asp Ala Leu Ala Leu Gln Leu Phe Asn Trp Asp Ala Ser Ala Ser Gln
    1090                1095                1100
Ser Ile Asn Ile Leu Glu Phe Asp Asp Lys Ala Tyr Lys Leu Arg
1105                1110                1115                1120
Val Tyr Ala Gln Gly Ser Gly Thr Ile Gln Phe Gly Asn Cys Glu Asp
                1125                1130                1135
Glu Ala Ile Gln Phe Asn Thr Asn Ser Phe Ile Tyr Gly Glu Lys Ile
            1140                1145                1150
Val Tyr Phe Asp Thr Pro Ser Val Asn Leu His Ile Gln Ser Glu Gly
        1155                1160                1165
Ser Glu Phe Ile Val Ser Ser Ile Asp Leu Ile Glu Leu Ser Asp Asp
    1170                1175                1180
Gln
1185

<210> SEQ ID NO 3
<211> LENGTH: 3984
<212> TYPE: DNA
<213> ORGANISM: Unknown
<220> FEATURE:
<223> OTHER INFORMATION: Isolated from soil sample
<221> NAME/KEY: CDS
<222> LOCATION: (1)...(3984)

<400> SEQUENCE: 3
```

```
atg gca aca ctt aat aat atg ttt tca gtt cct tat aat gta cta gct      48
Met Ala Thr Leu Asn Asn Met Phe Ser Val Pro Tyr Asn Val Leu Ala
1               5                   10                  15 cta ccc att atc ccc aat tct atc tta act ttt gaa gat aat cga aaa      96
Leu Pro Ile Ile Pro Asn Ser Ile Leu Thr Phe Glu Asp Asn Arg Lys
                20                  25                  30 aaa ata gaa gag ggt att aaa gag ttt gaa aag act gga cgt ata aaa     144
Lys Ile Glu Glu Gly Ile Lys Glu Phe Glu Lys Thr Gly Arg Ile Lys
            35                  40                  45 ccc ctt aaa gat tta ata gag ctc ata ttc aaa ggg tat agt gac gat     192
Pro Leu Lys Asp Leu Ile Glu Leu Ile Phe Lys Gly Tyr Ser Asp Asp
        50                  55                  60 gaa tct tct tac gca gca tta gtt caa act atg ctt gtc gtt att ccc     240
Glu Ser Ser Tyr Ala Ala Leu Val Gln Thr Met Leu Val Val Ile Pro
65                  70                  75                  80 ttg gcg ttc cct gaa tta gcc cca gtt ctt cca att att ggc gta gta     288
Leu Ala Phe Pro Glu Leu Ala Pro Val Leu Pro Ile Ile Gly Val Val
                85                  90                  95 att aat ttc gtt ttt cca ggt ttg aag ggt tct gct aaa tca acc tat     336
Ile Asn Phe Val Phe Pro Gly Leu Lys Gly Ser Ala Lys Ser Thr Tyr
                100                 105                 110 aca atg att aca gag atg gtt gat aaa gcc att aac caa tca ttc acg     384
Thr Met Ile Thr Glu Met Val Asp Lys Ala Ile Asn Gln Ser Phe Thr
            115                 120                 125 gcc cag att aca aat ata tta aca aac aat att act ggt ata caa aat     432
Ala Gln Ile Thr Asn Ile Leu Thr Asn Asn Ile Thr Gly Ile Gln Asn
        130                 135                 140 aat ata caa tct gtt tac gac gca atg agc aat gcc att gga aca aat     480
Asn Ile Gln Ser Val Tyr Asp Ala Met Ser Asn Ala Ile Gly Thr Asn
145                 150                 155                 160 gac aca att cat aat ttc atc aga aat aat gat aca aca cct tgc tct     528
Asp Thr Ile His Asn Phe Ile Arg Asn Asn Asp Thr Thr Pro Cys Ser
                165                 170                 175 caa aac aat cag cca gct tgt cct tgt cct cca aat aat caa tgt tta     576
Gln Asn Asn Gln Pro Ala Cys Pro Cys Pro Pro Asn Asn Gln Cys Leu
                180                 185                 190 caa aaa gtt gtt gat gaa tat act aaa gca ata gct aat atc gat ctc     624
Gln Lys Val Val Asp Glu Tyr Thr Lys Ala Ile Ala Asn Ile Asp Leu
            195                 200                 205 att atc cct caa ttt cat gat cca ctt act ggt gta att tcc gat tta     672
Ile Ile Pro Gln Phe His Asp Pro Leu Thr Gly Val Ile Ser Asp Leu
        210                 215                 220 gct act gca aac atg tat att tta cct tta tac gct caa act gtt aat     720
Ala Thr Ala Asn Met Tyr Ile Leu Pro Leu Tyr Ala Gln Thr Val Asn
225                 230                 235                 240 tta aaa tta att ttg cgt cag agt ttc att gaa ttt atg gag aaa tat     768
Leu Lys Leu Ile Leu Arg Gln Ser Phe Ile Glu Phe Met Glu Lys Tyr
                245                 250                 255 aaa tat gat gaa aaa gaa act gtt ttt cag gct ttt att aat gct gat     816
Lys Tyr Asp Glu Lys Glu Thr Val Phe Gln Ala Phe Ile Asn Ala Asp
                260                 265                 270 att cca gaa caa att aaa aaa ctt cgt caa gat att atc acg tat aca     864
Ile Pro Glu Gln Ile Lys Lys Leu Arg Gln Asp Ile Ile Thr Tyr Thr
            275                 280                 285 aaa gat att tat atg caa ttt gaa gct cac gct ccc tac ccg act tat     912
Lys Asp Ile Tyr Met Gln Phe Glu Ala His Ala Pro Tyr Pro Thr Tyr
        290                 295                 300 aat tca aaa aaa caa cta aat gac tat atc cgt tat aca aga att atc     960
Asn Ser Lys Lys Gln Leu Asn Asp Tyr Ile Arg Tyr Thr Arg Ile Ile
305                 310                 315                 320
```

```
caa gta tat tgt ttg gat tta gta gca atg tgg cct acg ctt gat cga      1008
Gln Val Tyr Cys Leu Asp Leu Val Ala Met Trp Pro Thr Leu Asp Arg
                325                 330                 335 gtg aat tat gca tta cct gtc caa caa aat atg aca cgc att ata ttt      1056
Val Asn Tyr Ala Leu Pro Val Gln Gln Asn Met Thr Arg Ile Ile Phe
            340                 345                 350 gga gat ctt att ggc cct gta gaa act gtg cct cag gtt ccc cgc caa      1104
Gly Asp Leu Ile Gly Pro Val Glu Thr Val Pro Gln Val Pro Arg Gln
        355                 360                 365 aat tca gat aac ttt cat ttt aat ttg tct gat gtt tat aga aac ccc      1152
Asn Ser Asp Asn Phe His Phe Asn Leu Ser Asp Val Tyr Arg Asn Pro
    370                 375                 380 tta cct aat aat gat att ttt aat tac cgt tat ggc ggg ctt caa att      1200
Leu Pro Asn Asn Asp Ile Phe Asn Tyr Arg Tyr Gly Gly Leu Gln Ile
385                 390                 395                 400 tct aaa gcg caa ttt atg aca tat tat aaa aaa ttc gga gct ttc agt      1248
Ser Lys Ala Gln Phe Met Thr Tyr Tyr Lys Lys Phe Gly Ala Phe Ser
                405                 410                 415 acc cat gat gaa tat tat tat gta gat ggg cat cgc cta agt ttt aat      1296
Thr His Asp Glu Tyr Tyr Tyr Val Asp Gly His Arg Leu Ser Phe Asn
            420                 425                 430 act tca gat aaa aaa aca att gaa atc aat gct cat caa aat tct cat      1344
Thr Ser Asp Lys Lys Thr Ile Glu Ile Asn Ala His Gln Asn Ser His
        435                 440                 445 gat act att gaa aag gat gta ata gat caa cta ggc ggc tat gtt aca      1392
Asp Thr Ile Glu Lys Asp Val Ile Asp Gln Leu Gly Gly Tyr Val Thr
    450                 455                 460 cgt atg aat atg gta agt caa gaa atc ggt agt ggc agt ata ttg ggt      1440
Arg Met Asn Met Val Ser Gln Glu Ile Gly Ser Gly Ser Ile Leu Gly
465                 470                 475                 480 gga aat gcc ata gat cga act gcc ctt act acc agt aca ggt gat aaa      1488
Gly Asn Ala Ile Asp Arg Thr Ala Leu Thr Thr Ser Thr Gly Asp Lys
                485                 490                 495 gac ata ctt gct gca gga ttt aac gcg ata aat aat gga aat tac aag      1536
Asp Ile Leu Ala Ala Gly Phe Asn Ala Ile Asn Asn Gly Asn Tyr Lys
            500                 505                 510 aca gaa ggt cgc ggt gcc tcc cat aat cag gat gtt cca aat cat aaa      1584
Thr Glu Gly Arg Gly Ala Ser His Asn Gln Asp Val Pro Asn His Lys
        515                 520                 525 gtt caa gcg att tat cct gtt caa ccg aat aaa tat gaa tat gac gat      1632
Val Gln Ala Ile Tyr Pro Val Gln Pro Asn Lys Tyr Glu Tyr Asp Asp
    530                 535                 540 tat gga tct gaa gaa aag tat gga tac ctt tat act tta att cca atg      1680
Tyr Gly Ser Glu Glu Lys Tyr Gly Tyr Leu Tyr Thr Leu Ile Pro Met
545                 550                 555                 560 gat gtg agt ttc att ccc caa ctc aat gca gaa gat gta att act act      1728
Asp Val Ser Phe Ile Pro Gln Leu Asn Ala Glu Asp Val Ile Thr Thr
                565                 570                 575 att cct gca gaa caa gca gtc aaa att aat ggt caa tct gta ata gat      1776
Ile Pro Ala Glu Gln Ala Val Lys Ile Asn Gly Gln Ser Val Ile Asp
            580                 585                 590 act gta aac acc aat tct tta ttg gaa ttt gtt aat ggt gca aat gca      1824
Thr Val Asn Thr Asn Ser Leu Leu Glu Phe Val Asn Gly Ala Asn Ala
        595                 600                 605 att aaa cta tct cct ggc gaa aca gca caa tac act atg att aat ccc      1872
Ile Lys Leu Ser Pro Gly Glu Thr Ala Gln Tyr Thr Met Ile Asn Pro
    610                 615                 620 gtc aat cgt tcc tac cag gtt aga gtt cgg gtt gct act gaa gga gaa      1920
Val Asn Arg Ser Tyr Gln Val Arg Val Arg Val Ala Thr Glu Gly Glu
625                 630                 635                 640
```

```
acc caa tta gat att ata gca ccc gtt gat agc aat acc ctt aat ctt    1968
Thr Gln Leu Asp Ile Ile Ala Pro Val Asp Ser Asn Thr Leu Asn Leu
            645                 650                 655 tca aac aca aaa aca aca gca aat gat caa aat ggg ata tta ggt aaa    2016
Ser Asn Thr Lys Thr Thr Ala Asn Asp Gln Asn Gly Ile Leu Gly Lys
        660                 665                 670 caa ggt aat tat ata gta ttt cca cag cca aac att gat act gtc aca    2064
Gln Gly Asn Tyr Ile Val Phe Pro Gln Pro Asn Ile Asp Thr Val Thr
    675                 680                 685 ggc acc agt tta cct cct acc gaa aac att atg aat ttt cca gta gga    2112
Gly Thr Ser Leu Pro Pro Thr Glu Asn Ile Met Asn Phe Pro Val Gly
690                 695                 700 aca ttt gat ttt acc att gta aat tct gga aac tca gat act att tta    2160
Thr Phe Asp Phe Thr Ile Val Asn Ser Gly Asn Ser Asp Thr Ile Leu
705                 710                 715                 720 gat cga att gaa ttt gtt cct att gta act tct aat aaa att caa caa    2208
Asp Arg Ile Glu Phe Val Pro Ile Val Thr Ser Asn Lys Ile Gln Gln
                725                 730                 735 gat ttc act att tct cct gga aca agt caa gta att tgg acc gga aat    2256
Asp Phe Thr Ile Ser Pro Gly Thr Ser Gln Val Ile Trp Thr Gly Asn
            740                 745                 750 tca gct aac act ata gat att aca att att gac aac gta gat aca agc    2304
Ser Ala Asn Thr Ile Asp Ile Thr Ile Ile Asp Asn Val Asp Thr Ser
        755                 760                 765 ggt tta ttc gtt caa att ttc caa aaa ggt aag caa ctg cat gga gaa    2352
Gly Leu Phe Val Gln Ile Phe Gln Lys Gly Lys Gln Leu His Gly Glu
    770                 775                 780 cta act ttg att gat ccc gct cat att caa cgt aca ttc tct gaa aaa    2400
Leu Thr Leu Ile Asp Pro Ala His Ile Gln Arg Thr Phe Ser Glu Lys
785                 790                 795                 800 ttt gat caa att gtt ttg tat aac cca ggt tat aat agt tct ata tct    2448
Phe Asp Gln Ile Val Leu Tyr Asn Pro Gly Tyr Asn Ser Ser Ile Ser
                805                 810                 815 ggt aca gtg agt ggt tca gta agc tct att cct aag aaa ttc gaa tta    2496
Gly Thr Val Ser Gly Ser Val Ser Ser Ile Pro Lys Lys Phe Glu Leu
            820                 825                 830 tct agc gac tta caa aat atc aca aac caa gtt aat aac tta ttt gca    2544
Ser Ser Asp Leu Gln Asn Ile Thr Asn Gln Val Asn Asn Leu Phe Ala
        835                 840                 845 tcg agc gaa cat gat aca ctt gcc aca gat gta agt gat tat gat att    2592
Ser Ser Glu His Asp Thr Leu Ala Thr Asp Val Ser Asp Tyr Asp Ile
    850                 855                 860 gaa gaa gtg att cta aaa gta gat gca tta tct gat gaa gtg ttt gga    2640
Glu Glu Val Ile Leu Lys Val Asp Ala Leu Ser Asp Glu Val Phe Gly
865                 870                 875                 880 aaa gag aaa aaa gca cta cgt aaa ttg gta aat caa gcg aag cgt tta    2688
Lys Glu Lys Lys Ala Leu Arg Lys Leu Val Asn Gln Ala Lys Arg Leu
                885                 890                 895 agt aaa gcg cgt aat ctt ctc cta gga gga agt ttt gat aat ttg gat    2736
Ser Lys Ala Arg Asn Leu Leu Leu Gly Gly Ser Phe Asp Asn Leu Asp
            900                 905                 910 gct tgg tat agg gga cga aat gta gta act gta tct gat cat gaa ctg    2784
Ala Trp Tyr Arg Gly Arg Asn Val Val Thr Val Ser Asp His Glu Leu
        915                 920                 925 ttt aaa agt gat cat ata tta tta cca cta cca aca aca ttg tat cca    2832
Phe Lys Ser Asp His Ile Leu Leu Pro Leu Pro Thr Thr Leu Tyr Pro
    930                 935                 940 tct tat ctt ttc caa aaa gta gag gaa tct aaa tta aaa gca aat aca    2880
Ser Tyr Leu Phe Gln Lys Val Glu Glu Ser Lys Leu Lys Ala Asn Thr
945                 950                 955                 960
```

```
cgt tat act gtc tct ggt ttc atc gcg cat gca gag gat tta gaa att    2928
Arg Tyr Thr Val Ser Gly Phe Ile Ala His Ala Glu Asp Leu Glu Ile
            965                 970                 975 gtt gtt tct cgt tat ggg caa gaa ata aag aaa gtg gtg caa gtt cca    2976
Val Val Ser Arg Tyr Gly Gln Glu Ile Lys Lys Val Val Gln Val Pro
            980                 985                 990 tat ggt gaa gca ttc cca ttg aca tcg agc gga cca att tgt tgt aga    3024
Tyr Gly Glu Ala Phe Pro Leu Thr Ser Ser Gly Pro Ile Cys Cys Arg
            995                 1000                1005 cca cgt tct aga gta aat ggt aaa cct gct gat cca cat ttc ttt agt    3072
Pro Arg Ser Arg Val Asn Gly Lys Pro Ala Asp Pro His Phe Phe Ser
        1010                1015                1020 tac agc att gat gta ggt gca tta gat gtg gaa gca aat cct ggt att    3120
Tyr Ser Ile Asp Val Gly Ala Leu Asp Val Glu Ala Asn Pro Gly Ile
1025                1030                1035                1040 gaa tta ggg ttt cgt att gta gag cca act gga atg gca cgt gta agt    3168
Glu Leu Gly Phe Arg Ile Val Glu Pro Thr Gly Met Ala Arg Val Ser
                1045                1050                1055 aac tta gaa att cgt gag gat cgc cca tta acg gca aat gaa ata cgt    3216
Asn Leu Glu Ile Arg Glu Asp Arg Pro Leu Thr Ala Asn Glu Ile Arg
            1060                1065                1070 aag gtg caa cgt gct gct aga gat tgg aaa caa aag tat gat caa gag    3264
Lys Val Gln Arg Ala Ala Arg Asp Trp Lys Gln Lys Tyr Asp Gln Glu
        1075                1080                1085 cgt gcg gaa gta aga gcc ctg att caa cct gtt tta aat caa atc aat    3312
Arg Ala Glu Val Arg Ala Leu Ile Gln Pro Val Leu Asn Gln Ile Asn
    1090                1095                1100 gcg ttg tat gaa aat gaa gat tgg aat gga gca att cgt tct gga gtt    3360
Ala Leu Tyr Glu Asn Glu Asp Trp Asn Gly Ala Ile Arg Ser Gly Val
1105                1110                1115                1120 tct tat cat gac tta gaa gca att gtt tta cca aca tta cca aaa tta    3408
Ser Tyr His Asp Leu Glu Ala Ile Val Leu Pro Thr Leu Pro Lys Leu
                1125                1130                1135 aat cat tgg ttt atg tcc gat atg tta ggg gaa caa ggt tcc att tta    3456
Asn His Trp Phe Met Ser Asp Met Leu Gly Glu Gln Gly Ser Ile Leu
            1140                1145                1150 gct caa ttc caa gaa gca tta aat cgt gcg tat acg caa ctc gaa gga    3504
Ala Gln Phe Gln Glu Ala Leu Asn Arg Ala Tyr Thr Gln Leu Glu Gly
        1155                1160                1165 agt aca att ctg cat aat ggc cat ttc aca aca gat gca gca aat tgg    3552
Ser Thr Ile Leu His Asn Gly His Phe Thr Thr Asp Ala Ala Asn Trp
    1170                1175                1180 acg ata gaa ggc gat gca cat cag gta gta tta gaa gat ggt aga cgt    3600
Thr Ile Glu Gly Asp Ala His Gln Val Val Leu Glu Asp Gly Arg Arg
1185                1190                1195                1200 gta tta cga ttg cca gat tgg tct tcg agt ttg tct caa acg att gaa    3648
Val Leu Arg Leu Pro Asp Trp Ser Ser Ser Leu Ser Gln Thr Ile Glu
                1205                1210                1215 atc gag aat ttt gat cca gat aaa gaa tat caa tta gta ttt cat ggg    3696
Ile Glu Asn Phe Asp Pro Asp Lys Glu Tyr Gln Leu Val Phe His Gly
            1220                1225                1230 caa gga gaa gga acg gtt acg ttg gag cat ggt gaa gaa gga gaa tat    3744
Gln Gly Glu Gly Thr Val Thr Leu Glu His Gly Glu Glu Gly Glu Tyr
        1235                1240                1245 gtg gaa aca cac ccg cat aag ttt gcg aat ttt aca act tct caa cgt    3792
Val Glu Thr His Pro His Lys Phe Ala Asn Phe Thr Thr Ser Gln Arg
    1250                1255                1260 caa gga att acg ttt gaa tca aat aaa gtg aca gtg act att tct tca    3840
Gln Gly Ile Thr Phe Glu Ser Asn Lys Val Thr Val Thr Ile Ser Ser
1265                1270                1275                1280
```

-continued

```
gaa gat gga gaa ttc tta gcg gat aat att gca att gtg gaa gtt cct       3888
Glu Asp Gly Glu Phe Leu Ala Asp Asn Ile Ala Ile Val Glu Val Pro
            1285                1290                1295 atg ttt aac aag aat caa atg gtc aat gaa aat aga ggt gta aat ata       3936
Met Phe Asn Lys Asn Gln Met Val Asn Glu Asn Arg Gly Val Asn Ile
1300                1305                1310 aat agc aat aca aat atg aat agt agc aat aac agc aat aac caa taa       3984
Asn Ser Asn Thr Asn Met Asn Ser Ser Asn Asn Ser Asn Asn Gln *
    1315                1320                1325
```

<210> SEQ ID NO 4
<211> LENGTH: 1327
<212> TYPE: PRT
<213> ORGANISM: Unknown
<220> FEATURE:
<223> OTHER INFORMATION: Isolated from soil sample

<400> SEQUENCE: 4

```
Met Ala Thr Leu Asn Asn Met Phe Ser Val Pro Tyr Asn Val Leu Ala
 1               5                   10                  15

Leu Pro Ile Ile Pro Asn Ser Ile Leu Thr Phe Glu Asp Asn Arg Lys
            20                  25                  30

Lys Ile Glu Glu Gly Ile Lys Glu Phe Glu Lys Thr Gly Arg Ile Lys
        35                  40                  45

Pro Leu Lys Asp Leu Ile Glu Leu Ile Phe Lys Gly Tyr Ser Asp Asp
    50                  55                  60

Glu Ser Ser Tyr Ala Ala Leu Val Gln Thr Met Leu Val Val Ile Pro
65                  70                  75                  80

Leu Ala Phe Pro Glu Leu Ala Pro Val Leu Pro Ile Ile Gly Val Val
                85                  90                  95

Ile Asn Phe Val Phe Pro Gly Leu Lys Gly Ser Ala Lys Ser Thr Tyr
            100                 105                 110

Thr Met Ile Thr Glu Met Val Asp Lys Ala Ile Asn Gln Ser Phe Thr
        115                 120                 125

Ala Gln Ile Thr Asn Ile Leu Thr Asn Asn Ile Thr Gly Ile Gln Asn
    130                 135                 140

Asn Ile Gln Ser Val Tyr Asp Ala Met Ser Asn Ala Ile Gly Thr Asn
145                 150                 155                 160

Asp Thr Ile His Asn Phe Ile Arg Asn Asn Asp Thr Thr Pro Cys Ser
                165                 170                 175

Gln Asn Asn Gln Pro Ala Cys Pro Cys Pro Asn Asn Gln Cys Leu
            180                 185                 190

Gln Lys Val Val Asp Glu Tyr Thr Lys Ala Ile Ala Asn Ile Asp Leu
        195                 200                 205

Ile Ile Pro Gln Phe His Asp Pro Leu Thr Gly Val Ile Ser Asp Leu
    210                 215                 220

Ala Thr Ala Asn Met Tyr Ile Leu Pro Leu Tyr Ala Gln Thr Val Asn
225                 230                 235                 240

Leu Lys Leu Ile Leu Arg Gln Ser Phe Ile Glu Phe Met Glu Lys Tyr
                245                 250                 255

Lys Tyr Asp Glu Lys Glu Thr Val Phe Gln Ala Phe Ile Asn Ala Asp
            260                 265                 270

Ile Pro Glu Gln Ile Lys Lys Leu Arg Gln Asp Ile Ile Thr Tyr Thr
        275                 280                 285

Lys Asp Ile Tyr Met Gln Phe Glu Ala His Ala Pro Tyr Pro Thr Tyr
    290                 295                 300

Asn Ser Lys Lys Gln Leu Asn Asp Tyr Ile Arg Tyr Thr Arg Ile Ile
```

```
            305                 310                 315                 320
Gln Val Tyr Cys Leu Asp Leu Val Ala Met Trp Pro Thr Leu Asp Arg
                325                 330                 335

Val Asn Tyr Ala Leu Pro Val Gln Gln Asn Met Thr Arg Ile Ile Phe
                340                 345                 350

Gly Asp Leu Ile Gly Pro Val Glu Thr Val Pro Gln Val Pro Arg Gln
                355                 360                 365

Asn Ser Asp Asn Phe His Phe Asn Leu Ser Asp Val Tyr Arg Asn Pro
            370                 375                 380

Leu Pro Asn Asn Asp Ile Phe Asn Tyr Arg Tyr Gly Gly Leu Gln Ile
385                 390                 395                 400

Ser Lys Ala Gln Phe Met Thr Tyr Tyr Lys Lys Phe Gly Ala Phe Ser
                405                 410                 415

Thr His Asp Glu Tyr Tyr Val Asp Gly His Arg Leu Ser Phe Asn
                420                 425                 430

Thr Ser Asp Lys Lys Thr Ile Glu Ile Asn Ala His Gln Asn Ser His
            435                 440                 445

Asp Thr Ile Glu Lys Asp Val Ile Asp Gln Leu Gly Gly Tyr Val Thr
450                 455                 460

Arg Met Asn Met Val Ser Gln Glu Ile Gly Ser Gly Ser Ile Leu Gly
465                 470                 475                 480

Gly Asn Ala Ile Asp Arg Thr Ala Leu Thr Thr Ser Thr Gly Asp Lys
                485                 490                 495

Asp Ile Leu Ala Ala Gly Phe Asn Ala Ile Asn Asn Gly Asn Tyr Lys
            500                 505                 510

Thr Glu Gly Arg Gly Ala Ser His Asn Gln Asp Val Pro Asn His Lys
            515                 520                 525

Val Gln Ala Ile Tyr Pro Val Gln Pro Asn Lys Tyr Glu Tyr Asp Asp
            530                 535                 540

Tyr Gly Ser Glu Glu Lys Tyr Gly Tyr Leu Tyr Thr Leu Ile Pro Met
545                 550                 555                 560

Asp Val Ser Phe Ile Pro Gln Leu Asn Ala Glu Asp Val Ile Thr Thr
                565                 570                 575

Ile Pro Ala Glu Gln Ala Val Lys Ile Asn Gly Gln Ser Val Ile Asp
            580                 585                 590

Thr Val Asn Thr Asn Ser Leu Leu Glu Phe Val Asn Gly Ala Asn Ala
            595                 600                 605

Ile Lys Leu Ser Pro Gly Glu Thr Ala Gln Tyr Thr Met Ile Asn Pro
610                 615                 620

Val Asn Arg Ser Tyr Gln Val Arg Val Arg Val Ala Thr Glu Gly Glu
625                 630                 635                 640

Thr Gln Leu Asp Ile Ile Ala Pro Val Asp Ser Asn Thr Leu Asn Leu
                645                 650                 655

Ser Asn Thr Lys Thr Thr Ala Asn Asp Gln Asn Gly Ile Leu Gly Lys
            660                 665                 670

Gln Gly Asn Tyr Ile Val Phe Pro Gln Pro Asn Ile Asp Thr Val Thr
            675                 680                 685

Gly Thr Ser Leu Pro Pro Thr Glu Asn Ile Met Asn Phe Pro Val Gly
            690                 695                 700

Thr Phe Asp Phe Thr Ile Val Asn Ser Gly Asn Ser Asp Thr Ile Leu
705                 710                 715                 720

Asp Arg Ile Glu Phe Val Pro Ile Val Thr Ser Asn Lys Ile Gln Gln
                725                 730                 735
```

```
Asp Phe Thr Ile Ser Pro Gly Thr Ser Gln Val Ile Trp Thr Gly Asn
            740                 745                 750

Ser Ala Asn Thr Ile Asp Ile Thr Ile Ile Asp Asn Val Asp Thr Ser
            755                 760                 765

Gly Leu Phe Val Gln Ile Phe Gln Lys Gly Lys Gln Leu His Gly Glu
            770                 775                 780

Leu Thr Leu Ile Asp Pro Ala His Ile Gln Arg Thr Phe Ser Glu Lys
785                 790                 795                 800

Phe Asp Gln Ile Val Leu Tyr Asn Pro Gly Tyr Asn Ser Ser Ile Ser
                805                 810                 815

Gly Thr Val Ser Gly Ser Val Ser Ile Pro Lys Lys Phe Glu Leu
            820                 825                 830

Ser Ser Asp Leu Gln Asn Ile Thr Asn Gln Val Asn Asn Leu Phe Ala
            835                 840                 845

Ser Ser Glu His Asp Thr Leu Ala Thr Asp Val Ser Asp Tyr Asp Ile
            850                 855                 860

Glu Glu Val Ile Leu Lys Val Asp Ala Leu Ser Asp Glu Val Phe Gly
865                 870                 875                 880

Lys Glu Lys Lys Ala Leu Arg Lys Leu Val Asn Gln Ala Lys Arg Leu
                885                 890                 895

Ser Lys Ala Arg Asn Leu Leu Leu Gly Gly Ser Phe Asp Asn Leu Asp
            900                 905                 910

Ala Trp Tyr Arg Gly Arg Asn Val Val Thr Val Ser Asp His Glu Leu
            915                 920                 925

Phe Lys Ser Asp His Ile Leu Leu Pro Leu Pro Thr Thr Leu Tyr Pro
            930                 935                 940

Ser Tyr Leu Phe Gln Lys Val Glu Glu Ser Lys Leu Lys Ala Asn Thr
945                 950                 955                 960

Arg Tyr Thr Val Ser Gly Phe Ile Ala His Ala Glu Asp Leu Glu Ile
                965                 970                 975

Val Val Ser Arg Tyr Gly Gln Glu Ile Lys Lys Val Val Gln Val Pro
            980                 985                 990

Tyr Gly Glu Ala Phe Pro Leu Thr Ser Ser Gly Pro Ile Cys Cys Arg
            995                 1000                1005

Pro Arg Ser Arg Val Asn Gly Lys Pro Ala Asp Pro His Phe Phe Ser
            1010                1015                1020

Tyr Ser Ile Asp Val Gly Ala Leu Asp Val Glu Ala Asn Pro Gly Ile
1025                1030                1035                1040

Glu Leu Gly Phe Arg Ile Val Glu Pro Thr Gly Met Ala Arg Val Ser
                1045                1050                1055

Asn Leu Glu Ile Arg Glu Asp Arg Pro Leu Thr Ala Asn Glu Ile Arg
            1060                1065                1070

Lys Val Gln Arg Ala Ala Arg Asp Trp Lys Gln Lys Tyr Asp Gln Glu
            1075                1080                1085

Arg Ala Glu Val Arg Ala Leu Ile Gln Pro Val Leu Asn Gln Ile Asn
            1090                1095                1100

Ala Leu Tyr Glu Asn Glu Asp Trp Asn Gly Ala Ile Arg Ser Gly Val
1105                1110                1115                1120

Ser Tyr His Asp Leu Glu Ala Ile Val Leu Pro Thr Leu Pro Lys Leu
            1125                1130                1135

Asn His Trp Phe Met Ser Asp Met Leu Gly Glu Gln Gly Ser Ile Leu
            1140                1145                1150

Ala Gln Phe Gln Glu Ala Leu Asn Arg Ala Tyr Thr Gln Leu Glu Gly
            1155                1160                1165
```

```
Ser Thr Ile Leu His Asn Gly His Phe Thr Thr Asp Ala Ala Asn Trp
    1170                1175                1180

Thr Ile Glu Gly Asp Ala His Gln Val Val Leu Glu Asp Gly Arg Arg
1185                1190                1195                1200

Val Leu Arg Leu Pro Asp Trp Ser Ser Ser Leu Ser Gln Thr Ile Glu
                1205                1210                1215

Ile Glu Asn Phe Asp Pro Asp Lys Glu Tyr Gln Leu Val Phe His Gly
            1220                1225                1230

Gln Gly Glu Gly Thr Val Thr Leu Glu His Gly Glu Gly Glu Tyr
        1235                1240                1245

Val Glu Thr His Pro His Lys Phe Ala Asn Phe Thr Thr Ser Gln Arg
    1250                1255                1260

Gln Gly Ile Thr Phe Glu Ser Asn Lys Val Thr Val Thr Ile Ser Ser
1265                1270                1275                1280

Glu Asp Gly Glu Phe Leu Ala Asp Asn Ile Ala Ile Val Glu Val Pro
                1285                1290                1295

Met Phe Asn Lys Asn Gln Met Val Asn Glu Asn Arg Gly Val Asn Ile
            1300                1305                1310

Asn Ser Asn Thr Asn Met Asn Ser Ser Asn Asn Ser Asn Asn Gln
        1315                1320                1325

<210> SEQ ID NO 5
<211> LENGTH: 3720
<212> TYPE: DNA
<213> ORGANISM: Unknown
<220> FEATURE:
<223> OTHER INFORMATION: Isolated from soil sample
<221> NAME/KEY: CDS
<222> LOCATION: (1)...(3720)

<400> SEQUENCE: 5 atg aat gat atg aca aat tta tct aaa tta tat tca cct gta cca tac      48
Met Asn Asp Met Thr Asn Leu Ser Lys Leu Tyr Ser Pro Val Pro Tyr
1               5                   10                  15 aat gtg tta gca act cca aat gtc tta gca aca aac aaa caa cca cta      96
Asn Val Leu Ala Thr Pro Asn Val Leu Ala Thr Asn Lys Gln Pro Leu
            20                  25                  30 gca gat aca gat gca tta aat aaa ttt tac aac gat ttg caa att gga     144
Ala Asp Thr Asp Ala Leu Asn Lys Phe Tyr Asn Asp Leu Gln Ile Gly
        35                  40                  45 aaa gtt tca gct ttt aca att gat gca tta tgg agc ctt atg aca acc     192
Lys Val Ser Ala Phe Thr Ile Asp Ala Leu Trp Ser Leu Met Thr Thr
    50                  55                  60 gga aaa tat gac tgg tcg tca att gct aaa ttt tgt tgg tct ctt gga     240
Gly Lys Tyr Asp Trp Ser Ser Ile Ala Lys Phe Cys Trp Ser Leu Gly
65                  70                  75                  80 act ggt gta aca cct ctg tta ggt ata ttt tca cct att ata gat ata     288
Thr Gly Val Thr Pro Leu Leu Gly Ile Phe Ser Pro Ile Ile Asp Ile
                85                  90                  95 att ttc cct gct tta ttc ggt ggt aac aaa cta agt cta ttt gaa caa     336
Ile Phe Pro Ala Leu Phe Gly Gly Asn Lys Leu Ser Leu Phe Glu Gln
            100                 105                 110 cta aaa cct caa ata gaa aaa ctg att att gaa aaa tta aca gat gaa     384
Leu Lys Pro Gln Ile Glu Lys Leu Ile Ile Glu Lys Leu Thr Asp Glu
        115                 120                 125 gaa aaa aat ttc tta gct caa aaa act agt gat att caa tcc tat tta     432
Glu Lys Asn Phe Leu Ala Gln Lys Thr Ser Asp Ile Gln Ser Tyr Leu
    130                 135                 140 aat gat tat aaa agt gca gtt tct aaa att aat aat cca aat gtt ata     480
```

```
                Asn Asp Tyr Lys Ser Ala Val Ser Lys Ile Asn Asn Pro Asn Val Ile
                145                 150                 155                 160 gat agc gat ttt gaa tct tta cat gca aca att aat cta aca tta tca         528
Asp Ser Asp Phe Glu Ser Leu His Ala Thr Ile Asn Leu Thr Leu Ser
                165                 170                 175 aaa ata aaa gga tca tta tct tat ttc tct atc ttt aac cag cca gat         576
Lys Ile Lys Gly Ser Leu Ser Tyr Phe Ser Ile Phe Asn Gln Pro Asp
                180                 185                 190 gat aga aaa cca att tat aca ata cta ggt tta cct tat tat acc ctt         624
Asp Arg Lys Pro Ile Tyr Thr Ile Leu Gly Leu Pro Tyr Tyr Thr Leu
                195                 200                 205 atg gcc act atg tat tta aca tta tta cga gac gtt att tta aat aca         672
Met Ala Thr Met Tyr Leu Thr Leu Leu Arg Asp Val Ile Leu Asn Thr
210                 215                 220 aca aaa tgg aaa ata tca cca gct tct aat att tcc tat cgt caa caa         720
Thr Lys Trp Lys Ile Ser Pro Ala Ser Asn Ile Ser Tyr Arg Gln Gln
225                 230                 235                 240 ttt aaa caa aac atg aat tca ttt gtt ctt aca att aaa aat aat tat         768
Phe Lys Gln Asn Met Asn Ser Phe Val Leu Thr Ile Lys Asn Asn Tyr
                245                 250                 255 caa act ggt ttt aat tat ata aca aat gaa gct tac aaa gca cat cct         816
Gln Thr Gly Phe Asn Tyr Ile Thr Asn Glu Ala Tyr Lys Ala His Pro
                260                 265                 270 aca aat cct tca aag act ata ctt cca ttt gaa aat aaa atg aca ttg         864
Thr Asn Pro Ser Lys Thr Ile Leu Pro Phe Glu Asn Lys Met Thr Leu
                275                 280                 285 gac tgt ttt gac tat gtt gca atg tgg ccc act tta tat cca gat gat         912
Asp Cys Phe Asp Tyr Val Ala Met Trp Pro Thr Leu Tyr Pro Asp Asp
                290                 295                 300 tat tat act gaa aaa aca aat ttg caa aaa act cgc tta tta ttt tcc         960
Tyr Tyr Thr Glu Lys Thr Asn Leu Gln Lys Thr Arg Leu Leu Phe Ser
305                 310                 315                 320 cca ata tta ggt cgt atg cca gat tct cga agt caa tgg ctt cat agt        1008
Pro Ile Leu Gly Arg Met Pro Asp Ser Arg Ser Gln Trp Leu His Ser
                325                 330                 335 aaa cct tat tcc tgg gat agt aat aaa act ttt acg ttc gat cac tat        1056
Lys Pro Tyr Ser Trp Asp Ser Asn Lys Thr Phe Thr Phe Asp His Tyr
                340                 345                 350 tat atg gct gaa ctc aca cac att gac act aaa gaa ttt gat cga gta        1104
Tyr Met Ala Glu Leu Thr His Ile Asp Thr Lys Glu Phe Asp Arg Val
                355                 360                 365 gac aga atc cgt cag att tat caa gaa gga tat caa aaa gaa caa caa        1152
Asp Arg Ile Arg Gln Ile Tyr Gln Glu Gly Tyr Gln Lys Glu Gln Gln
                370                 375                 380 acg tat gat gat tat tac act tat ggc gga gat tct gct caa aat act        1200
Thr Tyr Asp Asp Tyr Tyr Thr Tyr Gly Gly Asp Ser Ala Gln Asn Thr
385                 390                 395                 400 tct ttt aca aca gat aat cca ctt gca atc atg tat cct act cga ggt        1248
Ser Phe Thr Thr Asp Asn Pro Leu Ala Ile Met Tyr Pro Thr Arg Gly
                405                 410                 415 ggt aat tat gta ggt acc gct att aaa tgg ttt gat gac aca gtg caa        1296
Gly Asn Tyr Val Gly Thr Ala Ile Lys Trp Phe Asp Asp Thr Val Gln
                420                 425                 430 ggt ggt cga tct tca gga tat aca act cca tat tct gga gac cct gat        1344
Gly Gly Arg Ser Ser Gly Tyr Thr Thr Pro Tyr Ser Gly Asp Pro Asp
                435                 440                 445 cct ata ata act cct gat gat cat aaa gtt aat ttt ctc tat aca gta        1392
Pro Ile Ile Thr Pro Asp Asp His Lys Val Asn Phe Leu Tyr Thr Val
450                 455                 460 aaa gat gaa tta aaa gga att gat gca tgg gtc aat tca tgg gtt ccc        1440
```

|  |  |  |  |  |  |  |  |  |  |  |  |  |  |  |  |
|---|---|---|---|---|---|---|---|---|---|---|---|---|---|---|---|
| Lys | Asp | Glu | Leu | Lys | Gly | Ile | Asp | Ala | Trp | Val | Asn | Ser | Trp | Val | Pro |
| 465 |  |  |  | 470 |  |  |  | 475 |  |  |  | 480 |  |  |  |

| att | tat | aca | act | gtt | cca | aat | ata | att | gaa | aat | gaa | atg | ttc | ctc | act | 1488 |
|---|---|---|---|---|---|---|---|---|---|---|---|---|---|---|---|---|
| Ile | Tyr | Thr | Thr | Val | Pro | Asn | Ile | Ile | Glu | Asn | Glu | Met | Phe | Leu | Thr |  |
|  |  |  |  | 485 |  |  |  |  | 490 |  |  |  |  | 495 |  |  |

| aca | cta | ggt | ttt | cct | ttt | gaa | aaa | gga | ata | att | gat | aca | ggc | gga | gct | 1536 |
|---|---|---|---|---|---|---|---|---|---|---|---|---|---|---|---|---|
| Thr | Leu | Gly | Phe | Pro | Phe | Glu | Lys | Gly | Ile | Ile | Asp | Thr | Gly | Gly | Ala |  |
|  |  |  |  | 500 |  |  |  |  | 505 |  |  |  |  | 510 |  |  |

| ggt | gga | gat | aaa | ata | tat | caa | cta | gaa | cga | tta | aat | gga | tcc | atg | gct | 1584 |
|---|---|---|---|---|---|---|---|---|---|---|---|---|---|---|---|---|
| Gly | Gly | Asp | Lys | Ile | Tyr | Gln | Leu | Glu | Arg | Leu | Asn | Gly | Ser | Met | Ala |  |
|  |  |  | 515 |  |  |  |  | 520 |  |  |  |  | 525 |  |  |  |

| atc | aac | tta | aaa | ttt | aaa | caa | ata | att | aaa | tta | cca | ttt | aca | aat | cta | 1632 |
|---|---|---|---|---|---|---|---|---|---|---|---|---|---|---|---|---|
| Ile | Asn | Leu | Lys | Phe | Lys | Gln | Ile | Ile | Lys | Leu | Pro | Phe | Thr | Asn | Leu |  |
|  |  |  | 530 |  |  |  |  | 535 |  |  |  |  | 540 |  |  |  |

| aca | acc | ggt | aat | tat | cta | att | cgt | tta | cgt | tat | gca | agt | cat | tcg | gat | 1680 |
|---|---|---|---|---|---|---|---|---|---|---|---|---|---|---|---|---|
| Thr | Thr | Gly | Asn | Tyr | Leu | Ile | Arg | Leu | Arg | Tyr | Ala | Ser | His | Ser | Asp |  |
| 545 |  |  |  |  | 550 |  |  |  |  | 555 |  |  |  |  | 560 |  |

| ata | aat | gca | ttt | act | cac | att | cac | tct | gaa | aat | gga | gct | gat | atc | agc | 1728 |
|---|---|---|---|---|---|---|---|---|---|---|---|---|---|---|---|---|
| Ile | Asn | Ala | Phe | Thr | His | Ile | His | Ser | Glu | Asn | Gly | Ala | Asp | Ile | Ser |  |
|  |  |  |  | 565 |  |  |  |  | 570 |  |  |  |  | 575 |  |  |

| agt | act | cct | tta | gga | aat | att | act | ctt | cct | aac | acg | caa | aat | ttc | act | 1776 |
|---|---|---|---|---|---|---|---|---|---|---|---|---|---|---|---|---|
| Ser | Thr | Pro | Leu | Gly | Asn | Ile | Thr | Leu | Pro | Asn | Thr | Gln | Asn | Phe | Thr |  |
|  |  |  | 580 |  |  |  |  | 585 |  |  |  |  | 590 |  |  |  |

| ttt | cct | act | aac | gat | gaa | tac | caa | ccc | aat | caa | ccc | caa | tat | acg | acc | 1824 |
|---|---|---|---|---|---|---|---|---|---|---|---|---|---|---|---|---|
| Phe | Pro | Thr | Asn | Asp | Glu | Tyr | Gln | Pro | Asn | Gln | Pro | Gln | Tyr | Thr | Thr |  |
|  |  | 595 |  |  |  |  | 600 |  |  |  |  | 605 |  |  |  |  |

| tat | ata | gag | gga | aat | gct | ggt | aaa | tat | gct | tta | tat | caa | ttt | aca | caa | 1872 |
|---|---|---|---|---|---|---|---|---|---|---|---|---|---|---|---|---|
| Tyr | Ile | Glu | Gly | Asn | Ala | Gly | Lys | Tyr | Ala | Leu | Tyr | Gln | Phe | Thr | Gln |  |
| 610 |  |  |  |  | 615 |  |  |  |  | 620 |  |  |  |  |  |  |

| aat | atc | tcg | ctc | aca | tct | gga | caa | tat | act | ttc | tat | att | caa | aat | aat | 1920 |
|---|---|---|---|---|---|---|---|---|---|---|---|---|---|---|---|---|
| Asn | Ile | Ser | Leu | Thr | Ser | Gly | Gln | Tyr | Thr | Phe | Tyr | Ile | Gln | Asn | Asn |  |
| 625 |  |  |  |  | 630 |  |  |  |  | 635 |  |  |  |  | 640 |  |

| agt | aat | act | gat | ctc | ttt | tta | gat | cgg | att | gaa | ttt | gtt | cct | atg | ccg | 1968 |
|---|---|---|---|---|---|---|---|---|---|---|---|---|---|---|---|---|
| Ser | Asn | Thr | Asp | Leu | Phe | Leu | Asp | Arg | Ile | Glu | Phe | Val | Pro | Met | Pro |  |
|  |  |  |  | 645 |  |  |  |  | 650 |  |  |  |  | 655 |  |  |

| cct | tct | tca | ata | tca | tta | cct | gat | att | gaa | ata | act | aac | aca | gat | tat | 2016 |
|---|---|---|---|---|---|---|---|---|---|---|---|---|---|---|---|---|
| Pro | Ser | Ser | Ile | Ser | Leu | Pro | Asp | Ile | Glu | Ile | Thr | Asn | Thr | Asp | Tyr |  |
|  |  |  | 660 |  |  |  |  | 665 |  |  |  |  | 670 |  |  |  |

| gaa | att | tgg | aaa | agt | gat | cgt | cca | tat | ggc | cat | tct | ata | aat | gga | ata | 2064 |
|---|---|---|---|---|---|---|---|---|---|---|---|---|---|---|---|---|
| Glu | Ile | Trp | Lys | Ser | Asp | Arg | Pro | Tyr | Gly | His | Ser | Ile | Asn | Gly | Ile |  |
|  |  | 675 |  |  |  |  | 680 |  |  |  |  | 685 |  |  |  |  |

| ttc | ata | gtc | agc | gtg | cca | ttt | gga | aac | cag | aca | gat | act | gta | act | ata | 2112 |
|---|---|---|---|---|---|---|---|---|---|---|---|---|---|---|---|---|
| Phe | Ile | Val | Ser | Val | Pro | Phe | Gly | Asn | Gln | Thr | Asp | Thr | Val | Thr | Ile |  |
|  | 690 |  |  |  |  | 695 |  |  |  |  | 700 |  |  |  |  |  |

| aca | tat | tgg | aat | aat | ggg | gaa | aaa | gtc | cat | aca | gac | tct | caa | aca | ttt | 2160 |
|---|---|---|---|---|---|---|---|---|---|---|---|---|---|---|---|---|
| Thr | Tyr | Trp | Asn | Asn | Gly | Glu | Lys | Val | His | Thr | Asp | Ser | Gln | Thr | Phe |  |
| 705 |  |  |  | 710 |  |  |  |  | 715 |  |  |  |  | 720 |  |  |

| gat | atg | gca | aga | ttc | caa | ggt | caa | gat | ctt | aca | caa | tgg | caa | gga | gct | 2208 |
|---|---|---|---|---|---|---|---|---|---|---|---|---|---|---|---|---|
| Asp | Met | Ala | Arg | Phe | Gln | Gly | Gln | Asp | Leu | Thr | Gln | Trp | Gln | Gly | Ala |  |
|  |  |  |  | 725 |  |  |  |  | 730 |  |  |  |  | 735 |  |  |

| ttt | gat | cgt | gta | act | att | cgt | aga | act | cat | tct | gat | ggt | aca | ttg | tca | 2256 |
|---|---|---|---|---|---|---|---|---|---|---|---|---|---|---|---|---|
| Phe | Asp | Arg | Val | Thr | Ile | Arg | Arg | Thr | His | Ser | Asp | Gly | Thr | Leu | Ser |  |
|  |  |  | 740 |  |  |  |  | 745 |  |  |  |  | 750 |  |  |  |

| tta | aca | agt | gca | acc | cta | tac | ttt | gtt | atc | cca | aaa | tca | tcc | ttt | agt | 2304 |
|---|---|---|---|---|---|---|---|---|---|---|---|---|---|---|---|---|
| Leu | Thr | Ser | Ala | Thr | Leu | Tyr | Phe | Val | Ile | Pro | Lys | Ser | Ser | Phe | Ser |  |
|  |  | 755 |  |  |  |  | 760 |  |  |  |  | 765 |  |  |  |  |

| acc | cca | gaa | gat | tta | gaa | aaa | atc | aca | aac | caa | gtc | aat | cag | tta | ttt | 2352 |
|---|---|---|---|---|---|---|---|---|---|---|---|---|---|---|---|---|
| Thr | Pro | Glu | Asp | Leu | Glu | Lys | Ile | Thr | Asn | Gln | Val | Asn | Gln | Leu | Phe |  |
| 770 |  |  |  |  | 775 |  |  |  |  | 780 |  |  |  |  |  |  |

| act | tcc | tca | tcc | caa | aca | gaa | tta | gct | aac | acc | gta | acc | gat | tac | gga | 2400 |
|---|---|---|---|---|---|---|---|---|---|---|---|---|---|---|---|---|

-continued

| | | | | | | | | | | | | | | | |
|---|---|---|---|---|---|---|---|---|---|---|---|---|---|---|---|
| | Thr | Ser | Ser | Ser | Gln | Thr | Glu | Leu | Ala | Asn | Thr | Val | Thr | Asp | Tyr | Gly |
| | 785 | | | | 790 | | | | | 795 | | | | | 800 |

| att | gat | caa | gtt | ttg | atg | aaa | gta | gat | gcg | tta | tca | gac | gat | gta | ttt | 2448 |
|---|---|---|---|---|---|---|---|---|---|---|---|---|---|---|---|---|
| Ile | Asp | Gln | Val | Leu | Met | Lys | Val | Asp | Ala | Leu | Ser | Asp | Asp | Val | Phe | |
| | | | | 805 | | | | | 810 | | | | | 815 | | |

| ggg | gta | gag | aaa | aaa | gca | tta | cgt | aaa | ctt | gtc | aat | cag | gcc | aaa | caa | 2496 |
|---|---|---|---|---|---|---|---|---|---|---|---|---|---|---|---|---|
| Gly | Val | Glu | Lys | Lys | Ala | Leu | Arg | Lys | Leu | Val | Asn | Gln | Ala | Lys | Gln | |
| | | | 820 | | | | | 825 | | | | | 830 | | | |

| ctg | agt | aaa | gca | cgc | aat | gta | tta | gtc | ggt | gga | aac | ttt | gaa | gga | aat | 2544 |
|---|---|---|---|---|---|---|---|---|---|---|---|---|---|---|---|---|
| Leu | Ser | Lys | Ala | Arg | Asn | Val | Leu | Val | Gly | Gly | Asn | Phe | Glu | Gly | Asn | |
| | | 835 | | | | | 840 | | | | | 845 | | | | |

| cat | gaa | tgg | gta | ctc | ggt | cgt | aaa | gcg | gtc | atg | gtc | gca | aat | gat | gag | 2592 |
|---|---|---|---|---|---|---|---|---|---|---|---|---|---|---|---|---|
| His | Glu | Trp | Val | Leu | Gly | Arg | Lys | Ala | Val | Met | Val | Ala | Asn | Asp | Glu | |
| 850 | | | | | 855 | | | | | 860 | | | | | | |

| tta | ttt | aaa | ggc | aat | cat | tta | tta | tta | cca | cct | cca | agt | cta | tat | cca | 2640 |
|---|---|---|---|---|---|---|---|---|---|---|---|---|---|---|---|---|
| Leu | Phe | Lys | Gly | Asn | His | Leu | Leu | Leu | Pro | Pro | Pro | Ser | Leu | Tyr | Pro | |
| 865 | | | | | 870 | | | | | 875 | | | | | 880 | |

| tcg | tat | gcg | tat | caa | aaa | gtg | gat | gaa | tcc | aaa | tta | aaa | ccg | aat | aca | 2688 |
|---|---|---|---|---|---|---|---|---|---|---|---|---|---|---|---|---|
| Ser | Tyr | Ala | Tyr | Gln | Lys | Val | Asp | Glu | Ser | Lys | Leu | Lys | Pro | Asn | Thr | |
| | | | | 885 | | | | | 890 | | | | | 895 | | |

| cga | tat | acc | gtt | tct | ggt | ttt | gtg | gcg | caa | agt | gaa | caa | tta | gaa | gtc | 2736 |
|---|---|---|---|---|---|---|---|---|---|---|---|---|---|---|---|---|
| Arg | Tyr | Thr | Val | Ser | Gly | Phe | Val | Ala | Gln | Ser | Glu | Gln | Leu | Glu | Val | |
| | | | 900 | | | | | 905 | | | | | 910 | | | |

| gtt | gtt | tcc | cgt | tat | ggt | aaa | gaa | gta | cat | gac | atg | tta | aat | gtt | cct | 2784 |
|---|---|---|---|---|---|---|---|---|---|---|---|---|---|---|---|---|
| Val | Val | Ser | Arg | Tyr | Gly | Lys | Glu | Val | His | Asp | Met | Leu | Asn | Val | Pro | |
| | | 915 | | | | | 920 | | | | | 925 | | | | |

| tat | gaa | gaa | gcg | tta | ccg | att | tct | tca | aat | gaa | aag | tca | aat | tgt | tgt | 2832 |
|---|---|---|---|---|---|---|---|---|---|---|---|---|---|---|---|---|
| Tyr | Glu | Glu | Ala | Leu | Pro | Ile | Ser | Ser | Asn | Glu | Lys | Ser | Asn | Cys | Cys | |
| 930 | | | | | 935 | | | | | 940 | | | | | | |

| aaa | ccg | gct | act | tgc | aac | tat | aca | tct | tgt | gag | ggg | aaa | gaa | cca | gat | 2880 |
|---|---|---|---|---|---|---|---|---|---|---|---|---|---|---|---|---|
| Lys | Pro | Ala | Thr | Cys | Asn | Tyr | Thr | Ser | Cys | Glu | Gly | Lys | Glu | Pro | Asp | |
| 945 | | | | | 950 | | | | | 955 | | | | | 960 | |

| tct | cat | ttc | ttc | cgt | tat | agt | atc | gat | gtc | ggt | gct | tta | caa | cca | gaa | 2928 |
|---|---|---|---|---|---|---|---|---|---|---|---|---|---|---|---|---|
| Ser | His | Phe | Phe | Arg | Tyr | Ser | Ile | Asp | Val | Gly | Ala | Leu | Gln | Pro | Glu | |
| | | | | 965 | | | | | 970 | | | | | 975 | | |

| gca | aat | cta | gga | att | gaa | ttc | ggt | ctt | cgt | att | gtg | aaa | tca | aat | gga | 2976 |
|---|---|---|---|---|---|---|---|---|---|---|---|---|---|---|---|---|
| Ala | Asn | Leu | Gly | Ile | Glu | Phe | Gly | Leu | Arg | Ile | Val | Lys | Ser | Asn | Gly | |
| | | | 980 | | | | | 985 | | | | | 990 | | | |

| ttt | gca | aaa | atc | agt | aat | tta | gaa | atc | aaa | gaa | gat | cgt | cca | tta | aca | 3024 |
|---|---|---|---|---|---|---|---|---|---|---|---|---|---|---|---|---|
| Phe | Ala | Lys | Ile | Ser | Asn | Leu | Glu | Ile | Lys | Glu | Asp | Arg | Pro | Leu | Thr | |
| | | | 995 | | | | | 1000 | | | | | 1005 | | | |

| gac | caa | gaa | att | aaa | aaa | gta | caa | cac | aaa | gaa | caa | aag | tgg | aaa | aaa | 3072 |
|---|---|---|---|---|---|---|---|---|---|---|---|---|---|---|---|---|
| Asp | Gln | Glu | Ile | Lys | Lys | Val | Gln | His | Lys | Glu | Gln | Lys | Trp | Lys | Lys | |
| 1010 | | | | | 1015 | | | | | 1020 | | | | | | |

| gca | ttt | aac | aaa | gaa | caa | gca | gag | tta | acg | gca | aca | ctc | caa | cca | aca | 3120 |
|---|---|---|---|---|---|---|---|---|---|---|---|---|---|---|---|---|
| Ala | Phe | Asn | Lys | Glu | Gln | Ala | Glu | Leu | Thr | Ala | Thr | Leu | Gln | Pro | Thr | |
| 1025 | | | | | 1030 | | | | | 1035 | | | | | 1040 | |

| ctg | aat | caa | atc | aat | gcc | ttg | tat | caa | cag | gaa | gat | tgg | aat | ggt | tcg | 3168 |
|---|---|---|---|---|---|---|---|---|---|---|---|---|---|---|---|---|
| Leu | Asn | Gln | Ile | Asn | Ala | Leu | Tyr | Gln | Gln | Glu | Asp | Trp | Asn | Gly | Ser | |
| | | | | 1045 | | | | | 1050 | | | | | 1055 | | |

| att | cat | cct | cat | gtg | acg | tat | caa | cat | ctg | tct | gat | gtt | gtc | tta | cca | 3216 |
|---|---|---|---|---|---|---|---|---|---|---|---|---|---|---|---|---|
| Ile | His | Pro | His | Val | Thr | Tyr | Gln | His | Leu | Ser | Asp | Val | Val | Leu | Pro | |
| | | | 1060 | | | | | 1065 | | | | | 1070 | | | |

| acg | tta | cca | aaa | caa | aca | cat | tgg | ttt | atg | gaa | aat | cga | gaa | ggc | gaa | 3264 |
|---|---|---|---|---|---|---|---|---|---|---|---|---|---|---|---|---|
| Thr | Leu | Pro | Lys | Gln | Thr | His | Trp | Phe | Met | Glu | Asn | Arg | Glu | Gly | Glu | |
| | | | 1075 | | | | | 1080 | | | | | 1085 | | | |

| cat | gtt | gtt | ctg | acg | caa | caa | ttc | caa | caa | gca | tta | gat | cgt | gct | ttc | 3312 |
|---|---|---|---|---|---|---|---|---|---|---|---|---|---|---|---|---|
| His | Val | Val | Leu | Thr | Gln | Gln | Phe | Gln | Gln | Ala | Leu | Asp | Arg | Ala | Phe | |
| | | | 1090 | | | | | 1095 | | | | | 1100 | | | |

| caa | caa | atc | gaa | gaa | caa | aac | ttg | atc | cac | aat | ggt | agc | ttt | aca | agt | 3360 |

```
Gln Gln Ile Glu Glu Gln Asn Leu Ile His Asn Gly Ser Phe Thr Ser
1105                1110                1115                1120 gga tta aca gat tgg act gta aca gga gat gca cag att act atc tat    3408
Gly Leu Thr Asp Trp Thr Val Thr Gly Asp Ala Gln Ile Thr Ile Tyr
                1125                1130                1135 gat gaa gat cca gta tta gaa cta gca cat tgg gat gca agc gtc tct    3456
Asp Glu Asp Pro Val Leu Glu Leu Ala His Trp Asp Ala Ser Val Ser
                1140                1145                1150 caa acg att gag att act gat ttt gaa gaa aaa gaa tac aaa ctt        3504
Gln Thr Ile Glu Ile Thr Asp Phe Glu Glu Lys Glu Tyr Lys Leu
                1155                1160                1165 cgt gta cgc gga aaa ggc aaa gga acg gtt acc gtt caa cat gaa gaa    3552
Arg Val Arg Gly Lys Gly Lys Gly Thr Val Thr Val Gln His Glu Glu
                1170                1175                1180 gag tta gaa aca atg aca ttt aac aca act agt ttt aca acg aaa gaa    3600
Glu Leu Glu Thr Met Thr Phe Asn Thr Thr Ser Phe Thr Thr Lys Glu
1185                1190                1195                1200 caa acc ttc tat ttc gaa gga aat aca ata gat gta cac gtt caa tca    3648
Gln Thr Phe Tyr Phe Glu Gly Asn Thr Ile Asp Val His Val Gln Ser
                1205                1210                1215 gag aat aat gca ttc ctt gta gac agt gtg gaa ctc att gaa gtt gta    3696
Glu Asn Asn Ala Phe Leu Val Asp Ser Val Glu Leu Ile Glu Val Val
                1220                1225                1230 aaa gaa caa gaa gaa aaa caa taa                                    3720
Lys Glu Gln Glu Glu Lys Gln *
                1235

<210> SEQ ID NO 6
<211> LENGTH: 1239
<212> TYPE: PRT
<213> ORGANISM: Unknown
<220> FEATURE:
<223> OTHER INFORMATION: Isolated from soil sample

<400> SEQUENCE: 6

Met Asn Asp Met Thr Asn Leu Ser Lys Leu Tyr Ser Pro Val Pro Tyr
1               5                   10                  15

Asn Val Leu Ala Thr Pro Asn Val Leu Ala Thr Asn Lys Gln Pro Leu
            20                  25                  30

Ala Asp Thr Asp Ala Leu Asn Lys Phe Tyr Asn Asp Leu Gln Ile Gly
        35                  40                  45

Lys Val Ser Ala Phe Thr Ile Asp Ala Leu Trp Ser Leu Met Thr Thr
    50                  55                  60

Gly Lys Tyr Asp Trp Ser Ser Ile Ala Lys Phe Cys Trp Ser Leu Gly
65                  70                  75                  80

Thr Gly Val Thr Pro Leu Leu Gly Ile Phe Ser Pro Ile Ile Asp Ile
                85                  90                  95

Ile Phe Pro Ala Leu Phe Gly Gly Asn Lys Leu Ser Leu Phe Glu Gln
            100                 105                 110

Leu Lys Pro Gln Ile Glu Lys Leu Ile Glu Lys Leu Thr Asp Glu
        115                 120                 125

Glu Lys Asn Phe Leu Ala Gln Lys Thr Ser Asp Ile Gln Ser Tyr Leu
    130                 135                 140

Asn Asp Tyr Lys Ser Ala Val Ser Lys Ile Asn Asn Pro Asn Val Ile
145                 150                 155                 160

Asp Ser Asp Phe Glu Ser Leu His Ala Thr Ile Asn Leu Thr Leu Ser
                165                 170                 175

Lys Ile Lys Gly Ser Leu Ser Tyr Phe Ser Ile Phe Asn Gln Pro Asp
            180                 185                 190
```

Asp Arg Lys Pro Ile Tyr Thr Ile Leu Gly Leu Pro Tyr Tyr Thr Leu
        195                 200                 205

Met Ala Thr Met Tyr Leu Thr Leu Leu Arg Asp Val Ile Leu Asn Thr
        210                 215                 220

Thr Lys Trp Lys Ile Ser Pro Ala Ser Asn Ile Ser Tyr Arg Gln Gln
225                 230                 235                 240

Phe Lys Gln Asn Met Asn Ser Phe Val Leu Thr Ile Lys Asn Asn Tyr
                245                 250                 255

Gln Thr Gly Phe Asn Tyr Ile Thr Asn Glu Ala Tyr Lys Ala His Pro
                260                 265                 270

Thr Asn Pro Ser Lys Thr Ile Leu Pro Phe Glu Asn Lys Met Thr Leu
        275                 280                 285

Asp Cys Phe Asp Tyr Val Ala Met Trp Pro Thr Leu Tyr Pro Asp Asp
        290                 295                 300

Tyr Tyr Thr Glu Lys Thr Asn Leu Gln Lys Thr Arg Leu Leu Phe Ser
305                 310                 315                 320

Pro Ile Leu Gly Arg Met Pro Asp Ser Arg Ser Gln Trp Leu His Ser
                325                 330                 335

Lys Pro Tyr Ser Trp Asp Ser Asn Lys Thr Phe Thr Phe Asp His Tyr
                340                 345                 350

Tyr Met Ala Glu Leu Thr His Ile Asp Thr Lys Glu Phe Asp Arg Val
        355                 360                 365

Asp Arg Ile Arg Gln Ile Tyr Gln Glu Gly Tyr Gln Lys Glu Gln Gln
        370                 375                 380

Thr Tyr Asp Asp Tyr Tyr Thr Tyr Gly Gly Asp Ser Ala Gln Asn Thr
385                 390                 395                 400

Ser Phe Thr Thr Asp Asn Pro Leu Ala Ile Met Tyr Pro Thr Arg Gly
                405                 410                 415

Gly Asn Tyr Val Gly Thr Ala Ile Lys Trp Phe Asp Asp Thr Val Gln
                420                 425                 430

Gly Gly Arg Ser Ser Gly Tyr Thr Thr Pro Tyr Ser Gly Asp Pro Asp
        435                 440                 445

Pro Ile Ile Thr Pro Asp Asp His Lys Val Asn Phe Leu Tyr Thr Val
        450                 455                 460

Lys Asp Glu Leu Lys Gly Ile Asp Ala Trp Val Asn Ser Trp Val Pro
465                 470                 475                 480

Ile Tyr Thr Thr Val Pro Asn Ile Ile Glu Asn Glu Met Phe Leu Thr
                485                 490                 495

Thr Leu Gly Phe Pro Phe Glu Lys Gly Ile Ile Asp Thr Gly Gly Ala
                500                 505                 510

Gly Gly Asp Lys Ile Tyr Gln Leu Glu Arg Leu Asn Gly Ser Met Ala
        515                 520                 525

Ile Asn Leu Lys Phe Lys Gln Ile Ile Lys Leu Pro Phe Thr Asn Leu
        530                 535                 540

Thr Thr Gly Asn Tyr Leu Ile Arg Leu Arg Tyr Ala Ser His Ser Asp
545                 550                 555                 560

Ile Asn Ala Phe Thr His Ile His Ser Glu Asn Gly Ala Asp Ile Ser
                565                 570                 575

Ser Thr Pro Leu Gly Asn Ile Thr Leu Pro Asn Thr Gln Asn Phe Thr
        580                 585                 590

Phe Pro Thr Asn Asp Glu Tyr Gln Pro Asn Gln Pro Gln Tyr Thr Thr
        595                 600                 605

Tyr Ile Glu Gly Asn Ala Gly Lys Tyr Ala Leu Tyr Gln Phe Thr Gln

```
                610                 615                 620
Asn Ile Ser Leu Thr Ser Gly Gln Tyr Thr Phe Tyr Ile Gln Asn Asn
625                 630                 635                 640

Ser Asn Thr Asp Leu Phe Leu Asp Arg Ile Glu Phe Val Pro Met Pro
                645                 650                 655

Pro Ser Ser Ile Ser Leu Pro Asp Ile Glu Ile Thr Asn Thr Asp Tyr
                660                 665                 670

Glu Ile Trp Lys Ser Asp Arg Pro Tyr Gly His Ser Ile Asn Gly Ile
                675                 680                 685

Phe Ile Val Ser Val Pro Phe Gly Asn Gln Thr Asp Thr Val Thr Ile
690                 695                 700

Thr Tyr Trp Asn Asn Gly Glu Lys Val His Thr Asp Ser Gln Thr Phe
705                 710                 715                 720

Asp Met Ala Arg Phe Gln Gly Gln Asp Leu Thr Gln Trp Gln Gly Ala
                725                 730                 735

Phe Asp Arg Val Thr Ile Arg Arg Thr His Ser Asp Gly Thr Leu Ser
                740                 745                 750

Leu Thr Ser Ala Thr Leu Tyr Phe Val Ile Pro Lys Ser Ser Phe Ser
                755                 760                 765

Thr Pro Glu Asp Leu Glu Lys Ile Thr Asn Gln Val Asn Gln Leu Phe
770                 775                 780

Thr Ser Ser Ser Gln Thr Glu Leu Ala Asn Thr Val Thr Asp Tyr Gly
785                 790                 795                 800

Ile Asp Gln Val Leu Met Lys Val Asp Ala Leu Ser Asp Asp Val Phe
                805                 810                 815

Gly Val Glu Lys Lys Ala Leu Arg Lys Leu Val Asn Gln Ala Lys Gln
                820                 825                 830

Leu Ser Lys Ala Arg Asn Val Leu Val Gly Gly Asn Phe Glu Gly Asn
                835                 840                 845

His Glu Trp Val Leu Gly Arg Lys Ala Val Met Val Ala Asn Asp Glu
                850                 855                 860

Leu Phe Lys Gly Asn His Leu Leu Pro Pro Pro Ser Leu Tyr Pro
865                 870                 875                 880

Ser Tyr Ala Tyr Gln Lys Val Asp Glu Ser Lys Leu Lys Pro Asn Thr
                885                 890                 895

Arg Tyr Thr Val Ser Gly Phe Val Ala Gln Ser Glu Gln Leu Glu Val
                900                 905                 910

Val Val Ser Arg Tyr Gly Lys Glu Val His Asp Met Leu Asn Val Pro
                915                 920                 925

Tyr Glu Glu Ala Leu Pro Ile Ser Ser Asn Glu Lys Ser Asn Cys Cys
930                 935                 940

Lys Pro Ala Thr Cys Asn Tyr Thr Ser Cys Glu Gly Lys Glu Pro Asp
945                 950                 955                 960

Ser His Phe Phe Arg Tyr Ser Ile Asp Val Gly Ala Leu Gln Pro Glu
                965                 970                 975

Ala Asn Leu Gly Ile Glu Phe Gly Leu Arg Ile Val Lys Ser Asn Gly
                980                 985                 990

Phe Ala Lys Ile Ser Asn Leu Glu Ile Lys Glu Asp Arg Pro Leu Thr
                995                 1000                1005

Asp Gln Glu Ile Lys Lys Val Gln His Lys Glu Gln Lys Trp Lys Lys
                1010                1015                1020

Ala Phe Asn Lys Glu Gln Ala Glu Leu Thr Ala Thr Leu Gln Pro Thr
1025                1030                1035                1040
```

```
Leu Asn Gln Ile Asn Ala Leu Tyr Gln Gln Glu Asp Trp Asn Gly Ser
            1045                1050                1055

Ile His Pro His Val Thr Tyr Gln His Leu Ser Asp Val Val Leu Pro
        1060                1065                1070

Thr Leu Pro Lys Gln Thr His Trp Phe Met Glu Asn Arg Glu Gly Glu
        1075                1080                1085

His Val Val Leu Thr Gln Gln Phe Gln Gln Ala Leu Asp Arg Ala Phe
        1090                1095                1100

Gln Gln Ile Glu Glu Gln Asn Leu Ile His Asn Gly Ser Phe Thr Ser
1105                1110                1115                1120

Gly Leu Thr Asp Trp Thr Val Thr Gly Asp Ala Gln Ile Thr Ile Tyr
            1125                1130                1135

Asp Glu Asp Pro Val Leu Glu Leu Ala His Trp Asp Ala Ser Val Ser
            1140                1145                1150

Gln Thr Ile Glu Ile Thr Asp Phe Glu Glu Glu Lys Glu Tyr Lys Leu
            1155                1160                1165

Arg Val Arg Gly Lys Gly Lys Gly Thr Val Thr Val Gln His Glu Glu
        1170                1175                1180

Glu Leu Glu Thr Met Thr Phe Asn Thr Thr Ser Phe Thr Thr Lys Glu
1185                1190                1195                1200

Gln Thr Phe Tyr Phe Glu Gly Asn Thr Ile Asp Val His Val Gln Ser
            1205                1210                1215

Glu Asn Asn Ala Phe Leu Val Asp Ser Val Glu Leu Ile Glu Val Val
            1220                1225                1230

Lys Glu Gln Glu Glu Lys Gln
        1235

<210> SEQ ID NO 7
<211> LENGTH: 2059
<212> TYPE: DNA
<213> ORGANISM: Artificial Sequence
<220> FEATURE:
<223> OTHER INFORMATION: synaxmi-031
<221> NAME/KEY: CDS
<222> LOCATION: (1)...(2058)

<400> SEQUENCE: 7 atg gat tgc aat ctc cag agc cag cag aat atc cca tac aat gtg ctt      48
Met Asp Cys Asn Leu Gln Ser Gln Gln Asn Ile Pro Tyr Asn Val Leu
1               5                   10                  15 gct atc cct gtt agc aat gtt aat agc ctt acg gat acg gtt ggc gat      96
Ala Ile Pro Val Ser Asn Val Asn Ser Leu Thr Asp Thr Val Gly Asp
            20                  25                  30 cta aag aag gca tgg gaa gag ttc cag aag acg ggc agc ttc tcc ctt     144
Leu Lys Lys Ala Trp Glu Glu Phe Gln Lys Thr Gly Ser Phe Ser Leu
        35                  40                  45 acc gca ctc cag cag ggc ttc agc gct tcc cag ggc ggg acg ttc aat     192
Thr Ala Leu Gln Gln Gly Phe Ser Ala Ser Gln Gly Gly Thr Phe Asn
    50                  55                  60 tac ctc acc ctc ctc cag tcc ggg atc tcc ctg gct ggc agc ttc gtg     240
Tyr Leu Thr Leu Leu Gln Ser Gly Ile Ser Leu Ala Gly Ser Phe Val
65                  70                  75                  80 cct ggc ggc acc ttc gtt gct cca atc atc aat atg gtg atc ggc tgg     288
Pro Gly Gly Thr Phe Val Ala Pro Ile Ile Asn Met Val Ile Gly Trp
                85                  90                  95 ctc tgg cct cat aag aat aag aat gca gat acg gaa aat ctg atc aat     336
Leu Trp Pro His Lys Asn Lys Asn Ala Asp Thr Glu Asn Leu Ile Asn
            100                 105                 110 ctg atc gat tca gaa atc cag aag cag ctg aat aag gct ctg ctg gat     384
```

```
                Leu Ile Asp Ser Glu Ile Gln Lys Gln Leu Asn Lys Ala Leu Leu Asp
                    115                 120                 125 gct gat cgc aat gaa tgg agc agc tac ctc gag tcc atc ttc gat agc       432
Ala Asp Arg Asn Glu Trp Ser Ser Tyr Leu Glu Ser Ile Phe Asp Ser
130                 135                 140 agc aat aat ctg aat ggc gca atc gtt gat gct cag tgg tcc ggc acc       480
Ser Asn Asn Leu Asn Gly Ala Ile Val Asp Ala Gln Trp Ser Gly Thr
145                 150                 155                 160 gtg aat acg acc aat cgt acg ctt cgt aat cct acg gaa tca gat tac       528
Val Asn Thr Thr Asn Arg Thr Leu Arg Asn Pro Thr Glu Ser Asp Tyr
                165                 170                 175 acc aat gtg gtg acg aat ttc atc gca gca gat ggg gat atc gct aat       576
Thr Asn Val Val Thr Asn Phe Ile Ala Ala Asp Gly Asp Ile Ala Asn
                180                 185                 190 aat gaa aat cat atc atg aat ggg aat ttc gat gtg gca gca gct cca       624
Asn Glu Asn His Ile Met Asn Gly Asn Phe Asp Val Ala Ala Ala Pro
                195                 200                 205 tac ttc gtt atc ggg gct acc gct aga ttc gca gct atg cag tcc tac       672
Tyr Phe Val Ile Gly Ala Thr Ala Arg Phe Ala Ala Met Gln Ser Tyr
210                 215                 220 atc aag ttc tgc aat gca tgg atc gat aag gtt ggg ctg tca gat gct       720
Ile Lys Phe Cys Asn Ala Trp Ile Asp Lys Val Gly Leu Ser Asp Ala
225                 230                 235                 240 cag ctg acc acg cag aag gct aat ctg gat aga acg aag cag aat atg       768
Gln Leu Thr Thr Gln Lys Ala Asn Leu Asp Arg Thr Lys Gln Asn Met
                245                 250                 255 cgt aat gct atc ctt aat tac acc cag cag gtt atg aag gtt ttc aag       816
Arg Asn Ala Ile Leu Asn Tyr Thr Gln Gln Val Met Lys Val Phe Lys
                260                 265                 270 gat tcc aag aat atg cca acg atc ggc acg aat aag ttc agc gtt gat       864
Asp Ser Lys Asn Met Pro Thr Ile Gly Thr Asn Lys Phe Ser Val Asp
                275                 280                 285 acc tac aat gtt tac atc aag ggg atg acg ctt aat gtg ctt gat atc       912
Thr Tyr Asn Val Tyr Ile Lys Gly Met Thr Leu Asn Val Leu Asp Ile
            290                 295                 300 gtt gct atc tgg cca agc ctg tac cca gat gat tac acg tca cag acg       960
Val Ala Ile Trp Pro Ser Leu Tyr Pro Asp Asp Tyr Thr Ser Gln Thr
305                 310                 315                 320 gct ctg gaa cag acc cgc gtg acg ttc tcc aat atg gtg ggg cag gaa      1008
Ala Leu Glu Gln Thr Arg Val Thr Phe Ser Asn Met Val Gly Gln Glu
                325                 330                 335 gaa ggc acg gat ggc agc ctc aga atc tac aat acc ttc gat agc ttc      1056
Glu Gly Thr Asp Gly Ser Leu Arg Ile Tyr Asn Thr Phe Asp Ser Phe
                340                 345                 350 tcc tac cag cat agc cct atc cct aat aat aat gtg aat ctc atc agc      1104
Ser Tyr Gln His Ser Pro Ile Pro Asn Asn Asn Val Asn Leu Ile Ser
                355                 360                 365 tac tac aat gat gaa ctt cag aat ctg gaa ctc ggg gtt tac acc cca      1152
Tyr Tyr Asn Asp Glu Leu Gln Asn Leu Glu Leu Gly Val Tyr Thr Pro
370                 375                 380 cca aag aag ggc tca ggc tac agc tac cca tac ggg ttc gtg ctg aat      1200
Pro Lys Lys Gly Ser Gly Tyr Ser Tyr Pro Tyr Gly Phe Val Leu Asn
385                 390                 395                 400 tac gca aat agc aag tac aag tac ggc gat tcc aat gat cca gaa tcc      1248
Tyr Ala Asn Ser Lys Tyr Lys Tyr Gly Asp Ser Asn Asp Pro Glu Ser
                405                 410                 415 ctc ggc ggg ctt tcc acc ctt agc gct cca atc caa cag gtt aat gct      1296
Leu Gly Gly Leu Ser Thr Leu Ser Ala Pro Ile Gln Gln Val Asn Ala
                420                 425                 430 gct acc cag aat agc aag tac ctt gat ggc gaa atc ctg aat ggg atc      1344
Ala Thr Gln Asn Ser Lys Tyr Leu Asp Gly Glu Ile Leu Asn Gly Ile
```

```
                Ala Thr Gln Asn Ser Lys Tyr Leu Asp Gly Glu Ile Leu Asn Gly Ile
                        435                 440                 445 ggc gca agc ctg cct ggc tac tgc acg acc ggg tgc tca cct acc gaa    1392
Gly Ala Ser Leu Pro Gly Tyr Cys Thr Thr Gly Cys Ser Pro Thr Glu
450                 455                 460 cca cca ttc agc tgc acg agc acg gca aat ggg tac aag gca agc tgc    1440
Pro Pro Phe Ser Cys Thr Ser Thr Ala Asn Gly Tyr Lys Ala Ser Cys
465                 470                 475                 480 aat cca agc gat acc aat cag aag atc aat gct ctc tac cca ttc acg    1488
Asn Pro Ser Asp Thr Asn Gln Lys Ile Asn Ala Leu Tyr Pro Phe Thr
                485                 490                 495 cag gca aat gtg aag ggg aat acc ggg aag ctg ggc gtt ctc gca agc    1536
Gln Ala Asn Val Lys Gly Asn Thr Gly Lys Leu Gly Val Leu Ala Ser
                500                 505                 510 ctt gtt agc tac gat ctg aat cct aag aat gtt ttc ggg gaa ctc gat    1584
Leu Val Ser Tyr Asp Leu Asn Pro Lys Asn Val Phe Gly Glu Leu Asp
                515                 520                 525 tca gat acc aat aat gtt atc ctt aag ggc atc cca gca gaa aag ggc    1632
Ser Asp Thr Asn Asn Val Ile Leu Lys Gly Ile Pro Ala Glu Lys Gly
530                 535                 540 tac ttc cca aat aat gca aga cca acc gtt gtg aag gaa tgg atc aat    1680
Tyr Phe Pro Asn Asn Ala Arg Pro Thr Val Val Lys Glu Trp Ile Asn
545                 550                 555                 560 ggg gct tcc gca gtt cca ctt gat tcc ggc aat acc ctg ttc atg acg    1728
Gly Ala Ser Ala Val Pro Leu Asp Ser Gly Asn Thr Leu Phe Met Thr
                565                 570                 575 gct acg aac ctg acg gct acc cag tac aga atc cgc atc cgt tac gct    1776
Ala Thr Asn Leu Thr Ala Thr Gln Tyr Arg Ile Arg Ile Arg Tyr Ala
                580                 585                 590 aac cca aac tca aac acg cag atc ggc gtt aga atc acg cag aac ggg    1824
Asn Pro Asn Ser Asn Thr Gln Ile Gly Val Arg Ile Thr Gln Asn Gly
                595                 600                 605 agc ctc atc tcc tcc tcc aac ctc acg ctg tac tca acc acc gat atg    1872
Ser Leu Ile Ser Ser Ser Asn Leu Thr Leu Tyr Ser Thr Thr Asp Met
610                 615                 620 aac aac acc ctg cca ctg aac gtt tac gtg atc ggg gaa aac ggg aac    1920
Asn Asn Thr Leu Pro Leu Asn Val Tyr Val Ile Gly Glu Asn Gly Asn
625                 630                 635                 640 tac acc ctc cag gat ctc tac aac acg acg aac gtt ctg tcc acg ggc    1968
Tyr Thr Leu Gln Asp Leu Tyr Asn Thr Thr Asn Val Leu Ser Thr Gly
                645                 650                 655 gat atc acc ctg cag atc acc ggc ggg gat cag aag ata ttc atc gat    2016
Asp Ile Thr Leu Gln Ile Thr Gly Gly Asp Gln Lys Ile Phe Ile Asp
                660                 665                 670 cgc atc gag ttc gtg cct acg atg cca gtg cca ggc aac taa            2058
Arg Ile Glu Phe Val Pro Thr Met Pro Val Pro Gly Asn *
                675                 680                 685 a                                                                  2059

<210> SEQ ID NO 8
<211> LENGTH: 685
<212> TYPE: PRT
<213> ORGANISM: Artificial Sequence
<220> FEATURE:
<223> OTHER INFORMATION: SYNAXMI-031

<400> SEQUENCE: 8

Met Asp Cys Asn Leu Gln Ser Gln Gln Asn Ile Pro Tyr Asn Val Leu
1               5                   10                  15

Ala Ile Pro Val Ser Asn Val Asn Ser Leu Thr Asp Thr Val Gly Asp
            20                  25                  30
```

-continued

```
Leu Lys Lys Ala Trp Glu Glu Phe Gln Lys Thr Gly Ser Phe Ser Leu
         35                  40                  45

Thr Ala Leu Gln Gln Gly Phe Ser Ala Ser Gln Gly Gly Thr Phe Asn
 50                  55                  60

Tyr Leu Thr Leu Leu Gln Ser Gly Ile Ser Leu Ala Gly Ser Phe Val
 65                  70                  75                  80

Pro Gly Gly Thr Phe Val Ala Pro Ile Ile Asn Met Val Ile Gly Trp
                 85                  90                  95

Leu Trp Pro His Lys Asn Lys Asn Ala Asp Thr Glu Asn Leu Ile Asn
                100                 105                 110

Leu Ile Asp Ser Glu Ile Gln Lys Gln Leu Asn Lys Ala Leu Leu Asp
                115                 120                 125

Ala Asp Arg Asn Glu Trp Ser Ser Tyr Leu Glu Ser Ile Phe Asp Ser
                130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
                180                 185                 190

Asn Glu Asn His Ile Met Asn Gly Asn Phe Asp Val Ala Ala Ala Pro
                195                 200                 205

Tyr Phe Val Ile Gly Ala Thr Ala Arg Phe Ala Ala Met Gln Ser Tyr
                210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
                260                 265                 270

Asp Ser Lys Asn Met Pro Thr Ile Gly Thr Asn Lys Phe Ser Val Asp
                275                 280                 285

Thr Tyr Asn Val Tyr Ile Lys Gly Met Thr Leu Asn Val Leu Asp Ile
                290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                325                 330                 335

Glu Gly Thr Asp Gly Ser Leu Arg Ile Tyr Asn Thr Phe Asp Ser Phe
                340                 345                 350

Ser Tyr Gln His Ser Pro Ile Pro Asn Asn Val Asn Leu Ile Ser
                355                 360                 365

Tyr Tyr Asn Asp Glu Leu Gln Asn Leu Glu Leu Gly Val Tyr Thr Pro
                370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Gln Val Asn Ala
                420                 425                 430

Ala Thr Gln Asn Ser Lys Tyr Leu Asp Gly Glu Ile Leu Asn Gly Ile
                435                 440                 445

Gly Ala Ser Leu Pro Gly Tyr Cys Thr Thr Gly Cys Ser Pro Thr Glu
```

-continued

```
                   450                 455                 460
Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
                485                 490                 495

Gln Ala Asn Val Lys Gly Asn Thr Gly Lys Leu Gly Val Leu Ala Ser
                500                 505                 510

Leu Val Ser Tyr Asp Leu Asn Pro Lys Asn Val Phe Gly Glu Leu Asp
                515                 520                 525

Ser Asp Thr Asn Asn Val Ile Leu Lys Gly Ile Pro Ala Glu Lys Gly
530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575

Ala Thr Asn Leu Thr Ala Thr Gln Tyr Arg Ile Arg Ile Arg Tyr Ala
                580                 585                 590

Asn Pro Asn Ser Asn Thr Gln Ile Gly Val Arg Ile Thr Gln Asn Gly
                595                 600                 605

Ser Leu Ile Ser Ser Ser Asn Leu Thr Leu Tyr Ser Thr Thr Asp Met
                610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Asn Val Leu Ser Thr Gly
                645                 650                 655

Asp Ile Thr Leu Gln Ile Thr Gly Gly Asp Gln Lys Ile Phe Ile Asp
                660                 665                 670

Arg Ile Glu Phe Val Pro Thr Met Pro Val Pro Gly Asn
                675                 680                 685

<210> SEQ ID NO 9
<211> LENGTH: 2148
<212> TYPE: DNA
<213> ORGANISM: Artificial Sequence
<220> FEATURE:
<223> OTHER INFORMATION: synaxmi-031(apo)
<221> NAME/KEY: CDS
<222> LOCATION: (1)...(2148)

<400> SEQUENCE: 9 atg ggg tac tcc agc ttc gtt gct atc gct ctt ctt atg agc gtg gtt      48
Met Gly Tyr Ser Ser Phe Val Ala Ile Ala Leu Leu Met Ser Val Val
1               5                   10                  15 gtt gtt tgc aat ggg ggc aag acg tcc acc tac gtg cgt aat ctg gat      96
Val Val Cys Asn Gly Gly Lys Thr Ser Thr Tyr Val Arg Asn Leu Asp
            20                  25                  30 tgc aat ctc cag agc cag cag aat atc cca tac aat gtg ctt gct atc     144
Cys Asn Leu Gln Ser Gln Gln Asn Ile Pro Tyr Asn Val Leu Ala Ile
        35                  40                  45 cct gtt agc aat gtt aat agc ctt acg gat acg gtt ggc gat cta aag     192
Pro Val Ser Asn Val Asn Ser Leu Thr Asp Thr Val Gly Asp Leu Lys
    50                  55                  60 aag gca tgg gaa gag ttc cag aag acg ggc agc ttc tcc ctt acc gca     240
Lys Ala Trp Glu Glu Phe Gln Lys Thr Gly Ser Phe Ser Leu Thr Ala
65                  70                  75                  80 ctc cag cag ggc ttc agc gct tcc cag ggc ggg acg ttc aat tac ctc     288
Leu Gln Gln Gly Phe Ser Ala Ser Gln Gly Gly Thr Phe Asn Tyr Leu
                85                  90                  95
```

| | |
|---|---|
| acc ctc ctc cag tcc ggg atc tcc ctg gct ggc agc ttc gtg cct ggc<br>Thr Leu Leu Gln Ser Gly Ile Ser Leu Ala Gly Ser Phe Val Pro Gly<br>            100                    105                   110 | 336 |
| ggc acc ttc gtt gct cca atc atc aat atg gtg atc ggc tgg ctc tgg<br>Gly Thr Phe Val Ala Pro Ile Ile Asn Met Val Ile Gly Trp Leu Trp<br>     115                    120                    125 | 384 |
| cct cat aag aat aag aat gca gat acg gaa aat ctg atc aat ctg atc<br>Pro His Lys Asn Lys Asn Ala Asp Thr Glu Asn Leu Ile Asn Leu Ile<br>130                    135                    140 | 432 |
| gat tca gaa atc cag aag cag ctg aat aag gct ctg ctg gat gct gat<br>Asp Ser Glu Ile Gln Lys Gln Leu Asn Lys Ala Leu Leu Asp Ala Asp<br>145                    150                    155                    160 | 480 |
| cgc aat gaa tgg agc agc tac ctc gag tcc atc ttc gat agc agc aat<br>Arg Asn Glu Trp Ser Ser Tyr Leu Glu Ser Ile Phe Asp Ser Ser Asn<br>                    165                    170                    175 | 528 |
| aat ctg aat ggc gca atc gtt gat gct cag tgg tcc ggc acc gtg aat<br>Asn Leu Asn Gly Ala Ile Val Asp Ala Gln Trp Ser Gly Thr Val Asn<br>                        180                    185                    190 | 576 |
| acg acc aat cgt acg ctt cgt aat cct acg gaa tca gat tac acc aat<br>Thr Thr Asn Arg Thr Leu Arg Asn Pro Thr Glu Ser Asp Tyr Thr Asn<br>                 195                    200                    205 | 624 |
| gtg gtg acg aat ttc atc gca gca gat ggg gat atc gct aat aat gaa<br>Val Val Thr Asn Phe Ile Ala Ala Asp Gly Asp Ile Ala Asn Asn Glu<br>210                    215                    220 | 672 |
| aat cat atc atg aat ggg aat ttc gat gtg gca gca gct cca tac ttc<br>Asn His Ile Met Asn Gly Asn Phe Asp Val Ala Ala Ala Pro Tyr Phe<br>225                    230                    235                    240 | 720 |
| gtt atc ggg gct acc gct aga ttc gca gct atg cag tcc tac atc aag<br>Val Ile Gly Ala Thr Ala Arg Phe Ala Ala Met Gln Ser Tyr Ile Lys<br>                        245                    250                    255 | 768 |
| ttc tgc aat gca tgg atc gat aag gtt ggg ctg tca gat gct cag ctg<br>Phe Cys Asn Ala Trp Ile Asp Lys Val Gly Leu Ser Asp Ala Gln Leu<br>          260                    265                    270 | 816 |
| acc acg cag aag gct aat ctg gat aga acg aag cag aat atg cgt aat<br>Thr Thr Gln Lys Ala Asn Leu Asp Arg Thr Lys Gln Asn Met Arg Asn<br>               275                    280                    285 | 864 |
| gct atc ctt aat tac acc cag cag gtt atg aag gtt ttc aag gat tcc<br>Ala Ile Leu Asn Tyr Thr Gln Gln Val Met Lys Val Phe Lys Asp Ser<br>290                    295                    300 | 912 |
| aag aat atg cca acg atc ggc acg aat aag ttc agc gtt gat acc tac<br>Lys Asn Met Pro Thr Ile Gly Thr Asn Lys Phe Ser Val Asp Thr Tyr<br>305                    310                    315                    320 | 960 |
| aat gtt tac atc aag ggg atg acg ctt aat gtg ctt gat atc gtt gct<br>Asn Val Tyr Ile Lys Gly Met Thr Leu Asn Val Leu Asp Ile Val Ala<br>                        325                    330                    335 | 1008 |
| atc tgg cca agc ctg tac cca gat gat tac acg tca cag acg gct ctg<br>Ile Trp Pro Ser Leu Tyr Pro Asp Asp Tyr Thr Ser Gln Thr Ala Leu<br>          340                    345                    350 | 1056 |
| gaa cag acc cgc gtg acg ttc tcc aat atg gtg ggg cag gaa gaa ggc<br>Glu Gln Thr Arg Val Thr Phe Ser Asn Met Val Gly Gln Glu Glu Gly<br>               355                    360                    365 | 1104 |
| acg gat ggc agc ctc aga atc tac aat acc ttc gat agc ttc tcc tac<br>Thr Asp Gly Ser Leu Arg Ile Tyr Asn Thr Phe Asp Ser Phe Ser Tyr<br>370                    375                    380 | 1152 |
| cag cat agc cct atc cct aat aat aat gtg aat ctc atc agc tac tac<br>Gln His Ser Pro Ile Pro Asn Asn Asn Val Asn Leu Ile Ser Tyr Tyr<br>385                    390                    395                    400 | 1200 |
| aat gat gaa ctt cag aat ctg gaa ctc ggg gtt tac acc cca cca aag<br>Asn Asp Glu Leu Gln Asn Leu Glu Leu Gly Val Tyr Thr Pro Pro Lys<br>                        405                    410                    415 | 1248 |

| | |
|---|---|
| aag ggc tca ggc tac agc tac cca tac ggg ttc gtg ctg aat tac gca<br>Lys Gly Ser Gly Tyr Ser Tyr Pro Tyr Gly Phe Val Leu Asn Tyr Ala<br>420                      425                        430 | 1296 |
| aat agc aag tac aag tac ggg gat tcc aat gat cca gaa tcc ctc ggc<br>Asn Ser Lys Tyr Lys Tyr Gly Asp Ser Asn Asp Pro Glu Ser Leu Gly<br>        435                    440                    445 | 1344 |
| ggg ctt tcc acc ctt agc gct cca atc caa cag gtt aat gct gct acc<br>Gly Leu Ser Thr Leu Ser Ala Pro Ile Gln Gln Val Asn Ala Ala Thr<br>450                      455                      460 | 1392 |
| cag aat agc aag tac ctt gat ggc gaa atc ctg aat ggg atc ggc gca<br>Gln Asn Ser Lys Tyr Leu Asp Gly Glu Ile Leu Asn Gly Ile Gly Ala<br>465                  470                    475                  480 | 1440 |
| agc ctg cct ggc tac tgc acg acc ggg tgc tca cct acc gaa cca cca<br>Ser Leu Pro Gly Tyr Cys Thr Thr Gly Cys Ser Pro Thr Glu Pro Pro<br>                485                    490                    495 | 1488 |
| ttc agc tgc acg agc acg gca aat ggg tac aag gca agc tgc aat cca<br>Phe Ser Cys Thr Ser Thr Ala Asn Gly Tyr Lys Ala Ser Cys Asn Pro<br>500                      505                      510 | 1536 |
| agc gat acc aat cag aag atc aat gct ctc tac cca ttc acg cag gca<br>Ser Asp Thr Asn Gln Lys Ile Asn Ala Leu Tyr Pro Phe Thr Gln Ala<br>                515                    520                    525 | 1584 |
| aat gtg aag ggg aat acc ggg aag ctg ggc gtt ctc gca agc ctt gtt<br>Asn Val Lys Gly Asn Thr Gly Lys Leu Gly Val Leu Ala Ser Leu Val<br>530                      535                      540 | 1632 |
| agc tac gat ctg aat cct aag aat gtt ttc ggg gaa ctc gat tca gat<br>Ser Tyr Asp Leu Asn Pro Lys Asn Val Phe Gly Glu Leu Asp Ser Asp<br>545                  550                    555                  560 | 1680 |
| acc aat aat gtt atc ctt aag ggc atc cca gca gaa aag ggc tac ttc<br>Thr Asn Asn Val Ile Leu Lys Gly Ile Pro Ala Glu Lys Gly Tyr Phe<br>                565                    570                    575 | 1728 |
| cca aat aat gca aga cca acc gtt gtg aag gaa tgg atc aat ggg gct<br>Pro Asn Asn Ala Arg Pro Thr Val Val Lys Glu Trp Ile Asn Gly Ala<br>                    580                    585                  590 | 1776 |
| tcc gca gtt cca ctt gat tcc ggc aat acc ctg ttc atg acg gct acg<br>Ser Ala Val Pro Leu Asp Ser Gly Asn Thr Leu Phe Met Thr Ala Thr<br>        595                    600                    605 | 1824 |
| aac ctg acg gct acc cag tac aga atc cgc atc cgt tac gct aac cca<br>Asn Leu Thr Ala Thr Gln Tyr Arg Ile Arg Ile Arg Tyr Ala Asn Pro<br>610                      615                      620 | 1872 |
| aac tca aac acg cag atc ggc gtt aga atc acg cag aac ggg agc ctc<br>Asn Ser Asn Thr Gln Ile Gly Val Arg Ile Thr Gln Asn Gly Ser Leu<br>625                      630                    635                  640 | 1920 |
| atc tcc tcc tcc aac ctc acg ctg tac tca acc acc gat atg aac aac<br>Ile Ser Ser Ser Asn Leu Thr Leu Tyr Ser Thr Thr Asp Met Asn Asn<br>                645                    650                    655 | 1968 |
| acc ctg cca ctg aac gtt tac gtg atc ggg gaa aac ggg aac tac acc<br>Thr Leu Pro Leu Asn Val Tyr Val Ile Gly Glu Asn Gly Asn Tyr Thr<br>                    660                    665                  670 | 2016 |
| ctc cag gat ctc tac aac acg acg aac gtt ctg tcc acg ggc gat atc<br>Leu Gln Asp Leu Tyr Asn Thr Thr Asn Val Leu Ser Thr Gly Asp Ile<br>        675                    680                    685 | 2064 |
| acc ctg cag atc acc ggc ggg gat cag aag ata ttc atc gat cgc atc<br>Thr Leu Gln Ile Thr Gly Gly Asp Gln Lys Ile Phe Ile Asp Arg Ile<br>690                      695                    700 | 2112 |
| gag ttc gtg cct acg atg cca gtg cca ggc aac taa<br>Glu Phe Val Pro Thr Met Pro Val Pro Gly Asn  *<br>705                      710                    715 | 2148 |

<210> SEQ ID NO 10
<211> LENGTH: 715
<212> TYPE: PRT

<213> ORGANISM: Artificial Sequence
<220> FEATURE:
<223> OTHER INFORMATION: SYNAXMI-031(APO)

<400> SEQUENCE: 10

```
Met Gly Tyr Ser Ser Phe Val Ala Ile Ala Leu Leu Met Ser Val Val
 1               5                   10                  15

Val Val Cys Asn Gly Gly Lys Thr Ser Thr Tyr Val Arg Asn Leu Asp
             20                  25                  30

Cys Asn Leu Gln Ser Gln Gln Asn Ile Pro Tyr Asn Val Leu Ala Ile
         35                  40                  45

Pro Val Ser Asn Val Asn Ser Leu Thr Asp Thr Val Gly Asp Leu Lys
     50                  55                  60

Lys Ala Trp Glu Glu Phe Gln Lys Thr Gly Ser Phe Ser Leu Thr Ala
 65                  70                  75                  80

Leu Gln Gln Gly Phe Ser Ala Ser Gln Gly Gly Thr Phe Asn Tyr Leu
                 85                  90                  95

Thr Leu Leu Gln Ser Gly Ile Ser Leu Ala Gly Ser Phe Val Pro Gly
             100                 105                 110

Gly Thr Phe Val Ala Pro Ile Ile Asn Met Val Ile Gly Trp Leu Trp
         115                 120                 125

Pro His Lys Asn Lys Asn Ala Asp Thr Glu Asn Leu Ile Asn Leu Ile
     130                 135                 140

Asp Ser Glu Ile Gln Lys Gln Leu Asn Lys Ala Leu Leu Asp Ala Asp
145                 150                 155                 160

Arg Asn Glu Trp Ser Ser Tyr Leu Glu Ser Ile Phe Asp Ser Ser Asn
                165                 170                 175

Asn Leu Asn Gly Ala Ile Val Asp Ala Gln Trp Ser Gly Thr Val Asn
            180                 185                 190

Thr Thr Asn Arg Thr Leu Arg Asn Pro Thr Glu Ser Asp Tyr Thr Asn
        195                 200                 205

Val Val Thr Asn Phe Ile Ala Ala Asp Gly Asp Ile Ala Asn Asn Glu
    210                 215                 220

Asn His Ile Met Asn Gly Asn Phe Asp Val Ala Ala Pro Tyr Phe
225                 230                 235                 240

Val Ile Gly Ala Thr Ala Arg Phe Ala Ala Met Gln Ser Tyr Ile Lys
                245                 250                 255

Phe Cys Asn Ala Trp Ile Asp Lys Val Gly Leu Ser Asp Ala Gln Leu
            260                 265                 270

Thr Thr Gln Lys Ala Asn Leu Asp Arg Thr Lys Gln Asn Met Arg Asn
        275                 280                 285

Ala Ile Leu Asn Tyr Thr Gln Gln Val Met Lys Val Phe Lys Asp Ser
    290                 295                 300

Lys Asn Met Pro Thr Ile Gly Thr Asn Lys Phe Ser Val Asp Thr Tyr
305                 310                 315                 320

Asn Val Tyr Ile Lys Gly Met Thr Leu Asn Val Leu Asp Ile Val Ala
                325                 330                 335

Ile Trp Pro Ser Leu Tyr Pro Asp Asp Tyr Thr Ser Gln Thr Ala Leu
            340                 345                 350

Glu Gln Thr Arg Val Thr Phe Ser Asn Met Val Gly Gln Glu Glu Gly
        355                 360                 365

Thr Asp Gly Ser Leu Arg Ile Tyr Asn Thr Phe Asp Ser Phe Ser Tyr
    370                 375                 380

Gln His Ser Pro Ile Pro Asn Asn Asn Val Asn Leu Ile Ser Tyr Tyr
385                 390                 395                 400
```

Asn Asp Glu Leu Gln Asn Leu Glu Leu Gly Val Tyr Thr Pro Pro Lys
            405                 410                 415

Lys Gly Ser Gly Tyr Ser Tyr Pro Tyr Gly Phe Val Leu Asn Tyr Ala
        420                 425                 430

Asn Ser Lys Tyr Lys Tyr Gly Asp Ser Asn Asp Pro Glu Ser Leu Gly
    435                 440                 445

Gly Leu Ser Thr Leu Ser Ala Pro Ile Gln Gln Val Asn Ala Ala Thr
450                 455                 460

Gln Asn Ser Lys Tyr Leu Asp Gly Glu Ile Leu Asn Gly Ile Gly Ala
465                 470                 475                 480

Ser Leu Pro Gly Tyr Cys Thr Thr Gly Cys Ser Pro Thr Glu Pro Pro
                485                 490                 495

Phe Ser Cys Thr Ser Thr Ala Asn Gly Tyr Lys Ala Ser Cys Asn Pro
            500                 505                 510

Ser Asp Thr Asn Gln Lys Ile Asn Ala Leu Tyr Pro Phe Thr Gln Ala
        515                 520                 525

Asn Val Lys Gly Asn Thr Gly Lys Leu Gly Val Leu Ala Ser Leu Val
    530                 535                 540

Ser Tyr Asp Leu Asn Pro Lys Asn Val Phe Gly Leu Asp Ser Asp
545                 550                 555                 560

Thr Asn Asn Val Ile Leu Lys Gly Ile Pro Ala Glu Lys Gly Tyr Phe
                565                 570                 575

Pro Asn Asn Ala Arg Pro Thr Val Val Lys Glu Trp Ile Asn Gly Ala
            580                 585                 590

Ser Ala Val Pro Leu Asp Ser Gly Asn Thr Leu Phe Met Thr Ala Thr
        595                 600                 605

Asn Leu Thr Ala Thr Gln Tyr Arg Ile Arg Ile Arg Tyr Ala Asn Pro
    610                 615                 620

Asn Ser Asn Thr Gln Ile Gly Val Arg Ile Thr Gln Asn Gly Ser Leu
625                 630                 635                 640

Ile Ser Ser Ser Asn Leu Thr Leu Tyr Ser Thr Thr Asp Met Asn Asn
                645                 650                 655

Thr Leu Pro Leu Asn Val Tyr Val Ile Gly Glu Asn Gly Asn Tyr Thr
            660                 665                 670

Leu Gln Asp Leu Tyr Asn Thr Thr Asn Val Leu Ser Thr Gly Asp Ile
        675                 680                 685

Thr Leu Gln Ile Thr Gly Gly Asp Gln Lys Ile Phe Ile Asp Arg Ile
    690                 695                 700

Glu Phe Val Pro Thr Met Pro Val Pro Gly Asn
705                 710                 715

<210> SEQ ID NO 11
<211> LENGTH: 2160
<212> TYPE: DNA
<213> ORGANISM: Artificial Sequence
<220> FEATURE:
<223> OTHER INFORMATION: synaxmi-031(ER)
<221> NAME/KEY: CDS
<222> LOCATION: (1)...(2160)

<400> SEQUENCE: 11 atg ggg tac tcc agc ttc gtt gct atc gct ctt ctt atg agc gtg gtt      48
Met Gly Tyr Ser Ser Phe Val Ala Ile Ala Leu Leu Met Ser Val Val
1               5                   10                  15 gtt gtt tgc aat ggg ggc aag acg tcc acc tac gtg cgt aat ctg gat      96
Val Val Cys Asn Gly Gly Lys Thr Ser Thr Tyr Val Arg Asn Leu Asp
            20                  25                  30

-continued

| | | |
|---|---|---|
| tgc aat ctc cag agc cag cag aat atc cca tac aat gtg ctt gct atc<br>Cys Asn Leu Gln Ser Gln Gln Asn Ile Pro Tyr Asn Val Leu Ala Ile<br>35                     40                   45 | 144 |
| cct gtt agc aat gtt aat agc ctt acg gat acg gtt ggc gat cta aag<br>Pro Val Ser Asn Val Asn Ser Leu Thr Asp Thr Val Gly Asp Leu Lys<br>50                     55                   60 | 192 |
| aag gca tgg gaa gag ttc cag aag acg ggc agc ttc tcc ctt acc gca<br>Lys Ala Trp Glu Glu Phe Gln Lys Thr Gly Ser Phe Ser Leu Thr Ala<br>65                     70                   75                   80 | 240 |
| ctc cag cag ggc ttc agc gct tcc cag ggc ggg acg ttc aat tac ctc<br>Leu Gln Gln Gly Phe Ser Ala Ser Gln Gly Gly Thr Phe Asn Tyr Leu<br>                   85                   90                   95 | 288 |
| acc ctc ctc cag tcc ggg atc tcc ctg gct ggc agc ttc gtg cct ggc<br>Thr Leu Leu Gln Ser Gly Ile Ser Leu Ala Gly Ser Phe Val Pro Gly<br>                 100                  105                  110 | 336 |
| ggc acc ttc gtt gct cca atc atc aat atg gtg atc ggc tgg ctc tgg<br>Gly Thr Phe Val Ala Pro Ile Ile Asn Met Val Ile Gly Trp Leu Trp<br>            115                     120                  125 | 384 |
| cct cat aag aat aag aat gca gat acg gaa aat ctg atc aat ctg atc<br>Pro His Lys Asn Lys Asn Ala Asp Thr Glu Asn Leu Ile Asn Leu Ile<br>130                    135                  140 | 432 |
| gat tca gaa atc cag aag cag ctg aat aag gct ctg ctg gat gct gat<br>Asp Ser Glu Ile Gln Lys Gln Leu Asn Lys Ala Leu Leu Asp Ala Asp<br>145                    150                  155                  160 | 480 |
| cgc aat gaa tgg agc agc tac ctc gag tcc atc ttc gat agc agc aat<br>Arg Asn Glu Trp Ser Ser Tyr Leu Glu Ser Ile Phe Asp Ser Ser Asn<br>                   165                  170                  175 | 528 |
| aat ctg aat ggc gca atc gtt gat gct cag tgg tcc ggc acc gtg aat<br>Asn Leu Asn Gly Ala Ile Val Asp Ala Gln Trp Ser Gly Thr Val Asn<br>            180                     185                  190 | 576 |
| acg acc aat cgt acg ctt cgt aat cct acg gaa tca gat tac acc aat<br>Thr Thr Asn Arg Thr Leu Arg Asn Pro Thr Glu Ser Asp Tyr Thr Asn<br>               195                  200                  205 | 624 |
| gtg gtg acg aat ttc atc gca gca gat ggg gat atc gct aat aat gaa<br>Val Val Thr Asn Phe Ile Ala Ala Asp Gly Asp Ile Ala Asn Asn Glu<br>210                    215                  220 | 672 |
| aat cat atc atg aat ggg aat ttc gat gtg gca gca gct cca tac ttc<br>Asn His Ile Met Asn Gly Asn Phe Asp Val Ala Ala Ala Pro Tyr Phe<br>225                    230                  235                  240 | 720 |
| gtt atc ggg gct acc gct aga ttc gca gct atg cag tcc tac atc aag<br>Val Ile Gly Ala Thr Ala Arg Phe Ala Ala Met Gln Ser Tyr Ile Lys<br>            245                     250                  255 | 768 |
| ttc tgc aat gca tgg atc gat aag gtt ggg ctg tca gat gct cag ctg<br>Phe Cys Asn Ala Trp Ile Asp Lys Val Gly Leu Ser Asp Ala Gln Leu<br>                   260                  265                  270 | 816 |
| acc acg cag aag gct aat ctg gat aga acg aag cag aat atg cgt aat<br>Thr Thr Gln Lys Ala Asn Leu Asp Arg Thr Lys Gln Asn Met Arg Asn<br>            275                     280                  285 | 864 |
| gct atc ctt aat tac acc cag cag gtt atg aag gtt ttc aag gat tcc<br>Ala Ile Leu Asn Tyr Thr Gln Gln Val Met Lys Val Phe Lys Asp Ser<br>290                    295                  300 | 912 |
| aag aat atg cca acg atc ggc acg aat aag ttc agc gtt gat acc tac<br>Lys Asn Met Pro Thr Ile Gly Thr Asn Lys Phe Ser Val Asp Thr Tyr<br>305                    310                  315                  320 | 960 |
| aat gtt tac atc aag ggg atg acg ctt aat gtg ctt gat atc gtt gct<br>Asn Val Tyr Ile Lys Gly Met Thr Leu Asn Val Leu Asp Ile Val Ala<br>                   325                  330                  335 | 1008 |
| atc tgg cca agc ctg tac cca gat gat tac acg tca cag acg gct ctg<br>Ile Trp Pro Ser Leu Tyr Pro Asp Asp Tyr Thr Ser Gln Thr Ala Leu<br>            340                     345                  350 | 1056 |

```
gaa cag acc cgc gtg acg ttc tcc aat atg gtg ggg cag gaa gaa ggc    1104
Glu Gln Thr Arg Val Thr Phe Ser Asn Met Val Gly Gln Glu Glu Gly
            355                 360                 365 acg gat ggc agc ctc aga atc tac aat acc ttc gat agc ttc tcc tac    1152
Thr Asp Gly Ser Leu Arg Ile Tyr Asn Thr Phe Asp Ser Phe Ser Tyr
        370                 375                 380 cag cat agc cct atc cct aat aat aat gtg aat ctc atc agc tac tac    1200
Gln His Ser Pro Ile Pro Asn Asn Asn Val Asn Leu Ile Ser Tyr Tyr
385                 390                 395                 400 aat gat gaa ctt cag aat ctg gaa ctc ggg gtt tac acc cca cca aag    1248
Asn Asp Glu Leu Gln Asn Leu Glu Leu Gly Val Tyr Thr Pro Pro Lys
                405                 410                 415 aag ggc tca ggc tac agc tac cca tac ggg ttc gtg ctg aat tac gca    1296
Lys Gly Ser Gly Tyr Ser Tyr Pro Tyr Gly Phe Val Leu Asn Tyr Ala
            420                 425                 430 aat agc aag tac aag tac ggc gat tcc aat gat cca gaa tcc ctc ggc    1344
Asn Ser Lys Tyr Lys Tyr Gly Asp Ser Asn Asp Pro Glu Ser Leu Gly
        435                 440                 445 ggg ctt tcc acc ctt agc gct cca atc caa cag gtt aat gct gct acc    1392
Gly Leu Ser Thr Leu Ser Ala Pro Ile Gln Gln Val Asn Ala Ala Thr
450                 455                 460 cag aat agc aag tac ctt gat ggc gaa atc ctg aat ggg atc ggc gca    1440
Gln Asn Ser Lys Tyr Leu Asp Gly Glu Ile Leu Asn Gly Ile Gly Ala
465                 470                 475                 480 agc ctg cct ggc tac tgc acg acc ggg tgc tca cct acc gaa cca cca    1488
Ser Leu Pro Gly Tyr Cys Thr Thr Gly Cys Ser Pro Thr Glu Pro Pro
            485                 490                 495 ttc agc tgc acg agc acg gca aat ggg tac aag gca agc tgc aat cca    1536
Phe Ser Cys Thr Ser Thr Ala Asn Gly Tyr Lys Ala Ser Cys Asn Pro
        500                 505                 510 agc gat acc aat cag aag atc aat gct ctc tac cca ttc acg cag gca    1584
Ser Asp Thr Asn Gln Lys Ile Asn Ala Leu Tyr Pro Phe Thr Gln Ala
    515                 520                 525 aat gtg aag ggg aat acc ggg aag ctg ggc gtt ctc gca agc ctt gtt    1632
Asn Val Lys Gly Asn Thr Gly Lys Leu Gly Val Leu Ala Ser Leu Val
530                 535                 540 agc tac gat ctg aat cct aag aat gtt ttc ggg gaa ctc gat tca gat    1680
Ser Tyr Asp Leu Asn Pro Lys Asn Val Phe Gly Glu Leu Asp Ser Asp
545                 550                 555                 560 acc aat aat gtt atc ctt aag ggc atc cca gca gaa aag ggc tac ttc    1728
Thr Asn Asn Val Ile Leu Lys Gly Ile Pro Ala Glu Lys Gly Tyr Phe
            565                 570                 575 cca aat aat gca aga cca acc gtt gtg aag gaa tgg atc aat ggg gct    1776
Pro Asn Asn Ala Arg Pro Thr Val Val Lys Glu Trp Ile Asn Gly Ala
        580                 585                 590 tcc gca gtt cca ctt gat tcc ggc aat acc ctg ttc atg acg gct acg    1824
Ser Ala Val Pro Leu Asp Ser Gly Asn Thr Leu Phe Met Thr Ala Thr
    595                 600                 605 aac ctg acg gct acc cag tac aga atc cgc atc cgt tac gct aac cca    1872
Asn Leu Thr Ala Thr Gln Tyr Arg Ile Arg Ile Arg Tyr Ala Asn Pro
610                 615                 620 aac tca aac acg cag atc ggc gtt aga atc acg cag aac ggg agc ctc    1920
Asn Ser Asn Thr Gln Ile Gly Val Arg Ile Thr Gln Asn Gly Ser Leu
625                 630                 635                 640 atc tcc tcc tcc aac ctc acg ctg tac tca acc acc gat atg aac aac    1968
Ile Ser Ser Ser Asn Leu Thr Leu Tyr Ser Thr Thr Asp Met Asn Asn
            645                 650                 655 acc ctg cca ctg aac gtt tac gtg atc ggg gaa aac ggg aac tac acc    2016
Thr Leu Pro Leu Asn Val Tyr Val Ile Gly Glu Asn Gly Asn Tyr Thr
        660                 665                 670
```

```
ctc cag gat ctc tac aac acg acg aac gtt ctg tcc acg ggc gat atc    2064
Leu Gln Asp Leu Tyr Asn Thr Thr Asn Val Leu Ser Thr Gly Asp Ile
            675                 680                 685 acc ctg cag atc acc ggc ggg gat cag aag ata ttc atc gat cgc atc    2112
Thr Leu Gln Ile Thr Gly Gly Asp Gln Lys Ile Phe Ile Asp Arg Ile
690                 695                 700 gag ttc gtg cct acg atg cca gtg cca ggc aac aag gat gaa ctg taa    2160
Glu Phe Val Pro Thr Met Pro Val Pro Gly Asn Lys Asp Glu Leu *
705                 710                 715
```

<210> SEQ ID NO 12
<211> LENGTH: 719
<212> TYPE: PRT
<213> ORGANISM: Artificial Sequence
<220> FEATURE:
<223> OTHER INFORMATION: SYNAXMI-031(ER)

<400> SEQUENCE: 12

```
Met Gly Tyr Ser Ser Phe Val Ala Ile Ala Leu Leu Met Ser Val Val
 1               5                  10                  15

Val Val Cys Asn Gly Gly Lys Thr Ser Thr Tyr Val Arg Asn Leu Asp
            20                  25                  30

Cys Asn Leu Gln Ser Gln Gln Asn Ile Pro Tyr Asn Val Leu Ala Ile
        35                  40                  45

Pro Val Ser Asn Val Asn Ser Leu Thr Asp Thr Val Gly Asp Leu Lys
    50                  55                  60

Lys Ala Trp Glu Glu Phe Gln Lys Thr Gly Ser Phe Ser Leu Thr Ala
65                  70                  75                  80

Leu Gln Gln Gly Phe Ser Ala Ser Gln Gly Gly Thr Phe Asn Tyr Leu
                85                  90                  95

Thr Leu Leu Gln Ser Gly Ile Ser Leu Ala Gly Ser Phe Val Pro Gly
            100                 105                 110

Gly Thr Phe Val Ala Pro Ile Ile Asn Met Val Ile Gly Trp Leu Trp
        115                 120                 125

Pro His Lys Asn Lys Asn Ala Asp Thr Glu Asn Leu Ile Asn Leu Ile
    130                 135                 140

Asp Ser Glu Ile Gln Lys Gln Leu Asn Lys Ala Leu Leu Asp Ala Asp
145                 150                 155                 160

Arg Asn Glu Trp Ser Ser Tyr Leu Glu Ser Ile Phe Asp Ser Ser Asn
                165                 170                 175

Asn Leu Asn Gly Ala Ile Val Asp Ala Gln Trp Ser Gly Thr Val Asn
            180                 185                 190

Thr Thr Asn Arg Thr Leu Arg Asn Pro Thr Glu Ser Asp Tyr Thr Asn
        195                 200                 205

Val Val Thr Asn Phe Ile Ala Ala Asp Gly Asp Ile Ala Asn Asn Glu
    210                 215                 220

Asn His Ile Met Asn Gly Asn Phe Asp Val Ala Ala Pro Tyr Phe
225                 230                 235                 240

Val Ile Gly Ala Thr Ala Arg Phe Ala Ala Met Gln Ser Tyr Ile Lys
                245                 250                 255

Phe Cys Asn Ala Trp Ile Asp Lys Val Gly Leu Ser Asp Ala Gln Leu
            260                 265                 270

Thr Thr Gln Lys Ala Asn Leu Asp Arg Thr Lys Gln Asn Met Arg Asn
        275                 280                 285

Ala Ile Leu Asn Tyr Thr Gln Gln Val Met Lys Val Phe Lys Asp Ser
    290                 295                 300
```

```
Lys Asn Met Pro Thr Ile Gly Thr Asn Lys Phe Ser Val Asp Thr Tyr
305                 310                 315                 320

Asn Val Tyr Ile Lys Gly Met Thr Leu Asn Val Leu Asp Ile Val Ala
                325                 330                 335

Ile Trp Pro Ser Leu Tyr Pro Asp Asp Tyr Thr Ser Gln Thr Ala Leu
            340                 345                 350

Glu Gln Thr Arg Val Thr Phe Ser Asn Met Val Gly Gln Glu Glu Gly
        355                 360                 365

Thr Asp Gly Ser Leu Arg Ile Tyr Asn Thr Phe Asp Ser Phe Ser Tyr
    370                 375                 380

Gln His Ser Pro Ile Pro Asn Asn Val Asn Leu Ile Ser Tyr Tyr
385                 390                 395                 400

Asn Asp Glu Leu Gln Asn Leu Glu Leu Gly Val Tyr Thr Pro Pro Lys
                405                 410                 415

Lys Gly Ser Gly Tyr Ser Tyr Pro Tyr Gly Phe Val Leu Asn Tyr Ala
            420                 425                 430

Asn Ser Lys Tyr Lys Tyr Gly Asp Ser Asn Asp Pro Glu Ser Leu Gly
        435                 440                 445

Gly Leu Ser Thr Leu Ser Ala Pro Ile Gln Gln Val Asn Ala Ala Thr
450                 455                 460

Gln Asn Ser Lys Tyr Leu Asp Gly Glu Ile Leu Asn Gly Ile Gly Ala
465                 470                 475                 480

Ser Leu Pro Gly Tyr Cys Thr Thr Gly Cys Ser Pro Thr Glu Pro Pro
            485                 490                 495

Phe Ser Cys Thr Ser Thr Ala Asn Gly Tyr Lys Ala Ser Cys Asn Pro
            500                 505                 510

Ser Asp Thr Asn Gln Lys Ile Asn Ala Leu Tyr Pro Phe Thr Gln Ala
            515                 520                 525

Asn Val Lys Gly Asn Thr Gly Lys Leu Gly Val Leu Ala Ser Leu Val
530                 535                 540

Ser Tyr Asp Leu Asn Pro Lys Asn Val Phe Gly Glu Leu Asp Ser Asp
545                 550                 555                 560

Thr Asn Asn Val Ile Leu Lys Gly Ile Pro Ala Glu Lys Gly Tyr Phe
                565                 570                 575

Pro Asn Asn Ala Arg Pro Thr Val Val Lys Glu Trp Ile Asn Gly Ala
            580                 585                 590

Ser Ala Val Pro Leu Asp Ser Gly Asn Thr Leu Phe Met Thr Ala Thr
            595                 600                 605

Asn Leu Thr Ala Thr Gln Tyr Arg Ile Arg Ile Arg Tyr Ala Asn Pro
            610                 615                 620

Asn Ser Asn Thr Gln Ile Gly Val Arg Ile Thr Gln Asn Gly Ser Leu
625                 630                 635                 640

Ile Ser Ser Ser Asn Leu Thr Leu Tyr Ser Thr Thr Asp Met Asn Asn
                645                 650                 655

Thr Leu Pro Leu Asn Val Tyr Val Ile Gly Glu Asn Gly Asn Tyr Thr
            660                 665                 670

Leu Gln Asp Leu Tyr Asn Thr Thr Asn Val Leu Ser Thr Gly Asp Ile
            675                 680                 685

Thr Leu Gln Ile Thr Gly Gly Asp Gln Lys Ile Phe Ile Asp Arg Ile
            690                 695                 700

Glu Phe Val Pro Thr Met Pro Val Pro Gly Asn Lys Asp Glu Leu
705                 710                 715
```

<210> SEQ ID NO 13

```
<211> LENGTH: 1186
<212> TYPE: PRT
<213> ORGANISM: Bacillus thuringiensis

<400> SEQUENCE: 13

Met Asp Cys Asn Leu Gln Ser Gln Gln Asn Ile Pro Tyr Asn Val Leu
 1               5                  10                  15

Ala Ile Pro Val Ser Asn Val Asn Ala Leu Val Asp Thr Ala Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Ala Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Val Asn Met Val Ile Gly Trp
                85                  90                  95

Leu Trp Pro His Lys Asn Lys Thr Ala Asp Thr Glu Asn Leu Ile Lys
            100                 105                 110

Leu Ile Asp Glu Glu Ile Gln Lys Gln Leu Asn Lys Ala Leu Leu Asp
        115                 120                 125

Gln Asp Arg Asn Asn Trp Thr Ser Phe Leu Glu Ser Ile Phe Asp Thr
    130                 135                 140

Ser Ala Thr Val Ser Asn Ala Ile Ile Asp Ala Gln Trp Ser Gly Thr
145                 150                 155                 160

Val Asp Thr Thr Asn Arg Gln Gln Lys Thr Pro Thr Thr Ser Asp Tyr
                165                 170                 175

Leu Asn Val Val Gly Lys Phe Asp Ser Ala Asp Ser Ser Ile Ile Thr
            180                 185                 190

Asn Glu Asn Gln Ile Met Asn Gly Asn Phe Asp Val Ala Ala Ala Pro
        195                 200                 205

Tyr Phe Val Ile Gly Ala Thr Leu Arg Leu Ser Leu Tyr Gln Ser Tyr
    210                 215                 220

Ile Lys Phe Cys Asn Ser Trp Ile Asp Ala Val Gly Phe Ser Thr Asn
225                 230                 235                 240

Asp Ala Asn Thr Gln Lys Ala Asn Leu Ala Arg Thr Lys Leu Thr Met
                245                 250                 255

Arg Thr Thr Ile Asn Glu Tyr Thr Gln Arg Val Met Lys Val Phe Lys
            260                 265                 270

Asp Ser Lys Asn Met Pro Thr Ile Gly Thr Asn Lys Phe Ser Val Asp
        275                 280                 285

Ala Tyr Asn Val Tyr Val Lys Gly Met Thr Leu Asn Val Leu Asp Met
    290                 295                 300

Val Ala Ile Trp Ser Ser Leu Tyr Pro Asn Asp Tyr Thr Ser Gln Thr
305                 310                 315                 320

Ala Ile Glu Gln Thr Arg Val Thr Phe Ser Asn Met Val Gly Gln Glu
                325                 330                 335

Glu Gly Thr Asp Gly Thr Leu Lys Ile Tyr Asn Thr Phe Asp Ser Leu
            340                 345                 350

Ser Tyr Gln His Ser Leu Ile Pro Asn Asn Val Asn Leu Ile Ser
        355                 360                 365

Tyr Tyr Thr Asp Glu Leu Gln Asn Leu Glu Leu Ala Val Tyr Thr Pro
    370                 375                 380

Lys Gly Gly Ser Gly Tyr Ala Tyr Pro Tyr Gly Phe Ile Leu Asn Tyr
385                 390                 395                 400
```

```
Ala Asn Ser Asn Tyr Lys Tyr Gly Asp Asn Asp Pro Thr Gly Lys Pro
            405                 410                 415

Leu Asn Lys Gln Asp Gly Pro Ile Gln Gln Ile Asn Ala Ala Thr Gln
            420                 425                 430

Asn Ser Lys Tyr Leu Asp Gly Glu Thr Ile Asn Gly Ile Gly Ala Ser
            435                 440                 445

Leu Pro Gly Tyr Cys Thr Thr Gly Cys Ser Ala Thr Glu Gln Pro Phe
            450                 455                 460

Ser Cys Thr Ser Thr Ala Asn Ser Tyr Lys Ala Ser Cys Asn Pro Ser
465                 470                 475                 480

Asp Thr Asn Gln Lys Ile Asn Ala Leu Tyr Ala Phe Thr Gln Thr Asn
                485                 490                 495

Val Lys Gly Ser Thr Gly Lys Leu Gly Val Leu Ala Ser Leu Val Pro
            500                 505                 510

Tyr Asp Leu Asn Pro Lys Asn Val Phe Gly Glu Leu Asp Ser Asp Thr
            515                 520                 525

Asn Asn Val Ile Leu Lys Gly Ile Pro Ala Glu Lys Gly Tyr Phe Pro
530                 535                 540

Asn Asn Ala Arg Pro Thr Val Val Lys Glu Trp Ile Asn Gly Ala Ser
545                 550                 555                 560

Ala Val Pro Phe Tyr Ser Gly Asn Thr Leu Phe Met Thr Ala Thr Asn
                565                 570                 575

Leu Thr Ala Thr Gln Tyr Lys Ile Arg Ile Arg Tyr Ala Asn Pro Asn
            580                 585                 590

Ser Asp Thr Gln Ile Gly Val Leu Ile Thr Gln Asn Gly Ser Gln Ile
            595                 600                 605

Ser Asn Ser Asn Leu Thr Leu Tyr Ser Thr Thr Asp Ser Ser Met Ser
            610                 615                 620

Ser Asn Leu Pro Gln Asn Val Tyr Val Thr Gly Glu Asn Gly Asn Tyr
625                 630                 635                 640

Thr Leu Leu Asp Leu Tyr Ser Thr Thr Asn Val Leu Ser Thr Gly Asp
                645                 650                 655

Ile Thr Leu Lys Leu Thr Gly Gly Asn Gln Lys Ile Phe Ile Asp Arg
            660                 665                 670

Ile Glu Phe Ile Pro Thr Met Pro Val Pro Ala Pro Thr Asn Asn Thr
            675                 680                 685

Asn Asn Asn Asn Gly Asp Asn Gly Asn Asn Pro Pro His His Gly
            690                 695                 700

Cys Ala Ile Ala Gly Thr Gln Gln Leu Cys Ser Gly Pro Pro Lys Phe
705                 710                 715                 720

Glu Gln Val Ser Asp Leu Glu Lys Ile Thr Thr Gln Val Tyr Met Leu
                725                 730                 735

Phe Lys Ser Ser Tyr Glu Glu Leu Ala Leu Lys Val Ser Ser Tyr
            740                 745                 750

Gln Ile Asn Gln Val Ala Leu Lys Val Met Ala Leu Ser Asp Glu Lys
            755                 760                 765

Phe Cys Glu Glu Lys Arg Leu Leu Arg Lys Leu Val Asn Lys Ala Asn
            770                 775                 780

Gln Leu Leu Glu Ala Arg Asn Leu Leu Val Gly Gly Asn Phe Glu Thr
785                 790                 795                 800

Thr Gln Asn Trp Val Leu Gly Thr Asn Ala Tyr Ile Asn Tyr Asp Ser
                805                 810                 815

Phe Leu Phe Asn Gly Asn Tyr Leu Ser Leu Gln Pro Ala Ser Gly Phe
```

820                 825                 830
Phe Thr Ser Tyr Ala Tyr Gln Lys Ile Asp Glu Ser Thr Leu Lys Pro
        835                 840                 845

Tyr Thr Arg Tyr Lys Val Ser Gly Phe Ile Gly Gln Ser Asn Gln Val
        850                 855                 860

Glu Leu Ile Ile Ser Arg Tyr Gly Lys Glu Ile Asp Lys Ile Leu Asn
865                 870                 875                 880

Val Pro Tyr Ala Gly Pro Leu Pro Ile Thr Ala Asp Ala Ser Ile Thr
                885                 890                 895

Cys Cys Ala Pro Glu Ile Asp Gln Cys Asp Gly Gly Gln Ser Asp Ser
        900                 905                 910

His Phe Phe Asn Tyr Ser Ile Asp Val Gly Ala Leu His Pro Glu Leu
        915                 920                 925

Asn Pro Gly Ile Glu Ile Gly Leu Lys Ile Val Gln Ser Asn Gly Tyr
        930                 935                 940

Ile Thr Ile Ser Asn Leu Glu Ile Ile Glu Arg Pro Leu Thr Glu
945                 950                 955                 960

Met Glu Ile Gln Ala Val Asn Arg Lys Asp Gln Lys Trp Lys Arg Glu
                965                 970                 975

Lys Leu Leu Glu Cys Ala Ser Val Ser Glu Leu Leu Gln Pro Ile Ile
        980                 985                 990

Asn Gln Ile Asp Ser Leu Phe Lys Asp Ala Asn Trp Tyr Asn Asp Ile
        995                 1000                1005

Leu Pro His Val Thr Tyr Gln Thr Leu Lys Asn Ile Ile Val Pro Asp
        1010                1015                1020

Leu Pro Lys Leu Lys His Trp Phe Ile Asp His Leu Pro Gly Glu Tyr
1025                1030                1035                1040

His Glu Ile Glu Gln Lys Met Lys Glu Ala Leu Lys His Ala Phe Thr
                1045                1050                1055

Gln Leu Asp Glu Lys Asn Leu Ile His Asn Gly His Phe Ala Thr Asn
        1060                1065                1070

Leu Ile Asp Trp Gln Val Glu Gly Asp Ala Arg Met Lys Val Leu Glu
        1075                1080                1085

Asn Asn Ala Leu Ala Leu Gln Leu Ser Asn Trp Asp Ser Ser Val Ser
        1090                1095                1100

Gln Ser Ile Asp Ile Leu Glu Phe Asp Glu Asp Lys Ala Tyr Lys Leu
1105                1110                1115                1120

Arg Val Tyr Ala Gln Gly Ser Gly Thr Ile Gln Phe Gly Asn Cys Glu
                1125                1130                1135

Asp Glu Ala Ile Gln Phe Asn Thr Asn Ser Phe Val Tyr Lys Glu Lys
        1140                1145                1150

Ile Ile Tyr Phe Asp Thr Pro Ser Ile Asn Leu His Ile Gln Ser Glu
        1155                1160                1165

Gly Ser Glu Phe Val Val Ser Ser Ile Asp Leu Val Gly Leu Ser Asp
        1170                1175                1180

Asp Glu
1185

<210> SEQ ID NO 14
<211> LENGTH: 2190
<212> TYPE: DNA
<213> ORGANISM: Artificial Sequence
<220> FEATURE:
<223> OTHER INFORMATION: axmi-031(truncated)
<221> NAME/KEY: CDS
<222> LOCATION: (1)...(2190)

<400> SEQUENCE: 14

```
atg tcg tac tac cat cac cat cac cat cac ctc gaa tca aca agt ttg      48
Met Ser Tyr Tyr His His His His His His Leu Glu Ser Thr Ser Leu
1               5                   10                  15 tac aaa aaa gca ggc ttc att gaa gga cgt atg gat tgt aat tta caa      96
Tyr Lys Lys Ala Gly Phe Ile Glu Gly Arg Met Asp Cys Asn Leu Gln
            20                  25                  30 tca caa caa aat att cca tat aat gta tta gca ata cca gta tct aat     144
Ser Gln Gln Asn Ile Pro Tyr Asn Val Leu Ala Ile Pro Val Ser Asn
        35                  40                  45 gtt aat tcg ttg act gat aca gtt gga gat tta aaa aaa gca tgg gaa     192
Val Asn Ser Leu Thr Asp Thr Val Gly Asp Leu Lys Lys Ala Trp Glu
50                  55                  60 gaa ttt caa aaa act ggt tct ttt tca tta aca gct tta caa caa gga     240
Glu Phe Gln Lys Thr Gly Ser Phe Ser Leu Thr Ala Leu Gln Gln Gly
65                  70                  75                  80 ttt tct gct tca caa gga gga aca ttc aat tat tta aca tta cta caa     288
Phe Ser Ala Ser Gln Gly Gly Thr Phe Asn Tyr Leu Thr Leu Leu Gln
                85                  90                  95 tca gga ata tca tta gct ggt tct ttt gtt cct gga ggt act ttt gta     336
Ser Gly Ile Ser Leu Ala Gly Ser Phe Val Pro Gly Gly Thr Phe Val
            100                 105                 110 gca cct att att aat atg gtt att ggt tgg tta tgg cca cat aaa aac     384
Ala Pro Ile Ile Asn Met Val Ile Gly Trp Leu Trp Pro His Lys Asn
        115                 120                 125 aaa aat gcg gat aca gaa aat tta ata aat tta att gat tca gaa att     432
Lys Asn Ala Asp Thr Glu Asn Leu Ile Asn Leu Ile Asp Ser Glu Ile
130                 135                 140 caa aaa caa tta aac aaa gct tta tta gat gca gat aga aat gag tgg     480
Gln Lys Gln Leu Asn Lys Ala Leu Leu Asp Ala Asp Arg Asn Glu Trp
145                 150                 155                 160 agc tct tat tta gaa tct ata ttt gat tct tca aat aac cta aat ggt     528
Ser Ser Tyr Leu Glu Ser Ile Phe Asp Ser Ser Asn Asn Leu Asn Gly
                165                 170                 175 gca att gta gat gca cag tgg tca ggc act gta aat act aca aat aga     576
Ala Ile Val Asp Ala Gln Trp Ser Gly Thr Val Asn Thr Thr Asn Arg
            180                 185                 190 aca cta aga aat cca aca gaa tca gat tat aca aat gtt gtt aca aat     624
Thr Leu Arg Asn Pro Thr Glu Ser Asp Tyr Thr Asn Val Val Thr Asn
        195                 200                 205 ttt att gca gcg gat ggt gac att gca aat aat gaa aat cac ata atg     672
Phe Ile Ala Ala Asp Gly Asp Ile Ala Asn Asn Glu Asn His Ile Met
210                 215                 220 aat ggc aac ttt gac gta gct gca gca cct tat ttt gtt ata gga gca     720
Asn Gly Asn Phe Asp Val Ala Ala Ala Pro Tyr Phe Val Ile Gly Ala
225                 230                 235                 240 aca gca cgt ttt gca gca atg caa tct tat att aaa ttt tgt aat gct     768
Thr Ala Arg Phe Ala Ala Met Gln Ser Tyr Ile Lys Phe Cys Asn Ala
                245                 250                 255 tgg att gat aaa gtt gga ttg agt gac gca cag ctt act aca caa aag     816
Trp Ile Asp Lys Val Gly Leu Ser Asp Ala Gln Leu Thr Thr Gln Lys
            260                 265                 270 gct aat tta gat cgc acg aaa caa aat atg cgt aat gca att ctt aac     864
Ala Asn Leu Asp Arg Thr Lys Gln Asn Met Arg Asn Ala Ile Leu Asn
        275                 280                 285 tat aca caa caa gtt atg aaa gtt ttt aaa gat tcc aaa aat atg cct     912
Tyr Thr Gln Gln Val Met Lys Val Phe Lys Asp Ser Lys Asn Met Pro
290                 295                 300 aca ata ggt act aat aaa ttt agt gtt gat acc tat aat gta tat att     960
```

-continued

| | | | | | | | | | | | | | | | |
|---|---|---|---|---|---|---|---|---|---|---|---|---|---|---|---|
| Thr | Ile | Gly | Thr | Asn | Lys | Phe | Ser | Val | Asp | Thr | Tyr | Asn | Val | Tyr | Ile |
| 305 | | | | 310 | | | | | 315 | | | | | 320 | |

```
aaa gga atg aca tta aat gtt tta gat att gta gca ata tgg cct tca      1008
Lys Gly Met Thr Leu Asn Val Leu Asp Ile Val Ala Ile Trp Pro Ser
                    325                 330                 335 tta tat cca gat gat tat act tca caa aca gcc tta gaa caa aca cgt      1056
Leu Tyr Pro Asp Asp Tyr Thr Ser Gln Thr Ala Leu Glu Gln Thr Arg
                    340                 345                 350 gtc act ttt tca aat atg gtt ggc caa gaa gaa ggt aca gat gga agc      1104
Val Thr Phe Ser Asn Met Val Gly Gln Glu Glu Gly Thr Asp Gly Ser
                355                 360                 365 cta aga att tac aat act ttt gat tct ttt agt tat caa cat agt cca      1152
Leu Arg Ile Tyr Asn Thr Phe Asp Ser Phe Ser Tyr Gln His Ser Pro
370                 375                 380 ata cct aat aat aat gtt aat tta att tct tat tat aat gat gaa tta      1200
Ile Pro Asn Asn Asn Val Asn Leu Ile Ser Tyr Tyr Asn Asp Glu Leu
385                 390                 395                 400 caa aat cta gaa tta gga gta tat acc cct cct aaa aaa gga agt gga      1248
Gln Asn Leu Glu Leu Gly Val Tyr Thr Pro Pro Lys Lys Gly Ser Gly
                    405                 410                 415 tac tct tat cct tat gga ttt gtt tta aat tat gca aac agt aaa tat      1296
Tyr Ser Tyr Pro Tyr Gly Phe Val Leu Asn Tyr Ala Asn Ser Lys Tyr
                420                 425                 430 aaa tat ggt gat agc aat gat cca gaa tct cta gga gga tta tct aca      1344
Lys Tyr Gly Asp Ser Asn Asp Pro Glu Ser Leu Gly Gly Leu Ser Thr
                    435                 440                 445 cta tct gca cct ata caa caa gtt aat gca gca act caa aac agt aaa      1392
Leu Ser Ala Pro Ile Gln Gln Val Asn Ala Ala Thr Gln Asn Ser Lys
450                 455                 460 tat cta gat gga gaa atc cta aat gga ata gga gca tcc tta cct ggt      1440
Tyr Leu Asp Gly Glu Ile Leu Asn Gly Ile Gly Ala Ser Leu Pro Gly
465                 470                 475                 480 tat tgt act aca gga tgt tca cca aca gaa cca cct ttt agt tgt act      1488
Tyr Cys Thr Thr Gly Cys Ser Pro Thr Glu Pro Pro Phe Ser Cys Thr
                    485                 490                 495 tct acc gct aat ggc tat aaa gca agc tgt aat cct tca gat aca aat      1536
Ser Thr Ala Asn Gly Tyr Lys Ala Ser Cys Asn Pro Ser Asp Thr Asn
                500                 505                 510 caa aaa att aac gct tta tat cct ttt aca caa gct aat gta aag gga      1584
Gln Lys Ile Asn Ala Leu Tyr Pro Phe Thr Gln Ala Asn Val Lys Gly
                    515                 520                 525 aac aca gga aaa tta gga gta ctg gca agt ctt gtt tca tat gat tta      1632
Asn Thr Gly Lys Leu Gly Val Leu Ala Ser Leu Val Ser Tyr Asp Leu
                    530                 535                 540 aat cct aaa aat gta ttt ggt gaa tta gat tca gat aca aat aat gtt      1680
Asn Pro Lys Asn Val Phe Gly Glu Leu Asp Ser Asp Thr Asn Asn Val
545                 550                 555                 560 atc tta aaa gga att cct gca gaa aaa gga tat ttt cct aat aat gcg      1728
Ile Leu Lys Gly Ile Pro Ala Glu Lys Gly Tyr Phe Pro Asn Asn Ala
                    565                 570                 575 cgt cct act gtt gta aaa gaa tgg att aat ggt gca agt gct gta cca      1776
Arg Pro Thr Val Val Lys Glu Trp Ile Asn Gly Ala Ser Ala Val Pro
                    580                 585                 590 ctt gat tca gga aat acc tta ttt atg acg gct acg aat tta aca gct      1824
Leu Asp Ser Gly Asn Thr Leu Phe Met Thr Ala Thr Asn Leu Thr Ala
                595                 600                 605 act caa tat aga att aga ata cgt tat gca aat cca aat tca aat act      1872
Thr Gln Tyr Arg Ile Arg Ile Arg Tyr Ala Asn Pro Asn Ser Asn Thr
                    610                 615                 620 caa atc ggt gta cga att aca caa aat ggt tct cta att tcc agt agt      1920
Gln Ile Gly Val Arg Ile Thr Gln Asn Gly Ser Leu Ile Ser Ser Ser
```

```
Gln Ile Gly Val Arg Ile Thr Gln Asn Gly Ser Leu Ile Ser Ser Ser
625                 630                 635                 640 aat cta aca ctt tat agt act act gat atg aat aat act tta cca cta    1968
Asn Leu Thr Leu Tyr Ser Thr Thr Asp Met Asn Asn Thr Leu Pro Leu
                645                 650                 655 aat gta tat gta ata gga gaa aat gga aat tat aca ctt caa gat tta    2016
Asn Val Tyr Val Ile Gly Glu Asn Gly Asn Tyr Thr Leu Gln Asp Leu
                660                 665                 670 tat aat act act aat gtt tta tca aca gga gat att aca tta caa att    2064
Tyr Asn Thr Thr Asn Val Leu Ser Thr Gly Asp Ile Thr Leu Gln Ile
            675                 680                 685 aca gga gga gat caa aaa ata ttt att gat cga ata gaa ttt gtt cct    2112
Thr Gly Gly Asp Gln Lys Ile Phe Ile Asp Arg Ile Glu Phe Val Pro
    690                 695                 700 act atg cct gta cct ggt aat act aac aac aat aac ggt aat aat aac    2160
Thr Met Pro Val Pro Gly Asn Thr Asn Asn Asn Asn Gly Asn Asn Asn
705                 710                 715                 720 ggt aat aat aat ccc cca cac cac gtc tag                             2190
Gly Asn Asn Asn Pro Pro His His Val *
                725

<210> SEQ ID NO 15
<211> LENGTH: 729
<212> TYPE: PRT
<213> ORGANISM: Artificial Sequence
<220> FEATURE:
<223> OTHER INFORMATION: AXMI-031(TRUNCATED)

<400> SEQUENCE: 15

Met Ser Tyr Tyr His His His His His Leu Glu Ser Thr Ser Leu
 1               5                  10                  15

Tyr Lys Lys Ala Gly Phe Ile Glu Gly Arg Met Asp Cys Asn Leu Gln
                20                  25                  30

Ser Gln Gln Asn Ile Pro Tyr Asn Val Leu Ala Ile Pro Val Ser Asn
            35                  40                  45

Val Asn Ser Leu Thr Asp Thr Val Gly Asp Leu Lys Lys Ala Trp Glu
    50                  55                  60

Glu Phe Gln Lys Thr Gly Ser Phe Ser Leu Thr Ala Leu Gln Gln Gly
65                  70                  75                  80

Phe Ser Ala Ser Gln Gly Gly Thr Phe Asn Tyr Leu Thr Leu Leu Gln
                85                  90                  95

Ser Gly Ile Ser Leu Ala Gly Ser Phe Val Pro Gly Gly Thr Phe Val
            100                 105                 110

Ala Pro Ile Ile Asn Met Val Ile Gly Trp Leu Trp Pro His Lys Asn
    115                 120                 125

Lys Asn Ala Asp Thr Glu Asn Leu Ile Asn Leu Ile Asp Ser Glu Ile
130                 135                 140

Gln Lys Gln Leu Asn Lys Ala Leu Leu Asp Ala Asp Arg Asn Glu Trp
145                 150                 155                 160

Ser Ser Tyr Leu Glu Ser Ile Phe Asp Ser Ser Asn Leu Asn Gly
                165                 170                 175

Ala Ile Val Asp Ala Gln Trp Ser Gly Thr Val Asn Thr Thr Asn Arg
            180                 185                 190

Thr Leu Arg Asn Pro Thr Glu Ser Asp Tyr Thr Asn Val Val Thr Asn
    195                 200                 205

Phe Ile Ala Ala Asp Gly Asp Ile Ala Asn Asn Glu Asn His Ile Met
    210                 215                 220

Asn Gly Asn Phe Asp Val Ala Ala Ala Pro Tyr Phe Val Ile Gly Ala
```

```
                225                 230                 235                 240
Thr Ala Arg Phe Ala Met Gln Ser Tyr Ile Lys Phe Cys Asn Ala
            245                 250                 255
Trp Ile Asp Lys Val Gly Leu Ser Asp Ala Gln Leu Thr Thr Gln Lys
            260                 265                 270
Ala Asn Leu Asp Arg Thr Lys Gln Asn Met Arg Asn Ala Ile Leu Asn
            275                 280                 285
Tyr Thr Gln Gln Val Met Lys Val Phe Lys Asp Ser Lys Asn Met Pro
        290                 295                 300
Thr Ile Gly Thr Asn Lys Phe Ser Val Asp Thr Tyr Asn Val Tyr Ile
305                 310                 315                 320
Lys Gly Met Thr Leu Asn Val Leu Asp Ile Val Ala Ile Trp Pro Ser
                325                 330                 335
Leu Tyr Pro Asp Asp Tyr Thr Ser Gln Thr Ala Leu Glu Gln Thr Arg
                340                 345                 350
Val Thr Phe Ser Asn Met Val Gly Gln Glu Gly Thr Asp Gly Ser
        355                 360                 365
Leu Arg Ile Tyr Asn Thr Phe Asp Ser Phe Ser Tyr Gln His Ser Pro
    370                 375                 380
Ile Pro Asn Asn Asn Val Asn Leu Ile Ser Tyr Tyr Asn Asp Glu Leu
385                 390                 395                 400
Gln Asn Leu Glu Leu Gly Val Tyr Thr Pro Pro Lys Lys Gly Ser Gly
                405                 410                 415
Tyr Ser Tyr Pro Tyr Gly Phe Val Leu Asn Tyr Ala Asn Ser Lys Tyr
                420                 425                 430
Lys Tyr Gly Asp Ser Asn Asp Pro Glu Ser Leu Gly Gly Leu Ser Thr
            435                 440                 445
Leu Ser Ala Pro Ile Gln Gln Val Asn Ala Ala Thr Gln Asn Ser Lys
        450                 455                 460
Tyr Leu Asp Gly Glu Ile Leu Asn Gly Ile Gly Ala Ser Leu Pro Gly
465                 470                 475                 480
Tyr Cys Thr Thr Gly Cys Ser Pro Thr Glu Pro Pro Phe Ser Cys Thr
                485                 490                 495
Ser Thr Ala Asn Gly Tyr Lys Ala Ser Cys Asn Pro Ser Asp Thr Asn
            500                 505                 510
Gln Lys Ile Asn Ala Leu Tyr Pro Phe Thr Gln Ala Asn Val Lys Gly
        515                 520                 525
Asn Thr Gly Lys Leu Gly Val Leu Ala Ser Leu Val Ser Tyr Asp Leu
530                 535                 540
Asn Pro Lys Asn Val Phe Gly Glu Leu Asp Ser Asp Thr Asn Asn Val
545                 550                 555                 560
Ile Leu Lys Gly Ile Pro Ala Glu Lys Gly Tyr Phe Pro Asn Asn Ala
                565                 570                 575
Arg Pro Thr Val Val Lys Glu Trp Ile Asn Gly Ala Ser Ala Val Pro
                580                 585                 590
Leu Asp Ser Gly Asn Thr Leu Phe Met Thr Ala Thr Asn Leu Thr Ala
        595                 600                 605
Thr Gln Tyr Arg Ile Arg Ile Arg Tyr Ala Asn Pro Asn Ser Asn Thr
        610                 615                 620
Gln Ile Gly Val Arg Ile Thr Gln Asn Gly Ser Leu Ile Ser Ser Ser
625                 630                 635                 640
Asn Leu Thr Leu Tyr Ser Thr Thr Asp Met Asn Asn Thr Leu Pro Leu
                645                 650                 655
```

```
Asn Val Tyr Val Ile Gly Glu Asn Gly Asn Tyr Thr Leu Gln Asp Leu
                660                 665                 670

Tyr Asn Thr Thr Asn Val Leu Ser Thr Gly Asp Ile Thr Leu Gln Ile
            675                 680                 685

Thr Gly Gly Asp Gln Lys Ile Phe Ile Asp Arg Ile Glu Phe Val Pro
        690                 695                 700

Thr Met Pro Val Pro Gly Asn Thr Asn Asn Asn Gly Asn Asn Asn
705                 710                 715                 720

Gly Asn Asn Asn Pro Pro His His Val
                725

<210> SEQ ID NO 16
<211> LENGTH: 3558
<212> TYPE: DNA
<213> ORGANISM: Artificial Sequence
<220> FEATURE:
<223> OTHER INFORMATION: axmi-031(m1)
<221> NAME/KEY: CDS
<222> LOCATION: (1)...(3558)

<400> SEQUENCE: 16
```

| | | | | | | | | | | | | | | | | |
|---|---|---|---|---|---|---|---|---|---|---|---|---|---|---|---|---|
| atg | gat | tgt | aat | tta | caa | tca | caa | caa | aat | att | cca | tat | aat | gta | tta | 48 |
| Met | Asp | Cys | Asn | Leu | Gln | Ser | Gln | Gln | Asn | Ile | Pro | Tyr | Asn | Val | Leu | |
| 1 | | | | 5 | | | | | 10 | | | | | 15 | | |
| gca | ata | cca | gta | tct | aat | gtt | aat | tcg | ttg | act | gat | aca | gtt | gga | gat | 96 |
| Ala | Ile | Pro | Val | Ser | Asn | Val | Asn | Ser | Leu | Thr | Asp | Thr | Val | Gly | Asp | |
| | | | 20 | | | | | 25 | | | | | 30 | | | |
| tta | aaa | aaa | gca | tgg | gaa | gaa | ttt | caa | aaa | act | ggt | tct | ttt | tca | tta | 144 |
| Leu | Lys | Lys | Ala | Trp | Glu | Glu | Phe | Gln | Lys | Thr | Gly | Ser | Phe | Ser | Leu | |
| | 35 | | | | | 40 | | | | | 45 | | | | | |
| aca | gct | tta | caa | caa | gga | ttt | tct | gct | tca | caa | gga | gga | aca | ttc | aat | 192 |
| Thr | Ala | Leu | Gln | Gln | Gly | Phe | Ser | Ala | Ser | Gln | Gly | Gly | Thr | Phe | Asn | |
| 50 | | | | | 55 | | | | | 60 | | | | | | |
| tat | tta | aca | tta | cta | caa | tca | gga | ata | tca | tta | gct | ggt | tct | ttt | gtt | 240 |
| Tyr | Leu | Thr | Leu | Leu | Gln | Ser | Gly | Ile | Ser | Leu | Ala | Gly | Ser | Phe | Val | |
| 65 | | | | 70 | | | | | 75 | | | | | 80 | | |
| cct | gga | ggt | act | ttt | gta | gca | cct | att | att | aat | atg | gtt | att | ggt | tgg | 288 |
| Pro | Gly | Gly | Thr | Phe | Val | Ala | Pro | Ile | Ile | Asn | Met | Val | Ile | Gly | Trp | |
| | | | 85 | | | | | 90 | | | | | 95 | | | |
| tta | tgg | cca | cat | aaa | aac | aaa | aat | gcg | gat | aca | gaa | aat | tta | ata | aat | 336 |
| Leu | Trp | Pro | His | Lys | Asn | Lys | Asn | Ala | Asp | Thr | Glu | Asn | Leu | Ile | Asn | |
| | | 100 | | | | | 105 | | | | | 110 | | | | |
| tta | att | gat | tca | gaa | att | caa | aaa | caa | tta | aac | aaa | gct | tta | tta | gat | 384 |
| Leu | Ile | Asp | Ser | Glu | Ile | Gln | Lys | Gln | Leu | Asn | Lys | Ala | Leu | Leu | Asp | |
| | 115 | | | | | 120 | | | | | 125 | | | | | |
| gca | gat | aga | aat | gag | tgg | agc | tct | tat | tta | gaa | tct | ata | ttt | gat | tct | 432 |
| Ala | Asp | Arg | Asn | Glu | Trp | Ser | Ser | Tyr | Leu | Glu | Ser | Ile | Phe | Asp | Ser | |
| 130 | | | | | 135 | | | | | 140 | | | | | | |
| tca | aat | aac | cta | aat | ggt | gca | att | gta | gat | gca | cag | tgg | tca | ggc | act | 480 |
| Ser | Asn | Asn | Leu | Asn | Gly | Ala | Ile | Val | Asp | Ala | Gln | Trp | Ser | Gly | Thr | |
| 145 | | | | 150 | | | | | 155 | | | | | 160 | | |
| gta | aat | act | aca | aat | aga | aca | cta | aga | aat | cca | aca | gaa | tca | gat | tat | 528 |
| Val | Asn | Thr | Thr | Asn | Arg | Thr | Leu | Arg | Asn | Pro | Thr | Glu | Ser | Asp | Tyr | |
| | | | | 165 | | | | | 170 | | | | | 175 | | |
| aca | aat | gtt | gtt | aca | aat | ttt | att | gca | gcg | gat | ggt | gac | att | gca | aat | 576 |
| Thr | Asn | Val | Val | Thr | Asn | Phe | Ile | Ala | Ala | Asp | Gly | Asp | Ile | Ala | Asn | |
| | | | 180 | | | | | 185 | | | | | 190 | | | |
| aat | gaa | aat | cac | ata | atg | aat | ggc | aac | ttt | gac | gta | gct | gca | gca | cct | 624 |
| Asn | Glu | Asn | His | Ile | Met | Asn | Gly | Asn | Phe | Asp | Val | Ala | Ala | Ala | Pro | |
| | | | | 195 | | | | | 200 | | | | | 205 | | |
| tat | ttt | gct | ata | gga | gca | aca | gca | cgt | ttt | gca | gca | atg | caa | tct | tat | 672 |

```
              Tyr Phe Ala Ile Gly Ala Thr Ala Arg Phe Ala Ala Met Gln Ser Tyr
                  210                 215                 220 att aaa ttt tgt aat gct tgg att gat aaa gtt gga ttg agt gac gca          720
Ile Lys Phe Cys Asn Ala Trp Ile Asp Lys Val Gly Leu Ser Asp Ala
225                 230                 235                 240 cag ctt act aca caa aag gct aat tta gat cgc acg aaa caa aat atg          768
Gln Leu Thr Thr Gln Lys Ala Asn Leu Asp Arg Thr Lys Gln Asn Met
                245                 250                 255 cgt aat gca att ctt aac tat aca caa caa gtt atg aaa gtt ttt aaa          816
Arg Asn Ala Ile Leu Asn Tyr Thr Gln Gln Val Met Lys Val Phe Lys
                260                 265                 270 gat tcc aaa aat atg cct aca ata ggt act aat aaa ttt agt gtt gat          864
Asp Ser Lys Asn Met Pro Thr Ile Gly Thr Asn Lys Phe Ser Val Asp
            275                 280                 285 acc tat aat gta tat att aaa gga atg aca tta aat gtt tta gat att          912
Thr Tyr Asn Val Tyr Ile Lys Gly Met Thr Leu Asn Val Leu Asp Ile
        290                 295                 300 gta gca ata tgg cct tca tta tat cca gat gat tat act tca caa aca          960
Val Ala Ile Trp Pro Ser Leu Tyr Pro Asp Asp Tyr Thr Ser Gln Thr
305                 310                 315                 320 gcc tta gaa caa aca cgt gtc act ttt tca aat atg gtt ggc caa gaa         1008
Ala Leu Glu Gln Thr Arg Val Thr Phe Ser Asn Met Val Gly Gln Glu
                325                 330                 335 gaa ggt aca gat gga agc cta aga att tac aat act ttt gat tct ttt         1056
Glu Gly Thr Asp Gly Ser Leu Arg Ile Tyr Asn Thr Phe Asp Ser Phe
                340                 345                 350 agt tat caa cat agt cca ata cct aat aat aat gtt aat tta att tct         1104
Ser Tyr Gln His Ser Pro Ile Pro Asn Asn Asn Val Asn Leu Ile Ser
            355                 360                 365 tat tat aat gat gaa tta caa aat cta gaa tta gga gta tat acc cct         1152
Tyr Tyr Asn Asp Glu Leu Gln Asn Leu Glu Leu Gly Val Tyr Thr Pro
        370                 375                 380 cct aaa aaa gga agt gga tac tct tat cct tat gga ttt gtt tta aat         1200
Pro Lys Lys Gly Ser Gly Tyr Ser Tyr Pro Tyr Gly Phe Val Leu Asn
385                 390                 395                 400 tat gca aac agt aaa tat aaa tat ggt gat agc aat gat cca gaa tct         1248
Tyr Ala Asn Ser Lys Tyr Lys Tyr Gly Asp Ser Asn Asp Pro Glu Ser
                405                 410                 415 cta gga gga tta tct aca cta tct gca cct ata caa caa gtt aat gca         1296
Leu Gly Gly Leu Ser Thr Leu Ser Ala Pro Ile Gln Gln Val Asn Ala
                420                 425                 430 gca act caa aac agt aaa tat cta gat gga gaa atc cta aat gga ata         1344
Ala Thr Gln Asn Ser Lys Tyr Leu Asp Gly Glu Ile Leu Asn Gly Ile
            435                 440                 445 gga gca tcc tta cct ggt tat tgt act aca gga tgt tca cca aca gaa         1392
Gly Ala Ser Leu Pro Gly Tyr Cys Thr Thr Gly Cys Ser Pro Thr Glu
        450                 455                 460 cca cct ttt agt tgt act tct acc gct aat ggc tat aaa gca agc tgt         1440
Pro Pro Phe Ser Cys Thr Ser Thr Ala Asn Gly Tyr Lys Ala Ser Cys
465                 470                 475                 480 aat cct tca gat aca aat caa aaa att aac gct tta tat cct ttt aca         1488
Asn Pro Ser Asp Thr Asn Gln Lys Ile Asn Ala Leu Tyr Pro Phe Thr
                485                 490                 495 caa gct aat gta aag gga aac aca gga aaa tta gga gta ctg gca agt         1536
Gln Ala Asn Val Lys Gly Asn Thr Gly Lys Leu Gly Val Leu Ala Ser
                500                 505                 510 ctt gtt tca tat gat tta aat cct aaa aat gta ttt ggt gag tta gat         1584
Leu Val Ser Tyr Asp Leu Asn Pro Lys Asn Val Phe Gly Glu Leu Asp
            515                 520                 525 tca gat aca aat aat gtt atc tta aaa gga att cct gca gaa aaa gga         1632
```

```
Ser Asp Thr Asn Asn Val Ile Leu Lys Gly Ile Pro Ala Glu Lys Gly
    530                 535                 540 tat ttt cct aat aat gcg cgt cct act gtt gta aaa gaa tgg att aat    1680
Tyr Phe Pro Asn Asn Ala Arg Pro Thr Val Val Lys Glu Trp Ile Asn
545                 550                 555                 560 ggt gca agt gct gta cca ctt gat tca gga aat acc tta ttt atg acg    1728
Gly Ala Ser Ala Val Pro Leu Asp Ser Gly Asn Thr Leu Phe Met Thr
                565                 570                 575 gct acg aat tta aca gct act caa tat aga att aga ata cgt tat gca    1776
Ala Thr Asn Leu Thr Ala Thr Gln Tyr Arg Ile Arg Ile Arg Tyr Ala
            580                 585                 590 aat cca aat tca aat act caa atc ggt gta cga att aca caa aat ggt    1824
Asn Pro Asn Ser Asn Thr Gln Ile Gly Val Arg Ile Thr Gln Asn Gly
        595                 600                 605 tct cta att tcc agt agt aat cta aca ctt tat agt act act gat atg    1872
Ser Leu Ile Ser Ser Ser Asn Leu Thr Leu Tyr Ser Thr Thr Asp Met
610                 615                 620 aat aat act tta cca cta aat gta tat gta ata gga gaa aat gga aat    1920
Asn Asn Thr Leu Pro Leu Asn Val Tyr Val Ile Gly Glu Asn Gly Asn
625                 630                 635                 640 tat aca ctt caa gat tta tat aat act act aat gtt tta tca aca gga    1968
Tyr Thr Leu Gln Asp Leu Tyr Asn Thr Thr Asn Val Leu Ser Thr Gly
                645                 650                 655 gat att aca tta caa att aca gga gga gat caa aaa ata ttt att gat    2016
Asp Ile Thr Leu Gln Ile Thr Gly Gly Asp Gln Lys Ile Phe Ile Asp
            660                 665                 670 cga ata gaa ttt gtt cct act atg cct gta cct ggt aat act aac aac    2064
Arg Ile Glu Phe Val Pro Thr Met Pro Val Pro Gly Asn Thr Asn Asn
        675                 680                 685 aat aac ggt aat aat aac ggt aat aat aat ccc cca cac cac gtt tgt    2112
Asn Asn Gly Asn Asn Asn Gly Asn Asn Asn Pro Pro His His Val Cys
690                 695                 700 gca ata gct ggt aca caa caa tct tgt tct gga ccg ccc aaa ttt gaa    2160
Ala Ile Ala Gly Thr Gln Gln Ser Cys Ser Gly Pro Pro Lys Phe Glu
705                 710                 715                 720 caa gta agt gat tta gaa aaa att aca aca caa gta tat atg tta ttc    2208
Gln Val Ser Asp Leu Glu Lys Ile Thr Thr Gln Val Tyr Met Leu Phe
                725                 730                 735 aaa tct tct ccg tat gaa gaa tta gct cta gaa gtt tcc agc tat caa    2256
Lys Ser Ser Pro Tyr Glu Glu Leu Ala Leu Glu Val Ser Ser Tyr Gln
            740                 745                 750 att agt caa gta gca tta aaa gtt atg gca tta tct gat gaa cta ttt    2304
Ile Ser Gln Val Ala Leu Lys Val Met Ala Leu Ser Asp Glu Leu Phe
        755                 760                 765 tgt gaa gaa aaa aac gta tta cga aaa tta gtc aat aaa gca aaa caa    2352
Cys Glu Glu Lys Asn Val Leu Arg Lys Leu Val Asn Lys Ala Lys Gln
770                 775                 780 tta tta gaa gca agt aac tta cta gta ggt gga aat ttt gaa aca act    2400
Leu Leu Glu Ala Ser Asn Leu Leu Val Gly Gly Asn Phe Glu Thr Thr
785                 790                 795                 800 caa aat tgg gta ctt gga aca aat gct tat ata aat tat gat tcg ttt    2448
Gln Asn Trp Val Leu Gly Thr Asn Ala Tyr Ile Asn Tyr Asp Ser Phe
                805                 810                 815 tta ttt aat gga aat tat tta tct tta caa cca gca agt gga ttt ttc    2496
Leu Phe Asn Gly Asn Tyr Leu Ser Leu Gln Pro Ala Ser Gly Phe Phe
            820                 825                 830 aca tct tat gct tat caa aaa ata gat gag tca aca tta aaa cca tat    2544
Thr Ser Tyr Ala Tyr Gln Lys Ile Asp Glu Ser Thr Leu Lys Pro Tyr
        835                 840                 845 aca cga tat aaa gtt tct ggg ttc att ggg caa agt aat caa gta gaa    2592
Thr Arg Tyr Lys Val Ser Gly Phe Ile Gly Gln Ser Asn Gln Val Glu
```

-continued

```
Thr Arg Tyr Lys Val Ser Gly Phe Ile Gly Gln Ser Asn Gln Val Glu
850                 855                 860 ctt att att tct cgt tat gga aaa gaa att gat aaa ata tta aat gtt      2640
Leu Ile Ile Ser Arg Tyr Gly Lys Glu Ile Asp Lys Ile Leu Asn Val
865                 870                 875                 880 cca tat gca gga cct ctt cct atc act gct gat gca tca ata act tgt      2688
Pro Tyr Ala Gly Pro Leu Pro Ile Thr Ala Asp Ala Ser Ile Thr Cys
                885                 890                 895 tgt gca cca gaa ata ggc caa tgt gat ggg gaa caa tct gat tct cat      2736
Cys Ala Pro Glu Ile Gly Gln Cys Asp Gly Glu Gln Ser Asp Ser His
900                 905                 910 ttc ttt aac tat agc atc gat gta ggt gca ctt cac cca gaa tta aac      2784
Phe Phe Asn Tyr Ser Ile Asp Val Gly Ala Leu His Pro Glu Leu Asn
            915                 920                 925 cct ggc att gaa att ggt ctt aaa att gtg caa tca aat ggt tat ata      2832
Pro Gly Ile Glu Ile Gly Leu Lys Ile Val Gln Ser Asn Gly Tyr Ile
930                 935                 940 aca att agt aat cta gaa att att gaa gaa cgt cca ctt aca gaa atg      2880
Thr Ile Ser Asn Leu Glu Ile Ile Glu Glu Arg Pro Leu Thr Glu Met
945                 950                 955                 960 gaa att caa gca gtc aat cga aaa aat caa aaa tgg gaa aga gaa aaa      2928
Glu Ile Gln Ala Val Asn Arg Lys Asn Gln Lys Trp Glu Arg Glu Lys
                965                 970                 975 ctt cta gaa tgt gca agt att agt gaa ctt tta caa cca att att aat      2976
Leu Leu Glu Cys Ala Ser Ile Ser Glu Leu Leu Gln Pro Ile Ile Asn
            980                 985                 990 caa atc gat tca ttg ttt aaa gat gga aac tgg tat aat gat att ctt      3024
Gln Ile Asp Ser Leu Phe Lys Asp Gly Asn Trp Tyr Asn Asp Ile Leu
995                 1000                1005 cct cat gtc aca tat caa gat tta aaa aat att ata ata ccc gag tta      3072
Pro His Val Thr Tyr Gln Asp Leu Lys Asn Ile Ile Ile Pro Glu Leu
    1010                1015                1020 cca aaa tta aaa cat tgg ttc ata gag aat ctc cca ggt gaa tat cat      3120
Pro Lys Leu Lys His Trp Phe Ile Glu Asn Leu Pro Gly Glu Tyr His
1025                1030                1035                1040 gaa att gaa caa aaa atg aaa gaa gct cta aaa tat gca ttt aca caa      3168
Glu Ile Glu Gln Lys Met Lys Glu Ala Leu Lys Tyr Ala Phe Thr Gln
                1045                1050                1055 tta gac gag aaa aat tta atc cac aat ggt cac ttt aca act aac tta      3216
Leu Asp Glu Lys Asn Leu Ile His Asn Gly His Phe Thr Thr Asn Leu
            1060                1065                1070 ata gat tgg caa gta gaa ggt gat gct caa atg aaa gta tta gaa aat      3264
Ile Asp Trp Gln Val Glu Gly Asp Ala Gln Met Lys Val Leu Glu Asn
1075                1080                1085 gat gct ctt gca tta caa ctt ttc aac tgg gat gct aat gct tca caa      3312
Asp Ala Leu Ala Leu Gln Leu Phe Asn Trp Asp Ala Asn Ala Ser Gln
    1090                1095                1100 tct ata aat ata tta gaa ttt gat gaa gat aag gca tat aaa ctt cgc      3360
Ser Ile Asn Ile Leu Glu Phe Asp Glu Asp Lys Ala Tyr Lys Leu Arg
1105                1110                1115                1120 gta tat gct caa gga agc gga aca atc caa ttt gga aac tgt gaa gat      3408
Val Tyr Ala Gln Gly Ser Gly Thr Ile Gln Phe Gly Asn Cys Glu Asp
                1125                1130                1135 gaa gct atc caa ttt aat aca aac tca ttc ata tat caa gaa aaa ata      3456
Glu Ala Ile Gln Phe Asn Thr Asn Ser Phe Ile Tyr Gln Glu Lys Ile
            1140                1145                1150 gtc tat ttc gat acc cca tca gtt aat tta cac ata caa tca gaa ggt      3504
Val Tyr Phe Asp Thr Pro Ser Val Asn Leu His Ile Gln Ser Glu Gly
1155                1160                1165 tct gaa ttt att gta agt agt atc gat cta att gaa tta tca gac gac      3552
```

```
Ser Glu Phe Ile Val Ser Ser Ile Asp Leu Ile Glu Leu Ser Asp Asp
    1170                1175                1180 caa taa                                                              3558
Gln *
1185

<210> SEQ ID NO 17
<211> LENGTH: 1185
<212> TYPE: PRT
<213> ORGANISM: Artificial Sequence
<220> FEATURE:
<223> OTHER INFORMATION: AXMI-031(M1)

<400> SEQUENCE: 17

Met Asp Cys Asn Leu Gln Ser Gln Gln Asn Ile Pro Tyr Asn Val Leu
1               5                   10                  15

Ala Ile Pro Val Ser Asn Val Asn Ser Leu Thr Asp Thr Val Gly Asp
                20                  25                  30

Leu Lys Lys Ala Trp Glu Glu Phe Gln Lys Thr Gly Ser Phe Ser Leu
            35                  40                  45

Thr Ala Leu Gln Gln Gly Phe Ser Ala Ser Gln Gly Gly Thr Phe Asn
        50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
    130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Ala Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
    290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                325                 330                 335
```

-continued

```
Glu Gly Thr Asp Gly Ser Leu Arg Ile Tyr Asn Thr Phe Asp Ser Phe
            340                 345                 350
Ser Tyr Gln His Ser Pro Ile Pro Asn Asn Asn Val Asn Leu Ile Ser
            355                 360                 365
Tyr Tyr Asn Asp Glu Leu Gln Asn Leu Glu Leu Gly Val Tyr Thr Pro
        370                 375                 380
Pro Lys Lys Gly Ser Gly Tyr Ser Tyr Pro Tyr Gly Phe Val Leu Asn
385                 390                 395                 400
Tyr Ala Asn Ser Lys Tyr Lys Tyr Gly Asp Ser Asn Asp Pro Glu Ser
                405                 410                 415
Leu Gly Gly Leu Ser Thr Leu Ser Ala Pro Ile Gln Gln Val Asn Ala
            420                 425                 430
Ala Thr Gln Asn Ser Lys Tyr Leu Asp Gly Glu Ile Leu Asn Gly Ile
            435                 440                 445
Gly Ala Ser Leu Pro Gly Tyr Cys Thr Thr Gly Cys Ser Pro Thr Glu
        450                 455                 460
Pro Pro Phe Ser Cys Thr Ser Thr Ala Asn Gly Tyr Lys Ala Ser Cys
465                 470                 475                 480
Asn Pro Ser Asp Thr Asn Gln Lys Ile Asn Ala Leu Tyr Pro Phe Thr
                485                 490                 495
Gln Ala Asn Val Lys Gly Asn Thr Gly Lys Leu Gly Val Leu Ala Ser
            500                 505                 510
Leu Val Ser Tyr Asp Leu Asn Pro Lys Asn Val Phe Gly Glu Leu Asp
            515                 520                 525
Ser Asp Thr Asn Asn Val Ile Leu Lys Gly Ile Pro Ala Glu Lys Gly
        530                 535                 540
Tyr Phe Pro Asn Asn Ala Arg Pro Thr Val Val Lys Glu Trp Ile Asn
545                 550                 555                 560
Gly Ala Ser Ala Val Pro Leu Asp Ser Gly Asn Thr Leu Phe Met Thr
                565                 570                 575
Ala Thr Asn Leu Thr Ala Thr Gln Tyr Arg Ile Arg Ile Arg Tyr Ala
            580                 585                 590
Asn Pro Asn Ser Asn Thr Gln Ile Gly Val Arg Ile Thr Gln Asn Gly
            595                 600                 605
Ser Leu Ile Ser Ser Ser Asn Leu Thr Leu Tyr Ser Thr Thr Asp Met
        610                 615                 620
Asn Asn Thr Leu Pro Leu Asn Val Tyr Val Ile Gly Glu Asn Gly Asn
625                 630                 635                 640
Tyr Thr Leu Gln Asp Leu Tyr Asn Thr Asn Val Leu Ser Thr Gly
                645                 650                 655
Asp Ile Thr Leu Gln Ile Thr Gly Gly Asp Gln Lys Ile Phe Ile Asp
            660                 665                 670
Arg Ile Glu Phe Val Pro Thr Met Pro Val Pro Gly Asn Thr Asn Asn
            675                 680                 685
Asn Asn Gly Asn Asn Asn Gly Asn Asn Asn Pro Pro His His Val Cys
        690                 695                 700
Ala Ile Ala Gly Thr Gln Gln Ser Cys Ser Gly Pro Pro Lys Phe Glu
705                 710                 715                 720
Gln Val Ser Asp Leu Glu Lys Ile Thr Thr Gln Val Tyr Met Leu Phe
                725                 730                 735
Lys Ser Ser Pro Tyr Glu Glu Leu Ala Leu Glu Val Ser Ser Tyr Gln
            740                 745                 750
Ile Ser Gln Val Ala Leu Lys Val Met Ala Leu Ser Asp Glu Leu Phe
            755                 760                 765
```

```
Cys Glu Glu Lys Asn Val Leu Arg Lys Leu Val Asn Lys Ala Lys Gln
    770                 775                 780

Leu Leu Glu Ala Ser Asn Leu Val Gly Gly Asn Phe Glu Thr Thr
785                 790                 795                 800

Gln Asn Trp Val Leu Gly Thr Asn Ala Tyr Ile Asn Tyr Asp Ser Phe
                805                 810                 815

Leu Phe Asn Gly Asn Tyr Leu Ser Leu Gln Pro Ala Ser Gly Phe Phe
            820                 825                 830

Thr Ser Tyr Ala Tyr Gln Lys Ile Asp Glu Ser Thr Leu Lys Pro Tyr
            835                 840                 845

Thr Arg Tyr Lys Val Ser Gly Phe Ile Gly Gln Ser Asn Gln Val Glu
            850                 855                 860

Leu Ile Ile Ser Arg Tyr Gly Lys Glu Ile Asp Lys Ile Leu Asn Val
865                 870                 875                 880

Pro Tyr Ala Gly Pro Leu Pro Ile Thr Ala Asp Ala Ser Ile Thr Cys
                885                 890                 895

Cys Ala Pro Glu Ile Gly Gln Cys Asp Gly Glu Gln Ser Asp Ser His
            900                 905                 910

Phe Phe Asn Tyr Ser Ile Asp Val Gly Ala Leu His Pro Glu Leu Asn
            915                 920                 925

Pro Gly Ile Glu Ile Gly Leu Lys Ile Val Gln Ser Asn Gly Tyr Ile
            930                 935                 940

Thr Ile Ser Asn Leu Glu Ile Ile Glu Arg Pro Leu Thr Glu Met
945                 950                 955                 960

Glu Ile Gln Ala Val Asn Arg Lys Asn Gln Lys Trp Glu Arg Glu Lys
                965                 970                 975

Leu Leu Glu Cys Ala Ser Ile Ser Glu Leu Leu Gln Pro Ile Ile Asn
            980                 985                 990

Gln Ile Asp Ser Leu Phe Lys Asp Gly Asn Trp Tyr Asn Asp Ile Leu
            995                 1000                1005

Pro His Val Thr Tyr Gln Asp Leu Lys Asn Ile Ile Ile Pro Glu Leu
    1010                1015                1020

Pro Lys Leu Lys His Trp Phe Ile Glu Asn Leu Pro Gly Glu Tyr His
1025                1030                1035                1040

Glu Ile Glu Gln Lys Met Lys Glu Ala Leu Lys Tyr Ala Phe Thr Gln
                1045                1050                1055

Leu Asp Glu Lys Asn Leu Ile His Asn Gly His Phe Thr Thr Asn Leu
            1060                1065                1070

Ile Asp Trp Gln Val Glu Gly Asp Ala Gln Met Lys Val Leu Glu Asn
            1075                1080                1085

Asp Ala Leu Ala Leu Gln Leu Phe Asn Trp Asp Ala Asn Ala Ser Gln
    1090                1095                1100

Ser Ile Asn Ile Leu Glu Phe Asp Glu Asp Lys Ala Tyr Lys Leu Arg
1105                1110                1115                1120

Val Tyr Ala Gln Gly Ser Gly Thr Ile Gln Phe Gly Asn Cys Glu Asp
                1125                1130                1135

Glu Ala Ile Gln Phe Asn Thr Asn Ser Phe Ile Tyr Gln Glu Lys Ile
            1140                1145                1150

Val Tyr Phe Asp Thr Pro Ser Val Asn Leu His Ile Gln Ser Glu Gly
            1155                1160                1165

Ser Glu Phe Ile Val Ser Ser Ile Asp Leu Ile Glu Leu Ser Asp Asp
            1170                1175                1180

Gln
```

<210> SEQ ID NO 18
<211> LENGTH: 2112
<212> TYPE: DNA
<213> ORGANISM: Artificial Sequence
<220> FEATURE:
<223> OTHER INFORMATION: axmi-031(m1)truncated
<221> NAME/KEY: CDS
<222> LOCATION: (1)...(2112)

<400> SEQUENCE: 18

```
atg gat tgt aat tta caa tca caa caa aat att cca tat aat gta tta      48
Met Asp Cys Asn Leu Gln Ser Gln Gln Asn Ile Pro Tyr Asn Val Leu
1               5                   10                  15 gca ata cca gta tct aat gtt aat tcg ttg act gat aca gtt gga gat      96
Ala Ile Pro Val Ser Asn Val Asn Ser Leu Thr Asp Thr Val Gly Asp
            20                  25                  30 tta aaa aaa gca tgg gaa gaa ttt caa aaa act ggt tct ttt tca tta     144
Leu Lys Lys Ala Trp Glu Glu Phe Gln Lys Thr Gly Ser Phe Ser Leu
        35                  40                  45 aca gct tta caa caa gga ttt tct gct tca caa gga gga aca ttc aat     192
Thr Ala Leu Gln Gln Gly Phe Ser Ala Ser Gln Gly Gly Thr Phe Asn
    50                  55                  60 tat tta aca tta cta caa tca gga ata tca tta gct ggt tct ttt gtt     240
Tyr Leu Thr Leu Leu Gln Ser Gly Ile Ser Leu Ala Gly Ser Phe Val
65                  70                  75                  80 cct gga ggt act ttt gta gca cct att att aat atg gtt att ggt tgg     288
Pro Gly Gly Thr Phe Val Ala Pro Ile Ile Asn Met Val Ile Gly Trp
                85                  90                  95 tta tgg cca cat aaa aac aaa aat gcg gat aca gaa aat tta ata aat     336
Leu Trp Pro His Lys Asn Lys Asn Ala Asp Thr Glu Asn Leu Ile Asn
            100                 105                 110 tta att gat tca gaa att caa aaa caa tta aac aaa gct tta tta gat     384
Leu Ile Asp Ser Glu Ile Gln Lys Gln Leu Asn Lys Ala Leu Leu Asp
        115                 120                 125 gca gat aga aat gag tgg agc tct tat tta gaa tct ata ttt gat tct     432
Ala Asp Arg Asn Glu Trp Ser Ser Tyr Leu Glu Ser Ile Phe Asp Ser
    130                 135                 140 tca aat aac cta aat ggt gca att gta gat gca cag tgg tca ggc act     480
Ser Asn Asn Leu Asn Gly Ala Ile Val Asp Ala Gln Trp Ser Gly Thr
145                 150                 155                 160 gta aat act aca aat aga aca cta aga aat cca aca gaa tca gat tat     528
Val Asn Thr Thr Asn Arg Thr Leu Arg Asn Pro Thr Glu Ser Asp Tyr
                165                 170                 175 aca aat gtt gtt aca aat ttt att gca gcg gat ggt gac att gca aat     576
Thr Asn Val Val Thr Asn Phe Ile Ala Ala Asp Gly Asp Ile Ala Asn
            180                 185                 190 aat gaa aat cac ata atg aat ggc aac ttt gac gta gct gca gca cct     624
Asn Glu Asn His Ile Met Asn Gly Asn Phe Asp Val Ala Ala Ala Pro
        195                 200                 205 tat ttt gct ata gga gca aca gca cgt ttt gca gca atg caa tct tat     672
Tyr Phe Ala Ile Gly Ala Thr Ala Arg Phe Ala Ala Met Gln Ser Tyr
    210                 215                 220 att aaa ttt tgt aat gct tgg att gat aaa gtt gga ttg agt gac gca     720
Ile Lys Phe Cys Asn Ala Trp Ile Asp Lys Val Gly Leu Ser Asp Ala
225                 230                 235                 240 cag ctt act aca caa aag gct aat tta gat cgc acg aaa caa aat atg     768
Gln Leu Thr Thr Gln Lys Ala Asn Leu Asp Arg Thr Lys Gln Asn Met
                245                 250                 255 cgt aat gca att ctt aac tat aca caa caa gtt atg aaa gtt ttt aaa     816
Arg Asn Ala Ile Leu Asn Tyr Thr Gln Gln Val Met Lys Val Phe Lys
```

```
                    260                 265                 270
gat tcc aaa aat atg cct aca ata ggt act aat aaa ttt agt gtt gat    864
Asp Ser Lys Asn Met Pro Thr Ile Gly Thr Asn Lys Phe Ser Val Asp
        275                 280                 285 acc tat aat gta tat att aaa gga atg aca tta aat gtt tta gat att    912
Thr Tyr Asn Val Tyr Ile Lys Gly Met Thr Leu Asn Val Leu Asp Ile
    290                 295                 300 gta gca ata tgg cct tca tta tat cca gat gat tat act tca caa aca    960
Val Ala Ile Trp Pro Ser Leu Tyr Pro Asp Asp Tyr Thr Ser Gln Thr
305                 310                 315                 320 gcc tta gaa caa aca cgt gtc act ttt tca aat atg gtt ggc caa gaa   1008
Ala Leu Glu Gln Thr Arg Val Thr Phe Ser Asn Met Val Gly Gln Glu
                325                 330                 335 gaa ggt aca gat gga agc cta aga att tac aat act ttt gat tct ttt   1056
Glu Gly Thr Asp Gly Ser Leu Arg Ile Tyr Asn Thr Phe Asp Ser Phe
            340                 345                 350 agt tat caa cat agt cca ata cct aat aat aat gtt aat tta att tct   1104
Ser Tyr Gln His Ser Pro Ile Pro Asn Asn Asn Val Asn Leu Ile Ser
        355                 360                 365 tat tat aat gat gaa tta caa aat cta gaa tta gga gta tat acc cct   1152
Tyr Tyr Asn Asp Glu Leu Gln Asn Leu Glu Leu Gly Val Tyr Thr Pro
    370                 375                 380 cct aaa aaa gga agt gga tac tct tat cct tat gga ttt gtt tta aat   1200
Pro Lys Lys Gly Ser Gly Tyr Ser Tyr Pro Tyr Gly Phe Val Leu Asn
385                 390                 395                 400 tat gca aac agt aaa tat aaa tat ggt gat agc aat gat cca gaa tct   1248
Tyr Ala Asn Ser Lys Tyr Lys Tyr Gly Asp Ser Asn Asp Pro Glu Ser
                405                 410                 415 cta gga gga tta tct aca cta tct gca cct ata caa caa gtt aat gca   1296
Leu Gly Gly Leu Ser Thr Leu Ser Ala Pro Ile Gln Gln Val Asn Ala
            420                 425                 430 gca act caa aac agt aaa tat cta gat gga gaa atc cta aat gga ata   1344
Ala Thr Gln Asn Ser Lys Tyr Leu Asp Gly Glu Ile Leu Asn Gly Ile
        435                 440                 445 gga gca tcc tta cct ggt tat tgt act aca gga tgt tca cca aca gaa   1392
Gly Ala Ser Leu Pro Gly Tyr Cys Thr Thr Gly Cys Ser Pro Thr Glu
    450                 455                 460 cca cct ttt agt tgt act tct acc gct aat ggc tat aaa gca agc tgt   1440
Pro Pro Phe Ser Cys Thr Ser Thr Ala Asn Gly Tyr Lys Ala Ser Cys
465                 470                 475                 480 aat cct tca gat aca aat caa aaa att aac gct tta tat cct ttt aca   1488
Asn Pro Ser Asp Thr Asn Gln Lys Ile Asn Ala Leu Tyr Pro Phe Thr
                485                 490                 495 caa gct aat gta aag gga aac aca gga aaa tta gga gta ctg gca agt   1536
Gln Ala Asn Val Lys Gly Asn Thr Gly Lys Leu Gly Val Leu Ala Ser
            500                 505                 510 ctt gtt tca tat gat tta aat cct aaa aat gta ttt ggt gag tta gat   1584
Leu Val Ser Tyr Asp Leu Asn Pro Lys Asn Val Phe Gly Glu Leu Asp
        515                 520                 525 tca gat aca aat aat gtt atc tta aaa gga att cct gca gaa aaa gga   1632
Ser Asp Thr Asn Asn Val Ile Leu Lys Gly Ile Pro Ala Glu Lys Gly
    530                 535                 540 tat ttt cct aat aat gcg cgt cct act gtt gta aaa gaa tgg att aat   1680
Tyr Phe Pro Asn Asn Ala Arg Pro Thr Val Val Lys Glu Trp Ile Asn
545                 550                 555                 560 ggt gca agt gct gta cca ctt gat tca gga aat acc tta ttt atg acg   1728
Gly Ala Ser Ala Val Pro Leu Asp Ser Gly Asn Thr Leu Phe Met Thr
                565                 570                 575 gct acg aat tta aca gct act caa tat aga att aga ata cgt tat gca   1776
Ala Thr Asn Leu Thr Ala Thr Gln Tyr Arg Ile Arg Ile Arg Tyr Ala
```

```
                    580                 585                 590
aat cca aat tca aat act caa atc ggt gta cga att aca caa aat ggt       1824
Asn Pro Asn Ser Asn Thr Gln Ile Gly Val Arg Ile Thr Gln Asn Gly
        595                 600                 605 tct cta att tcc agt agt aat cta aca ctt tat agt act act gat atg       1872
Ser Leu Ile Ser Ser Ser Asn Leu Thr Leu Tyr Ser Thr Thr Asp Met
610                 615                 620 aat aat act tta cca cta aat gta tat gta ata gga gaa aat gga aat       1920
Asn Asn Thr Leu Pro Leu Asn Val Tyr Val Ile Gly Glu Asn Gly Asn
625                 630                 635                 640 tat aca ctt caa gat tta tat aat act act aat gtt tta tca aca gga       1968
Tyr Thr Leu Gln Asp Leu Tyr Asn Thr Thr Asn Val Leu Ser Thr Gly
            645                 650                 655 gat att aca tta caa att aca gga gga gat caa aaa ata ttt att gat       2016
Asp Ile Thr Leu Gln Ile Thr Gly Gly Asp Gln Lys Ile Phe Ile Asp
        660                 665                 670 cga ata gaa ttt gtt cct act atg cct gta cct ggt aat act aac aac       2064
Arg Ile Glu Phe Val Pro Thr Met Pro Val Pro Gly Asn Thr Asn Asn
    675                 680                 685 aat aac ggt aat aat aac ggt aat aat aat ccc cca cac cac gtc tag       2112
Asn Asn Gly Asn Asn Asn Gly Asn Asn Asn Pro Pro His His Val *
690                 695                 700

<210> SEQ ID NO 19
<211> LENGTH: 703
<212> TYPE: PRT
<213> ORGANISM: Artificial Sequence
<220> FEATURE:
<223> OTHER INFORMATION: AXMI-031(M1)TRUNCATED

<400> SEQUENCE: 19

Met Asp Cys Asn Leu Gln Ser Gln Gln Asn Ile Pro Tyr Asn Val Leu
1               5                   10                  15

Ala Ile Pro Val Ser Asn Val Asn Ser Leu Thr Asp Thr Val Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Thr Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
    130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Ala Ile Gly Ala Thr Ala Arg Phe Ala Ala Met Gln Ser Tyr
```

```
           210                 215                 220
Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
                260                 265                 270

Asp Ser Lys Asn Met Pro Thr Ile Gly Thr Asn Lys Phe Ser Val Asp
                275                 280                 285

Thr Tyr Asn Val Tyr Ile Lys Gly Met Thr Leu Asn Val Leu Asp Ile
                290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                325                 330                 335

Glu Gly Thr Asp Gly Ser Leu Arg Ile Tyr Asn Thr Phe Asp Ser Phe
                340                 345                 350

Ser Tyr Gln His Ser Pro Ile Pro Asn Asn Val Asn Leu Ile Ser
                355                 360                 365

Tyr Tyr Asn Asp Glu Leu Gln Asn Leu Glu Leu Gly Val Tyr Thr Pro
                370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Gln Val Asn Ala
                420                 425                 430

Ala Thr Gln Asn Ser Lys Tyr Leu Asp Gly Glu Ile Leu Asn Gly Ile
                435                 440                 445

Gly Ala Ser Leu Pro Gly Tyr Cys Thr Thr Gly Cys Ser Pro Thr Glu
                450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
                485                 490                 495

Gln Ala Asn Val Lys Gly Asn Thr Gly Lys Leu Gly Val Leu Ala Ser
                500                 505                 510

Leu Val Ser Tyr Asp Leu Asn Pro Lys Asn Val Phe Gly Glu Leu Asp
                515                 520                 525

Ser Asp Thr Asn Asn Val Ile Leu Lys Gly Ile Pro Ala Glu Lys Gly
                530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575

Ala Thr Asn Leu Thr Ala Thr Gln Tyr Arg Ile Arg Ile Arg Tyr Ala
                580                 585                 590

Asn Pro Asn Ser Asn Thr Gln Ile Gly Val Arg Ile Thr Gln Asn Gly
                595                 600                 605

Ser Leu Ile Ser Ser Ser Asn Leu Thr Leu Tyr Ser Thr Thr Asp Met
                610                 615                 620

Asn Asn Thr Leu Pro Leu Asn Val Tyr Val Ile Gly Glu Asn Gly Asn
625                 630                 635                 640
```

```
Tyr Thr Leu Gln Asp Leu Tyr Asn Thr Thr Asn Val Leu Ser Thr Gly
                645                 650                 655

Asp Ile Thr Leu Gln Ile Thr Gly Gly Asp Gln Lys Ile Phe Ile Asp
            660                 665                 670

Arg Ile Glu Phe Val Pro Thr Met Pro Val Pro Gly Asn Thr Asn Asn
        675                 680                 685

Asn Asn Gly Asn Asn Asn Gly Asn Asn Asn Pro Pro His His Val
    690                 695                 700

<210> SEQ ID NO 20
<211> LENGTH: 2219
<212> TYPE: DNA
<213> ORGANISM: Artificial Sequence
<220> FEATURE:
<223> OTHER INFORMATION: axmi-031(A-D)
<221> NAME/KEY: CDS
<222> LOCATION: (1)...(2216)

<400> SEQUENCE: 20 atg gat tgt aat tta caa tca caa caa aat att cca tat aat gta tta      48
Met Asp Cys Asn Leu Gln Ser Gln Gln Asn Ile Pro Tyr Asn Val Leu
1               5                   10                  15 gca ata cca gta tct aat gtt aat tcg ttg act gat aca gtt gga gat      96
Ala Ile Pro Val Ser Asn Val Asn Ser Leu Thr Asp Thr Val Gly Asp
            20                  25                  30 tta aaa aaa gca tgg gaa gaa ttt caa aaa act ggt tct ttt tca tta     144
Leu Lys Lys Ala Trp Glu Glu Phe Gln Lys Thr Gly Ser Phe Ser Leu
        35                  40                  45 aca gct tta caa caa gga ttt tct gct tca caa gga gga aca ttc aat     192
Thr Ala Leu Gln Gln Gly Phe Ser Ala Ser Gln Gly Gly Thr Phe Asn
    50                  55                  60 tat tta aca tta cta caa tca gga ata tca tta gct ggt tct ttt gtt     240
Tyr Leu Thr Leu Leu Gln Ser Gly Ile Ser Leu Ala Gly Ser Phe Val
65                  70                  75                  80 cct gga ggt act ttt gta gca cct att att aat atg gtt att ggt tgg     288
Pro Gly Gly Thr Phe Val Ala Pro Ile Ile Asn Met Val Ile Gly Trp
                85                  90                  95 tta tgg cca cat aaa aac aaa aat gcg gat aca gaa aat tta ata aat     336
Leu Trp Pro His Lys Asn Lys Asn Ala Asp Thr Glu Asn Leu Ile Asn
            100                 105                 110 tta att gat tca gaa att caa aaa caa tta aac aaa gct tta tta gat     384
Leu Ile Asp Ser Glu Ile Gln Lys Gln Leu Asn Lys Ala Leu Leu Asp
        115                 120                 125 gca gat aga aat gag tgg agc tct tat tta gaa tct ata ttt gat tct     432
Ala Asp Arg Asn Glu Trp Ser Ser Tyr Leu Glu Ser Ile Phe Asp Ser
    130                 135                 140 tca aat aac cta aat ggt gca att gta gat gca cag tgg tca ggc act     480
Ser Asn Asn Leu Asn Gly Ala Ile Val Asp Ala Gln Trp Ser Gly Thr
145                 150                 155                 160 gta aat act aca aat aga aca cta aga aat cca aca gaa tca gat tat     528
Val Asn Thr Thr Asn Arg Thr Leu Arg Asn Pro Thr Glu Ser Asp Tyr
                165                 170                 175 aca aat gtt gtt aca aat ttt att gca gcg gat ggt gac att gca aat     576
Thr Asn Val Val Thr Asn Phe Ile Ala Ala Asp Gly Asp Ile Ala Asn
            180                 185                 190 aat gaa aat cac ata atg aat ggc aac ttt gac gta gct gca gca cct     624
Asn Glu Asn His Ile Met Asn Gly Asn Phe Asp Val Ala Ala Ala Pro
        195                 200                 205 tat ttt gtt ata gga gca aca gca cgt ttt gca gca atg caa tct tat     672
Tyr Phe Val Ile Gly Ala Thr Ala Arg Phe Ala Ala Met Gln Ser Tyr
    210                 215                 220
```

```
att aaa ttt tgt aat gct tgg att gat aaa gtt gga ttg agt gac gca      720
Ile Lys Phe Cys Asn Ala Trp Ile Asp Lys Val Gly Leu Ser Asp Ala
225                 230                 235                 240 cag ctt act aca caa aag gct aat tta gat cgc acg aaa caa aat atg      768
Gln Leu Thr Thr Gln Lys Ala Asn Leu Asp Arg Thr Lys Gln Asn Met
            245                 250                 255 cgt aat gca att ctt aac tat aca caa caa gtt atg aaa gtt ttt aaa      816
Arg Asn Ala Ile Leu Asn Tyr Thr Gln Gln Val Met Lys Val Phe Lys
        260                 265                 270 gat tcc aaa aat atg cct aca ata ggt act aat aaa ttt agt gtt gat      864
Asp Ser Lys Asn Met Pro Thr Ile Gly Thr Asn Lys Phe Ser Val Asp
    275                 280                 285 acc tat aat gta tat att aaa gga atg aca tta aat gtt tta gat att      912
Thr Tyr Asn Val Tyr Ile Lys Gly Met Thr Leu Asn Val Leu Asp Ile
290                 295                 300 gta gca ata tgg cct tca tta tat cca gat gat tat act tca caa aca      960
Val Ala Ile Trp Pro Ser Leu Tyr Pro Asp Asp Tyr Thr Ser Gln Thr
305                 310                 315                 320 gcc tta gaa caa aca cgt gtc act ttt tca aat atg gtt ggc caa gaa     1008
Ala Leu Glu Gln Thr Arg Val Thr Phe Ser Asn Met Val Gly Gln Glu
            325                 330                 335 gaa ggt aca gat gga agc cta aga att tac aat act ttt gat tct ttt     1056
Glu Gly Thr Asp Gly Ser Leu Arg Ile Tyr Asn Thr Phe Asp Ser Phe
        340                 345                 350 agt tat caa cat agt cca ata cct aat aat aat gtt aat tta att tct     1104
Ser Tyr Gln His Ser Pro Ile Pro Asn Asn Asn Val Asn Leu Ile Ser
    355                 360                 365 tat tat aat gat gaa tta caa aat cta gaa tta gga gta tat acc cct     1152
Tyr Tyr Asn Asp Glu Leu Gln Asn Leu Glu Leu Gly Val Tyr Thr Pro
370                 375                 380 cct aaa aaa gga agt gga tac tct tat cct tat gga ttt gtt tta aat     1200
Pro Lys Lys Gly Ser Gly Tyr Ser Tyr Pro Tyr Gly Phe Val Leu Asn
385                 390                 395                 400 tat gca aac agt aaa tat aaa tat ggt gat agc aat gat cca gaa tct     1248
Tyr Ala Asn Ser Lys Tyr Lys Tyr Gly Asp Ser Asn Asp Pro Glu Ser
            405                 410                 415 cta gga gga tta tct aca cta tct gca cct ata caa caa gtt aat gca     1296
Leu Gly Gly Leu Ser Thr Leu Ser Ala Pro Ile Gln Gln Val Asn Ala
        420                 425                 430 gca act caa aac agt aaa tat cta gat gga gaa atc cta aat gga ata     1344
Ala Thr Gln Asn Ser Lys Tyr Leu Asp Gly Glu Ile Leu Asn Gly Ile
    435                 440                 445 gga gca tcc tta cct ggt tat tgt act aca gga tgt tca cca aca gaa     1392
Gly Ala Ser Leu Pro Gly Tyr Cys Thr Thr Gly Cys Ser Pro Thr Glu
450                 455                 460 cca cct ttt agt tgt act tct acc gct aat ggc tat aaa gca agc tgt     1440
Pro Pro Phe Ser Cys Thr Ser Thr Ala Asn Gly Tyr Lys Ala Ser Cys
465                 470                 475                 480 aat cct tca gat aca aat caa aaa att aac gct tta tat cct ttt aca     1488
Asn Pro Ser Asp Thr Asn Gln Lys Ile Asn Ala Leu Tyr Pro Phe Thr
            485                 490                 495 caa gct aat gta aag gga aac aca gga aaa tta gga gta ctg gca agt     1536
Gln Ala Asn Val Lys Gly Asn Thr Gly Lys Leu Gly Val Leu Ala Ser
        500                 505                 510 ctt gtt tca tat gat tta aat cct aaa aat gta ttt ggt gaa tta gat     1584
Leu Val Ser Tyr Asp Leu Asn Pro Lys Asn Val Phe Gly Glu Leu Asp
    515                 520                 525 tca gat aca aat aat gtt atc tta aaa gga att cct gca gaa aaa gga     1632
Ser Asp Thr Asn Asn Val Ile Leu Lys Gly Ile Pro Ala Glu Lys Gly
530                 535                 540
```

-continued

| | | | | | | | | | | | | | | | | |
|---|---|---|---|---|---|---|---|---|---|---|---|---|---|---|---|---|
| tat | ttt | cct | aat | aat | gcg | cgt | cct | act | gtt | gta | aaa | gaa | tgg | att | aat | 1680 |
| Tyr | Phe | Pro | Asn | Asn | Ala | Arg | Pro | Thr | Val | Val | Lys | Glu | Trp | Ile | Asn | |
| 545 | | | | 550 | | | | | 555 | | | | | 560 | | |
| ggt | gca | agt | gct | gta | cca | ctt | gat | tca | gga | aat | acc | tta | ttt | atg | acg | 1728 |
| Gly | Ala | Ser | Ala | Val | Pro | Leu | Asp | Ser | Gly | Asn | Thr | Leu | Phe | Met | Thr | |
| | | | | 565 | | | | | 570 | | | | | 575 | | |
| gct | acg | aat | tta | aca | gct | act | caa | tat | aga | att | aga | ata | cgt | tat | gca | 1776 |
| Ala | Thr | Asn | Leu | Thr | Ala | Thr | Gln | Tyr | Arg | Ile | Arg | Ile | Arg | Tyr | Ala | |
| | | | 580 | | | | | 585 | | | | | 590 | | | |
| aat | cca | aat | tca | aat | act | caa | atc | ggt | gta | cga | att | aca | caa | aat | ggt | 1824 |
| Asn | Pro | Asn | Ser | Asn | Thr | Gln | Ile | Gly | Val | Arg | Ile | Thr | Gln | Asn | Gly | |
| | | | 595 | | | | | 600 | | | | | 605 | | | |
| tct | cta | att | tcc | agt | agt | aat | cta | aca | ctt | tat | agt | act | act | gat | atg | 1872 |
| Ser | Leu | Ile | Ser | Ser | Ser | Asn | Leu | Thr | Leu | Tyr | Ser | Thr | Thr | Asp | Met | |
| | 610 | | | | | 615 | | | | | 620 | | | | | |
| aat | aat | act | tta | cca | cta | aat | gta | tat | gta | ata | gga | gaa | aat | gga | aat | 1920 |
| Asn | Asn | Thr | Leu | Pro | Leu | Asn | Val | Tyr | Val | Ile | Gly | Glu | Asn | Gly | Asn | |
| 625 | | | | | 630 | | | | | 635 | | | | | 640 | |
| tat | aca | ctt | caa | gat | tta | tat | aat | act | act | aat | gtt | tta | tca | aca | gga | 1968 |
| Tyr | Thr | Leu | Gln | Asp | Leu | Tyr | Asn | Thr | Thr | Asn | Val | Leu | Ser | Thr | Gly | |
| | | | | 645 | | | | | 650 | | | | | 655 | | |
| gat | att | aca | tta | caa | att | aca | gga | gga | gat | caa | aaa | ata | ttt | att | gat | 2016 |
| Asp | Ile | Thr | Leu | Gln | Ile | Thr | Gly | Gly | Asp | Gln | Lys | Ile | Phe | Ile | Asp | |
| | | | 660 | | | | | 665 | | | | | 670 | | | |
| cga | ata | gaa | ttt | gtt | cct | act | atg | cct | gta | cct | ggt | aat | act | aac | aac | 2064 |
| Arg | Ile | Glu | Phe | Val | Pro | Thr | Met | Pro | Val | Pro | Gly | Asn | Thr | Asn | Asn | |
| | | 675 | | | | | 680 | | | | | 685 | | | | |
| aat | aac | ggt | aat | aat | aac | ggt | aat | aat | aat | ccc | cca | cac | cac | gtt | tgt | 2112 |
| Asn | Asn | Gly | Asn | Asn | Asn | Gly | Asn | Asn | Asn | Pro | Pro | His | His | Val | Cys | |
| 690 | | | | | 695 | | | | | 700 | | | | | | |
| gca | ata | gct | ggt | aca | caa | caa | tct | tgt | tct | gga | ccg | ccc | aaa | ttt | gaa | 2160 |
| Ala | Ile | Ala | Gly | Thr | Gln | Gln | Ser | Cys | Ser | Gly | Pro | Pro | Lys | Phe | Glu | |
| 705 | | | | 710 | | | | | 715 | | | | | 720 | | |
| caa | gta | agt | gat | tta | gaa | aaa | att | aca | aca | caa | gta | tat | atg | tta | ttc | 2208 |
| Gln | Val | Ser | Asp | Leu | Glu | Lys | Ile | Thr | Thr | Gln | Val | Tyr | Met | Leu | Phe | |
| | | | 725 | | | | | 730 | | | | | 735 | | | |
| aaa | tct | ta tag | | | | | | | | | | | | | | 2219 |
| Lys | Ser | | | | | | | | | | | | | | | |

<210> SEQ ID NO 21
<211> LENGTH: 738
<212> TYPE: PRT
<213> ORGANISM: Artificial Sequence
<220> FEATURE:
<223> OTHER INFORMATION: AXMI-031(A-D)

<400> SEQUENCE: 21

Met Asp Cys Asn Leu Gln Ser Gln Gln Asn Ile Pro Tyr Asn Val Leu
1               5                   10                  15

Ala Ile Pro Val Ser Asn Val Asn Ser Leu Thr Asp Thr Val Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Thr Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn

-continued

```
                100                 105                 110
Leu Ile Asp Ser Glu Ile Gln Lys Gln Leu Asn Lys Ala Leu Leu Asp
            115                 120                 125

Ala Asp Arg Asn Glu Trp Ser Ser Tyr Leu Glu Ser Ile Phe Asp Ser
        130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Val Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
    290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Val Asn Leu Ile Ser
        355                 360                 365

Tyr Tyr Asn Asp Glu Leu Gln Asn Leu Glu Leu Gly Val Tyr Thr Pro
    370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Gln Val Asn Ala
            420                 425                 430

Ala Thr Gln Asn Ser Lys Tyr Leu Asp Gly Glu Ile Leu Asn Gly Ile
        435                 440                 445

Gly Ala Ser Leu Pro Gly Tyr Cys Thr Thr Gly Cys Ser Pro Thr Glu
    450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
                485                 490                 495

Gln Ala Asn Val Lys Gly Asn Thr Gly Lys Leu Gly Val Leu Ala Ser
            500                 505                 510

Leu Val Ser Tyr Asp Leu Asn Pro Lys Asn Val Phe Gly Glu Leu Asp
        515                 520                 525
```

```
Ser Asp Thr Asn Asn Val Ile Leu Lys Gly Ile Pro Ala Glu Lys Gly
    530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575

Ala Thr Asn Leu Thr Ala Thr Gln Tyr Arg Ile Arg Ile Arg Tyr Ala
            580                 585                 590

Asn Pro Asn Ser Asn Thr Gln Ile Gly Val Arg Ile Thr Gln Asn Gly
        595                 600                 605

Ser Leu Ile Ser Ser Ser Asn Leu Thr Leu Tyr Ser Thr Thr Asp Met
    610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Asn Val Leu Ser Thr Gly
                645                 650                 655

Asp Ile Thr Leu Gln Ile Thr Gly Gly Asp Gln Lys Ile Phe Ile Asp
            660                 665                 670

Arg Ile Glu Phe Val Pro Thr Met Pro Val Pro Gly Asn Thr Asn Asn
        675                 680                 685

Asn Asn Gly Asn Asn Asn Gly Asn Asn Asn Pro Pro His His Val Cys
690                 695                 700

Ala Ile Ala Gly Thr Gln Gln Ser Cys Ser Gly Pro Pro Lys Phe Glu
705                 710                 715                 720

Gln Val Ser Asp Leu Glu Lys Ile Thr Thr Gln Val Tyr Met Leu Phe
                725                 730                 735

Lys Ser

<210> SEQ ID NO 22
<211> LENGTH: 2015
<212> TYPE: DNA
<213> ORGANISM: Artificial Sequence
<220> FEATURE:
<223> OTHER INFORMATION: axmi-031(B-C)
<221> NAME/KEY: CDS
<222> LOCATION: (1)...(2012)

<400> SEQUENCE: 22 atg gca ata cca gta tct aat gtt aat tcg ttg act gat aca gtt gga      48
Met Ala Ile Pro Val Ser Asn Val Asn Ser Leu Thr Asp Thr Val Gly
1               5                   10                  15 gat tta aaa aaa gca tgg gaa gaa ttt caa aaa act ggt tct ttt tca      96
Asp Leu Lys Lys Ala Trp Glu Glu Phe Gln Lys Thr Gly Ser Phe Ser
            20                  25                  30 tta aca gct tta caa caa gga ttt tct gct tca caa gga gga aca ttc     144
Leu Thr Ala Leu Gln Gln Gly Phe Ser Ala Ser Gln Gly Gly Thr Phe
        35                  40                  45 aat tat tta aca tta cta caa tca gga ata tca tta gct ggt tct ttt     192
Asn Tyr Leu Thr Leu Leu Gln Ser Gly Ile Ser Leu Ala Gly Ser Phe
    50                  55                  60 gtt cct gga ggt act ttt gta gca cct att att aat atg gtt att ggt     240
Val Pro Gly Gly Thr Phe Val Ala Pro Ile Ile Asn Met Val Ile Gly
65                  70                  75                  80 tgg tta tgg cca cat aaa aac aaa aat gcg gat aca gaa aat tta ata     288
Trp Leu Trp Pro His Lys Asn Lys Asn Ala Asp Thr Glu Asn Leu Ile
                85                  90                  95 aat tta att gat tca gaa att caa aaa caa tta aac aaa gct tta tta     336
Asn Leu Ile Asp Ser Glu Ile Gln Lys Gln Leu Asn Lys Ala Leu Leu
            100                 105                 110
```

```
gat gca gat aga aat gag tgg agc tct tat tta gaa tct ata ttt gat      384
Asp Ala Asp Arg Asn Glu Trp Ser Ser Tyr Leu Glu Ser Ile Phe Asp
        115                 120                 125 tct tca aat aac cta aat ggt gca att gta gat gca cag tgg tca ggc      432
Ser Ser Asn Asn Leu Asn Gly Ala Ile Val Asp Ala Gln Trp Ser Gly
130                 135                 140 act gta aat act aca aat aga aca cta aga aat cca aca gaa tca gat      480
Thr Val Asn Thr Thr Asn Arg Thr Leu Arg Asn Pro Thr Glu Ser Asp
145                 150                 155                 160 tat aca aat gtt gtt aca aat ttt att gca gcg gat ggt gac att gca      528
Tyr Thr Asn Val Val Thr Asn Phe Ile Ala Ala Asp Gly Asp Ile Ala
            165                 170                 175 aat aat gaa aat cac ata atg aat ggc aac ttt gac gta gct gca gca      576
Asn Asn Glu Asn His Ile Met Asn Gly Asn Phe Asp Val Ala Ala Ala
        180                 185                 190 cct tat ttt gtt ata gga gca aca gca cgt ttt gca gca atg caa tct      624
Pro Tyr Phe Val Ile Gly Ala Thr Ala Arg Phe Ala Ala Met Gln Ser
        195                 200                 205 tat att aaa ttt tgt aat gct tgg att gat aaa gtt gga ttg agt gac      672
Tyr Ile Lys Phe Cys Asn Ala Trp Ile Asp Lys Val Gly Leu Ser Asp
        210                 215                 220 gca cag ctt act aca caa aag gct aat tta gat cgc acg aaa caa aat      720
Ala Gln Leu Thr Thr Gln Lys Ala Asn Leu Asp Arg Thr Lys Gln Asn
225                 230                 235                 240 atg cgt aat gca att ctt aac tat aca caa caa gtt atg aaa gtt ttt      768
Met Arg Asn Ala Ile Leu Asn Tyr Thr Gln Gln Val Met Lys Val Phe
            245                 250                 255 aaa gat tcc aaa aat atg cct aca ata ggt act aat aaa ttt agt gtt      816
Lys Asp Ser Lys Asn Met Pro Thr Ile Gly Thr Asn Lys Phe Ser Val
        260                 265                 270 gat acc tat aat gta tat att aaa gga atg aca tta aat gtt tta gat      864
Asp Thr Tyr Asn Val Tyr Ile Lys Gly Met Thr Leu Asn Val Leu Asp
        275                 280                 285 att gta gca ata tgg cct tca tta tat cca gat gat tat act tca caa      912
Ile Val Ala Ile Trp Pro Ser Leu Tyr Pro Asp Asp Tyr Thr Ser Gln
        290                 295                 300 aca gcc tta gaa caa aca cgt gtc act ttt tca aat atg gtt ggc caa      960
Thr Ala Leu Glu Gln Thr Arg Val Thr Phe Ser Asn Met Val Gly Gln
305                 310                 315                 320 gaa gaa ggt aca gat gga agc cta aga att tac aat act ttt gat tct     1008
Glu Glu Gly Thr Asp Gly Ser Leu Arg Ile Tyr Asn Thr Phe Asp Ser
            325                 330                 335 ttt agt tat caa cat agt cca ata cct aat aat aat gtt aat tta att     1056
Phe Ser Tyr Gln His Ser Pro Ile Pro Asn Asn Asn Val Asn Leu Ile
        340                 345                 350 tct tat tat aat gat gaa tta caa aat cta gaa tta gga gta tat acc     1104
Ser Tyr Tyr Asn Asp Glu Leu Gln Asn Leu Glu Leu Gly Val Tyr Thr
        355                 360                 365 cct cct aaa aaa gga agt gga tac tct tat cct tat gga ttt gtt tta     1152
Pro Pro Lys Lys Gly Ser Gly Tyr Ser Tyr Pro Tyr Gly Phe Val Leu
370                 375                 380 aat tat gca aac agt aaa tat aaa tat ggt gat agc aat gat cca gaa     1200
Asn Tyr Ala Asn Ser Lys Tyr Lys Tyr Gly Asp Ser Asn Asp Pro Glu
385                 390                 395                 400 tct cta gga gga tta tct aca cta tct gca cct ata caa caa gtt aat     1248
Ser Leu Gly Gly Leu Ser Thr Leu Ser Ala Pro Ile Gln Gln Val Asn
            405                 410                 415 gca gca act caa aac agt aaa tat cta gat gga gaa atc cta aat gga     1296
Ala Ala Thr Gln Asn Ser Lys Tyr Leu Asp Gly Glu Ile Leu Asn Gly
        420                 425                 430
```

```
ata gga gca tcc tta cct ggt tat tgt act aca gga tgt tca cca aca      1344
Ile Gly Ala Ser Leu Pro Gly Tyr Cys Thr Thr Gly Cys Ser Pro Thr
            435                 440                 445 gaa cca cct ttt agt tgt act tct acc gct aat ggc tat aaa gca agc      1392
Glu Pro Pro Phe Ser Cys Thr Ser Thr Ala Asn Gly Tyr Lys Ala Ser
        450                 455                 460 tgt aat cct tca gat aca aat caa aaa att aac gct tta tat cct ttt      1440
Cys Asn Pro Ser Asp Thr Asn Gln Lys Ile Asn Ala Leu Tyr Pro Phe
465                 470                 475                 480 aca caa gct aat gta aag gga aac aca gga aaa tta gga gta ctg gca      1488
Thr Gln Ala Asn Val Lys Gly Asn Thr Gly Lys Leu Gly Val Leu Ala
                485                 490                 495 agt ctt gtt tca tat gat tta aat cct aaa aat gta ttt ggt gaa tta      1536
Ser Leu Val Ser Tyr Asp Leu Asn Pro Lys Asn Val Phe Gly Glu Leu
            500                 505                 510 gat tca gat aca aat aat gtt atc tta aaa gga att cct gca gaa aaa      1584
Asp Ser Asp Thr Asn Asn Val Ile Leu Lys Gly Ile Pro Ala Glu Lys
        515                 520                 525 gga tat ttt cct aat aat gcg cgt cct act gtt gta aaa gaa tgg att      1632
Gly Tyr Phe Pro Asn Asn Ala Arg Pro Thr Val Val Lys Glu Trp Ile
530                 535                 540 aat ggt gca agt gct gta cca ctt gat tca gga aat acc tta ttt atg      1680
Asn Gly Ala Ser Ala Val Pro Leu Asp Ser Gly Asn Thr Leu Phe Met
545                 550                 555                 560 acg gct acg aat tta aca gct act caa tat aga att aga ata cgt tat      1728
Thr Ala Thr Asn Leu Thr Ala Thr Gln Tyr Arg Ile Arg Ile Arg Tyr
                565                 570                 575 gca aat cca aat tca aat act caa atc ggt gta cga att aca caa aat      1776
Ala Asn Pro Asn Ser Asn Thr Gln Ile Gly Val Arg Ile Thr Gln Asn
            580                 585                 590 ggt tct cta att tcc agt agt aat cta aca ctt tat agt act act gat      1824
Gly Ser Leu Ile Ser Ser Ser Asn Leu Thr Leu Tyr Ser Thr Thr Asp
        595                 600                 605 atg aat aat act tta cca cta aat gta tat gta ata gga gaa aat gga      1872
Met Asn Asn Thr Leu Pro Leu Asn Val Tyr Val Ile Gly Glu Asn Gly
    610                 615                 620 aat tat aca ctt caa gat tta tat aat act act aat gtt tta tca aca      1920
Asn Tyr Thr Leu Gln Asp Leu Tyr Asn Thr Thr Asn Val Leu Ser Thr
625                 630                 635                 640 gga gat att aca tta caa att aca gga gga gat caa aaa ata ttt att      1968
Gly Asp Ile Thr Leu Gln Ile Thr Gly Gly Asp Gln Lys Ile Phe Ile
                645                 650                 655 gat cga ata gaa ttt gtt cct act atg cct gta cct ggt aat ta           2012
Asp Arg Ile Glu Phe Val Pro Thr Met Pro Val Pro Gly Asn
            660                 665                 670 tag                                                                   2015

<210> SEQ ID NO 23
<211> LENGTH: 670
<212> TYPE: PRT
<213> ORGANISM: Artificial Sequence
<220> FEATURE:
<223> OTHER INFORMATION: AXMI-031(B-C)

<400> SEQUENCE: 23

Met Ala Ile Pro Val Ser Asn Val Asn Ser Leu Thr Asp Thr Val Gly
  1               5                  10                  15

Asp Leu Lys Lys Ala Trp Glu Glu Phe Gln Lys Thr Gly Ser Phe Ser
             20                  25                  30

Leu Thr Ala Leu Gln Gln Gly Phe Ser Ala Ser Gln Gly Gly Thr Phe
```

-continued

```
               35                  40                  45
Asn Tyr Leu Thr Leu Leu Gln Ser Gly Ile Ser Leu Ala Gly Ser Phe
 50                  55                  60
Val Pro Gly Gly Thr Phe Val Ala Pro Ile Ile Asn Met Val Ile Gly
 65                  70                  75                  80
Trp Leu Trp Pro His Lys Asn Lys Asn Ala Asp Thr Glu Asn Leu Ile
                 85                  90                  95
Asn Leu Ile Asp Ser Glu Ile Gln Lys Gln Leu Asn Lys Ala Leu Leu
                100                 105                 110
Asp Ala Asp Arg Asn Glu Trp Ser Ser Tyr Leu Glu Ser Ile Phe Asp
                115                 120                 125
Ser Ser Asn Asn Leu Asn Gly Ala Ile Val Asp Ala Gln Trp Ser Gly
                130                 135                 140
Thr Val Asn Thr Thr Asn Arg Thr Leu Arg Asn Pro Thr Glu Ser Asp
145                 150                 155                 160
Tyr Thr Asn Val Val Thr Asn Phe Ile Ala Ala Asp Gly Asp Ile Ala
                165                 170                 175
Asn Asn Glu Asn His Ile Met Asn Gly Asn Phe Asp Val Ala Ala Ala
                180                 185                 190
Pro Tyr Phe Val Ile Gly Ala Thr Ala Arg Phe Ala Ala Met Gln Ser
                195                 200                 205
Tyr Ile Lys Phe Cys Asn Ala Trp Ile Asp Lys Val Gly Leu Ser Asp
                210                 215                 220
Ala Gln Leu Thr Thr Gln Lys Ala Asn Leu Asp Arg Thr Lys Gln Asn
225                 230                 235                 240
Met Arg Asn Ala Ile Leu Asn Tyr Thr Gln Gln Val Met Lys Val Phe
                245                 250                 255
Lys Asp Ser Lys Asn Met Pro Thr Ile Gly Thr Asn Lys Phe Ser Val
                260                 265                 270
Asp Thr Tyr Asn Val Tyr Ile Lys Gly Met Thr Leu Asn Val Leu Asp
                275                 280                 285
Ile Val Ala Ile Trp Pro Ser Leu Tyr Pro Asp Asp Tyr Thr Ser Gln
290                 295                 300
Thr Ala Leu Glu Gln Thr Arg Val Thr Phe Ser Asn Met Val Gly Gln
305                 310                 315                 320
Glu Glu Gly Thr Asp Gly Ser Leu Arg Ile Tyr Asn Thr Phe Asp Ser
                325                 330                 335
Phe Ser Tyr Gln His Ser Pro Ile Pro Asn Asn Asn Val Asn Leu Ile
                340                 345                 350
Ser Tyr Tyr Asn Asp Glu Leu Gln Asn Leu Glu Leu Gly Val Tyr Thr
                355                 360                 365
Pro Pro Lys Lys Gly Ser Gly Tyr Ser Tyr Pro Tyr Gly Phe Val Leu
370                 375                 380
Asn Tyr Ala Asn Ser Lys Tyr Tyr Gly Asp Ser Asn Asp Pro Glu
385                 390                 395                 400
Ser Leu Gly Gly Leu Ser Thr Leu Ser Ala Pro Ile Gln Gln Val Asn
                405                 410                 415
Ala Ala Thr Gln Asn Ser Lys Tyr Leu Asp Gly Glu Ile Leu Asn Gly
                420                 425                 430
Ile Gly Ala Ser Leu Pro Gly Tyr Cys Thr Thr Gly Cys Ser Pro Thr
                435                 440                 445
Glu Pro Pro Phe Ser Cys Thr Ser Thr Ala Asn Gly Tyr Lys Ala Ser
450                 455                 460
```

```
Cys Asn Pro Ser Asp Thr Asn Gln Lys Ile Asn Ala Leu Tyr Pro Phe
465                 470                 475                 480

Thr Gln Ala Asn Val Lys Gly Asn Thr Gly Lys Leu Gly Val Leu Ala
            485                 490                 495

Ser Leu Val Ser Tyr Asp Leu Asn Pro Lys Asn Val Phe Gly Glu Leu
        500                 505                 510

Asp Ser Asp Thr Asn Asn Val Ile Leu Lys Gly Ile Pro Ala Glu Lys
    515                 520                 525

Gly Tyr Phe Pro Asn Asn Ala Arg Pro Thr Val Val Lys Glu Trp Ile
530                 535                 540

Asn Gly Ala Ser Ala Val Pro Leu Asp Ser Gly Asn Thr Leu Phe Met
545                 550                 555                 560

Thr Ala Thr Asn Leu Thr Ala Thr Gln Tyr Arg Ile Arg Ile Arg Tyr
                565                 570                 575

Ala Asn Pro Asn Ser Asn Thr Gln Ile Gly Val Arg Ile Thr Gln Asn
            580                 585                 590

Gly Ser Leu Ile Ser Ser Ser Asn Leu Thr Leu Tyr Ser Thr Thr Asp
        595                 600                 605

Met Asn Asn Thr Leu Pro Leu Asn Val Tyr Val Ile Gly Glu Asn Gly
    610                 615                 620

Asn Tyr Thr Leu Gln Asp Leu Tyr Asn Thr Thr Asn Val Leu Ser Thr
625                 630                 635                 640

Gly Asp Ile Thr Leu Gln Ile Thr Gly Gly Asp Gln Lys Ile Phe Ile
                645                 650                 655

Asp Arg Ile Glu Phe Val Pro Thr Met Pro Val Pro Gly Asn
            660                 665                 670

<210> SEQ ID NO 24
<211> LENGTH: 2174
<212> TYPE: DNA
<213> ORGANISM: Artificial Sequence
<220> FEATURE:
<223> OTHER INFORMATION: axmi-031(B-D)
<221> NAME/KEY: CDS
<222> LOCATION: (1)...(2171)

<400> SEQUENCE: 24 atg gca ata cca gta tct aat gtt aat tcg ttg act gat aca gtt gga     48
Met Ala Ile Pro Val Ser Asn Val Asn Ser Leu Thr Asp Thr Val Gly
1               5                   10                  15 gat tta aaa aaa gca tgg gaa gaa ttt caa aaa act ggt tct ttt tca     96
Asp Leu Lys Lys Ala Trp Glu Glu Phe Gln Lys Thr Gly Ser Phe Ser
            20                  25                  30 tta aca gct tta caa caa gga ttt tct gct tca caa gga gga aca ttc    144
Leu Thr Ala Leu Gln Gln Gly Phe Ser Ala Ser Gln Gly Gly Thr Phe
        35                  40                  45 aat tat tta aca tta cta caa tca gga ata tca tta gct ggt tct ttt    192
Asn Tyr Leu Thr Leu Leu Gln Ser Gly Ile Ser Leu Ala Gly Ser Phe
    50                  55                  60 gtt cct gga ggt act ttt gta gca cct att att aat atg gtt att ggt    240
Val Pro Gly Gly Thr Phe Val Ala Pro Ile Ile Asn Met Val Ile Gly
65                  70                  75                  80 tgg tta tgg cca cat aaa aac aaa aat gcg gat aca gaa aat tta ata    288
Trp Leu Trp Pro His Lys Asn Lys Asn Ala Asp Thr Glu Asn Leu Ile
                85                  90                  95 aat tta att gat tca gaa att caa aaa caa tta aac aaa gct tta tta    336
Asn Leu Ile Asp Ser Glu Ile Gln Lys Gln Leu Asn Lys Ala Leu Leu
            100                 105                 110 gat gca gat aga aat gag tgg agc tct tat tta gaa tct ata ttt gat    384
```

```
                Asp Ala Asp Arg Asn Glu Trp Ser Ser Tyr Leu Glu Ser Ile Phe Asp
                            115                 120                 125 tct tca aat aac cta aat ggt gca att gta gat gca cag tgg tca ggc       432
Ser Ser Asn Asn Leu Asn Gly Ala Ile Val Asp Ala Gln Trp Ser Gly
130                 135                 140 act gta aat act aca aat aga aca cta aga aat cca aca gaa tca gat       480
Thr Val Asn Thr Thr Asn Arg Thr Leu Arg Asn Pro Thr Glu Ser Asp
145                 150                 155                 160 tat aca aat gtt gtt aca aat ttt att gca gcg gat ggt gac att gca       528
Tyr Thr Asn Val Val Thr Asn Phe Ile Ala Ala Asp Gly Asp Ile Ala
            165                 170                 175 aat aat gaa aat cac ata atg aat ggc aac ttt gac gta gct gca gca       576
Asn Asn Glu Asn His Ile Met Asn Gly Asn Phe Asp Val Ala Ala Ala
            180                 185                 190 cct tat ttt gtt ata gga gca aca gca cgt ttt gca gca atg caa tct       624
Pro Tyr Phe Val Ile Gly Ala Thr Ala Arg Phe Ala Ala Met Gln Ser
            195                 200                 205 tat att aaa ttt tgt aat gct tgg att gat aaa gtt gga ttg agt gac       672
Tyr Ile Lys Phe Cys Asn Ala Trp Ile Asp Lys Val Gly Leu Ser Asp
210                 215                 220 gca cag ctt act aca caa aag gct aat tta gat cgc acg aaa caa aat       720
Ala Gln Leu Thr Thr Gln Lys Ala Asn Leu Asp Arg Thr Lys Gln Asn
225                 230                 235                 240 atg cgt aat gca att ctt aac tat aca caa caa gtt atg aaa gtt ttt       768
Met Arg Asn Ala Ile Leu Asn Tyr Thr Gln Gln Val Met Lys Val Phe
            245                 250                 255 aaa gat tcc aaa aat atg cct aca ata ggt act aat aaa ttt agt gtt       816
Lys Asp Ser Lys Asn Met Pro Thr Ile Gly Thr Asn Lys Phe Ser Val
            260                 265                 270 gat acc tat aat gta tat att aaa gga atg aca tta aat gtt tta gat       864
Asp Thr Tyr Asn Val Tyr Ile Lys Gly Met Thr Leu Asn Val Leu Asp
            275                 280                 285 att gta gca ata tgg cct tca tta tat cca gat gat tat act tca caa       912
Ile Val Ala Ile Trp Pro Ser Leu Tyr Pro Asp Asp Tyr Thr Ser Gln
290                 295                 300 aca gcc tta gaa caa aca cgt gtc act ttt tca aat atg gtt ggc caa       960
Thr Ala Leu Glu Gln Thr Arg Val Thr Phe Ser Asn Met Val Gly Gln
305                 310                 315                 320 gaa gaa ggt aca gat gga agc cta aga att tac aat act ttt gat tct      1008
Glu Glu Gly Thr Asp Gly Ser Leu Arg Ile Tyr Asn Thr Phe Asp Ser
            325                 330                 335 ttt agt tat caa cat agt cca ata cct aat aat aat gtt aat tta att      1056
Phe Ser Tyr Gln His Ser Pro Ile Pro Asn Asn Asn Val Asn Leu Ile
            340                 345                 350 tct tat tat aat gat gaa tta caa aat cta gaa tta gga gta tat acc      1104
Ser Tyr Tyr Asn Asp Glu Leu Gln Asn Leu Glu Leu Gly Val Tyr Thr
            355                 360                 365 cct cct aaa aaa gga agt gga tac tct tat cct tat gga ttt gtt tta      1152
Pro Pro Lys Lys Gly Ser Gly Tyr Ser Tyr Pro Tyr Gly Phe Val Leu
370                 375                 380 aat tat gca aac agt aaa tat aaa tat ggt gat agc aat gat cca gaa      1200
Asn Tyr Ala Asn Ser Lys Tyr Lys Tyr Gly Asp Ser Asn Asp Pro Glu
385                 390                 395                 400 tct cta gga gga tta tct aca cta tct gca cct ata caa caa gtt aat      1248
Ser Leu Gly Gly Leu Ser Thr Leu Ser Ala Pro Ile Gln Gln Val Asn
            405                 410                 415 gca gca act caa aac agt aaa tat cta gat gga gaa atc cta aat gga      1296
Ala Ala Thr Gln Asn Ser Lys Tyr Leu Asp Gly Glu Ile Leu Asn Gly
            420                 425                 430 ata gga gca tcc tta cct ggt tat tgt act aca gga tgt tca cca aca      1344
```

```
                Ile Gly Ala Ser Leu Pro Gly Tyr Cys Thr Thr Gly Cys Ser Pro Thr
                            435                 440                 445 gaa cca cct ttt agt tgt act tct acc gct aat ggc tat aaa gca agc            1392
Glu Pro Pro Phe Ser Cys Thr Ser Thr Ala Asn Gly Tyr Lys Ala Ser
450                 455                 460 tgt aat cct tca gat aca aat caa aaa att aac gct tta tat cct ttt            1440
Cys Asn Pro Ser Asp Thr Asn Gln Lys Ile Asn Ala Leu Tyr Pro Phe
465                 470                 475                 480 aca caa gct aat gta aag gga aac aca gga aaa tta gga gta ctg gca            1488
Thr Gln Ala Asn Val Lys Gly Asn Thr Gly Lys Leu Gly Val Leu Ala
                485                 490                 495 agt ctt gtt tca tat gat tta aat cct aaa aat gta ttt ggt gaa tta            1536
Ser Leu Val Ser Tyr Asp Leu Asn Pro Lys Asn Val Phe Gly Glu Leu
            500                 505                 510 gat tca gat aca aat aat gtt atc tta aaa gga att cct gca gaa aaa            1584
Asp Ser Asp Thr Asn Asn Val Ile Leu Lys Gly Ile Pro Ala Glu Lys
        515                 520                 525 gga tat ttt cct aat aat gcg cgt cct act gtt gta aaa gaa tgg att            1632
Gly Tyr Phe Pro Asn Asn Ala Arg Pro Thr Val Val Lys Glu Trp Ile
    530                 535                 540 aat ggt gca agt gct gta cca ctt gat tca gga aat acc tta ttt atg            1680
Asn Gly Ala Ser Ala Val Pro Leu Asp Ser Gly Asn Thr Leu Phe Met
545                 550                 555                 560 acg gct acg aat tta aca gct act caa tat aga att aga ata cgt tat            1728
Thr Ala Thr Asn Leu Thr Ala Thr Gln Tyr Arg Ile Arg Ile Arg Tyr
                565                 570                 575 gca aat cca aat tca aat act caa atc ggt gta cga att aca caa aat            1776
Ala Asn Pro Asn Ser Asn Thr Gln Ile Gly Val Arg Ile Thr Gln Asn
            580                 585                 590 ggt tct cta att tcc agt agt aat cta aca ctt tat agt act act gat            1824
Gly Ser Leu Ile Ser Ser Ser Asn Leu Thr Leu Tyr Ser Thr Thr Asp
        595                 600                 605 atg aat aat act tta cca cta aat gta tat gta ata gga gaa aat gga            1872
Met Asn Asn Thr Leu Pro Leu Asn Val Tyr Val Ile Gly Glu Asn Gly
    610                 615                 620 aat tat aca ctt caa gat tta tat aat act act aat gtt tta tca aca            1920
Asn Tyr Thr Leu Gln Asp Leu Tyr Asn Thr Thr Asn Val Leu Ser Thr
625                 630                 635                 640 gga gat att aca tta caa att aca gga gga gat caa aaa ata ttt att            1968
Gly Asp Ile Thr Leu Gln Ile Thr Gly Gly Asp Gln Lys Ile Phe Ile
                645                 650                 655 gat cga ata gaa ttt gtt cct act atg cct gta cct ggt aat act aac            2016
Asp Arg Ile Glu Phe Val Pro Thr Met Pro Val Pro Gly Asn Thr Asn
            660                 665                 670 aac aat aac ggt aat aat aac ggt aat aat aat ccc cca cac cac gtt            2064
Asn Asn Asn Gly Asn Asn Asn Gly Asn Asn Asn Pro Pro His His Val
        675                 680                 685 tgt gca ata gct ggt aca caa caa tct tgt tct gga ccg ccc aaa ttt            2112
Cys Ala Ile Ala Gly Thr Gln Gln Ser Cys Ser Gly Pro Pro Lys Phe
    690                 695                 700 gaa caa gta agt gat tta gaa aaa att aca aca caa gta tat atg tta            2160
Glu Gln Val Ser Asp Leu Glu Lys Ile Thr Thr Gln Val Tyr Met Leu
705                 710                 715                 720 ttc aaa tct ta tag                                                          2174
Phe Lys Ser <210> SEQ ID NO 25
<211> LENGTH: 723
<212> TYPE: PRT
<213> ORGANISM: Artificial Sequence
<220> FEATURE:
```

<223> OTHER INFORMATION: AXMI-031(B-D)

<400> SEQUENCE: 25

Met Ala Ile Pro Val Ser Asn Val Asn Ser Leu Thr Asp Thr Val Gly
1               5                   10                  15

Asp Leu Lys Lys Ala Trp Glu Glu Phe Gln Lys Thr Gly Ser Phe Ser
            20                  25                  30

Leu Thr Ala Leu Gln Gln Gly Phe Ser Ala Ser Gln Gly Gly Thr Phe
        35                  40                  45

Asn Tyr Leu Thr Leu Leu Gln Ser Gly Ile Ser Leu Ala Gly Ser Phe
    50                  55                  60

Val Pro Gly Gly Thr Phe Val Ala Pro Ile Ile Asn Met Val Ile Gly
65                  70                  75                  80

Trp Leu Trp Pro His Lys Asn Lys Asn Ala Asp Thr Glu Asn Leu Ile
                85                  90                  95

Asn Leu Ile Asp Ser Glu Ile Gln Lys Gln Leu Asn Lys Ala Leu Leu
            100                 105                 110

Asp Ala Asp Arg Asn Glu Trp Ser Ser Tyr Leu Glu Ser Ile Phe Asp
        115                 120                 125

Ser Ser Asn Asn Leu Asn Gly Ala Ile Val Asp Ala Gln Trp Ser Gly
    130                 135                 140

Thr Val Asn Thr Thr Asn Arg Thr Leu Arg Asn Pro Thr Glu Ser Asp
145                 150                 155                 160

Tyr Thr Asn Val Val Thr Asn Phe Ile Ala Ala Asp Gly Asp Ile Ala
                165                 170                 175

Asn Asn Glu Asn His Ile Met Asn Gly Asn Phe Asp Val Ala Ala Ala
            180                 185                 190

Pro Tyr Phe Val Ile Gly Ala Thr Ala Arg Phe Ala Ala Met Gln Ser
        195                 200                 205

Tyr Ile Lys Phe Cys Asn Ala Trp Ile Asp Lys Val Gly Leu Ser Asp
    210                 215                 220

Ala Gln Leu Thr Thr Gln Lys Ala Asn Leu Asp Arg Thr Lys Gln Asn
225                 230                 235                 240

Met Arg Asn Ala Ile Leu Asn Tyr Thr Gln Gln Val Met Lys Val Phe
                245                 250                 255

Lys Asp Ser Lys Asn Met Pro Thr Ile Gly Thr Asn Lys Phe Ser Val
            260                 265                 270

Asp Thr Tyr Asn Val Tyr Ile Lys Gly Met Thr Leu Asn Val Leu Asp
        275                 280                 285

Ile Val Ala Ile Trp Pro Ser Leu Tyr Pro Asp Asp Tyr Thr Ser Gln
    290                 295                 300

Thr Ala Leu Glu Gln Thr Arg Val Thr Phe Ser Asn Met Val Gly Gln
305                 310                 315                 320

Glu Glu Gly Thr Asp Gly Ser Leu Arg Ile Tyr Asn Thr Phe Asp Ser
                325                 330                 335

Phe Ser Tyr Gln His Ser Pro Ile Pro Asn Asn Val Asn Leu Ile
            340                 345                 350

Ser Tyr Tyr Asn Asp Glu Leu Gln Asn Leu Glu Leu Gly Val Tyr Thr
        355                 360                 365

Pro Pro Lys Lys Gly Ser Gly Tyr Ser Tyr Pro Tyr Gly Phe Val Leu
    370                 375                 380

Asn Tyr Ala Asn Ser Lys Tyr Lys Tyr Gly Asp Ser Asn Asp Pro Glu
385                 390                 395                 400

Ser Leu Gly Gly Leu Ser Thr Leu Ser Ala Pro Ile Gln Gln Val Asn

```
                    405                 410                 415
Ala Ala Thr Gln Asn Ser Lys Tyr Leu Asp Gly Glu Ile Leu Asn Gly
            420                 425                 430

Ile Gly Ala Ser Leu Pro Gly Tyr Cys Thr Thr Gly Cys Ser Pro Thr
        435                 440                 445

Glu Pro Pro Phe Ser Cys Thr Ser Thr Ala Asn Gly Tyr Lys Ala Ser
    450                 455                 460

Cys Asn Pro Ser Asp Thr Asn Gln Lys Ile Asn Ala Leu Tyr Pro Phe
465                 470                 475                 480

Thr Gln Ala Asn Val Lys Gly Asn Thr Gly Lys Leu Gly Val Leu Ala
                485                 490                 495

Ser Leu Val Ser Tyr Asp Leu Asn Pro Lys Asn Val Phe Gly Glu Leu
            500                 505                 510

Asp Ser Asp Thr Asn Asn Val Ile Leu Lys Gly Ile Pro Ala Glu Lys
        515                 520                 525

Gly Tyr Phe Pro Asn Asn Ala Arg Pro Thr Val Val Lys Glu Trp Ile
    530                 535                 540

Asn Gly Ala Ser Ala Val Pro Leu Asp Ser Gly Asn Thr Leu Phe Met
545                 550                 555                 560

Thr Ala Thr Asn Leu Thr Ala Thr Gln Tyr Arg Ile Arg Ile Arg Tyr
                565                 570                 575

Ala Asn Pro Asn Ser Asn Thr Gln Ile Gly Val Arg Ile Thr Gln Asn
            580                 585                 590

Gly Ser Leu Ile Ser Ser Ser Asn Leu Thr Leu Tyr Ser Thr Thr Asp
        595                 600                 605

Met Asn Asn Thr Leu Pro Leu Asn Val Tyr Val Ile Gly Glu Asn Gly
    610                 615                 620

Asn Tyr Thr Leu Gln Asp Leu Tyr Asn Thr Thr Asn Val Leu Ser Thr
625                 630                 635                 640

Gly Asp Ile Thr Leu Gln Ile Thr Gly Gly Asp Gln Lys Ile Phe Ile
                645                 650                 655

Asp Arg Ile Glu Phe Val Pro Thr Met Pro Val Pro Gly Asn Thr Asn
            660                 665                 670

Asn Asn Asn Gly Asn Asn Asn Gly Asn Asn Asn Pro Pro His His Val
        675                 680                 685

Cys Ala Ile Ala Gly Thr Gln Ser Cys Ser Gly Pro Pro Lys Phe
    690                 695                 700

Glu Gln Val Ser Asp Leu Glu Lys Ile Thr Thr Gln Val Tyr Met Leu
705                 710                 715                 720

Phe Lys Ser

<210> SEQ ID NO 26
<211> LENGTH: 2226
<212> TYPE: DNA
<213> ORGANISM: Artificial Sequence
<220> FEATURE:
<223> OTHER INFORMATION: synaxmi-031(A-D)
<221> NAME/KEY: CDS
<222> LOCATION: (1)...(2226)

<400> SEQUENCE: 26 atg cag atc ctt gat tgc aat ctc cag agc cag cag aat atc cca tac     48
Met Gln Ile Leu Asp Cys Asn Leu Gln Ser Gln Gln Asn Ile Pro Tyr
1               5                   10                  15 aat gtg ctt gct atc cct gtt agc aat gtt aat agc ctt acg gat acg     96
Asn Val Leu Ala Ile Pro Val Ser Asn Val Asn Ser Leu Thr Asp Thr
            20                  25                  30
```

| | | |
|---|---|---|
| gtt ggc gat cta aag aag gca tgg gaa gag ttc cag aag acg ggc agc<br>Val Gly Asp Leu Lys Lys Ala Trp Glu Glu Phe Gln Lys Thr Gly Ser<br>35             40                    45 | | 144 |
| ttc tcc ctt acc gca ctc cag cag ggc ttc agc gct tcc cag ggc ggg<br>Phe Ser Leu Thr Ala Leu Gln Gln Gly Phe Ser Ala Ser Gln Gly Gly<br>50             55                  60 | | 192 |
| acg ttc aat tac ctc acc ctc ctc cag tcc ggg atc tcc ctg gct ggc<br>Thr Phe Asn Tyr Leu Thr Leu Leu Gln Ser Gly Ile Ser Leu Ala Gly<br>65             70                 75              80 | | 240 |
| agc ttc gtg cct ggc ggc acc ttc gtt gct cca atc atc aat atg gtg<br>Ser Phe Val Pro Gly Gly Thr Phe Val Ala Pro Ile Ile Asn Met Val<br>             85                  90              95 | | 288 |
| atc ggc tgg ctc tgg cct cat aag aat aag aat gca gat acg gaa aat<br>Ile Gly Trp Leu Trp Pro His Lys Asn Lys Asn Ala Asp Thr Glu Asn<br>           100                105             110 | | 336 |
| ctg atc aat ctg atc gat tca gaa atc cag aag cag ctg aat aag gct<br>Leu Ile Asn Leu Ile Asp Ser Glu Ile Gln Lys Gln Leu Asn Lys Ala<br>115                 120                125 | | 384 |
| ctg ctg gat gct gat cgc aat gaa tgg agc agc tac ctc gag tcc atc<br>Leu Leu Asp Ala Asp Arg Asn Glu Trp Ser Ser Tyr Leu Glu Ser Ile<br>130                 135                140 | | 432 |
| ttc gat agc agc aat aat ctg aat ggc gca atc gtt gat gct cag tgg<br>Phe Asp Ser Ser Asn Asn Leu Asn Gly Ala Ile Val Asp Ala Gln Trp<br>145                 150                155              160 | | 480 |
| tcc ggc acc gtg aat acg acc aat cgt acg ctt cgt aat cct acg gaa<br>Ser Gly Thr Val Asn Thr Thr Asn Arg Thr Leu Arg Asn Pro Thr Glu<br>                 165                170             175 | | 528 |
| tca gat tac acc aat gtg gtg acg aat ttc atc gca gca gat ggg gat<br>Ser Asp Tyr Thr Asn Val Val Thr Asn Phe Ile Ala Ala Asp Gly Asp<br>           180                185             190 | | 576 |
| atc gct aat aat gaa aat cat atc atg aat ggg aat ttc gat gtg gca<br>Ile Ala Asn Asn Glu Asn His Ile Met Asn Gly Asn Phe Asp Val Ala<br>195                 200                205 | | 624 |
| gca gct cca tac ttc gtt atc ggg gct acc gct aga ttc gca gct atg<br>Ala Ala Pro Tyr Phe Val Ile Gly Ala Thr Ala Arg Phe Ala Ala Met<br>210                 215                220 | | 672 |
| cag tcc tac atc aag ttc tgc aat gca tgg atc gat aag gtt ggg ctg<br>Gln Ser Tyr Ile Lys Phe Cys Asn Ala Trp Ile Asp Lys Val Gly Leu<br>225                 230                235              240 | | 720 |
| tca gat gct cag ctg acc acg cag aag gct aat ctg gat aga acg aag<br>Ser Asp Ala Gln Leu Thr Thr Gln Lys Ala Asn Leu Asp Arg Thr Lys<br>                 245                250             255 | | 768 |
| cag aat atg cgt aat gct atc ctt aat tac acc cag cag gtt atg aag<br>Gln Asn Met Arg Asn Ala Ile Leu Asn Tyr Thr Gln Gln Val Met Lys<br>           260                265             270 | | 816 |
| gtt ttc aag gat tcc aag aat atg cca acg atc ggc acg aat aag ttc<br>Val Phe Lys Asp Ser Lys Asn Met Pro Thr Ile Gly Thr Asn Lys Phe<br>275                 280                285 | | 864 |
| agc gtt gat acc tac aat gtt tac atc aag ggg atg acg ctt aat gtg<br>Ser Val Asp Thr Tyr Asn Val Tyr Ile Lys Gly Met Thr Leu Asn Val<br>290                 295                300 | | 912 |
| ctt gat atc gtt gct atc tgg cca agc ctg tac cca gat gat tac acg<br>Leu Asp Ile Val Ala Ile Trp Pro Ser Leu Tyr Pro Asp Asp Tyr Thr<br>305                 310                315              320 | | 960 |
| tca cag acg gct ctg gaa cag acc cgc gtg acg ttc tcc aat atg gtg<br>Ser Gln Thr Ala Leu Glu Gln Thr Arg Val Thr Phe Ser Asn Met Val<br>                 325                330             335 | | 1008 |
| ggg cag gaa gaa ggc acg gat ggc agc ctc aga atc tac aat acc ttc<br>Gly Gln Glu Glu Gly Thr Asp Gly Ser Leu Arg Ile Tyr Asn Thr Phe<br>           340                345             350 | | 1056 |

```
gat agc ttc tcc tac cag cat agc cct atc cct aat aat aat gtg aat    1104
Asp Ser Phe Ser Tyr Gln His Ser Pro Ile Pro Asn Asn Asn Val Asn
        355                 360                 365 ctc atc agc tac tac aat gat gaa ctt cag aat ctg gaa ctc ggg gtt    1152
Leu Ile Ser Tyr Tyr Asn Asp Glu Leu Gln Asn Leu Glu Leu Gly Val
370                 375                 380 tac acc cca cca aag aag ggc tca ggc tac agc tac cca tac ggg ttc    1200
Tyr Thr Pro Pro Lys Lys Gly Ser Gly Tyr Ser Tyr Pro Tyr Gly Phe
385                 390                 395                 400 gtg ctg aat tac gca aat agc aag tac aag tac ggc gat tcc aat gat    1248
Val Leu Asn Tyr Ala Asn Ser Lys Tyr Lys Tyr Gly Asp Ser Asn Asp
            405                 410                 415 cca gaa tcc ctc ggc ggg ctt tcc acc ctt agc gct cca atc caa cag    1296
Pro Glu Ser Leu Gly Gly Leu Ser Thr Leu Ser Ala Pro Ile Gln Gln
        420                 425                 430 gtt aat gct gct acc cag aat agc aag tac ctt gat ggc gaa atc ctg    1344
Val Asn Ala Ala Thr Gln Asn Ser Lys Tyr Leu Asp Gly Glu Ile Leu
    435                 440                 445 aat ggg atc ggc gca agc ctg cct ggc tac tgc acg acc ggg tgc tca    1392
Asn Gly Ile Gly Ala Ser Leu Pro Gly Tyr Cys Thr Thr Gly Cys Ser
450                 455                 460 cct acc gaa cca cca ttc agc tgc acg agc acg gca aat ggg tac aag    1440
Pro Thr Glu Pro Pro Phe Ser Cys Thr Ser Thr Ala Asn Gly Tyr Lys
465                 470                 475                 480 gca agc tgc aat cca agc gat acc aat cag aag atc aat gct ctc tac    1488
Ala Ser Cys Asn Pro Ser Asp Thr Asn Gln Lys Ile Asn Ala Leu Tyr
            485                 490                 495 cca ttc acg cag gca aat gtg aag ggg aat acc ggg aag ctg ggc gtt    1536
Pro Phe Thr Gln Ala Asn Val Lys Gly Asn Thr Gly Lys Leu Gly Val
        500                 505                 510 ctc gca agc ctt gtt agc tac gat ctg aat cct aag aat gtt ttc ggg    1584
Leu Ala Ser Leu Val Ser Tyr Asp Leu Asn Pro Lys Asn Val Phe Gly
    515                 520                 525 gaa ctc gat tca gat acc aat aat gtt atc ctt aag ggc atc cca gca    1632
Glu Leu Asp Ser Asp Thr Asn Asn Val Ile Leu Lys Gly Ile Pro Ala
530                 535                 540 gaa aag ggc tac ttc cca aat aat gca aga cca acc gtt gtg aag gaa    1680
Glu Lys Gly Tyr Phe Pro Asn Asn Ala Arg Pro Thr Val Val Lys Glu
545                 550                 555                 560 tgg atc aat ggg gct tcc gca gtt cca ctt gat tcc ggc aat acc ctg    1728
Trp Ile Asn Gly Ala Ser Ala Val Pro Leu Asp Ser Gly Asn Thr Leu
            565                 570                 575 ttc atg acg gct acg aac ctg acg gct acc cag tac aga atc cgc atc    1776
Phe Met Thr Ala Thr Asn Leu Thr Ala Thr Gln Tyr Arg Ile Arg Ile
        580                 585                 590 cgt tac gct aac cca aac tca aac acg cag atc ggc gtt aga atc acg    1824
Arg Tyr Ala Asn Pro Asn Ser Asn Thr Gln Ile Gly Val Arg Ile Thr
    595                 600                 605 cag aac ggg agc ctc atc tcc tcc tcc aac ctc acg ctg tac tca acc    1872
Gln Asn Gly Ser Leu Ile Ser Ser Ser Asn Leu Thr Leu Tyr Ser Thr
610                 615                 620 acc gat atg aac aac acc ctg cca ctg aac gtt tac gtg atc ggg gaa    1920
Thr Asp Met Asn Asn Thr Leu Pro Leu Asn Val Tyr Val Ile Gly Glu
625                 630                 635                 640 aac ggg aac tac acc ctc cag gat ctc tac aac acg acg aac gtt ctg    1968
Asn Gly Asn Tyr Thr Leu Gln Asp Leu Tyr Asn Thr Thr Asn Val Leu
            645                 650                 655 tcc acg ggc gat atc acc ctg cag atc acc ggc ggg gat cag aag ata    2016
Ser Thr Gly Asp Ile Thr Leu Gln Ile Thr Gly Gly Asp Gln Lys Ile
        660                 665                 670
```

-continued

```
ttc atc gat cgc atc gag ttc gtg cct acg atg cca gtg cca ggc aac      2064
Phe Ile Asp Arg Ile Glu Phe Val Pro Thr Met Pro Val Pro Gly Asn
            675                 680                 685 acc aac aac aac aac ggc aac aac ggc aac aac aac ccc ccc cat          2112
Thr Asn Asn Asn Asn Gly Asn Asn Gly Asn Asn Asn Pro Pro His
        690                 695                 700 cat gtc tgc gct ata gct ggt act cag cag tct tgc tca ggt cct cct      2160
His Val Cys Ala Ile Ala Gly Thr Gln Gln Ser Cys Ser Gly Pro Pro
705                 710                 715                 720 aag ttc gag cag gtt tct gat ctc gag aag atc acc acc cag gtc tac      2208
Lys Phe Glu Gln Val Ser Asp Leu Glu Lys Ile Thr Thr Gln Val Tyr
                725                 730                 735 atg ctg ttc aag tcc taa                                              2226
Met Leu Phe Lys Ser *
740
```

<210> SEQ ID NO 27
<211> LENGTH: 741
<212> TYPE: PRT
<213> ORGANISM: Artificial Sequence
<220> FEATURE:
<223> OTHER INFORMATION: SYNAXMI-031(A-D)

<400> SEQUENCE: 27

```
Met Gln Ile Leu Asp Cys Asn Leu Gln Ser Gln Gln Asn Ile Pro Tyr
1               5                   10                  15

Asn Val Leu Ala Ile Pro Val Ser Asn Val Asn Ser Leu Thr Asp Thr
            20                  25                  30

Val Gly Asp Leu Lys Lys Ala Trp Glu Glu Phe Gln Lys Thr Gly Ser
        35                  40                  45

Phe Ser Leu Thr Ala Leu Gln Gln Gly Phe Ser Ala Ser Gln Gly Gly
    50                  55                  60

Thr Phe Asn Tyr Leu Thr Leu Leu Gln Ser Gly Ile Ser Leu Ala Gly
65                  70                  75                  80

Ser Phe Val Pro Gly Gly Thr Phe Val Ala Pro Ile Ile Asn Met Val
                85                  90                  95

Ile Gly Trp Leu Trp Pro His Lys Asn Lys Asn Ala Asp Thr Glu Asn
            100                 105                 110

Leu Ile Asn Leu Ile Asp Ser Glu Ile Gln Lys Gln Leu Asn Lys Ala
        115                 120                 125

Leu Leu Asp Ala Asp Arg Asn Glu Trp Ser Ser Tyr Leu Glu Ser Ile
    130                 135                 140

Phe Asp Ser Ser Asn Asn Leu Asn Gly Ala Ile Val Asp Ala Gln Trp
145                 150                 155                 160

Ser Gly Thr Val Asn Thr Thr Asn Arg Thr Leu Arg Asn Pro Thr Glu
                165                 170                 175

Ser Asp Tyr Thr Asn Val Val Thr Asn Phe Ile Ala Ala Asp Gly Asp
            180                 185                 190

Ile Ala Asn Asn Glu Asn His Ile Met Asn Gly Asn Phe Asp Val Ala
        195                 200                 205

Ala Ala Pro Tyr Phe Val Ile Gly Ala Thr Ala Arg Phe Ala Ala Met
    210                 215                 220

Gln Ser Tyr Ile Lys Phe Cys Asn Ala Trp Ile Asp Lys Val Gly Leu
225                 230                 235                 240

Ser Asp Ala Gln Leu Thr Thr Gln Lys Ala Asn Leu Asp Arg Thr Lys
                245                 250                 255

Gln Asn Met Arg Asn Ala Ile Leu Asn Tyr Thr Gln Gln Val Met Lys
```

-continued

```
                260                 265                 270
Val Phe Lys Asp Ser Lys Asn Met Pro Thr Ile Gly Thr Asn Lys Phe
            275                 280                 285

Ser Val Asp Thr Tyr Asn Val Tyr Ile Lys Gly Met Thr Leu Asn Val
            290                 295                 300

Leu Asp Ile Val Ala Ile Trp Pro Ser Leu Tyr Pro Asp Asp Tyr Thr
305                 310                 315                 320

Ser Gln Thr Ala Leu Glu Gln Thr Arg Val Thr Phe Ser Asn Met Val
            325                 330                 335

Gly Gln Glu Glu Gly Thr Asp Gly Ser Leu Arg Ile Tyr Asn Thr Phe
            340                 345                 350

Asp Ser Phe Ser Tyr Gln His Ser Pro Ile Pro Asn Asn Asn Val Asn
            355                 360                 365

Leu Ile Ser Tyr Tyr Asn Asp Glu Leu Gln Asn Leu Glu Leu Gly Val
            370                 375                 380

Tyr Thr Pro Pro Lys Lys Gly Ser Gly Tyr Ser Tyr Pro Tyr Gly Phe
385                 390                 395                 400

Val Leu Asn Tyr Ala Asn Ser Lys Tyr Lys Tyr Gly Asp Ser Asn Asp
            405                 410                 415

Pro Glu Ser Leu Gly Gly Leu Ser Thr Leu Ser Ala Pro Ile Gln Gln
            420                 425                 430

Val Asn Ala Ala Thr Gln Asn Ser Lys Tyr Leu Asp Gly Glu Ile Leu
            435                 440                 445

Asn Gly Ile Gly Ala Ser Leu Pro Gly Tyr Cys Thr Thr Gly Cys Ser
450                 455                 460

Pro Thr Glu Pro Pro Phe Ser Cys Thr Ser Thr Ala Asn Gly Tyr Lys
465                 470                 475                 480

Ala Ser Cys Asn Pro Ser Asp Thr Asn Gln Lys Ile Asn Ala Leu Tyr
            485                 490                 495

Pro Phe Thr Gln Ala Asn Val Lys Gly Asn Thr Gly Lys Leu Gly Val
            500                 505                 510

Leu Ala Ser Leu Val Ser Tyr Asp Leu Asn Pro Lys Asn Val Phe Gly
            515                 520                 525

Glu Leu Asp Ser Asp Thr Asn Asn Val Ile Leu Lys Gly Ile Pro Ala
            530                 535                 540

Glu Lys Gly Tyr Phe Pro Asn Asn Ala Arg Pro Thr Val Val Lys Glu
545                 550                 555                 560

Trp Ile Asn Gly Ala Ser Ala Val Pro Leu Asp Ser Gly Asn Thr Leu
            565                 570                 575

Phe Met Thr Ala Thr Asn Leu Thr Ala Thr Gln Tyr Arg Ile Arg Ile
            580                 585                 590

Arg Tyr Ala Asn Pro Asn Ser Asn Thr Gln Ile Gly Val Arg Ile Thr
            595                 600                 605

Gln Asn Gly Ser Leu Ile Ser Ser Asn Leu Thr Leu Tyr Ser Thr
            610                 615                 620

Thr Asp Met Asn Asn Thr Leu Pro Leu Asn Val Tyr Val Ile Gly Glu
625                 630                 635                 640

Asn Gly Asn Tyr Thr Leu Gln Asp Leu Tyr Asn Thr Asn Val Leu
            645                 650                 655

Ser Thr Gly Asp Ile Thr Leu Gln Ile Thr Gly Gly Asp Gln Lys Ile
            660                 665                 670

Phe Ile Asp Arg Ile Glu Phe Val Pro Thr Met Pro Val Pro Gly Asn
            675                 680                 685
```

-continued

```
Thr Asn Asn Asn Asn Gly Asn Asn Gly Asn Asn Asn Pro Pro His
    690                 695                 700
His Val Cys Ala Ile Ala Gly Thr Gln Gln Ser Cys Ser Gly Pro Pro
705                 710                 715                 720
Lys Phe Glu Gln Val Ser Asp Leu Glu Lys Ile Thr Thr Gln Val Tyr
                725                 730                 735
Met Leu Phe Lys Ser
            740

<210> SEQ ID NO 28
<211> LENGTH: 2316
<212> TYPE: DNA
<213> ORGANISM: Artificial Sequence
<220> FEATURE:
<223> OTHER INFORMATION: aposynaxmi-031(A-D)
<221> NAME/KEY: CDS
<222> LOCATION: (1)...(2316)

<400> SEQUENCE: 28 atg cag atc ctt ggg tac tcc agc ttc gtt gct atc gct ctt ctt atg    48
Met Gln Ile Leu Gly Tyr Ser Ser Phe Val Ala Ile Ala Leu Leu Met
1               5                   10                  15 agc gtg gtt gtt gtt tgc aat ggg ggc aag acg tcc acc tac gtg cgt    96
Ser Val Val Val Val Cys Asn Gly Gly Lys Thr Ser Thr Tyr Val Arg
                20                  25                  30 aat ctg gat tgc aat ctc cag agc cag cag aat atc cca tac aat gtg   144
Asn Leu Asp Cys Asn Leu Gln Ser Gln Gln Asn Ile Pro Tyr Asn Val
            35                  40                  45 ctt gct atc cct gtt agc aat gtt aat agc ctt acg gat acg gtt ggc   192
Leu Ala Ile Pro Val Ser Asn Val Asn Ser Leu Thr Asp Thr Val Gly
        50                  55                  60 gat cta aag aag gca tgg gaa gag ttc cag aag acg ggc agc ttc tcc   240
Asp Leu Lys Lys Ala Trp Glu Glu Phe Gln Lys Thr Gly Ser Phe Ser
65                  70                  75                  80 ctt acc gca ctc cag cag ggc ttc agc gct tcc cag ggc ggg acg ttc   288
Leu Thr Ala Leu Gln Gln Gly Phe Ser Ala Ser Gln Gly Gly Thr Phe
                85                  90                  95 aat tac ctc acc ctc ctc cag tcc ggg atc tcc ctg gct ggc agc ttc   336
Asn Tyr Leu Thr Leu Leu Gln Ser Gly Ile Ser Leu Ala Gly Ser Phe
            100                 105                 110 gtg cct ggc ggc acc ttc gtt gct cca atc atc aat atg gtg atc ggc   384
Val Pro Gly Gly Thr Phe Val Ala Pro Ile Ile Asn Met Val Ile Gly
        115                 120                 125 tgg ctc tgg cct cat aag aat aag aat gca gat acg gaa aat ctg atc   432
Trp Leu Trp Pro His Lys Asn Lys Asn Ala Asp Thr Glu Asn Leu Ile
130                 135                 140 aat ctg atc gat tca gaa atc cag aag cag ctg aat aag gct ctg ctg   480
Asn Leu Ile Asp Ser Glu Ile Gln Lys Gln Leu Asn Lys Ala Leu Leu
145                 150                 155                 160 gat gct gat cgc aat gaa tgg agc agc tac ctc gag tcc atc ttc gat   528
Asp Ala Asp Arg Asn Glu Trp Ser Ser Tyr Leu Glu Ser Ile Phe Asp
                165                 170                 175 agc agc aat aat ctg aat ggc gca atc gtt gat gct cag tgg tcc ggc   576
Ser Ser Asn Asn Leu Asn Gly Ala Ile Val Asp Ala Gln Trp Ser Gly
            180                 185                 190 acc gtg aat acg acc aat cgt acg ctt cgt aat cct acg gaa tca gat   624
Thr Val Asn Thr Thr Asn Arg Thr Leu Arg Asn Pro Thr Glu Ser Asp
        195                 200                 205 tac acc aat gtg gtg acg aat ttc atc gca gca gat ggg gat atc gct   672
Tyr Thr Asn Val Val Thr Asn Phe Ile Ala Ala Asp Gly Asp Ile Ala
            210                 215                 220
```

```
aat aat gaa aat cat atc atg aat ggg aat ttc gat gtg gca gca gct    720
Asn Asn Glu Asn His Ile Met Asn Gly Asn Phe Asp Val Ala Ala Ala
225                 230                 235                 240 cca tac ttc gtt atc ggg gct acc gct aga ttc gca gct atg cag tcc    768
Pro Tyr Phe Val Ile Gly Ala Thr Ala Arg Phe Ala Ala Met Gln Ser
            245                 250                 255 tac atc aag ttc tgc aat gca tgg atc gat aag gtt ggg ctg tca gat    816
Tyr Ile Lys Phe Cys Asn Ala Trp Ile Asp Lys Val Gly Leu Ser Asp
        260                 265                 270 gct cag ctg acc acg cag aag gct aat ctg gat aga acg aag cag aat    864
Ala Gln Leu Thr Thr Gln Lys Ala Asn Leu Asp Arg Thr Lys Gln Asn
    275                 280                 285 atg cgt aat gct atc ctt aat tac acc cag cag gtt atg aag gtt ttc    912
Met Arg Asn Ala Ile Leu Asn Tyr Thr Gln Gln Val Met Lys Val Phe
290                 295                 300 aag gat tcc aag aat atg cca acg atc ggc acg aat aag ttc agc gtt    960
Lys Asp Ser Lys Asn Met Pro Thr Ile Gly Thr Asn Lys Phe Ser Val
305                 310                 315                 320 gat acc tac aat gtt tac atc aag ggg atg acg ctt aat gtg ctt gat    1008
Asp Thr Tyr Asn Val Tyr Ile Lys Gly Met Thr Leu Asn Val Leu Asp
            325                 330                 335 atc gtt gct atc tgg cca agc ctg tac cca gat gat tac acg tca cag    1056
Ile Val Ala Ile Trp Pro Ser Leu Tyr Pro Asp Asp Tyr Thr Ser Gln
        340                 345                 350 acg gct ctg gaa cag acc cgc gtg acg ttc tcc aat atg gtg ggg cag    1104
Thr Ala Leu Glu Gln Thr Arg Val Thr Phe Ser Asn Met Val Gly Gln
    355                 360                 365 gaa gaa ggc acg gat ggc agc ctc aga atc tac aat acc ttc gat agc    1152
Glu Glu Gly Thr Asp Gly Ser Leu Arg Ile Tyr Asn Thr Phe Asp Ser
370                 375                 380 ttc tcc tac cag cat agc cct atc cct aat aat aat gtg aat ctc atc    1200
Phe Ser Tyr Gln His Ser Pro Ile Pro Asn Asn Asn Val Asn Leu Ile
385                 390                 395                 400 agc tac tac aat gat gaa ctt cag aat ctg gaa ctc ggg gtt tac acc    1248
Ser Tyr Tyr Asn Asp Glu Leu Gln Asn Leu Glu Leu Gly Val Tyr Thr
            405                 410                 415 cca cca aag aag ggc tca ggc tac agc tac cca tac ggg ttc gtg ctg    1296
Pro Pro Lys Lys Gly Ser Gly Tyr Ser Tyr Pro Tyr Gly Phe Val Leu
        420                 425                 430 aat tac gca aat agc aag tac aag tac ggc gat tcc aat gat cca gaa    1344
Asn Tyr Ala Asn Ser Lys Tyr Lys Tyr Gly Asp Ser Asn Asp Pro Glu
    435                 440                 445 tcc ctc ggc ggg ctt tcc acc ctt agc gct cca atc caa cag gtt aat    1392
Ser Leu Gly Gly Leu Ser Thr Leu Ser Ala Pro Ile Gln Gln Val Asn
450                 455                 460 gct gct acc cag aat agc aag tac ctt gat ggc gaa atc ctg aat ggg    1440
Ala Ala Thr Gln Asn Ser Lys Tyr Leu Asp Gly Glu Ile Leu Asn Gly
465                 470                 475                 480 atc ggc gca agc ctg cct ggc tac tgc acg acc ggg tgc tca cct acc    1488
Ile Gly Ala Ser Leu Pro Gly Tyr Cys Thr Thr Gly Cys Ser Pro Thr
            485                 490                 495 gaa cca cca ttc agc tgc acg agc acg gca aat ggg tac aag gca agc    1536
Glu Pro Pro Phe Ser Cys Thr Ser Thr Ala Asn Gly Tyr Lys Ala Ser
        500                 505                 510 tgc aat cca agc gat acc aat cag aag atc aat gct ctc tac cca ttc    1584
Cys Asn Pro Ser Asp Thr Asn Gln Lys Ile Asn Ala Leu Tyr Pro Phe
    515                 520                 525 acg cag gca aat gtg aag ggg aat acc ggg aag ctg ggc gtt ctc gca    1632
Thr Gln Ala Asn Val Lys Gly Asn Thr Gly Lys Leu Gly Val Leu Ala
530                 535                 540
```

```
agc ctt gtt agc tac gat ctg aat cct aag aat gtt ttc ggg gaa ctc    1680
Ser Leu Val Ser Tyr Asp Leu Asn Pro Lys Asn Val Phe Gly Glu Leu
545                 550                 555                 560 gat tca gat acc aat aat gtt atc ctt aag ggc atc cca gca gaa aag    1728
Asp Ser Asp Thr Asn Asn Val Ile Leu Lys Gly Ile Pro Ala Glu Lys
                565                 570                 575 ggc tac ttc cca aat aat gca aga cca acc gtt gtg aag gaa tgg atc    1776
Gly Tyr Phe Pro Asn Asn Ala Arg Pro Thr Val Val Lys Glu Trp Ile
            580                 585                 590 aat ggg gct tcc gca gtt cca ctt gat tcc ggc aat acc ctg ttc atg    1824
Asn Gly Ala Ser Ala Val Pro Leu Asp Ser Gly Asn Thr Leu Phe Met
        595                 600                 605 acg gct acg aac ctg acg gct acc cag tac aga atc gcc atc cgt tac    1872
Thr Ala Thr Asn Leu Thr Ala Thr Gln Tyr Arg Ile Arg Ile Arg Tyr
    610                 615                 620 gct aac cca aac tca aac acg cag atc ggc gtt aga atc acg cag aac    1920
Ala Asn Pro Asn Ser Asn Thr Gln Ile Gly Val Arg Ile Thr Gln Asn
625                 630                 635                 640 ggg agc ctc atc tcc tcc tcc aac ctc acg ctg tac tca acc acc gat    1968
Gly Ser Leu Ile Ser Ser Ser Asn Leu Thr Leu Tyr Ser Thr Thr Asp
                645                 650                 655 atg aac aac acc ctg cca ctg aac gtt tac gtg atc ggg gaa aac ggg    2016
Met Asn Asn Thr Leu Pro Leu Asn Val Tyr Val Ile Gly Glu Asn Gly
                660                 665                 670 aac tac acc ctc cag gat ctc tac aac acg acg aac gtt ctg tcc acg    2064
Asn Tyr Thr Leu Gln Asp Leu Tyr Asn Thr Thr Asn Val Leu Ser Thr
            675                 680                 685 ggc gat atc acc ctg cag atc acc ggg gat cag aag ata ttc atc        2112
Gly Asp Ile Thr Leu Gln Ile Thr Gly Gly Asp Gln Lys Ile Phe Ile
        690                 695                 700 gat cgc atc gag ttc gtg cct acg atg cca gtg cca ggc aac acc aac    2160
Asp Arg Ile Glu Phe Val Pro Thr Met Pro Val Pro Gly Asn Thr Asn
705                 710                 715                 720 aac aac aac ggc aac aac aac ggc aac aac aac ccc ccc cat cat gtc    2208
Asn Asn Asn Gly Asn Asn Asn Gly Asn Asn Asn Pro Pro His His Val
                725                 730                 735 tgc gct ata gct ggt act cag cag tct tgc tca ggt cct cct aag ttc    2256
Cys Ala Ile Ala Gly Thr Gln Gln Ser Cys Ser Gly Pro Pro Lys Phe
                740                 745                 750 gag cag gtt tct gat ctc gag aag atc acc acc cag gtc tac atg ctg    2304
Glu Gln Val Ser Asp Leu Glu Lys Ile Thr Thr Gln Val Tyr Met Leu
            755                 760                 765 ttc aag tcc taa                                                    2316
Phe Lys Ser *
    770

<210> SEQ ID NO 29
<211> LENGTH: 771
<212> TYPE: PRT
<213> ORGANISM: Artificial Sequence
<220> FEATURE:
<223> OTHER INFORMATION: APOSYNAXMI-031(A-D)

<400> SEQUENCE: 29

Met Gln Ile Leu Gly Tyr Ser Ser Phe Val Ala Ile Ala Leu Leu Met
1               5                   10                  15

Ser Val Val Val Cys Asn Gly Gly Lys Thr Ser Thr Tyr Val Arg
            20                  25                  30

Asn Leu Asp Cys Asn Leu Gln Ser Gln Gln Asn Ile Pro Tyr Asn Val
            35                  40                  45

Leu Ala Ile Pro Val Ser Asn Val Asn Ser Leu Thr Asp Thr Val Gly
```

```
                 50                  55                  60
Asp Leu Lys Lys Ala Trp Glu Glu Phe Gln Lys Thr Gly Ser Phe Ser
 65                  70                  75                  80

Leu Thr Ala Leu Gln Gln Gly Phe Ser Ala Ser Gln Gly Gly Thr Phe
                 85                  90                  95

Asn Tyr Leu Thr Leu Leu Gln Ser Gly Ile Ser Leu Ala Gly Ser Phe
                100                 105                 110

Val Pro Gly Gly Thr Phe Val Ala Pro Ile Ile Asn Met Val Ile Gly
                115                 120                 125

Trp Leu Trp Pro His Lys Asn Lys Asn Ala Asp Thr Glu Asn Leu Ile
130                 135                 140

Asn Leu Ile Asp Ser Glu Ile Gln Lys Gln Leu Asn Lys Ala Leu Leu
145                 150                 155                 160

Asp Ala Asp Arg Asn Glu Trp Ser Ser Tyr Leu Glu Ser Ile Phe Asp
                165                 170                 175

Ser Ser Asn Asn Leu Asn Gly Ala Ile Val Asp Ala Gln Trp Ser Gly
                180                 185                 190

Thr Val Asn Thr Thr Asn Arg Thr Leu Arg Asn Pro Thr Glu Ser Asp
                195                 200                 205

Tyr Thr Asn Val Val Thr Asn Phe Ile Ala Ala Asp Gly Asp Ile Ala
                210                 215                 220

Asn Asn Glu Asn His Ile Met Asn Gly Asn Phe Asp Val Ala Ala Ala
225                 230                 235                 240

Pro Tyr Phe Val Ile Gly Ala Thr Ala Arg Phe Ala Ala Met Gln Ser
                245                 250                 255

Tyr Ile Lys Phe Cys Asn Ala Trp Ile Asp Lys Val Gly Leu Ser Asp
                260                 265                 270

Ala Gln Leu Thr Thr Gln Lys Ala Asn Leu Asp Arg Thr Lys Gln Asn
                275                 280                 285

Met Arg Asn Ala Ile Leu Asn Tyr Thr Gln Gln Val Met Lys Val Phe
290                 295                 300

Lys Asp Ser Lys Asn Met Pro Thr Ile Gly Thr Asn Lys Phe Ser Val
305                 310                 315                 320

Asp Thr Tyr Asn Val Tyr Ile Lys Gly Met Thr Leu Asn Val Leu Asp
                325                 330                 335

Ile Val Ala Ile Trp Pro Ser Leu Tyr Pro Asp Tyr Thr Ser Gln
                340                 345                 350

Thr Ala Leu Glu Gln Thr Arg Val Thr Phe Ser Asn Met Val Gly Gln
                355                 360                 365

Glu Glu Gly Thr Asp Gly Ser Leu Arg Ile Tyr Asn Thr Phe Asp Ser
370                 375                 380

Phe Ser Tyr Gln His Ser Pro Ile Pro Asn Asn Val Asn Leu Ile
385                 390                 395                 400

Ser Tyr Tyr Asn Asp Glu Leu Gln Asn Leu Glu Leu Gly Val Tyr Thr
                405                 410                 415

Pro Pro Lys Lys Gly Ser Gly Tyr Ser Tyr Pro Tyr Gly Phe Val Leu
                420                 425                 430

Asn Tyr Ala Asn Ser Lys Tyr Lys Tyr Gly Asp Ser Asn Asp Pro Glu
                435                 440                 445

Ser Leu Gly Gly Leu Ser Thr Leu Ser Ala Pro Ile Gln Gln Val Asn
                450                 455                 460

Ala Ala Thr Gln Asn Ser Lys Tyr Leu Asp Gly Glu Ile Leu Asn Gly
465                 470                 475                 480
```

```
Ile Gly Ala Ser Leu Pro Gly Tyr Cys Thr Thr Cys Ser Pro Thr
            485                 490                 495

Glu Pro Pro Phe Ser Cys Thr Ser Thr Ala Asn Gly Tyr Lys Ala Ser
            500                 505                 510

Cys Asn Pro Ser Asp Thr Asn Gln Lys Ile Asn Ala Leu Tyr Pro Phe
            515                 520                 525

Thr Gln Ala Asn Val Lys Gly Asn Thr Gly Lys Leu Gly Val Leu Ala
            530                 535                 540

Ser Leu Val Ser Tyr Asp Leu Asn Pro Lys Asn Val Phe Gly Glu Leu
545                 550                 555                 560

Asp Ser Asp Thr Asn Asn Val Ile Leu Lys Gly Ile Pro Ala Glu Lys
                565                 570                 575

Gly Tyr Phe Pro Asn Asn Ala Arg Pro Thr Val Val Lys Glu Trp Ile
                580                 585                 590

Asn Gly Ala Ser Ala Val Pro Leu Asp Ser Gly Asn Thr Leu Phe Met
                595                 600                 605

Thr Ala Thr Asn Leu Thr Ala Thr Gln Tyr Arg Ile Arg Ile Arg Tyr
            610                 615                 620

Ala Asn Pro Asn Ser Asn Thr Gln Ile Gly Val Arg Ile Thr Gln Asn
625                 630                 635                 640

Gly Ser Leu Ile Ser Ser Ser Asn Leu Thr Leu Tyr Ser Thr Thr Asp
                645                 650                 655

Met Asn Asn Thr Leu Pro Leu Asn Val Tyr Val Ile Gly Glu Asn Gly
                660                 665                 670

Asn Tyr Thr Leu Gln Asp Leu Tyr Asn Thr Thr Asn Val Leu Ser Thr
                675                 680                 685

Gly Asp Ile Thr Leu Gln Ile Thr Gly Gly Asp Gln Lys Ile Phe Ile
            690                 695                 700

Asp Arg Ile Glu Phe Val Pro Thr Met Pro Val Pro Gly Asn Thr Asn
705                 710                 715                 720

Asn Asn Asn Gly Asn Asn Gly Asn Asn Asn Pro Pro His His Val
                725                 730                 735

Cys Ala Ile Ala Gly Thr Gln Gln Ser Cys Ser Gly Pro Pro Lys Phe
            740                 745                 750

Glu Gln Val Ser Asp Leu Glu Lys Ile Thr Thr Gln Val Tyr Met Leu
            755                 760                 765

Phe Lys Ser
770

<210> SEQ ID NO 30
<211> LENGTH: 2307
<212> TYPE: DNA
<213> ORGANISM: Artificial Sequence
<220> FEATURE:
<223> OTHER INFORMATION: aposyn2axmi-031(A-D)
<221> NAME/KEY: CDS
<222> LOCATION: (1)...(2307)

<400> SEQUENCE: 30 atg ggc tac agc agc ttc gtc gcc atc gcg ctg ctg atg agc gtg gtg      48
Met Gly Tyr Ser Ser Phe Val Ala Ile Ala Leu Leu Met Ser Val Val
1               5                   10                  15 gtg gtg tgc aac ggc ggc aag aca agc acc tat gtg agg aac ctg gac      96
Val Val Cys Asn Gly Gly Lys Thr Ser Thr Tyr Val Arg Asn Leu Asp
                20                  25                  30 tgc aac ctc cag agc cag cag aac atc ccc tac aat gtg ctg gcc atc     144
Cys Asn Leu Gln Ser Gln Gln Asn Ile Pro Tyr Asn Val Leu Ala Ile
            35                  40                  45
```

-continued

| | |
|---|---|
| ccc gtc tca aat gtc aac agc ttg aca gat act gtt ggt gat ttg aag<br>Pro Val Ser Asn Val Asn Ser Leu Thr Asp Thr Val Gly Asp Leu Lys<br>50 55 60 | 192 |
| aag gca tgg gag gag ttc cag aag acc ggc agc ttc agc ttg acg gcg<br>Lys Ala Trp Glu Glu Phe Gln Lys Thr Gly Ser Phe Ser Leu Thr Ala<br>65 70 75 80 | 240 |
| ctg caa caa ggc ttc tca gca agc caa gga ggc acc ttc aac tac ctc<br>Leu Gln Gln Gly Phe Ser Ala Ser Gln Gly Gly Thr Phe Asn Tyr Leu<br>85 90 95 | 288 |
| acc ttg ctg caa agc ggc atc agc ttg gcc ggc agc ttc gtg ccc ggc<br>Thr Leu Leu Gln Ser Gly Ile Ser Leu Ala Gly Ser Phe Val Pro Gly<br>100 105 110 | 336 |
| ggc acc ttc gtg gcg ccc atc atc aac atg gtg att gga tgg ctg tgg<br>Gly Thr Phe Val Ala Pro Ile Ile Asn Met Val Ile Gly Trp Leu Trp<br>115 120 125 | 384 |
| ccg cac aag aac aag aat gct gac aca gaa aat ttg atc aac ctc att<br>Pro His Lys Asn Lys Asn Ala Asp Thr Glu Asn Leu Ile Asn Leu Ile<br>130 135 140 | 432 |
| gat tca gag atc cag aag cag ctc aac aag gcg ctg ctg gat gct gac<br>Asp Ser Glu Ile Gln Lys Gln Leu Asn Lys Ala Leu Leu Asp Ala Asp<br>145 150 155 160 | 480 |
| aga aat gaa tgg agc agc tac ctg gag agc atc ttt gat tca agc aac<br>Arg Asn Glu Trp Ser Ser Tyr Leu Glu Ser Ile Phe Asp Ser Ser Asn<br>165 170 175 | 528 |
| aac ctc aac ggc gcc atc gtg gat gct caa tgg tca ggc acc gtc aac<br>Asn Leu Asn Gly Ala Ile Val Asp Ala Gln Trp Ser Gly Thr Val Asn<br>180 185 190 | 576 |
| acc acc aac agg acg ctg agg aat cca aca gaa agt gac tac acc aat<br>Thr Thr Asn Arg Thr Leu Arg Asn Pro Thr Glu Ser Asp Tyr Thr Asn<br>195 200 205 | 624 |
| gtg gtg acc aac ttc att gct gct gat gga gac atc gcc aac aat gag<br>Val Val Thr Asn Phe Ile Ala Ala Asp Gly Asp Ile Ala Asn Asn Glu<br>210 215 220 | 672 |
| aac cac atc atg aat gga aat ttt gat gtt gct gct gct cca tat ttt<br>Asn His Ile Met Asn Gly Asn Phe Asp Val Ala Ala Ala Pro Tyr Phe<br>225 230 235 240 | 720 |
| gtg att gga gca aca gca aga ttt gct gcc atg caa tca tac atc aag<br>Val Ile Gly Ala Thr Ala Arg Phe Ala Ala Met Gln Ser Tyr Ile Lys<br>245 250 255 | 768 |
| ttc tgc aat gca tgg atc gac aag gtg ggc ctc tct gat gct cag ctc<br>Phe Cys Asn Ala Trp Ile Asp Lys Val Gly Leu Ser Asp Ala Gln Leu<br>260 265 270 | 816 |
| acc acc cag aag gcc aac ctg gac agg acc aag cag aac atg agg aat<br>Thr Thr Gln Lys Ala Asn Leu Asp Arg Thr Lys Gln Asn Met Arg Asn<br>275 280 285 | 864 |
| gcc atc ttg aat tac acc cag cag gtg atg aag gtg ttc aag gac agc<br>Ala Ile Leu Asn Tyr Thr Gln Gln Val Met Lys Val Phe Lys Asp Ser<br>290 295 300 | 912 |
| aag aac atg cca acc atc ggc acc aac aag ttc tca gtg gac acc tac<br>Lys Asn Met Pro Thr Ile Gly Thr Asn Lys Phe Ser Val Asp Thr Tyr<br>305 310 315 320 | 960 |
| aat gtc tac atc aag ggc atg acg ctc aat gtg ctg gac atc gtc gcc<br>Asn Val Tyr Ile Lys Gly Met Thr Leu Asn Val Leu Asp Ile Val Ala<br>325 330 335 | 1008 |
| atc tgg cca agc ctc tac cct gat gac tac acc tca cag acg gcg ctg<br>Ile Trp Pro Ser Leu Tyr Pro Asp Asp Tyr Thr Ser Gln Thr Ala Leu<br>340 345 350 | 1056 |
| gag caa aca agg gtg acc ttc agc aac atg gtg ggc caa gaa gaa gga<br>Glu Gln Thr Arg Val Thr Phe Ser Asn Met Val Gly Gln Glu Glu Gly<br>355 360 365 | 1104 |

```
act gat ggc agc ttg agg atc tac aac acc ttc gac agc ttc agc tac      1152
Thr Asp Gly Ser Leu Arg Ile Tyr Asn Thr Phe Asp Ser Phe Ser Tyr
370                 375                 380 cag cat tct ccc atc ccc aac aac aat gtc aac ctc atc agc tac tac      1200
Gln His Ser Pro Ile Pro Asn Asn Asn Val Asn Leu Ile Ser Tyr Tyr
385                 390                 395                 400 aat gat gag ctg caa aat ttg gag cta gga gtc tac acg ccg cca aag      1248
Asn Asp Glu Leu Gln Asn Leu Glu Leu Gly Val Tyr Thr Pro Pro Lys
                405                 410                 415 aaa gga agt gga tat tct tat cct tat ggc ttc gtg ctc aac tac gcc      1296
Lys Gly Ser Gly Tyr Ser Tyr Pro Tyr Gly Phe Val Leu Asn Tyr Ala
            420                 425                 430 aac agc aag tac aag tat gga gat tca aat gat cca gaa agc ctc ggc      1344
Asn Ser Lys Tyr Lys Tyr Gly Asp Ser Asn Asp Pro Glu Ser Leu Gly
        435                 440                 445 ggc ctc tcc acc ttg tcg gcg ccc atc cag cag gtg aac gcc gcc acc      1392
Gly Leu Ser Thr Leu Ser Ala Pro Ile Gln Gln Val Asn Ala Ala Thr
    450                 455                 460 cag aac agc aag tac ctt gat gga gag atc ctc aat ggc att gga gct      1440
Gln Asn Ser Lys Tyr Leu Asp Gly Glu Ile Leu Asn Gly Ile Gly Ala
465                 470                 475                 480 tct ctt cct ggc tac tgc acc acc ggc tgc tcg ccg acg gag ccg ccc      1488
Ser Leu Pro Gly Tyr Cys Thr Thr Gly Cys Ser Pro Thr Glu Pro Pro
                485                 490                 495 ttc agc tgc acc tca aca gca aat ggc tac aag gca agc tgc aac ccc      1536
Phe Ser Cys Thr Ser Thr Ala Asn Gly Tyr Lys Ala Ser Cys Asn Pro
            500                 505                 510 tcc gac acc aac cag aag atc aac gcg ctc tac ccc ttc acc caa gct      1584
Ser Asp Thr Asn Gln Lys Ile Asn Ala Leu Tyr Pro Phe Thr Gln Ala
        515                 520                 525 aat gtg aag ggc aac acc ggc aag ctc ggc gtg ctg gcc agc ttg gtg      1632
Asn Val Lys Gly Asn Thr Gly Lys Leu Gly Val Leu Ala Ser Leu Val
    530                 535                 540 agc tac gac ctc aac ccc aag aat gtt ttt gga gag ctg gac agc gac      1680
Ser Tyr Asp Leu Asn Pro Lys Asn Val Phe Gly Glu Leu Asp Ser Asp
545                 550                 555                 560 acc aac aat gtc atc cta aag ggc atc ccg gcg gag aag ggc tac ttc      1728
Thr Asn Asn Val Ile Leu Lys Gly Ile Pro Ala Glu Lys Gly Tyr Phe
                565                 570                 575 ccc aac aat gca agg ccg acg gtg gtg aag gag tgg atc aat gga gct      1776
Pro Asn Asn Ala Arg Pro Thr Val Val Lys Glu Trp Ile Asn Gly Ala
            580                 585                 590 tcg gcg gtg cct ctt gat tca ggc aac acc ttg ttc atg aca gca aca      1824
Ser Ala Val Pro Leu Asp Ser Gly Asn Thr Leu Phe Met Thr Ala Thr
        595                 600                 605 aat ttg acg gcg acg cag tac agg atc agg atc aga tat gcc aac ccc      1872
Asn Leu Thr Ala Thr Gln Tyr Arg Ile Arg Ile Arg Tyr Ala Asn Pro
    610                 615                 620 aac agc aac acc cag atc ggc gtg agg atc acc caa aat gga agc ctc      1920
Asn Ser Asn Thr Gln Ile Gly Val Arg Ile Thr Gln Asn Gly Ser Leu
625                 630                 635                 640 atc agc agc agc aac ctc acc ctc tac tca aca act gac atg aac aac      1968
Ile Ser Ser Ser Asn Leu Thr Leu Tyr Ser Thr Thr Asp Met Asn Asn
                645                 650                 655 acc ttg ccg ctc aat gtt tat gtg att gga gaa aat ggc aac tac acc      2016
Thr Leu Pro Leu Asn Val Tyr Val Ile Gly Glu Asn Gly Asn Tyr Thr
            660                 665                 670 ttg caa gat ctc tac aac acc acc aac gtg ctg agc acc ggc gac atc      2064
Leu Gln Asp Leu Tyr Asn Thr Thr Asn Val Leu Ser Thr Gly Asp Ile
        675                 680                 685
```

| | | | | | | | | | | | | | | | |
|---|---|---|---|---|---|---|---|---|---|---|---|---|---|---|---|
| acc | cta | cag | atc | act | gga | gga | gat | cag | aag | atc | ttc | atc | gac | agg | att | 2112 |
| Thr | Leu | Gln | Ile | Thr | Gly | Gly | Asp | Gln | Lys | Ile | Phe | Ile | Asp | Arg | Ile | |
| | 690 | | | | | 695 | | | | 700 | | | | | | |
| gaa | ttt | gtt | cca | aca | atg | cca | gtt | cct | ggc | aac | acc | aac | aac | aac | aat | 2160 |
| Glu | Phe | Val | Pro | Thr | Met | Pro | Val | Pro | Gly | Asn | Thr | Asn | Asn | Asn | Asn | |
| 705 | | | | | 710 | | | | | 715 | | | | | 720 | |
| ggc | aac | aac | aat | ggc | aac | aac | aac | ccg | ccg | cac | cat | gtt | tgt | gcc | ata | 2208 |
| Gly | Asn | Asn | Asn | Gly | Asn | Asn | Asn | Pro | Pro | His | His | Val | Cys | Ala | Ile | |
| | | | | 725 | | | | | 730 | | | | | 735 | | |
| gct | gga | act | caa | caa | agc | tgc | tct | ggg | ccg | cca | aaa | ttt | gag | caa | gtt | 2256 |
| Ala | Gly | Thr | Gln | Gln | Ser | Cys | Ser | Gly | Pro | Pro | Lys | Phe | Glu | Gln | Val | |
| | | | 740 | | | | | 745 | | | | | 750 | | | |
| tca | gat | ctg | gag | aag | atc | acc | acc | caa | gtc | tac | atg | ctc | ttc | aag | agc | 2304 |
| Ser | Asp | Leu | Glu | Lys | Ile | Thr | Thr | Gln | Val | Tyr | Met | Leu | Phe | Lys | Ser | |
| | | 755 | | | | | 760 | | | | | 765 | | | | |
| taa | | | | | | | | | | | | | | | | 2307 |
| * | | | | | | | | | | | | | | | | |

<210> SEQ ID NO 31
<211> LENGTH: 768
<212> TYPE: PRT
<213> ORGANISM: Artificial Sequence
<220> FEATURE:
<223> OTHER INFORMATION: APOSYN2AXMI-031(A-D)

<400> SEQUENCE: 31

```
Met Gly Tyr Ser Ser Phe Val Ala Ile Ala Leu Leu Met Ser Val Val
 1               5                  10                  15

Val Val Cys Asn Gly Gly Lys Thr Ser Thr Tyr Val Arg Asn Leu Asp
                20                  25                  30

Cys Asn Leu Gln Ser Gln Gln Asn Ile Pro Tyr Asn Val Leu Ala Ile
            35                  40                  45

Pro Val Ser Asn Val Asn Ser Leu Thr Asp Thr Val Gly Asp Leu Lys
        50                  55                  60

Lys Ala Trp Glu Glu Phe Gln Lys Thr Gly Ser Phe Ser Leu Thr Ala
65                  70                  75                  80

Leu Gln Gln Gly Phe Ser Ala Ser Gln Gly Gly Thr Phe Asn Tyr Leu
                85                  90                  95

Thr Leu Leu Gln Ser Gly Ile Ser Leu Ala Gly Ser Phe Val Pro Gly
            100                 105                 110

Gly Thr Phe Val Ala Pro Ile Ile Asn Met Val Ile Gly Trp Leu Trp
        115                 120                 125

Pro His Lys Asn Lys Asn Ala Asp Thr Glu Asn Leu Ile Asn Leu Ile
    130                 135                 140

Asp Ser Glu Ile Gln Lys Gln Leu Asn Lys Ala Leu Leu Asp Ala Asp
145                 150                 155                 160

Arg Asn Glu Trp Ser Ser Tyr Leu Glu Ser Ile Phe Asp Ser Ser Asn
                165                 170                 175

Asn Leu Asn Gly Ala Ile Val Asp Ala Gln Trp Ser Gly Thr Val Asn
            180                 185                 190

Thr Thr Asn Arg Thr Leu Arg Asn Pro Thr Glu Ser Asp Tyr Thr Asn
        195                 200                 205

Val Val Thr Asn Phe Ile Ala Ala Asp Gly Asp Ile Ala Asn Asn Glu
    210                 215                 220

Asn His Ile Met Asn Gly Asn Phe Asp Val Ala Ala Ala Pro Tyr Phe
225                 230                 235                 240

Val Ile Gly Ala Thr Ala Arg Phe Ala Ala Met Gln Ser Tyr Ile Lys
```

```
              245                 250                 255
Phe Cys Asn Ala Trp Ile Asp Lys Val Gly Leu Ser Asp Ala Gln Leu
            260                 265                 270

Thr Thr Gln Lys Ala Asn Leu Asp Arg Thr Lys Gln Asn Met Arg Asn
        275                 280                 285

Ala Ile Leu Asn Tyr Thr Gln Gln Val Met Lys Val Phe Lys Asp Ser
    290                 295                 300

Lys Asn Met Pro Thr Ile Gly Thr Asn Lys Phe Ser Val Asp Thr Tyr
305                 310                 315                 320

Asn Val Tyr Ile Lys Gly Met Thr Leu Asn Val Leu Asp Ile Val Ala
                325                 330                 335

Ile Trp Pro Ser Leu Tyr Pro Asp Asp Tyr Thr Ser Gln Thr Ala Leu
            340                 345                 350

Glu Gln Thr Arg Val Thr Phe Ser Asn Met Val Gly Gln Glu Glu Gly
        355                 360                 365

Thr Asp Gly Ser Leu Arg Ile Tyr Asn Thr Phe Asp Ser Phe Ser Tyr
    370                 375                 380

Gln His Ser Pro Ile Pro Asn Asn Asn Val Asn Leu Ile Ser Tyr Tyr
385                 390                 395                 400

Asn Asp Glu Leu Gln Asn Leu Glu Leu Gly Val Tyr Thr Pro Pro Lys
                405                 410                 415

Lys Gly Ser Gly Tyr Ser Tyr Pro Tyr Gly Phe Val Leu Asn Tyr Ala
            420                 425                 430

Asn Ser Lys Tyr Lys Tyr Gly Asp Ser Asn Asp Pro Glu Ser Leu Gly
        435                 440                 445

Gly Leu Ser Thr Leu Ser Ala Pro Ile Gln Gln Val Asn Ala Ala Thr
    450                 455                 460

Gln Asn Ser Lys Tyr Leu Asp Gly Glu Ile Leu Asn Gly Ile Gly Ala
465                 470                 475                 480

Ser Leu Pro Gly Tyr Cys Thr Thr Gly Cys Ser Pro Thr Glu Pro Pro
                485                 490                 495

Phe Ser Cys Thr Ser Thr Ala Asn Gly Tyr Lys Ala Ser Cys Asn Pro
            500                 505                 510

Ser Asp Thr Asn Gln Lys Ile Asn Ala Leu Tyr Pro Phe Thr Gln Ala
        515                 520                 525

Asn Val Lys Gly Asn Thr Gly Lys Leu Gly Val Leu Ala Ser Leu Val
    530                 535                 540

Ser Tyr Asp Leu Asn Pro Lys Asn Val Phe Gly Glu Leu Asp Ser Asp
545                 550                 555                 560

Thr Asn Asn Val Ile Leu Lys Gly Ile Pro Ala Glu Lys Gly Tyr Phe
                565                 570                 575

Pro Asn Asn Ala Arg Pro Thr Val Val Lys Glu Trp Ile Asn Gly Ala
            580                 585                 590

Ser Ala Val Pro Leu Asp Ser Gly Asn Thr Leu Phe Met Thr Ala Thr
        595                 600                 605

Asn Leu Thr Ala Thr Gln Tyr Arg Ile Arg Ile Arg Tyr Ala Asn Pro
    610                 615                 620

Asn Ser Asn Thr Gln Ile Gly Val Arg Ile Thr Gln Asn Gly Ser Leu
625                 630                 635                 640

Ile Ser Ser Ser Asn Leu Thr Leu Tyr Ser Thr Thr Asp Met Asn Asn
                645                 650                 655

Thr Leu Pro Leu Asn Val Tyr Val Ile Gly Glu Asn Gly Asn Tyr Thr
            660                 665                 670
```

-continued

```
Leu Gln Asp Leu Tyr Asn Thr Thr Asn Val Leu Ser Thr Gly Asp Ile
        675                 680                 685

Thr Leu Gln Ile Thr Gly Gly Asp Gln Lys Ile Phe Ile Asp Arg Ile
    690                 695                 700

Glu Phe Val Pro Thr Met Pro Val Pro Gly Asn Thr Asn Asn Asn Asn
705                 710                 715                 720

Gly Asn Asn Asn Gly Asn Asn Asn Pro His His Val Cys Ala Ile
                725                 730                 735

Ala Gly Thr Gln Gln Ser Cys Ser Gly Pro Pro Lys Phe Glu Gln Val
            740                 745                 750

Ser Asp Leu Glu Lys Ile Thr Thr Gln Val Tyr Met Leu Phe Lys Ser
        755                 760                 765

<210> SEQ ID NO 32
<211> LENGTH: 3570
<212> TYPE: DNA
<213> ORGANISM: Artificial Sequence
<220> FEATURE:
<223> OTHER INFORMATION: synaxmi-031(fl)-ER
<221> NAME/KEY: CDS
<222> LOCATION: (1)...(3570)

<400> SEQUENCE: 32 atg gat tgc aat ctc cag agc cag cag aat atc cca tac aat gtg ctt      48
Met Asp Cys Asn Leu Gln Ser Gln Gln Asn Ile Pro Tyr Asn Val Leu
1               5                  10                  15 gct atc cct gtt agc aat gtt aat agc ctt acg gat acg gtt ggc gat      96
Ala Ile Pro Val Ser Asn Val Asn Ser Leu Thr Asp Thr Val Gly Asp
            20                  25                  30 cta aag aag gca tgg gaa gag ttc cag aag acg ggc agc ttc tcc ctt     144
Leu Lys Lys Ala Trp Glu Glu Phe Gln Lys Thr Gly Ser Phe Ser Leu
        35                  40                  45 acc gca ctc cag cag ggc ttc agc gct tcc cag ggc ggg acg ttc aat     192
Thr Ala Leu Gln Gln Gly Phe Ser Ala Ser Gln Gly Gly Thr Phe Asn
    50                  55                  60 tac ctc acc ctc ctc cag tcc ggg atc tcc ctg gct ggc agc ttc gtg     240
Tyr Leu Thr Leu Leu Gln Ser Gly Ile Ser Leu Ala Gly Ser Phe Val
65                  70                  75                  80 cct ggc ggc acc ttc gtt gct cca atc atc aat atg gtg atc ggc tgg     288
Pro Gly Gly Thr Phe Val Ala Pro Ile Ile Asn Met Val Ile Gly Trp
                85                  90                  95 ctc tgg cct cat aag aat aag aat gca gat acg gaa aat ctg atc aat     336
Leu Trp Pro His Lys Asn Lys Asn Ala Asp Thr Glu Asn Leu Ile Asn
            100                 105                 110 ctg atc gat tca gaa atc cag aag cag ctg aat aag gct ctg ctg gat     384
Leu Ile Asp Ser Glu Ile Gln Lys Gln Leu Asn Lys Ala Leu Leu Asp
        115                 120                 125 gct gat cgc aat gaa tgg agc agc tac ctc gag tcc atc ttc gat agc     432
Ala Asp Arg Asn Glu Trp Ser Ser Tyr Leu Glu Ser Ile Phe Asp Ser
    130                 135                 140 agc aat aat ctg aat ggc gca atc gtt gat gct cag tgg tcc ggc acc     480
Ser Asn Asn Leu Asn Gly Ala Ile Val Asp Ala Gln Trp Ser Gly Thr
145                 150                 155                 160 gtg aat acg acc aat cgt acg ctt cgt aat cct acg gaa tca gat tac     528
Val Asn Thr Thr Asn Arg Thr Leu Arg Asn Pro Thr Glu Ser Asp Tyr
                165                 170                 175 acc aat gtg gtg acg aat ttc atc gca gca gat ggg gat atc gct aat     576
Thr Asn Val Val Thr Asn Phe Ile Ala Ala Asp Gly Asp Ile Ala Asn
            180                 185                 190 aat gaa aat cat atc atg aat ggg aat ttc gat gtg gca gca gct cca     624
Asn Glu Asn His Ile Met Asn Gly Asn Phe Asp Val Ala Ala Ala Pro
```

```
                                            -continued
        195                  200                  205
tac ttc gtt atc ggg gct acc gct aga ttc gca gct atg cag tcc tac     672
Tyr Phe Val Ile Gly Ala Thr Ala Arg Phe Ala Ala Met Gln Ser Tyr
210                 215                 220 atc aag ttc tgc aat gca tgg atc gat aag gtt ggg ctg tca gat gct     720
Ile Lys Phe Cys Asn Ala Trp Ile Asp Lys Val Gly Leu Ser Asp Ala
225                 230                 235                 240 cag ctg acc acg cag aag gct aat ctg gat aga acg aag cag aat atg     768
Gln Leu Thr Thr Gln Lys Ala Asn Leu Asp Arg Thr Lys Gln Asn Met
                245                 250                 255 cgt aat gct atc ctt aat tac acc cag cag gtt atg aag gtt ttc aag     816
Arg Asn Ala Ile Leu Asn Tyr Thr Gln Gln Val Met Lys Val Phe Lys
        260                 265                 270 gat tcc aag aat atg cca acg atc ggc acg aat aag ttc agc gtt gat     864
Asp Ser Lys Asn Met Pro Thr Ile Gly Thr Asn Lys Phe Ser Val Asp
    275                 280                 285 acc tac aat gtt tac atc aag ggg atg acg ctt aat gtg ctt gat atc     912
Thr Tyr Asn Val Tyr Ile Lys Gly Met Thr Leu Asn Val Leu Asp Ile
290                 295                 300 gtt gct atc tgg cca agc ctg tac cca gat gat tac acg tca cag acg     960
Val Ala Ile Trp Pro Ser Leu Tyr Pro Asp Asp Tyr Thr Ser Gln Thr
305                 310                 315                 320 gct ctg gaa cag acc cgc gtg acg ttc tcc aat atg gtg ggg cag gaa    1008
Ala Leu Glu Gln Thr Arg Val Thr Phe Ser Asn Met Val Gly Gln Glu
                325                 330                 335 gaa ggc acg gat ggc agc ctc aga atc tac aat acc ttc gat agc ttc    1056
Glu Gly Thr Asp Gly Ser Leu Arg Ile Tyr Asn Thr Phe Asp Ser Phe
            340                 345                 350 tcc tac cag cat agc cct atc cct aat aat aat gtg aat ctc atc agc    1104
Ser Tyr Gln His Ser Pro Ile Pro Asn Asn Asn Val Asn Leu Ile Ser
        355                 360                 365 tac tac aat gat gaa ctt cag aat ctg gaa ctc ggg gtt tac acc cca    1152
Tyr Tyr Asn Asp Glu Leu Gln Asn Leu Glu Leu Gly Val Tyr Thr Pro
    370                 375                 380 cca aag aag ggc tca ggc tac agc tac cca tac ggg ttc gtg ctg aat    1200
Pro Lys Lys Gly Ser Gly Tyr Ser Tyr Pro Tyr Gly Phe Val Leu Asn
385                 390                 395                 400 tac gca aat agc aag tac aag tac ggc gat tcc aat gat cca gaa tcc    1248
Tyr Ala Asn Ser Lys Tyr Lys Tyr Gly Asp Ser Asn Asp Pro Glu Ser
                405                 410                 415 ctc ggc ggg ctt tcc acc ctt agc gct cca atc caa cag gtt aat gct    1296
Leu Gly Gly Leu Ser Thr Leu Ser Ala Pro Ile Gln Gln Val Asn Ala
            420                 425                 430 gct acc cag aat agc aag tac ctt gat ggc gaa atc ctg aat ggg atc    1344
Ala Thr Gln Asn Ser Lys Tyr Leu Asp Gly Glu Ile Leu Asn Gly Ile
        435                 440                 445 ggc gca agc ctg cct ggc tac tgc acg acc ggg tgc tca cct acc gaa    1392
Gly Ala Ser Leu Pro Gly Tyr Cys Thr Thr Gly Cys Ser Pro Thr Glu
    450                 455                 460 cca cca ttc agc tgc acg agc acg gca aat ggg tac aag gca agc tgc    1440
Pro Pro Phe Ser Cys Thr Ser Thr Ala Asn Gly Tyr Lys Ala Ser Cys
465                 470                 475                 480 aat cca agc gat acc aat cag aag atc aat gct ctc tac cca ttc acg    1488
Asn Pro Ser Asp Thr Asn Gln Lys Ile Asn Ala Leu Tyr Pro Phe Thr
                485                 490                 495 cag gca aat gtg aag ggg aat acc ggg aag ctg ggc gtt ctc gca agc    1536
Gln Ala Asn Val Lys Gly Asn Thr Gly Lys Leu Gly Val Leu Ala Ser
            500                 505                 510 ctt gtt agc tac gat ctg aat cct aag aat gtt ttc ggg gaa ctc gat    1584
Leu Val Ser Tyr Asp Leu Asn Pro Lys Asn Val Phe Gly Glu Leu Asp
```

-continued

```
              515                 520                 525
tca gat acc aat aat gtt atc ctt aag ggc atc cca gca gaa aag ggc      1632
Ser Asp Thr Asn Asn Val Ile Leu Lys Gly Ile Pro Ala Glu Lys Gly
    530                 535                 540 tac ttc cca aat aat gca aga cca acc gtt gtg aag gaa tgg atc aat      1680
Tyr Phe Pro Asn Asn Ala Arg Pro Thr Val Val Lys Glu Trp Ile Asn
545                 550                 555                 560 ggg gct tcc gca gtt cca ctt gat tcc ggc aat acc ctg ttc atg acg      1728
Gly Ala Ser Ala Val Pro Leu Asp Ser Gly Asn Thr Leu Phe Met Thr
                565                 570                 575 gct acg aac ctg acg gct acc cag tac aga atc cgc atc cgt tac gct      1776
Ala Thr Asn Leu Thr Ala Thr Gln Tyr Arg Ile Arg Ile Arg Tyr Ala
            580                 585                 590 aac cca aac tca aac acg cag atc ggc gtt aga atc acg cag aac ggg      1824
Asn Pro Asn Ser Asn Thr Gln Ile Gly Val Arg Ile Thr Gln Asn Gly
        595                 600                 605 agc ctc atc tcc tcc tcc aac ctc acg ctg tac tca acc acc gat atg      1872
Ser Leu Ile Ser Ser Ser Asn Leu Thr Leu Tyr Ser Thr Thr Asp Met
    610                 615                 620 aac aac acc ctg cca ctg aac gtt tac gtg atc ggg gaa aac ggg aac      1920
Asn Asn Thr Leu Pro Leu Asn Val Tyr Val Ile Gly Glu Asn Gly Asn
625                 630                 635                 640 tac acc ctc cag gat ctc tac aac acg acg aac gtt ctg tcc acg ggc      1968
Tyr Thr Leu Gln Asp Leu Tyr Asn Thr Thr Asn Val Leu Ser Thr Gly
                645                 650                 655 gat atc acc ctg cag atc acc ggc ggg gat cag aag ata ttc atc gat      2016
Asp Ile Thr Leu Gln Ile Thr Gly Gly Asp Gln Lys Ile Phe Ile Asp
            660                 665                 670 cgc atc gag ttc gtg cct acg atg cca gtg cca ggc aac acc aac aac      2064
Arg Ile Glu Phe Val Pro Thr Met Pro Val Pro Gly Asn Thr Asn Asn
        675                 680                 685 aac aac ggg aac aac aac ggc aac aac aac cct cct cat cat gtt tgc      2112
Asn Asn Gly Asn Asn Asn Gly Asn Asn Asn Pro Pro His His Val Cys
    690                 695                 700 gct atc gca ggc acc cag cag tcc tgc tcc ggc cca cca aag ttc gag      2160
Ala Ile Ala Gly Thr Gln Gln Ser Cys Ser Gly Pro Pro Lys Phe Glu
705                 710                 715                 720 cag gtg tcc gat tta gaa aag ata acc acg cag gtt tac atg ctc ttc      2208
Gln Val Ser Asp Leu Glu Lys Ile Thr Thr Gln Val Tyr Met Leu Phe
                725                 730                 735 aag tcc tcc cca tac gaa gaa ctt gct ctt gaa gtt agc agc tac cag      2256
Lys Ser Ser Pro Tyr Glu Glu Leu Ala Leu Glu Val Ser Ser Tyr Gln
            740                 745                 750 atc agc cag gtt gca ctg aag gtt atg gct ctc agc gat gaa cta ttc      2304
Ile Ser Gln Val Ala Leu Lys Val Met Ala Leu Ser Asp Glu Leu Phe
        755                 760                 765 tgc gaa gaa aag aac gtg ctg aga aag ctc gtg aac aag gca aag cag      2352
Cys Glu Glu Lys Asn Val Leu Arg Lys Leu Val Asn Lys Ala Lys Gln
    770                 775                 780 ctt ctc gaa gca agc aac ctt ctc gtt ggg ggg aac ttc gag acg act      2400
Leu Leu Glu Ala Ser Asn Leu Leu Val Gly Gly Asn Phe Glu Thr Thr
785                 790                 795                 800 cag aac tgg gtg ctc ggc acg aac gct tac atc aac tat gat tca ttc      2448
Gln Asn Trp Val Leu Gly Thr Asn Ala Tyr Ile Asn Tyr Asp Ser Phe
                805                 810                 815 ctg ttc aac ggg aac tac ctg agc ctc cag cca gca tcc ggc ttc ttc      2496
Leu Phe Asn Gly Asn Tyr Leu Ser Leu Gln Pro Ala Ser Gly Phe Phe
            820                 825                 830 acg agc tac gct tac cag aag atc gat gaa tcc acg ctt aag cct tac      2544
Thr Ser Tyr Ala Tyr Gln Lys Ile Asp Glu Ser Thr Leu Lys Pro Tyr
```

-continued

```
             835                 840                 845
acg cgc tac aag gtg tcc ggg ttc atc ggg cag tca aac cag gtt gaa    2592
Thr Arg Tyr Lys Val Ser Gly Phe Ile Gly Gln Ser Asn Gln Val Glu
850                 855                 860 ctg atc atc agc cgc tac ggg aag gaa atc gat aag atc ctt aac gtg    2640
Leu Ile Ile Ser Arg Tyr Gly Lys Glu Ile Asp Lys Ile Leu Asn Val
865                 870                 875                 880 cca tac gca ggg cca ctc cca atc acc gca gat gca agc atc acc tgc    2688
Pro Tyr Ala Gly Pro Leu Pro Ile Thr Ala Asp Ala Ser Ile Thr Cys
                885                 890                 895 tgc gct cca gaa ata ggg cag tgc gat ggg gaa cag tca gat tcc cat    2736
Cys Ala Pro Glu Ile Gly Gln Cys Asp Gly Glu Gln Ser Asp Ser His
            900                 905                 910 ttc ttc aac tac agc atc gat gtt ggc gca ctc cat cca gaa ctt aac    2784
Phe Phe Asn Tyr Ser Ile Asp Val Gly Ala Leu His Pro Glu Leu Asn
        915                 920                 925 cca ggg atc gaa atc ggg ctg aag atc gtt cag agc aac ggc tac atc    2832
Pro Gly Ile Glu Ile Gly Leu Lys Ile Val Gln Ser Asn Gly Tyr Ile
930                 935                 940 acc atc tcc aac ctt gaa atc atc gaa gaa aga cca tta acg gaa atg    2880
Thr Ile Ser Asn Leu Glu Ile Ile Glu Glu Arg Pro Leu Thr Glu Met
945                 950                 955                 960 gaa att caa gca gtg aac cgc aag aac cag aag tgg gaa cgc gaa aag    2928
Glu Ile Gln Ala Val Asn Arg Lys Asn Gln Lys Trp Glu Arg Glu Lys
                965                 970                 975 ctg ctt gaa tgc gca tcc atc tcc gaa ctc ctc cag cct atc atc aac    2976
Leu Leu Glu Cys Ala Ser Ile Ser Glu Leu Leu Gln Pro Ile Ile Asn
            980                 985                 990 cag ata gat agc ctc ttc aag gat ggc aac tgg tac aac gat atc cta    3024
Gln Ile Asp Ser Leu Phe Lys Asp Gly Asn Trp Tyr Asn Asp Ile Leu
        995                 1000                1005 cca cat gtt acc tac cag gat ctt aag aac atc atc atc cca gaa ctt    3072
Pro His Val Thr Tyr Gln Asp Leu Lys Asn Ile Ile Ile Pro Glu Leu
    1010                1015                1020 cct aag ctc aag cat tgg ttc atc gaa aac ctg cct ggg gaa tac cat    3120
Pro Lys Leu Lys His Trp Phe Ile Glu Asn Leu Pro Gly Glu Tyr His
1025                1030                1035                1040 gaa atc gaa cag aag atg aag gaa gca tta aag tac gca ttc act cag    3168
Glu Ile Glu Gln Lys Met Lys Glu Ala Leu Lys Tyr Ala Phe Thr Gln
                1045                1050                1055 ctc gat gaa aag aac ctg atc cat aac ggc cat ttc acc acc aac ctc    3216
Leu Asp Glu Lys Asn Leu Ile His Asn Gly His Phe Thr Thr Asn Leu
            1060                1065                1070 atc gat tgg cag gtg gaa ggc gat gct cag atg aag gtg ctt gaa aac    3264
Ile Asp Trp Gln Val Glu Gly Asp Ala Gln Met Lys Val Leu Glu Asn
        1075                1080                1085 gat gca ctc gct ctc cag cta ttc aac tgg gat gct tcc gca tcc cag    3312
Asp Ala Leu Ala Leu Gln Leu Phe Asn Trp Asp Ala Ser Ala Ser Gln
    1090                1095                1100 agc atc aac atc cta gag ttc gat gaa gat aag gct tac aag ctg cgt    3360
Ser Ile Asn Ile Leu Glu Phe Asp Glu Asp Lys Ala Tyr Lys Leu Arg
1105                1110                1115                1120 gtg tac gca cag ggc tcc ggg acg atc cag ttc ggc aac tgc gaa gat    3408
Val Tyr Ala Gln Gly Ser Gly Thr Ile Gln Phe Gly Asn Cys Glu Asp
                1125                1130                1135 gaa gct atc cag ttc aac acc aac tca ttc atc tac cag gaa aag ata    3456
Glu Ala Ile Gln Phe Asn Thr Asn Ser Phe Ile Tyr Gln Glu Lys Ile
            1140                1145                1150 gtg tac ttc gat acg cca tcc gtt aac ctt cat atc cag agc gaa ggc    3504
Val Tyr Phe Asp Thr Pro Ser Val Asn Leu His Ile Gln Ser Glu Gly
```

-continued

```
                    1155                1160                1165
tcc gag ttc atc gtg agc agc atc gat ctc atc gaa ctc agc gat gat       3552
Ser Glu Phe Ile Val Ser Ser Ile Asp Leu Ile Glu Leu Ser Asp Asp
    1170                1175                1180 cag aag gat gaa ctg taa                                               3570
Gln Lys Asp Glu Leu *
1185
```

<210> SEQ ID NO 33
<211> LENGTH: 1189
<212> TYPE: PRT
<213> ORGANISM: Artificial Sequence
<220> FEATURE:
<223> OTHER INFORMATION: SYNAXMI-031(FL)-ER

<400> SEQUENCE: 33

```
Met Asp Cys Asn Leu Gln Ser Gln Gln Asn Ile Pro Tyr Asn Val Leu
1               5                   10                  15

Ala Ile Pro Val Ser Asn Val Asn Ser Leu Thr Asp Thr Val Gly Asp
                20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Thr Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
    130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Val Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
    290                 295                 300

Val Ala Ile Trp Pro Ser Leu Tyr Pro Asp Asp Tyr Ser Gln Thr
305                 310                 315                 320
```

-continued

Ala Leu Glu Gln Thr Arg Val Thr Phe Ser Asn Met Val Gly Gln Glu
              325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Val Asn Leu Ile Ser
        355                 360                 365

Tyr Tyr Asn Asp Glu Leu Gln Asn Leu Glu Leu Gly Val Tyr Thr Pro
    370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Gln Val Asn Ala
            420                 425                 430

Ala Thr Gln Asn Ser Lys Tyr Leu Asp Gly Glu Ile Leu Asn Gly Ile
        435                 440                 445

Gly Ala Ser Leu Pro Gly Tyr Cys Thr Thr Gly Cys Ser Pro Thr Glu
    450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
                485                 490                 495

Gln Ala Asn Val Lys Gly Asn Thr Gly Lys Leu Gly Val Leu Ala Ser
            500                 505                 510

Leu Val Ser Tyr Asp Leu Asn Pro Lys Asn Val Phe Gly Glu Leu Asp
        515                 520                 525

Ser Asp Thr Asn Asn Val Ile Leu Lys Gly Ile Pro Ala Glu Lys Gly
    530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575

Ala Thr Asn Leu Thr Ala Thr Gln Tyr Arg Ile Arg Ile Arg Tyr Ala
            580                 585                 590

Asn Pro Asn Ser Asn Thr Gln Ile Gly Val Arg Ile Thr Gln Asn Gly
        595                 600                 605

Ser Leu Ile Ser Ser Ser Asn Leu Thr Leu Tyr Ser Thr Thr Asp Met
    610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Asn Val Leu Ser Thr Gly
                645                 650                 655

Asp Ile Thr Leu Gln Ile Thr Gly Gly Asp Gln Lys Ile Phe Ile Asp
            660                 665                 670

Arg Ile Glu Phe Val Pro Thr Met Pro Val Pro Gly Asn Thr Asn Asn
        675                 680                 685

Asn Asn Gly Asn Asn Asn Gly Asn Asn Asn Pro His His Val Cys
    690                 695                 700

Ala Ile Ala Gly Thr Gln Gln Ser Cys Ser Gly Pro Pro Lys Phe Glu
705                 710                 715                 720

Gln Val Ser Asp Leu Glu Lys Ile Thr Thr Gln Val Tyr Met Leu Phe
                725                 730                 735

Lys Ser Ser Pro Tyr Glu Glu Leu Ala Leu Glu Val Ser Ser Tyr Gln
            740                 745                 750

```
Ile Ser Gln Val Ala Leu Lys Val Met Ala Leu Ser Asp Glu Leu Phe
        755                 760                 765
Cys Glu Glu Lys Asn Val Leu Arg Lys Leu Val Asn Lys Ala Lys Gln
        770                 775                 780
Leu Leu Glu Ala Ser Asn Leu Val Gly Gly Asn Phe Glu Thr Thr
785                 790                 795                 800
Gln Asn Trp Val Leu Gly Thr Asn Ala Tyr Ile Asn Tyr Asp Ser Phe
                805                 810                 815
Leu Phe Asn Gly Asn Tyr Leu Ser Leu Gln Pro Ala Ser Gly Phe Phe
                820                 825                 830
Thr Ser Tyr Ala Tyr Gln Lys Ile Asp Glu Ser Thr Leu Lys Pro Tyr
                835                 840                 845
Thr Arg Tyr Lys Val Ser Gly Phe Ile Gly Gln Ser Asn Gln Val Glu
        850                 855                 860
Leu Ile Ile Ser Arg Tyr Gly Lys Glu Ile Asp Lys Ile Leu Asn Val
865                 870                 875                 880
Pro Tyr Ala Gly Pro Leu Pro Ile Thr Ala Asp Ala Ser Ile Thr Cys
                885                 890                 895
Cys Ala Pro Glu Ile Gly Gln Cys Asp Gly Glu Gln Ser Asp Ser His
                900                 905                 910
Phe Phe Asn Tyr Ser Ile Asp Val Gly Ala Leu His Pro Glu Leu Asn
                915                 920                 925
Pro Gly Ile Glu Ile Gly Leu Lys Ile Val Gln Ser Asn Gly Tyr Ile
        930                 935                 940
Thr Ile Ser Asn Leu Glu Ile Ile Glu Glu Arg Pro Leu Thr Glu Met
945                 950                 955                 960
Glu Ile Gln Ala Val Asn Arg Lys Asn Gln Lys Trp Glu Arg Glu Lys
                965                 970                 975
Leu Leu Glu Cys Ala Ser Ile Ser Glu Leu Leu Gln Pro Ile Ile Asn
                980                 985                 990
Gln Ile Asp Ser Leu Phe Lys Asp Gly Asn Trp Tyr Asn Asp Ile Leu
        995                 1000                1005
Pro His Val Thr Tyr Gln Asp Leu Lys Asn Ile Ile Ile Pro Glu Leu
        1010                1015                1020
Pro Lys Leu Lys His Trp Phe Ile Glu Asn Leu Pro Gly Glu Tyr His
1025                1030                1035                1040
Glu Ile Glu Gln Lys Met Lys Glu Ala Leu Lys Tyr Ala Phe Thr Gln
                1045                1050                1055
Leu Asp Glu Lys Asn Leu Ile His Asn Gly His Phe Thr Thr Asn Leu
        1060                1065                1070
Ile Asp Trp Gln Val Glu Gly Asp Ala Gln Met Lys Val Leu Glu Asn
        1075                1080                1085
Asp Ala Leu Ala Leu Gln Leu Phe Asn Trp Asp Ala Ser Ala Ser Gln
        1090                1095                1100
Ser Ile Asn Ile Leu Glu Phe Asp Glu Asp Lys Ala Tyr Lys Leu Arg
1105                1110                1115                1120
Val Tyr Ala Gln Gly Ser Gly Thr Ile Gln Phe Gly Asn Cys Glu Asp
                1125                1130                1135
Glu Ala Ile Gln Phe Asn Thr Asn Ser Phe Ile Tyr Gln Glu Lys Ile
                1140                1145                1150
Val Tyr Phe Asp Thr Pro Ser Val Asn Leu His Ile Gln Ser Glu Gly
        1155                1160                1165
Ser Glu Phe Ile Val Ser Ser Ile Asp Leu Ile Glu Leu Ser Asp Asp
```

```
                                            -continued
            1170              1175              1180

Gln Lys Asp Glu Leu
1185

<210> SEQ ID NO 34
<211> LENGTH: 3669
<212> TYPE: DNA
<213> ORGANISM: Unknown
<220> FEATURE:
<223> OTHER INFORMATION: isolated from soil sample (AXMI-049)
<221> NAME/KEY: CDS
<222> LOCATION: (1)...(3669)

<400> SEQUENCE: 34 atg gat gac atg aca aat tta tcc gat gta tat tca ccc gta cct tcc         48
Met Asp Asp Met Thr Asn Leu Ser Asp Val Tyr Ser Pro Val Pro Ser
1               5                   10                  15 aat gta tta gca gct cca ctt att ctt gaa gaa aca aag aaa aaa aca         96
Asn Val Leu Ala Ala Pro Leu Ile Leu Glu Glu Thr Lys Lys Lys Thr
            20                  25                  30 ccg gct gaa caa gca aaa gaa gat tta gaa aag gca ttg aga aca gga        144
Pro Ala Glu Gln Ala Lys Glu Asp Leu Glu Lys Ala Leu Arg Thr Gly
        35                  40                  45 aag ttt tcc gat gca att gca caa att tta aat gat gtt ctt att aac        192
Lys Phe Ser Asp Ala Ile Ala Gln Ile Leu Asn Asp Val Leu Ile Asn
    50                  55                  60 caa aag ttc agc tat caa aca gcg gtt aca gtt tcc tta tct ttg gct        240
Gln Lys Phe Ser Tyr Gln Thr Ala Val Thr Val Ser Leu Ser Leu Ala
65                  70                  75                  80 agt ata gtt ctt cca gaa ata ggt ttt ttt gcc ccc ttt gtt ggt tta        288
Ser Ile Val Leu Pro Glu Ile Gly Phe Phe Ala Pro Phe Val Gly Leu
                85                  90                  95 ttt ttt tct gct tta aat aaa tct caa aat ata cct acg act tca gat        336
Phe Phe Ser Ala Leu Asn Lys Ser Gln Asn Ile Pro Thr Thr Ser Asp
            100                 105                 110 att ttt gaa gcg atg aaa cca gct att caa aca atg att gat cgt agt        384
Ile Phe Glu Ala Met Lys Pro Ala Ile Gln Thr Met Ile Asp Arg Ser
        115                 120                 125 tta aca gat gct gaa aac aag gag atg gat gat cag gcg cac aac cta        432
Leu Thr Asp Ala Glu Asn Lys Glu Met Asp Asp Gln Ala His Asn Leu
    130                 135                 140 ttt acg cga tta caa act tat caa gag caa ata gat ctc tat aaa cat        480
Phe Thr Arg Leu Gln Thr Tyr Gln Glu Gln Ile Asp Leu Tyr Lys His
145                 150                 155                 160 att tta gat gca aaa caa aaa cca act ctt aac gat ata gga gat ctt        528
Ile Leu Asp Ala Lys Gln Lys Pro Thr Leu Asn Asp Ile Gly Asp Leu
                165                 170                 175 cac act tcg atc gac gaa act ctc aga aca tta gat tcc aat tta gca        576
His Thr Ser Ile Asp Glu Thr Leu Arg Thr Leu Asp Ser Asn Leu Ala
            180                 185                 190 ttt ttc caa aca gaa ggc tat caa gat ctc ggg tta cca tat tac aca        624
Phe Phe Gln Thr Glu Gly Tyr Gln Asp Leu Gly Leu Pro Tyr Tyr Thr
        195                 200                 205 att ttt gcc aca caa tat ttg tta atc ctt tca gat aaa att aaa act        672
Ile Phe Ala Thr Gln Tyr Leu Leu Ile Leu Ser Asp Lys Ile Lys Thr
    210                 215                 220 ggt atc aca tgg gga tat aat cct att aac att cca gat ttt caa aac        720
Gly Ile Thr Trp Gly Tyr Asn Pro Ile Asn Ile Pro Asp Phe Gln Asn
225                 230                 235                 240 caa ttt aat aat aga ata ctt cta ttt aca aaa tac att agt ggt caa        768
Gln Phe Asn Asn Arg Ile Leu Leu Phe Thr Lys Tyr Ile Ser Gly Gln
                245                 250                 255
```

```
ctt aag aaa atg tat gac aac ggt gta cat cca gca ctt tta tat caa      816
Leu Lys Lys Met Tyr Asp Asn Gly Val His Pro Ala Leu Leu Tyr Gln
        260                 265                 270 aac tgt atc caa ttt gtt gct tta tgg cct act ttt tct ccc gca gat      864
Asn Cys Ile Gln Phe Val Ala Leu Trp Pro Thr Phe Ser Pro Ala Asp
            275                 280                 285 tat aac ctt agt aac agc aca gat tta gaa caa aca ata agt ttt aag      912
Tyr Asn Leu Ser Asn Ser Thr Asp Leu Glu Gln Thr Ile Ser Phe Lys
        290                 295                 300 agt ttc atc tcc tat aag agt tta aat gat tat aat tat gca ctt cct      960
Ser Phe Ile Ser Tyr Lys Ser Leu Asn Asp Tyr Asn Tyr Ala Leu Pro
305                 310                 315                 320 gaa att aat aca tgg aca aat ttt gaa atg aca aaa tca ctt gat ttt     1008
Glu Ile Asn Thr Trp Thr Asn Phe Glu Met Thr Lys Ser Leu Asp Phe
            325                 330                 335 aac aac tgt aga tcc atg gat aat tat ggt atc gcg ggt gac ctt cgt     1056
Asn Asn Cys Arg Ser Met Asp Asn Tyr Gly Ile Ala Gly Asp Leu Arg
        340                 345                 350 ata aca aat cat aaa aat gaa atc cat gaa ata tct gct cct tcg gta     1104
Ile Thr Asn His Lys Asn Glu Ile His Glu Ile Ser Ala Pro Ser Val
        355                 360                 365 ctc tac atg aca tca aat cag tgt aac tca aga ctt gtt ttt cca ttc     1152
Leu Tyr Met Thr Ser Asn Gln Cys Asn Ser Arg Leu Val Phe Pro Phe
370                 375                 380 gat gat cct att gtt aaa ttc gaa gga aca agt agt gtt ttc ata ggg     1200
Asp Asp Pro Ile Val Lys Phe Glu Gly Thr Ser Ser Val Phe Ile Gly
385                 390                 395                 400 aca cct gga tta cct caa ttt tat aca aat ttt cag ttg act tct ggt     1248
Thr Pro Gly Leu Pro Gln Phe Tyr Thr Asn Phe Gln Leu Thr Ser Gly
            405                 410                 415 aaa agt tta ata ttc cct cct cct tca gga gtt aat caa caa ggt ttc     1296
Lys Ser Leu Ile Phe Pro Pro Pro Ser Gly Val Asn Gln Gln Gly Phe
        420                 425                 430 aca caa aat tat tcg gta atc cct cat cct gga ttt aaa ata gca ggt     1344
Thr Gln Asn Tyr Ser Val Ile Pro His Pro Gly Phe Lys Ile Ala Gly
        435                 440                 445 att aca aat atg tca tat tta cct act cat cac gat agt aat gcg cgg     1392
Ile Thr Asn Met Ser Tyr Leu Pro Thr His His Asp Ser Asn Ala Arg
450                 455                 460 aca caa ata gaa cat atc caa gtt cct gaa aaa atc ttt cca gaa aat     1440
Thr Gln Ile Glu His Ile Gln Val Pro Glu Lys Ile Phe Pro Glu Asn
465                 470                 475                 480 att atc ggg gtt cca gat cca gat aat aac aat cta atc cca atc aaa     1488
Ile Ile Gly Val Pro Asp Pro Asp Asn Asn Asn Leu Ile Pro Ile Lys
            485                 490                 495 ggt att ccc gca gaa aaa gga tat ggt gac tca att gca tat gtg tca     1536
Gly Ile Pro Ala Glu Lys Gly Tyr Gly Asp Ser Ile Ala Tyr Val Ser
        500                 505                 510 gaa ccg gta aat ggt gcg agt gca gtt aaa ctt act tca aat caa att     1584
Glu Pro Val Asn Gly Ala Ser Ala Val Lys Leu Thr Ser Asn Gln Ile
        515                 520                 525 ctc caa atg gaa att aca aat gta aca act caa aaa tat caa gtt cgc     1632
Leu Gln Met Glu Ile Thr Asn Val Thr Thr Gln Lys Tyr Gln Val Arg
530                 535                 540 ata cgt tat gct aca gct gga gat aca gag gct aat ata agg ttc cat     1680
Ile Arg Tyr Ala Thr Ala Gly Asp Thr Glu Ala Asn Ile Arg Phe His
545                 550                 555                 560 att att gat cca aat gaa aat aat tta ata aat ggg cct aat cat ttc     1728
Ile Ile Asp Pro Asn Glu Asn Asn Leu Ile Asn Gly Pro Asn His Phe
            565                 570                 575
```

```
aca gct gta tct aat act caa acg tct gtc caa ggt gaa aat gga aaa    1776
Thr Ala Val Ser Asn Thr Gln Thr Ser Val Gln Gly Glu Asn Gly Lys
        580                 585                 590 tat gta cta aac aca ctt gta aat tca ata ata tta cca tca gga aaa    1824
Tyr Val Leu Asn Thr Leu Val Asn Ser Ile Ile Leu Pro Ser Gly Lys
    595                 600                 605 caa aag gtc ttt att caa aac act ggt tct caa gat ctc ttt tta gac    1872
Gln Lys Val Phe Ile Gln Asn Thr Gly Ser Gln Asp Leu Phe Leu Asp
610                 615                 620 cgt att gaa ttt att cca tta caa cta gaa ctt cct ttc act tca aaa    1920
Arg Ile Glu Phe Ile Pro Leu Gln Leu Glu Leu Pro Phe Thr Ser Lys
625                 630                 635                 640 tta cct gaa act act aca caa cca aat aca aca aaa aca att tgg tca    1968
Leu Pro Glu Thr Thr Thr Gln Pro Asn Thr Thr Lys Thr Ile Trp Ser
                645                 650                 655 ggt caa aaa cct gct aat aca ctt tct ctt caa ggt aca gtt tat aat    2016
Gly Gln Lys Pro Ala Asn Thr Leu Ser Leu Gln Gly Thr Val Tyr Asn
            660                 665                 670 gat gct tct atc gaa tta caa ctt tat atg aac gat aac tta gtc caa    2064
Asp Ala Ser Ile Glu Leu Gln Leu Tyr Met Asn Asp Asn Leu Val Gln
        675                 680                 685 aaa atc cct gca caa ggt cct ggt cct agt ttt gac tgt gac gac caa    2112
Lys Ile Pro Ala Gln Gly Pro Gly Pro Ser Phe Asp Cys Asp Asp Gln
    690                 695                 700 tct aaa cct att aat caa cca aat ata aaa act gaa gaa ttt aac aaa    2160
Ser Lys Pro Ile Asn Gln Pro Asn Ile Lys Thr Glu Glu Phe Asn Lys
705                 710                 715                 720 ctt gtc tta aaa gaa tta agt agt acc tat tcg tat tgt atg gga gga    2208
Leu Val Leu Lys Glu Leu Ser Ser Thr Tyr Ser Tyr Cys Met Gly Gly
                725                 730                 735 gct ttt gaa aac act tac caa att gat att aca ata gac agc aaa tcc    2256
Ala Phe Glu Asn Thr Tyr Gln Ile Asp Ile Thr Ile Asp Ser Lys Ser
            740                 745                 750 caa tct ttt act act cca gaa gat tta gaa aaa atc aca aac caa gtc    2304
Gln Ser Phe Thr Thr Pro Glu Asp Leu Glu Lys Ile Thr Asn Gln Val
        755                 760                 765 aac cag tta ttt act tcc tca tcc caa aca aaa ttg gtt caa acc gta    2352
Asn Gln Leu Phe Thr Ser Ser Ser Gln Thr Lys Leu Val Gln Thr Val
    770                 775                 780 acg gat tat gga att gat caa atg gta atg aaa gta gat gcg tta tca    2400
Thr Asp Tyr Gly Ile Asp Gln Met Val Met Lys Val Asp Ala Leu Ser
785                 790                 795                 800 gac gat gta ttt ggt gtc gag aaa aaa gca tta cgt aaa ctt gtc aat    2448
Asp Asp Val Phe Gly Val Glu Lys Lys Ala Leu Arg Lys Leu Val Asn
                805                 810                 815 cag gcc aaa caa tta agt aaa gta cga aat gta ctg gtc ggt gga aac    2496
Gln Ala Lys Gln Leu Ser Lys Val Arg Asn Val Leu Val Gly Gly Asn
            820                 825                 830 ttt gaa aaa ggt cat aaa tgg gta cta ggt cgt aaa gcg aca acg gta    2544
Phe Glu Lys Gly His Lys Trp Val Leu Gly Arg Lys Ala Thr Thr Val
        835                 840                 845 gcg gat cat gat tta ttc aaa ggg gat cat tta tta tta cca cca cca    2592
Ala Asp His Asp Leu Phe Lys Gly Asp His Leu Leu Leu Pro Pro Pro
    850                 855                 860 acc ctg tat cca tcg tat gcg tat caa aaa atc gat gaa tct aaa tta    2640
Thr Leu Tyr Pro Ser Tyr Ala Tyr Gln Lys Ile Asp Glu Ser Lys Leu
865                 870                 875                 880 aaa tcc aat aca cgc tat acg gtt tcc ggt ttt gtt gcg caa agt gaa    2688
Lys Ser Asn Thr Arg Tyr Thr Val Ser Gly Phe Val Ala Gln Ser Glu
                885                 890                 895
```

```
cat tta gaa gtt gtt gtt tct cgc tat ggg aaa gaa gta aat acc ctg    2736
His Leu Glu Val Val Val Ser Arg Tyr Gly Lys Glu Val Asn Thr Leu
        900                 905                 910 tta cat gtc cct tat gaa gaa gca tta ccg att tct tcc gat gag cgt    2784
Leu His Val Pro Tyr Glu Glu Ala Leu Pro Ile Ser Ser Asp Glu Arg
            915                 920                 925 cca aat tgc tgt aaa cca gct gct tgt cag tgt cca tct tgc aat ggt    2832
Pro Asn Cys Cys Lys Pro Ala Ala Cys Gln Cys Pro Ser Cys Asn Gly
    930                 935                 940 gat gca cca gac tcc cat ttc ttt agc tat agt atc gat gtt ggt tcc    2880
Asp Ala Pro Asp Ser His Phe Phe Ser Tyr Ser Ile Asp Val Gly Ser
945                 950                 955                 960 tta caa gca gat gta aat tta gga att gag ttt ggt ctt cgt att gtg    2928
Leu Gln Ala Asp Val Asn Leu Gly Ile Glu Phe Gly Leu Arg Ile Val
                965                 970                 975 aaa tcc aac gga ttt gca aaa atc agt aac cta gaa atc aaa gaa gac    2976
Lys Ser Asn Gly Phe Ala Lys Ile Ser Asn Leu Glu Ile Lys Glu Asp
            980                 985                 990 cgt cca tta aca gaa aaa gaa att aag aaa ata caa cgc aaa gaa caa    3024
Arg Pro Leu Thr Glu Lys Glu Ile Lys Lys Ile Gln Arg Lys Glu Gln
        995                 1000                1005 aag tgg aaa aaa gca ttt gac aaa gaa cag gca gag tta acg gca aca    3072
Lys Trp Lys Lys Ala Phe Asp Lys Glu Gln Ala Glu Leu Thr Ala Thr
    1010                1015                1020 ctc caa cca acc ctg aac caa atc aat gcc tta tat caa aat gaa gat    3120
Leu Gln Pro Thr Leu Asn Gln Ile Asn Ala Leu Tyr Gln Asn Glu Asp
1025                1030                1035                1040 tgg aac ggt tcg att cac cct cat gta acg tat caa cat cta tcc gat    3168
Trp Asn Gly Ser Ile His Pro His Val Thr Tyr Gln His Leu Ser Asp
                1045                1050                1055 gtt gtc gta cca gca tta cca aaa caa aga cat tgg ttt atg gaa gat    3216
Val Val Val Pro Ala Leu Pro Lys Gln Arg His Trp Phe Met Glu Asp
            1060                1065                1070 cga caa ggt gaa cat tac aat gta aca caa caa ttc caa caa gca tta    3264
Arg Gln Gly Glu His Tyr Asn Val Thr Gln Gln Phe Gln Gln Ala Leu
        1075                1080                1085 gat cgt gct ttc caa caa atc gaa gaa caa aac tta att cac aat ggt    3312
Asp Arg Ala Phe Gln Gln Ile Glu Glu Gln Asn Leu Ile His Asn Gly
    1090                1095                1100 agc ttt gcg aat gga ttg aca gat tgg act gtc aca ggg gat gca cat    3360
Ser Phe Ala Asn Gly Leu Thr Asp Trp Thr Val Thr Gly Asp Ala His
1105                1110                1115                1120 gtt act atc cag gat gat gat caa gta tta gaa cta tct cat tgg gat    3408
Val Thr Ile Gln Asp Asp Asp Gln Val Leu Glu Leu Ser His Trp Asp
                1125                1130                1135 gca agt gtc tct caa acg att gaa att att gat ttt gaa gaa gaa aaa    3456
Ala Ser Val Ser Gln Thr Ile Glu Ile Ile Asp Phe Glu Glu Glu Lys
            1140                1145                1150 gaa tac aaa ctt cgt gta cgt gga aaa ggt aaa gga acg gta acc gtt    3504
Glu Tyr Lys Leu Arg Val Arg Gly Lys Gly Lys Gly Thr Val Thr Val
        1155                1160                1165 caa cat gga gaa gaa gag tta gaa aca atg aca ttt aat gca acg agt    3552
Gln His Gly Glu Glu Glu Leu Glu Thr Met Thr Phe Asn Ala Thr Ser
    1170                1175                1180 ttt aca acg caa gaa caa acc ttc tat ttc gaa gga aat aca gtg gat    3600
Phe Thr Thr Gln Glu Gln Thr Phe Tyr Phe Glu Gly Asn Thr Val Asp
1185                1190                1195                1200 ata cac gtt caa tca gag aat aat aca ttc ctg gta gac agt gta gaa    3648
Ile His Val Gln Ser Glu Asn Asn Thr Phe Leu Val Asp Ser Val Glu
                1205                1210                1215
```

```
ctc att gaa att ata gaa aag                                              3669
Leu Ile Glu Ile Ile Glu Lys
            1220
```

<210> SEQ ID NO 35
<211> LENGTH: 1223
<212> TYPE: PRT
<213> ORGANISM: Unknown
<220> FEATURE:
<223> OTHER INFORMATION: isolated from soil sample (AXMI-049)

<400> SEQUENCE: 35

```
Met Asp Asp Met Thr Asn Leu Ser Asp Val Tyr Ser Pro Val Pro Ser
 1               5                  10                  15

Asn Val Leu Ala Ala Pro Leu Ile Leu Glu Glu Thr Lys Lys Lys Thr
            20                  25                  30

Pro Ala Glu Gln Ala Lys Glu Asp Leu Glu Lys Ala Leu Arg Thr Gly
        35                  40                  45

Lys Phe Ser Asp Ala Ile Ala Gln Ile Leu Asn Asp Val Leu Ile Asn
 50                  55                  60

Gln Lys Phe Ser Tyr Gln Thr Ala Val Thr Val Ser Leu Ser Leu Ala
 65                  70                  75                  80

Ser Ile Val Leu Pro Glu Ile Gly Phe Phe Ala Pro Phe Val Gly Leu
                85                  90                  95

Phe Phe Ser Ala Leu Asn Lys Ser Gln Asn Ile Pro Thr Thr Ser Asp
            100                 105                 110

Ile Phe Glu Ala Met Lys Pro Ala Ile Gln Thr Met Ile Asp Arg Ser
        115                 120                 125

Leu Thr Asp Ala Glu Asn Lys Glu Met Asp Asp Gln Ala His Asn Leu
130                 135                 140

Phe Thr Arg Leu Gln Thr Tyr Gln Glu Gln Ile Asp Leu Tyr Lys His
145                 150                 155                 160

Ile Leu Asp Ala Lys Gln Lys Pro Thr Leu Asn Asp Ile Gly Asp Leu
                165                 170                 175

His Thr Ser Ile Asp Glu Thr Leu Arg Thr Leu Asp Ser Asn Leu Ala
            180                 185                 190

Phe Phe Gln Thr Glu Gly Tyr Gln Asp Leu Gly Leu Pro Tyr Tyr Thr
        195                 200                 205

Ile Phe Ala Thr Gln Tyr Leu Leu Ile Leu Ser Asp Lys Ile Lys Thr
    210                 215                 220

Gly Ile Thr Trp Gly Tyr Asn Pro Ile Asn Ile Pro Asp Phe Gln Asn
225                 230                 235                 240

Gln Phe Asn Asn Arg Ile Leu Leu Phe Thr Lys Tyr Ile Ser Gly Gln
                245                 250                 255

Leu Lys Lys Met Tyr Asp Asn Gly Val His Pro Ala Leu Leu Tyr Gln
            260                 265                 270

Asn Cys Ile Gln Phe Val Ala Leu Trp Pro Thr Phe Ser Pro Ala Asp
        275                 280                 285

Tyr Asn Leu Ser Asn Ser Thr Asp Leu Glu Gln Thr Ile Ser Phe Lys
    290                 295                 300

Ser Phe Ile Ser Tyr Lys Ser Leu Asn Asp Tyr Asn Tyr Ala Leu Pro
305                 310                 315                 320

Glu Ile Asn Thr Trp Thr Asn Phe Glu Met Thr Lys Ser Leu Asp Phe
                325                 330                 335

Asn Asn Cys Arg Ser Met Asp Asn Tyr Gly Ile Ala Gly Asp Leu Arg
            340                 345                 350
```

```
Ile Thr Asn His Lys Asn Glu Ile His Glu Ile Ser Ala Pro Ser Val
        355                 360                 365

Leu Tyr Met Thr Ser Asn Gln Cys Asn Ser Arg Leu Val Phe Pro Phe
        370                 375                 380

Asp Asp Pro Ile Val Lys Phe Glu Gly Thr Ser Ser Val Phe Ile Gly
385                 390                 395                 400

Thr Pro Gly Leu Pro Gln Phe Tyr Thr Asn Phe Gln Leu Thr Ser Gly
                405                 410                 415

Lys Ser Leu Ile Phe Pro Pro Ser Gly Val Asn Gln Gln Gly Phe
        420                 425                 430

Thr Gln Asn Tyr Ser Val Ile Pro His Pro Gly Phe Lys Ile Ala Gly
        435                 440                 445

Ile Thr Asn Met Ser Tyr Leu Pro Thr His His Asp Ser Asn Ala Arg
        450                 455                 460

Thr Gln Ile Glu His Ile Gln Val Pro Glu Lys Ile Phe Pro Glu Asn
465                 470                 475                 480

Ile Ile Gly Val Pro Asp Pro Asp Asn Asn Asn Leu Ile Pro Ile Lys
                485                 490                 495

Gly Ile Pro Ala Glu Lys Gly Tyr Gly Asp Ser Ile Ala Tyr Val Ser
        500                 505                 510

Glu Pro Val Asn Gly Ala Ser Ala Val Lys Leu Thr Ser Asn Gln Ile
        515                 520                 525

Leu Gln Met Glu Ile Thr Asn Val Thr Thr Gln Lys Tyr Gln Val Arg
        530                 535                 540

Ile Arg Tyr Ala Thr Ala Gly Asp Thr Glu Ala Asn Ile Arg Phe His
545                 550                 555                 560

Ile Ile Asp Pro Asn Glu Asn Asn Leu Ile Asn Gly Pro Asn His Phe
                565                 570                 575

Thr Ala Val Ser Asn Thr Gln Thr Ser Val Gln Gly Glu Asn Gly Lys
        580                 585                 590

Tyr Val Leu Asn Thr Leu Val Asn Ser Ile Ile Leu Pro Ser Gly Lys
        595                 600                 605

Gln Lys Val Phe Ile Gln Asn Thr Gly Ser Gln Asp Leu Phe Leu Asp
        610                 615                 620

Arg Ile Glu Phe Ile Pro Leu Gln Leu Glu Leu Pro Phe Thr Ser Lys
625                 630                 635                 640

Leu Pro Glu Thr Thr Gln Pro Asn Thr Lys Thr Ile Trp Ser
                645                 650                 655

Gly Gln Lys Pro Ala Asn Thr Leu Ser Leu Gln Gly Thr Val Tyr Asn
        660                 665                 670

Asp Ala Ser Ile Glu Leu Gln Leu Tyr Met Asn Asp Asn Leu Val Gln
        675                 680                 685

Lys Ile Pro Ala Gln Gly Pro Gly Pro Ser Phe Asp Cys Asp Asp Gln
        690                 695                 700

Ser Lys Pro Ile Asn Gln Pro Asn Ile Lys Thr Glu Glu Phe Asn Lys
705                 710                 715                 720

Leu Val Leu Lys Glu Leu Ser Ser Thr Tyr Ser Tyr Cys Met Gly Gly
                725                 730                 735

Ala Phe Glu Asn Thr Tyr Gln Ile Asp Ile Thr Ile Asp Ser Lys Ser
                740                 745                 750

Gln Ser Phe Thr Thr Pro Glu Asp Leu Glu Lys Ile Thr Asn Gln Val
        755                 760                 765

Asn Gln Leu Phe Thr Ser Ser Ser Gln Thr Lys Leu Val Gln Thr Val
```

-continued

```
                770                 775                 780
Thr Asp Tyr Gly Ile Asp Gln Met Val Met Lys Val Asp Ala Leu Ser
785                 790                 795                 800

Asp Asp Val Phe Gly Val Glu Lys Lys Ala Leu Arg Lys Leu Val Asn
                805                 810                 815

Gln Ala Lys Gln Leu Ser Lys Val Arg Asn Val Leu Val Gly Gly Asn
                820                 825                 830

Phe Glu Lys Gly His Lys Trp Val Leu Gly Arg Lys Ala Thr Thr Val
                835                 840                 845

Ala Asp His Asp Leu Phe Lys Gly Asp His Leu Leu Pro Pro
850                 855                 860

Thr Leu Tyr Pro Ser Tyr Ala Tyr Gln Lys Ile Asp Glu Ser Lys Leu
865                 870                 875                 880

Lys Ser Asn Thr Arg Tyr Thr Val Ser Gly Phe Val Ala Gln Ser Glu
                885                 890                 895

His Leu Glu Val Val Ser Arg Tyr Gly Lys Glu Val Asn Thr Leu
                900                 905                 910

Leu His Val Pro Tyr Glu Glu Ala Leu Pro Ile Ser Ser Asp Glu Arg
                915                 920                 925

Pro Asn Cys Cys Lys Pro Ala Ala Cys Gln Cys Pro Ser Cys Asn Gly
930                 935                 940

Asp Ala Pro Asp Ser His Phe Phe Ser Tyr Ser Ile Asp Val Gly Ser
945                 950                 955                 960

Leu Gln Ala Asp Val Asn Leu Gly Ile Glu Phe Gly Leu Arg Ile Val
                965                 970                 975

Lys Ser Asn Gly Phe Ala Lys Ile Ser Asn Leu Glu Ile Lys Glu Asp
                980                 985                 990

Arg Pro Leu Thr Glu Lys Glu Ile Lys Lys Ile Gln Arg Lys Glu Gln
                995                 1000                1005

Lys Trp Lys Lys Ala Phe Asp Lys Glu Gln Ala Glu Leu Thr Ala Thr
                1010                1015                1020

Leu Gln Pro Thr Leu Asn Gln Ile Asn Ala Leu Tyr Gln Asn Glu Asp
1025                1030                1035                1040

Trp Asn Gly Ser Ile His Pro His Val Thr Tyr Gln His Leu Ser Asp
                1045                1050                1055

Val Val Val Pro Ala Leu Pro Lys Gln Arg His Trp Phe Met Glu Asp
                1060                1065                1070

Arg Gln Gly Glu His Tyr Asn Val Thr Gln Gln Phe Gln Gln Ala Leu
                1075                1080                1085

Asp Arg Ala Phe Gln Gln Ile Glu Glu Gln Asn Leu Ile His Asn Gly
                1090                1095                1100

Ser Phe Ala Asn Gly Leu Thr Asp Trp Thr Val Thr Gly Asp Ala His
1105                1110                1115                1120

Val Thr Ile Gln Asp Asp Gln Val Leu Glu Leu Ser His Trp Asp
                1125                1130                1135

Ala Ser Val Ser Gln Thr Ile Glu Ile Ile Asp Phe Glu Glu Glu Lys
                1140                1145                1150

Glu Tyr Lys Leu Arg Val Arg Gly Lys Gly Lys Gly Thr Val Thr Val
                1155                1160                1165

Gln His Gly Glu Glu Leu Glu Thr Met Thr Phe Asn Ala Thr Ser
                1170                1175                1180

Phe Thr Thr Gln Glu Gln Thr Phe Tyr Phe Glu Gly Asn Thr Val Asp
1185                1190                1195                1200
```

```
Ile His Val Gln Ser Glu Asn Asn Thr Phe Leu Val Asp Ser Val Glu
            1205                1210                1215
Leu Ile Glu Ile Ile Glu Lys
        1220

<210> SEQ ID NO 36
<211> LENGTH: 4
<212> TYPE: PRT
<213> ORGANISM: Artificial Sequence
<220> FEATURE:
<223> OTHER INFORMATION: Targeting peptide

<400> SEQUENCE: 36

Lys Asp Glu Leu
 1

<210> SEQ ID NO 37
<211> LENGTH: 3657
<212> TYPE: DNA
<213> ORGANISM: Artificial Sequence
<220> FEATURE:
<223> OTHER INFORMATION: aposynaxmi-031(fl)
<221> NAME/KEY: CDS
<222> LOCATION: (1)...(3657)

<400> SEQUENCE: 37
```

| | | | | | | | | | | | | | | | | |
|---|---|---|---|---|---|---|---|---|---|---|---|---|---|---|---|---|
| atg | cag | atc | ctt | ggg | tac | tcc | agc | ttc | gtt | gct | atc | gct | ctt | ctt | atg | 48 |
| Met | Gln | Ile | Leu | Gly | Tyr | Ser | Ser | Phe | Val | Ala | Ile | Ala | Leu | Leu | Met | |
| 1 | | | | 5 | | | | | 10 | | | | | 15 | | |
| agc | gtg | gtt | gtt | gtt | tgc | aat | ggg | ggc | aag | acg | tcc | acc | tac | gtg | cgt | 96 |
| Ser | Val | Val | Val | Val | Cys | Asn | Gly | Gly | Lys | Thr | Ser | Thr | Tyr | Val | Arg | |
| | | 20 | | | | | 25 | | | | | 30 | | | | |
| aat | ctg | gat | tgc | aat | ctc | cag | agc | cag | cag | aat | atc | cca | tac | aat | gtg | 144 |
| Asn | Leu | Asp | Cys | Asn | Leu | Gln | Ser | Gln | Gln | Asn | Ile | Pro | Tyr | Asn | Val | |
| | 35 | | | | | 40 | | | | | 45 | | | | | |
| ctt | gct | atc | cct | gtt | agc | aat | gtt | aat | agc | ctt | acg | gat | acg | gtt | ggc | 192 |
| Leu | Ala | Ile | Pro | Val | Ser | Asn | Val | Asn | Ser | Leu | Thr | Asp | Thr | Val | Gly | |
| 50 | | | | | 55 | | | | | 60 | | | | | | |
| gat | cta | aag | aag | gca | tgg | gaa | gag | ttc | cag | aag | acg | ggc | agc | ttc | tcc | 240 |
| Asp | Leu | Lys | Lys | Ala | Trp | Glu | Glu | Phe | Gln | Lys | Thr | Gly | Ser | Phe | Ser | |
| 65 | | | | 70 | | | | | 75 | | | | | 80 | | |
| ctt | acc | gca | ctc | cag | cag | ggc | ttc | agc | gct | tcc | cag | ggc | ggg | acg | ttc | 288 |
| Leu | Thr | Ala | Leu | Gln | Gln | Gly | Phe | Ser | Ala | Ser | Gln | Gly | Gly | Thr | Phe | |
| | | | 85 | | | | | 90 | | | | | 95 | | | |
| aat | tac | ctc | acc | ctc | ctc | cag | tcc | ggg | atc | tcc | ctg | gct | ggc | agc | ttc | 336 |
| Asn | Tyr | Leu | Thr | Leu | Leu | Gln | Ser | Gly | Ile | Ser | Leu | Ala | Gly | Ser | Phe | |
| | | 100 | | | | | 105 | | | | | 110 | | | | |
| gtg | cct | ggc | ggc | acc | ttc | gtt | gct | cca | atc | atc | aat | atg | gtg | atc | ggc | 384 |
| Val | Pro | Gly | Gly | Thr | Phe | Val | Ala | Pro | Ile | Ile | Asn | Met | Val | Ile | Gly | |
| | 115 | | | | | 120 | | | | | 125 | | | | | |
| tgg | ctc | tgg | cct | cat | aag | aat | aag | aat | gca | gat | acg | gaa | aat | ctg | atc | 432 |
| Trp | Leu | Trp | Pro | His | Lys | Asn | Lys | Asn | Ala | Asp | Thr | Glu | Asn | Leu | Ile | |
| 130 | | | | | 135 | | | | | 140 | | | | | | |
| aat | ctg | atc | gat | tca | gaa | atc | cag | aag | cag | ctg | aat | aag | gct | ctg | ctg | 480 |
| Asn | Leu | Ile | Asp | Ser | Glu | Ile | Gln | Lys | Gln | Leu | Asn | Lys | Ala | Leu | Leu | |
| 145 | | | | 150 | | | | | 155 | | | | | 160 | | |
| gat | gct | gat | cgc | aat | gaa | tgg | agc | agc | tac | ctc | gag | tcc | atc | ttc | gat | 528 |
| Asp | Ala | Asp | Arg | Asn | Glu | Trp | Ser | Ser | Tyr | Leu | Glu | Ser | Ile | Phe | Asp | |
| | | | 165 | | | | | 170 | | | | | 175 | | | |
| agc | agc | aat | aat | ctg | aat | ggc | gca | atc | gtt | gat | gct | cag | tgg | tcc | ggc | 576 |
| Ser | Ser | Asn | Asn | Leu | Asn | Gly | Ala | Ile | Val | Asp | Ala | Gln | Trp | Ser | Gly | |
| | | 180 | | | | | 185 | | | | | 190 | | | | |
| acc | gtg | aat | acg | acc | aat | cgt | acg | ctt | cgt | aat | cct | acg | gaa | tca | gat | 624 |

```
                    -continued

Thr Val Asn Thr Thr Asn Arg Thr Leu Arg Asn Pro Thr Glu Ser Asp
        195                 200                 205 tac acc aat gtg gtg acg aat ttc atc gca gca gat ggg gat atc gct       672
Tyr Thr Asn Val Val Thr Asn Phe Ile Ala Ala Asp Gly Asp Ile Ala
210                 215                 220 aat aat gaa aat cat atc atg aat ggg aat ttc gat gtg gca gca gct       720
Asn Asn Glu Asn His Ile Met Asn Gly Asn Phe Asp Val Ala Ala Ala
225                 230                 235                 240 cca tac ttc gtt atc ggg gct acc gct aga ttc gca gct atg cag tcc       768
Pro Tyr Phe Val Ile Gly Ala Thr Ala Arg Phe Ala Ala Met Gln Ser
            245                 250                 255 tac atc aag ttc tgc aat gca tgg atc gat aag gtt ggg ctg tca gat       816
Tyr Ile Lys Phe Cys Asn Ala Trp Ile Asp Lys Val Gly Leu Ser Asp
        260                 265                 270 gct cag ctg acc acg cag aag gct aat ctg gat aga acg aag cag aat       864
Ala Gln Leu Thr Thr Gln Lys Ala Asn Leu Asp Arg Thr Lys Gln Asn
    275                 280                 285 atg cgt aat gct atc ctt aat tac acc cag cag gtt atg aag gtt ttc       912
Met Arg Asn Ala Ile Leu Asn Tyr Thr Gln Gln Val Met Lys Val Phe
290                 295                 300 aag gat tcc aag aat atg cca acg atc ggc acg aat aag ttc agc gtt       960
Lys Asp Ser Lys Asn Met Pro Thr Ile Gly Thr Asn Lys Phe Ser Val
305                 310                 315                 320 gat acc tac aat gtt tac atc aag ggg atg acg ctt aat gtg ctt gat      1008
Asp Thr Tyr Asn Val Tyr Ile Lys Gly Met Thr Leu Asn Val Leu Asp
            325                 330                 335 atc gtt gct atc tgg cca agc ctg tac cca gat gat tac acg tca cag      1056
Ile Val Ala Ile Trp Pro Ser Leu Tyr Pro Asp Asp Tyr Thr Ser Gln
        340                 345                 350 acg gct ctg gaa cag acc cgc gtg acg ttc tcc aat atg gtg ggg cag      1104
Thr Ala Leu Glu Gln Thr Arg Val Thr Phe Ser Asn Met Val Gly Gln
    355                 360                 365 gaa gaa ggc acg gat ggc agc ctc aga atc tac aat acc ttc gat agc      1152
Glu Glu Gly Thr Asp Gly Ser Leu Arg Ile Tyr Asn Thr Phe Asp Ser
370                 375                 380 ttc tcc tac cag cat agc cct atc cct aat aat aat gtg aat ctc atc      1200
Phe Ser Tyr Gln His Ser Pro Ile Pro Asn Asn Asn Val Asn Leu Ile
385                 390                 395                 400 agc tac tac aat gat gaa ctt cag aat ctg gaa ctc ggg gtt tac acc      1248
Ser Tyr Tyr Asn Asp Glu Leu Gln Asn Leu Glu Leu Gly Val Tyr Thr
            405                 410                 415 cca cca aag aag ggc tca ggc tac agc tac cca tac ggg ttc gtg ctg      1296
Pro Pro Lys Lys Gly Ser Gly Tyr Ser Tyr Pro Tyr Gly Phe Val Leu
        420                 425                 430 aat tac gca aat agc aag tac aag tac ggc gat tcc aat gat cca gaa      1344
Asn Tyr Ala Asn Ser Lys Tyr Lys Tyr Gly Asp Ser Asn Asp Pro Glu
    435                 440                 445 tcc ctc ggc ggg ctt tcc acc ctt agc gct cca atc caa cag gtt aat      1392
Ser Leu Gly Gly Leu Ser Thr Leu Ser Ala Pro Ile Gln Gln Val Asn
450                 455                 460 gct gct acc cag aat agc aag tac ctt gat ggc gaa atc ctg aat ggg      1440
Ala Ala Thr Gln Asn Ser Lys Tyr Leu Asp Gly Glu Ile Leu Asn Gly
465                 470                 475                 480 atc ggc gca agc ctg cct ggc tac tgc acg acc ggg tgc tca cct acc      1488
Ile Gly Ala Ser Leu Pro Gly Tyr Cys Thr Thr Gly Cys Ser Pro Thr
            485                 490                 495 gaa cca cca ttc agc tgc acg agc acg gca aat ggg tac aag gca agc      1536
Glu Pro Pro Phe Ser Cys Thr Ser Thr Ala Asn Gly Tyr Lys Ala Ser
        500                 505                 510 tgc aat cca agc gat acc aat cag aag atc aat gct ctc tac cca ttc      1584
```

-continued

| | | |
|---|---|---|
| Cys Asn Pro Ser Asp Thr Asn Gln Lys Ile Asn Ala Leu Tyr Pro Phe<br>515 520 525 | | |
| acg cag gca aat gtg aag ggg aat acc ggg aag ctg ggc gtt ctc gca<br>Thr Gln Ala Asn Val Lys Gly Asn Thr Gly Lys Leu Gly Val Leu Ala<br>530 535 540 | 1632 | |
| agc ctt gtt agc tac gat ctg aat cct aag aat gtt ttc ggg gaa ctc<br>Ser Leu Val Ser Tyr Asp Leu Asn Pro Lys Asn Val Phe Gly Glu Leu<br>545 550 555 560 | 1680 | |
| gat tca gat acc aat aat gtt atc ctt aag ggc atc cca gca gaa aag<br>Asp Ser Asp Thr Asn Asn Val Ile Leu Lys Gly Ile Pro Ala Glu Lys<br>565 570 575 | 1728 | |
| ggc tac ttc cca aat aat gca aga cca acc gtt gtg aag gaa tgg atc<br>Gly Tyr Phe Pro Asn Asn Ala Arg Pro Thr Val Val Lys Glu Trp Ile<br>580 585 590 | 1776 | |
| aat ggg gct tcc gca gtt cca ctt gat tcc ggc aat acc ctg ttc atg<br>Asn Gly Ala Ser Ala Val Pro Leu Asp Ser Gly Asn Thr Leu Phe Met<br>595 600 605 | 1824 | |
| acg gct acg aac ctg acg gct acc cag tac aga atc cgc atc cgt tac<br>Thr Ala Thr Asn Leu Thr Ala Thr Gln Tyr Arg Ile Arg Ile Arg Tyr<br>610 615 620 | 1872 | |
| gct aac cca aac tca aac acg cag atc ggc gtt aga atc acg cag aac<br>Ala Asn Pro Asn Ser Asn Thr Gln Ile Gly Val Arg Ile Thr Gln Asn<br>625 630 635 640 | 1920 | |
| ggg agc ctc atc tcc tcc tcc aac ctc acg ctg tac tca acc acc gat<br>Gly Ser Leu Ile Ser Ser Ser Asn Leu Thr Leu Tyr Ser Thr Thr Asp<br>645 650 655 | 1968 | |
| atg aac aac acc ctg cca ctg aac gtt tac gtg atc ggg gaa aac ggg<br>Met Asn Asn Thr Leu Pro Leu Asn Val Tyr Val Ile Gly Glu Asn Gly<br>660 665 670 | 2016 | |
| aac tac acc ctc cag gat ctc tac aac acg acg aac gtt ctg tcc acg<br>Asn Tyr Thr Leu Gln Asp Leu Tyr Asn Thr Thr Asn Val Leu Ser Thr<br>675 680 685 | 2064 | |
| ggc gat atc acc ctg cag atc acc ggc ggg gat cag aag ata ttc atc<br>Gly Asp Ile Thr Leu Gln Ile Thr Gly Gly Asp Gln Lys Ile Phe Ile<br>690 695 700 | 2112 | |
| gat cgc atc gag ttc gtg cct acg atg cca gtg cca ggc aac acc aac<br>Asp Arg Ile Glu Phe Val Pro Thr Met Pro Val Pro Gly Asn Thr Asn<br>705 710 715 720 | 2160 | |
| aac aac aac ggg aac aac aac ggc aac aac aac cct cct cat cat gtt<br>Asn Asn Asn Gly Asn Asn Asn Gly Asn Asn Asn Pro Pro His His Val<br>725 730 735 | 2208 | |
| tgc gct atc gca ggc acc cag cag tcc tgc tcc ggc cca cca aag ttc<br>Cys Ala Ile Ala Gly Thr Gln Gln Ser Cys Ser Gly Pro Pro Lys Phe<br>740 745 750 | 2256 | |
| gag cag gtg tcc gat tta gaa aag ata acc acg cag gtt tac atg ctc<br>Glu Gln Val Ser Asp Leu Glu Lys Ile Thr Thr Gln Val Tyr Met Leu<br>755 760 765 | 2304 | |
| ttc aag tcc tcc cca tac gaa gaa ctt gct ctt gaa gtt agc agc tac<br>Phe Lys Ser Ser Pro Tyr Glu Glu Leu Ala Leu Glu Val Ser Ser Tyr<br>770 775 780 | 2352 | |
| cag atc agc cag gtt gca ctg aag gtt atg gct ctc agc gat gaa cta<br>Gln Ile Ser Gln Val Ala Leu Lys Val Met Ala Leu Ser Asp Glu Leu<br>785 790 795 800 | 2400 | |
| ttc tgc gaa gaa aag aac gtg ctg aga aag ctc gtg aac aag gca aag<br>Phe Cys Glu Glu Lys Asn Val Leu Arg Lys Leu Val Asn Lys Ala Lys<br>805 810 815 | 2448 | |
| cag ctt ctc gaa gca agc aac ctt ctc gtt ggg ggg aac ttc gag acg<br>Gln Leu Leu Glu Ala Ser Asn Leu Leu Val Gly Gly Asn Phe Glu Thr<br>820 825 830 | 2496 | |
| act cag aac tgg gtg ctc ggc acg aac gct tac atc aac tat gat tca | 2544 | |

```
                Thr Gln Asn Trp Val Leu Gly Thr Asn Ala Tyr Ile Asn Tyr Asp Ser
                        835                 840                 845 ttc ctg ttc aac ggg aac tac ctg agc ctc cag cca gca tcc ggc ttc          2592
Phe Leu Phe Asn Gly Asn Tyr Leu Ser Leu Gln Pro Ala Ser Gly Phe
850                 855                 860 ttc acg agc tac gct tac cag aag atc gat gaa tcc acg ctt aag cct          2640
Phe Thr Ser Tyr Ala Tyr Gln Lys Ile Asp Glu Ser Thr Leu Lys Pro
865                 870                 875                 880 tac acg cgc tac aag gtg tcc ggg ttc atc ggg cag tca aac cag gtt          2688
Tyr Thr Arg Tyr Lys Val Ser Gly Phe Ile Gly Gln Ser Asn Gln Val
                885                 890                 895 gaa ctg atc atc agc cgc tac ggg aag gaa atc gat aag atc ctt aac          2736
Glu Leu Ile Ile Ser Arg Tyr Gly Lys Glu Ile Asp Lys Ile Leu Asn
                900                 905                 910 gtg cca tac gca ggg cca ctc cca atc acc gca gat gca agc atc acc          2784
Val Pro Tyr Ala Gly Pro Leu Pro Ile Thr Ala Asp Ala Ser Ile Thr
                915                 920                 925 tgc tgc gct cca gaa ata ggg cag tgc gat ggg gaa cag tca gat tcc          2832
Cys Cys Ala Pro Glu Ile Gly Gln Cys Asp Gly Glu Gln Ser Asp Ser
                930                 935                 940 cat ttc ttc aac tac agc atc gat gtt ggc gca ctc cat cca gaa ctt          2880
His Phe Phe Asn Tyr Ser Ile Asp Val Gly Ala Leu His Pro Glu Leu
945                 950                 955                 960 aac cca ggg atc gaa atc ggg ctg aag atc gtt cag agc aac ggc tac          2928
Asn Pro Gly Ile Glu Ile Gly Leu Lys Ile Val Gln Ser Asn Gly Tyr
                965                 970                 975 atc acc atc tcc aac ctt gaa atc atc gaa gaa aga cca tta acg gaa          2976
Ile Thr Ile Ser Asn Leu Glu Ile Ile Glu Glu Arg Pro Leu Thr Glu
                980                 985                 990 atg gaa att caa gca gtg aac cgc aag aac cag aag tgg gaa cgc gaa          3024
Met Glu Ile Gln Ala Val Asn Arg Lys Asn Gln Lys Trp Glu Arg Glu
                995                 1000                1005 aag ctg ctt gaa tgc gca tcc atc tcc gaa ctc ctc cag cct atc atc          3072
Lys Leu Leu Glu Cys Ala Ser Ile Ser Glu Leu Leu Gln Pro Ile Ile
        1010                1015                1020 aac cag ata gat agc ctc ttc aag gat ggc aac tgg tac aac gat atc          3120
Asn Gln Ile Asp Ser Leu Phe Lys Asp Gly Asn Trp Tyr Asn Asp Ile
1025                1030                1035                1040 cta cca cat gtt acc tac cag gat ctt aag aac atc atc atc cca gaa          3168
Leu Pro His Val Thr Tyr Gln Asp Leu Lys Asn Ile Ile Ile Pro Glu
                1045                1050                1055 ctt cct aag ctc aag cat tgg ttc atc gaa aac ctg cct ggg gaa tac          3216
Leu Pro Lys Leu Lys His Trp Phe Ile Glu Asn Leu Pro Gly Glu Tyr
        1060                1065                1070 cat gaa atc gaa cag aag atg aag gaa gca tta aag tac gca ttc act          3264
His Glu Ile Glu Gln Lys Met Lys Glu Ala Leu Lys Tyr Ala Phe Thr
        1075                1080                1085 cag ctc gat gaa aag aac ctg atc cat aac ggc cat ttc acc acc aac          3312
Gln Leu Asp Glu Lys Asn Leu Ile His Asn Gly His Phe Thr Thr Asn
        1090                1095                1100 ctc atc gat tgg cag gtg gaa ggc gat gct cag atg aag gtg ctt gaa          3360
Leu Ile Asp Trp Gln Val Glu Gly Asp Ala Gln Met Lys Val Leu Glu
1105                1110                1115                1120 aac gat gca ctc gct ctc cag cta ttc aac tgg gat gct tcc gca tcc          3408
Asn Asp Ala Leu Ala Leu Gln Leu Phe Asn Trp Asp Ala Ser Ala Ser
                1125                1130                1135 cag agc atc aac atc cta gag ttc gat gaa gat aag gct tac aag ctg          3456
Gln Ser Ile Asn Ile Leu Glu Phe Asp Glu Asp Lys Ala Tyr Lys Leu
        1140                1145                1150 cgt gtg tac gca cag ggc tcc ggg acg atc cag ttc ggc aac tgc gaa          3504
```

```
Arg Val Tyr Ala Gln Gly Ser Gly Thr Ile Gln Phe Gly Asn Cys Glu
        1155                1160                1165 gat gaa gct atc cag ttc aac acc aac tca ttc atc tac cag gaa aag      3552
Asp Glu Ala Ile Gln Phe Asn Thr Asn Ser Phe Ile Tyr Gln Glu Lys
        1170                1175                1180 ata gtg tac ttc gat acg cca tcc gtt aac ctt cat atc cag agc gaa      3600
Ile Val Tyr Phe Asp Thr Pro Ser Val Asn Leu His Ile Gln Ser Glu
1185                1190                1195                1200 ggc tcc gag ttc atc gtg agc agc atc gat ctc atc gaa ctc agc gat      3648
Gly Ser Glu Phe Ile Val Ser Ser Ile Asp Leu Ile Glu Leu Ser Asp
                    1205                1210                1215 gat cag tag                                                           3657
Asp Gln *

<210> SEQ ID NO 38
<211> LENGTH: 1218
<212> TYPE: PRT
<213> ORGANISM: Artificial Sequence
<220> FEATURE:
<223> OTHER INFORMATION: APOSYNAXMI-031(FL)

<400> SEQUENCE: 38

Met Gln Ile Leu Gly Tyr Ser Ser Phe Val Ala Ile Ala Leu Leu Met
 1               5                  10                  15

Ser Val Val Val Cys Asn Gly Gly Lys Thr Ser Thr Tyr Val Arg
            20                  25                  30

Asn Leu Asp Cys Asn Leu Gln Ser Gln Gln Asn Ile Pro Tyr Asn Val
        35                  40                  45

Leu Ala Ile Pro Val Ser Asn Val Asn Ser Leu Thr Asp Thr Val Gly
    50                  55                  60

Asp Leu Lys Lys Ala Trp Glu Glu Phe Gln Lys Thr Gly Ser Phe Ser
65                  70                  75                  80

Leu Thr Ala Leu Gln Gln Gly Phe Ser Ala Ser Gln Gly Gly Thr Phe
                85                  90                  95

Asn Tyr Leu Thr Leu Leu Gln Ser Gly Ile Ser Leu Ala Gly Ser Phe
            100                 105                 110

Val Pro Gly Gly Thr Phe Val Ala Pro Ile Ile Asn Met Val Ile Gly
        115                 120                 125

Trp Leu Trp Pro His Lys Asn Lys Asn Ala Asp Thr Glu Asn Leu Ile
    130                 135                 140

Asn Leu Ile Asp Ser Glu Ile Gln Lys Gln Leu Asn Lys Ala Leu Leu
145                 150                 155                 160

Asp Ala Asp Arg Asn Glu Trp Ser Ser Tyr Leu Glu Ser Ile Phe Asp
                165                 170                 175

Ser Ser Asn Asn Leu Asn Gly Ala Ile Val Asp Ala Gln Trp Ser Gly
            180                 185                 190

Thr Val Asn Thr Thr Asn Arg Thr Leu Arg Asn Pro Thr Glu Ser Asp
        195                 200                 205

Tyr Thr Asn Val Val Thr Asn Phe Ile Ala Ala Asp Gly Asp Ile Ala
    210                 215                 220

Asn Asn Glu Asn His Ile Met Asn Gly Asn Phe Asp Val Ala Ala Ala
225                 230                 235                 240

Pro Tyr Phe Val Ile Gly Ala Thr Ala Arg Phe Ala Ala Met Gln Ser
                245                 250                 255

Tyr Ile Lys Phe Cys Asn Ala Trp Ile Asp Lys Val Gly Leu Ser Asp
            260                 265                 270

Ala Gln Leu Thr Thr Gln Lys Ala Asn Leu Asp Arg Thr Lys Gln Asn
```

```
                275                 280                 285
Met Arg Asn Ala Ile Leu Asn Tyr Thr Gln Gln Val Met Lys Val Phe
290                 295                 300
Lys Asp Ser Lys Asn Met Pro Thr Ile Gly Thr Asn Lys Phe Ser Val
305                 310                 315                 320
Asp Thr Tyr Asn Val Tyr Ile Lys Gly Met Thr Leu Asn Val Leu Asp
                325                 330                 335
Ile Val Ala Ile Trp Pro Ser Leu Tyr Pro Asp Tyr Thr Ser Gln
                340                 345                 350
Thr Ala Leu Glu Gln Thr Arg Val Thr Phe Ser Asn Met Val Gly Gln
                355                 360                 365
Glu Glu Gly Thr Asp Gly Ser Leu Arg Ile Tyr Asn Thr Phe Asp Ser
370                 375                 380
Phe Ser Tyr Gln His Ser Pro Ile Pro Asn Asn Asn Val Asn Leu Ile
385                 390                 395                 400
Ser Tyr Tyr Asn Asp Glu Leu Gln Asn Leu Glu Leu Gly Val Tyr Thr
                405                 410                 415
Pro Pro Lys Lys Gly Ser Gly Tyr Ser Tyr Pro Tyr Gly Phe Val Leu
                420                 425                 430
Asn Tyr Ala Asn Ser Lys Tyr Lys Tyr Gly Asp Ser Asn Asp Pro Glu
                435                 440                 445
Ser Leu Gly Gly Leu Ser Thr Leu Ser Ala Pro Ile Gln Gln Val Asn
                450                 455                 460
Ala Ala Thr Gln Asn Ser Lys Tyr Leu Asp Gly Glu Ile Leu Asn Gly
465                 470                 475                 480
Ile Gly Ala Ser Leu Pro Gly Tyr Cys Thr Thr Gly Cys Ser Pro Thr
                485                 490                 495
Glu Pro Pro Phe Ser Cys Thr Ser Thr Ala Asn Gly Tyr Lys Ala Ser
                500                 505                 510
Cys Asn Pro Ser Asp Thr Asn Gln Lys Ile Asn Ala Leu Tyr Pro Phe
                515                 520                 525
Thr Gln Ala Asn Val Lys Gly Asn Thr Gly Lys Leu Gly Val Leu Ala
                530                 535                 540
Ser Leu Val Ser Tyr Asp Leu Asn Pro Lys Asn Val Phe Gly Glu Leu
545                 550                 555                 560
Asp Ser Asp Thr Asn Asn Val Ile Leu Lys Gly Ile Pro Ala Glu Lys
                565                 570                 575
Gly Tyr Phe Pro Asn Asn Ala Arg Pro Thr Val Val Lys Glu Trp Ile
                580                 585                 590
Asn Gly Ala Ser Ala Val Pro Leu Asp Ser Gly Asn Thr Leu Phe Met
                595                 600                 605
Thr Ala Thr Asn Leu Thr Ala Thr Gln Tyr Arg Ile Arg Ile Arg Tyr
                610                 615                 620
Ala Asn Pro Asn Ser Asn Thr Gln Ile Gly Val Arg Ile Thr Gln Asn
625                 630                 635                 640
Gly Ser Leu Ile Ser Ser Ser Asn Leu Thr Leu Tyr Ser Thr Thr Asp
                645                 650                 655
Met Asn Asn Thr Leu Pro Leu Asn Val Tyr Val Ile Gly Glu Asn Gly
                660                 665                 670
Asn Tyr Thr Leu Gln Asp Leu Tyr Asn Thr Asn Val Leu Ser Thr
                675                 680                 685
Gly Asp Ile Thr Leu Gln Ile Thr Gly Gly Asp Gln Lys Ile Phe Ile
                690                 695                 700
```

```
Asp Arg Ile Glu Phe Val Pro Thr Met Pro Val Pro Gly Asn Thr Asn
705                 710                 715                 720

Asn Asn Asn Gly Asn Asn Gly Asn Asn Asn Pro Pro His His Val
            725             730                 735

Cys Ala Ile Ala Gly Thr Gln Gln Ser Cys Ser Gly Pro Pro Lys Phe
            740             745                 750

Glu Gln Val Ser Asp Leu Glu Lys Ile Thr Thr Gln Val Tyr Met Leu
            755             760                 765

Phe Lys Ser Ser Pro Tyr Glu Glu Leu Ala Leu Glu Val Ser Ser Tyr
770             775                 780

Gln Ile Ser Gln Val Ala Leu Lys Val Met Ala Leu Ser Asp Glu Leu
785                 790                 795                 800

Phe Cys Glu Glu Lys Asn Val Leu Arg Lys Leu Val Asn Lys Ala Lys
                805                 810                 815

Gln Leu Leu Glu Ala Ser Asn Leu Leu Val Gly Gly Asn Phe Glu Thr
            820                 825                 830

Thr Gln Asn Trp Val Leu Gly Thr Asn Ala Tyr Ile Asn Tyr Asp Ser
            835                 840                 845

Phe Leu Phe Asn Gly Asn Tyr Leu Ser Leu Gln Pro Ala Ser Gly Phe
850                 855                 860

Phe Thr Ser Tyr Ala Tyr Gln Lys Ile Asp Glu Ser Thr Leu Lys Pro
865             870                 875                 880

Tyr Thr Arg Tyr Lys Val Ser Gly Phe Ile Gly Gln Ser Asn Gln Val
            885                 890                 895

Glu Leu Ile Ile Ser Arg Tyr Gly Lys Glu Ile Asp Lys Ile Leu Asn
                900                 905                 910

Val Pro Tyr Ala Gly Pro Leu Pro Ile Thr Ala Asp Ala Ser Ile Thr
            915                 920                 925

Cys Cys Ala Pro Glu Ile Gly Gln Cys Asp Gly Glu Gln Ser Asp Ser
            930                 935                 940

His Phe Phe Asn Tyr Ser Ile Asp Val Gly Ala Leu His Pro Glu Leu
945                 950                 955                 960

Asn Pro Gly Ile Glu Ile Gly Leu Lys Ile Val Gln Ser Asn Gly Tyr
                965                 970                 975

Ile Thr Ile Ser Asn Leu Glu Ile Ile Glu Glu Arg Pro Leu Thr Glu
            980                 985                 990

Met Glu Ile Gln Ala Val Asn Arg Lys Asn Gln Lys Trp Glu Arg Glu
            995                 1000                1005

Lys Leu Leu Glu Cys Ala Ser Ile Ser Glu Leu Leu Gln Pro Ile Ile
    1010                1015                1020

Asn Gln Ile Asp Ser Leu Phe Lys Asp Gly Asn Trp Tyr Asn Asp Ile
1025                1030                1035                1040

Leu Pro His Val Thr Tyr Gln Asp Leu Lys Asn Ile Ile Pro Glu
            1045                1050                1055

Leu Pro Lys Leu Lys His Trp Phe Ile Glu Asn Leu Pro Gly Glu Tyr
            1060                1065                1070

His Glu Ile Glu Gln Lys Met Lys Glu Ala Leu Lys Tyr Ala Phe Thr
            1075                1080                1085

Gln Leu Asp Glu Lys Asn Leu Ile His Asn Gly His Phe Thr Thr Asn
            1090                1095                1100

Leu Ile Asp Trp Gln Val Glu Gly Asp Ala Gln Met Lys Val Leu Glu
1105                1110                1115                1120

Asn Asp Ala Leu Ala Leu Gln Leu Phe Asn Trp Asp Ala Ser Ala Ser
            1125                1130                1135
```

```
Gln Ser Ile Asn Ile Leu Glu Phe Asp Glu Asp Lys Ala Tyr Lys Leu
            1140                1145                1150

Arg Val Tyr Ala Gln Gly Ser Gly Thr Ile Gln Phe Gly Asn Cys Glu
        1155                1160                1165

Asp Glu Ala Ile Gln Phe Asn Thr Asn Ser Phe Ile Tyr Gln Glu Lys
    1170                1175                1180

Ile Val Tyr Phe Asp Thr Pro Ser Val Asn Leu His Ile Gln Ser Glu
1185                1190                1195                1200

Gly Ser Glu Phe Ile Val Ser Ser Ile Asp Leu Ile Glu Leu Ser Asp
                1205                1210                1215

Asp Gln
```